US012599676B2

(12) United States Patent
Carr et al.

(10) Patent No.: US 12,599,676 B2
(45) Date of Patent: Apr. 14, 2026

(54) CYTOTOXIC IMIDAZO[1,2-A]PYRIDINE COMPOUNDS AND THEIR USE IN THERAPY

(71) Applicants: MyricX Pharma Limited, London (GB); Imperial College Innovations Limited, London (GB)

(72) Inventors: Robin Carr, London (GB); Roberto Solari, London (GB); Andrew Simon Bell, London (GB); Edward William Tate, London (GB); Roger Bonnert, Geneva (CH)

(73) Assignees: MyricX Pharma Limited, London (GB); Imperial College Innovations Limited, London (GB)

(*) Notice: Subject to any disclaimer, the term of this patent is extended or adjusted under 35 U.S.C. 154(b) by 0 days.

(21) Appl. No.: 19/072,750

(22) Filed: Mar. 6, 2025

(65) Prior Publication Data

US 2026/0048136 A1 Feb. 19, 2026

Related U.S. Application Data

(63) Continuation of application No. PCT/GB2023/052319, filed on Sep. 8, 2023.

(30) Foreign Application Priority Data

Sep. 9, 2022 (EP) .................................... 22194959
Sep. 9, 2022 (EP) .................................... 22194984
Apr. 14, 2023 (GB) .................................... 2305541
Apr. 14, 2023 (GB) .................................... 2305546

(51) Int. Cl.
*A61P 35/00* (2006.01)
*A61K 31/437* (2006.01)
*A61K 47/68* (2017.01)
*C07D 471/04* (2006.01)
*C07K 16/32* (2006.01)

(52) U.S. Cl.
CPC ........ *A61K 47/6851* (2017.08); *A61K 31/437* (2013.01); *A61K 47/6803* (2017.08); *A61P 35/00* (2018.01); *C07D 471/04* (2013.01); *C07K 16/32* (2013.01)

(58) Field of Classification Search
CPC ............ A61K 47/6851; A61K 47/6803; C07K 16/32; A61P 35/00
See application file for complete search history.

(56) References Cited

U.S. PATENT DOCUMENTS

| | | | |
|---|---|---|---|
| 2,917,511 | A | 12/1959 | Bicking et al. |
| 3,050,525 | A | 8/1962 | Bicking et al. |
| 3,145,215 | A | 8/1964 | Kirchner et al. |
| 3,457,269 | A | 7/1969 | Kirchner et al. |
| 3,678,059 | A | 7/1972 | Gschwend et al. |
| 3,705,175 | A | 12/1972 | Magdanyi et al. |
| 4,886,808 | A | 12/1989 | King et al. |
| 5,017,573 | A | 5/1991 | Kon et al. |
| 5,037,844 | A | 8/1991 | Hamminga et al. |
| 5,190,953 | A | 3/1993 | Munson, Jr. et al. |
| 5,246,945 | A | 9/1993 | Kikuchi et al. |
| 5,665,725 | A | 9/1997 | Moltzen et al. |
| 5,684,003 | A | 11/1997 | Kikuchi et al. |
| 5,798,367 | A | 8/1998 | Catlow et al. |
| 5,861,414 | A | 1/1999 | Allen et al. |
| 5,914,405 | A | 6/1999 | Wilson |
| 5,985,867 | A | 11/1999 | Rodgers et al. |
| 6,069,152 | A | 5/2000 | Schaus et al. |
| 6,096,746 | A | 8/2000 | Suzuki et al. |
| 6,303,625 | B1 | 10/2001 | Hoekstra et al. |
| 6,376,491 | B1 | 4/2002 | Aoki et al. |
| 6,458,781 | B1 | 10/2002 | Connor et al. |
| 8,557,841 | B2 | 10/2013 | Yu et al. |
| 10,759,804 | B2 | 9/2020 | Bell et al. |
| 11,466,011 | B2 | 10/2022 | Bell et al. |
| 2002/0103229 | A1 | 8/2002 | Bhagwat et al. |
| 2002/0119972 | A1 | 8/2002 | Leftheris et al. |

(Continued)

FOREIGN PATENT DOCUMENTS

| | | | |
|---|---|---|---|
| EP | 0261964 | A2 | 3/1988 |
| EP | 0494774 | A1 | 7/1992 |

(Continued)

OTHER PUBLICATIONS

Rackham et al., "Discovery of Novel and Ligand-Efficient Inhibitors of Plasmodium falciparum and Plasmodium vivax N-myristoyltransferase," Journal of Medicinal Chemistry, 2013, 56, pp. 371-375.

(Continued)

*Primary Examiner* — Timothy R Rozof

(74) *Attorney, Agent, or Firm* — Morgan, Lewis & Bockius LLP

(57) ABSTRACT

The present invention relates to compounds of formula (I) and related aspects.

(I)

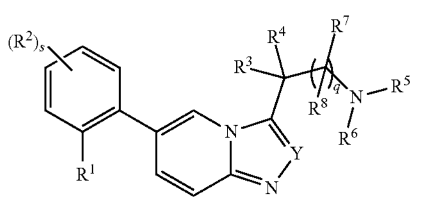

23 Claims, 14 Drawing Sheets

Specification includes a Sequence Listing.

(56) References Cited

U.S. PATENT DOCUMENTS

| | | | | |
|---|---|---|---|---|
| 2002/0161022 | A1 | 10/2002 | Reich et al. | |
| 2003/0096838 | A1 | 5/2003 | McClure et al. | |
| 2003/0109550 | A1 | 6/2003 | Clare et al. | |
| 2003/0149034 | A1 | 8/2003 | Lee et al. | |
| 2003/0153507 | A1 | 8/2003 | Canan-Koch et al. | |
| 2003/0207883 | A1 | 11/2003 | Renhowe et al. | |
| 2004/0009968 | A1 | 1/2004 | Binch et al. | |
| 2004/0014764 | A1 | 1/2004 | Smith et al. | |
| 2004/0014802 | A1 | 1/2004 | Dutruc-Rosset et al. | |
| 2004/0053958 | A1 | 3/2004 | Dombroski et al. | |
| 2004/0058912 | A1 | 3/2004 | Aissaoui et al. | |
| 2004/0106667 | A1 | 6/2004 | Damour et al. | |
| 2004/0138286 | A1 | 7/2004 | Imazaki et al. | |
| 2004/0157877 | A1 | 8/2004 | Dombroski et al. | |
| 2004/0176325 | A1 | 9/2004 | Munson et al. | |
| 2004/0204591 | A1 | 10/2004 | Kucera et al. | |
| 2005/0070546 | A1 | 3/2005 | Arrington et al. | |
| 2005/0075365 | A1 | 4/2005 | Braganza et al. | |
| 2006/0004000 | A1 | 1/2006 | D'Orchymont et al. | |
| 2006/0035922 | A1 | 2/2006 | Mathias et al. | |
| 2006/0100248 | A1 | 5/2006 | Garthwaite et al. | |
| 2006/0135589 | A1 | 6/2006 | Berdino et al. | |
| 2006/0135764 | A1 | 6/2006 | Fatheree et al. | |
| 2006/0142345 | A1 | 6/2006 | Kephart et al. | |
| 2006/0281789 | A1 | 12/2006 | Shiotsu et al. | |
| 2006/0287324 | A1 | 12/2006 | Sun et al. | |
| 2007/0197522 | A1 | 8/2007 | Edwards et al. | |
| 2008/0039457 | A1 | 2/2008 | Zhuo et al. | |
| 2009/0082348 | A1 | 3/2009 | Ohta et al. | |
| 2009/0124612 | A1 | 5/2009 | Albrecht et al. | |
| 2009/0203690 | A1 | 8/2009 | Akritopoulou-Zanze et al. | |
| 2009/0209577 | A1 | 8/2009 | Rucker et al. | |
| 2009/0215817 | A1 | 8/2009 | Rucker et al. | |
| 2009/0247504 | A1 | 10/2009 | Churcher et al. | |
| 2009/0270402 | A1 | 10/2009 | Calderwood et al. | |
| 2009/0291968 | A1 | 11/2009 | Georges et al. | |
| 2009/0318436 | A1 | 12/2009 | Albrecht et al. | |
| 2010/0113421 | A1 | 5/2010 | Williams et al. | |
| 2010/0120731 | A1 | 5/2010 | Vidal Juan et al. | |
| 2010/0222331 | A1 | 9/2010 | Engelhardt et al. | |
| 2010/0240662 | A1 | 9/2010 | Moon et al. | |
| 2011/0039891 | A1 | 2/2011 | Hagihara et al. | |
| 2011/0124626 | A1 | 5/2011 | Pooni et al. | |
| 2013/0039906 | A1 | 2/2013 | Do et al. | |
| 2013/0280245 | A1 | 10/2013 | Cai et al. | |
| 2013/0303529 | A1 | 11/2013 | Albrecht et al. | |
| 2013/0310373 | A1 | 11/2013 | Matsushima et al. | |
| 2014/0031360 | A1 | 1/2014 | Wang et al. | |
| 2014/0227284 | A1 | 8/2014 | Berthiaume et al. | |
| 2014/0378474 | A1 | 12/2014 | Flohr et al. | |
| 2016/0002224 | A1 | 1/2016 | Acton, III et al. | |
| 2016/0060224 | A1 | 3/2016 | Brand et al. | |
| 2017/0081315 | A1 | 3/2017 | Berger et al. | |
| 2018/0237416 | A1 | 8/2018 | Hood et al. | |
| 2022/0064158 | A1 | 3/2022 | Tate et al. | |
| 2022/0071960 | A1* | 3/2022 | Tate ..................... | A61K 31/437 |
| 2022/0411431 | A1 | 12/2022 | Bell et al. | |

FOREIGN PATENT DOCUMENTS

| | | | |
|---|---|---|---|
| EP | 0517984 | A1 | 12/1992 |
| EP | 0623621 | A1 | 11/1994 |
| EP | 0765873 | B1 | 4/2002 |
| EP | 1674464 | A1 | 6/2006 |
| GB | 2208862 | A | 4/1989 |
| GB | 2345486 | A | 7/2000 |
| JP | 63310891 | A | 12/1988 |
| JP | 03223280 | A | 10/1991 |
| JP | 05230057 | A | 9/1993 |
| JP | 06135960 | A | 5/1994 |
| JP | 11279156 | A | 10/1999 |
| WO | 92/04025 | A1 | 3/1992 |
| WO | 92/05174 | A1 | 4/1992 |
| WO | 93/03725 | A1 | 3/1993 |
| WO | 99/61426 | A1 | 12/1999 |
| WO | 00/37464 | A2 | 6/2000 |
| WO | 00/63215 | A2 | 10/2000 |
| WO | 01/02369 | A2 | 1/2001 |
| WO | 2004/077682 | A2 | 9/2004 |
| WO | 2005/014554 | A1 | 2/2005 |
| WO | 2008/040995 | A1 | 4/2008 |
| WO | 2008/153858 | A1 | 12/2008 |
| WO | 2010/026365 | A1 | 3/2010 |
| WO | 2011/019738 | A1 | 2/2011 |
| WO | 2012/095781 | A1 | 7/2012 |
| WO | 2013/083991 | A1 | 6/2013 |
| WO | 2013/133556 | A1 | 9/2013 |
| WO | 2017/001812 | A1 | 1/2017 |
| WO | 2017/011907 | A1 | 1/2017 |
| WO | 2020/128473 | A1 | 6/2020 |
| WO | 2020/128475 | A1 | 6/2020 |
| WO | 2021/008512 | A1 | 1/2021 |
| WO | 2022/058745 | A3 | 3/2022 |
| WO | 2022/090746 | A1 | 5/2022 |
| WO | 2024/052685 | A1 | 3/2024 |
| WO | 2025/007800 | A1 | 1/2025 |

OTHER PUBLICATIONS

Rackham et al., "Discovery of high affinity inhibitors of Leishmania donovani N-myristoyltransferase," Med. Chem. Commun., 2015, DOI: 10.1039/c5md00241a. (6 pages).

Ramljak et al., "Cellular N-myristoyltransferasees play a crucial picornavirus genus-specific role in viral assembly, virion maturation, and infectivity", PLoS Pathogens, vol. 14, No. 8, Aug. 6, 2018, pp. 1-39.

Resh, M., "Interaction of tyrosine kinase oncoproteins with cellular membranes," Biochimica et Biophysica Acta, 1993, 1155, pp. 307-322.

Robinson et al., "Identification and structure solution of fragment hits against kinetoplastid N-myristoyltransferase," Acta Cryst., 2015, F71, pp. 586-593.

Rudnick et al., "Kinetic and Structural Evidence for a Sequential Ordered Bi Bi mechanism of Catalysis by *Saccharyomyces cervisiae* Myristoyl-CoA:Protein N-Myristoyltransferase," The Journal of Biological Chemistry, 1991, vol. 266, No. 15, pp. 9732-9739.

Sheng et al., "Homology modelling and molecular dynamics simulation of N-myristoyltransferase from protozoan parasites: active site characterization and insights into reational inhibito design," J Comput Aided Mol Des, 2009, 23, pp. 375-389.

Sheng et al., "Design, synthesis and antifungal activity of isosteric analogues of benzoheterocyclic N-myristoyltransferase inhibitors," European Journal of Medicinal Chemistry, 2010, 45, pp. 3531-3540.

Sikorski et al., "Selective Peptidic and Peptidomimetic Inhibitors of Candida albicans MyristoylCoA : Protein N-Myristoyltransferase: A New Approach to Antifungal Therapy," Biopolymers, 1997, 43, pp. 43-71.

Snyder et al., "The Synthesis of an Indazole Analog of DL-Tryptophan," JACS, 1952, vol. 74, pp. 2009-2012.

Snyder et al., "The Synthesis of DL-alpha-Amino-beta-6-methyl-3-indazolyl)-propionic Acid," JACS, 1954, vol. 76, 1298-1301.

Sogabe et al., "Crystal Structures of Candida albicans N-Myristoyltransferase with two Distinct inhibitors," Chemistry & Biology, 2002, vol. 9, pp. 1119-1128.

Tate et al., "Peptide-based inhibitors of N-myristoyl transferase generated from a lipid/combinatorial peptide chimera library," Signal Transduction, 2006, 6, pp. 60-166.

Wang et al., "Expeditious one-pot synthesis of C3-piperazinyl-substituted quinolines: key precursors to potent c-Met inhibitors," Org. Biomol. Chem., 2011, 9, pp. 5930-5933.

Wang et al., "The role of N-myristoyltransferase 1 in tumour development", Annals of Medicine, Vo. 55, No. 1, pp. 1422-1430.

Wiegand et al., "The Candida albicans Myristoyl-CoA:Protein N-Myristoyltransferase Gene," The Journal of Biological Chemistry, 1992, vol. 267, No. 12, pp. 8591-8598.

Wright et al., "Validation of N-Myristoyltransferase as an antimalarial drug target using an integrated chemical biology approach," Nature Chemistry, 2013, DOI: 10.1038/NCHEM.1830, pp. 1-10.

(56) References Cited

OTHER PUBLICATIONS

Wu et al., "A versatile linkage strategy for solid-phase synthesis of N,N-dimethyltryptamines and β-carbolines", Organic Letters, Vo. 4, No. 23, pp. 4033-4036.
Wu et al., "Multisubstituted quinoxalines and pyrido[2,3-d]pyrimidines: Synthesis and SAR study as tyrosine kinase c-Met inhibitors," Bioorganic and Medicinal chemistry Letters 22, 2012, pp. 6368-6372.
Yamazaki et al., "Synthesis of potent and selective inhibitors of Candida albicans N-myristoyltransferase based on benzothiazole structure," Bioorganic & medicinal Chemistry 13, 2005, pp. 2509-2522.
Yu et al., "Design and Synthesis of Inhibitors of Plasmodium falciparum N-Myristoyltransferase, A Promising target for Antimalarial Drug Discover," Journal of Medicinal Chemistry, 2012, 55, pp. 8879-8890.
Yu et al., "Discovery of pyridyl-based inhibitors of Plasmodium falciparum N-myristoyltransferase ." Med. Chem. Commun., 2015,: DOI: 10.1039/c5md00242g, (6pages).
Armour, D., "Discovery of a novel Series of Non-Peptidic Fungal N-Myristoyl Transferase (NMT) Inhibitors," Slides from Pfizer, 221 ACS meeting, 2001, MEDI 349, (21 pages).
Abstract Book, "Emerging Paradigms in Anti-Infective Drug Design," London School of Hygiene and Tropical Medicine, British Society for Parasitology and Royal Society of Chemistry (Biological and Medicinal Chemistry Sector) Symposium, Sep. 17 and 18, 2012, (76 pages).
Basta et al., "Modeling of human rhinovirus C capsid suggests a novel topography with insights on receptor preference and immunogenicity," Virology, 2014, 448, pp. 176-144.
Bell et al., "Selective Inhibitors of Protozoan Protein N-myristoyltransferases as Starting Points for Tropical Disease Medicinal Chemistry Programs," PLOS Neglected Tropical Diseases, 2012, vol. 6, Issue 4, e1625, pp. 1-9.
Bell et al., Slides from "Selective Inhibitors of Protozoan Protein N-myristoyltransferases as Starting Points for Tropical Disease Medicinal Chemistry Programs," Emerging Paradigms in Anti-Infective Drug Design, London School of Hygiene and Tropical Medicine, Sep. 18, 2012 (16 pages).
Bell et al., "Discovery of Fungicidal N-Myristoyl Transferase (NMT) Inhibitors," Slides from Pfizer, 221 ACS meeting, 2001, MEDI 350, (20 pages).
Boezio, et al., "Discovery and optimization of potent and selective triazolopyridazine series of c-Met inhibitors," Bioorganic & Medicinal Chemistry Letters 19, 2009, pp. 6307-6312.
Bowyer et al., "Molecules incorporating a benzothiazole core scaffold inhibit the N-myristoyltransferase of Plasmodium falciparum," Biochem. J., 2007, 408, pp. 173-180, DOI: 10.1042/BJ20070692 (8 pages).
Bowyer et al., "N-Myristoyltransferase: a Prospective Drug Target for Protozoan Parasites," ChemMedChem, 2008, 3, pp. 402-408, DOI: 10.1002/cmdc.200700301 (7 pages).
Brand et al., "Discovery of a Novel Class of Orally Active Trypanocidal N-Myristoyltransferase Inhibitors," Journal of Medicinal Chemistry, 2012, 55, pp. 140-152.
Brand et al., "Lead Optimizatin of a Pyrazole Sulfonamide Series of Trypanosoma brucei N-Myristoyltransferase Inhibitors: Identification and Evaluation of CNS Penetrant Compounds as Potential Treatments for Stage 2 Human African Trypanosomiasis," Journal of Medicinal Chemistry, 2014, 57, pp. 9855-9869.
Brannigan et al., "Diverse modes of binding in structures of Leishmania major N-myristoyltransferase with selective inhibitors," IUCrJ, 2014, 1, pp. 250-266.
Brannigan et al., "N-Myristoyltransferase from Leishmania donovani: Structural and Functional Characterisation of a Potential Drug Target for Visceral Leishmaniasis." J. Mol. Biol. 2010, 396, pp. 985-999.
Bryant et al., "Myristoylation-dependent replication and assembly of human immunodeficiency virus 1," Proc. Natl. Acad. Sci. USA, 1990, vol. 87, pp. 523-527.
Davis et al., "Recombinant VP4 of Human Rhinovirus Induces Permeability in Model Membranes," Journal of Virology, 2008, vol. 82, No. 8, pp. 4169-4174.
Devadas et al., "Design and Synthesis of Novel Imidazole-Substituted Dipeptide Amides as Potent and Selective Inhibitors of Candida albicans MyristoylCoA:Protein N-Myristoyltransferase and Identification of Related Tripeptide Inhibitors with Mechanism-Based Antifungal Activity," Journal of Medicinal Chemistry, 1997, vol. 40, No. 16, pp. 2609-2625.
Devadas et al., "Design and Synthesis of Potent and Selective Dipeptide Inhibitors of Candida albicans Myristoyl-CoA: Protein N-Myristoyltransferase," Journal of Medicinal Chemistry, 1995, vol. 38, No. 11, pp. 1837-1840.
Duronio et al., "Disruption of the Yeast N-Myristoyl Transferase gene Causes Recessive Lethality," Science, 1989, vol. 243, pp. 796-800.
Ebara et al., "FTR1335 Is a Novel Synthetic Inhibitor of Candida albicans N-Myristoyltransferase with Fungicidal Activity," Biol. Pharm. Bull., 2005, vol. 28, No. 4, pp. 591-595.
Ebiike et al., "Design and Synthesis of Novel Benzofurans as a New Class of Antifungal Agents Targeting Fungal N-Myristoyltransferase. Part 2," Bioorganic & Medicinal Chemistry Letters 12, 2002, pp. 607-610.
Fang et al., "N-Myristoyltransferase Is a Cell Wall Target in Aspergillus fumigatus," ACS Chem. Biol., 2015, 10, pp. 1425-1434.
Farazi et al., "The Biology and Enzymology of Protein N-Myristoylation," The Journal of Biological Chemistry, 2001, vol. 276, No. 43, pp. 39501-39504.
Frearson et al., "N-myristoyltransferase inhibitors as new leads to treat sleeping sickness," Nature, 2010, vol. 464, pp. 728-732 (7 pages).
Galvin et al., "A Target Repurposing Approach Identifies N-myristoyltransferase as a New Candidate Drug Target in Filarial Nematodes," PLOS Neglected Tropical Diseases, 2014, vol. 8, Issue 9, e3145, pp. 1-13.
Giang et al., "A Second Mammalian N-Myristoyltransferase," The Journal of Biological Chemistry, 1998, vol. 273, No. 12, pp. 6595-6598.
Goncalves et al., "A fluorescence-based assay for N-Myristoyltransferase activity," Anal Biochem., 2012, 421(1), pp. 1-7.
Goncalves et al., "Discovery of Plasmodium vivax N-Myristoyltransferase Inhibitors: Screening, Synthesis, and Structural Characterization of their Binding Mode," Journal of Medicinal Chemistry, 2012, 55, pp. 3578-3582.
Gottlinger et al., "Role of capsid precursor processing and myristoylation in morphogenesis and infectivity of human immunodeficiency virus type 1," Proc. Natl. Acad. Sci. USA, 1989, vol. 86, pp. 5781-5785.
Grundt et al., "Analogues of the dopamine D2 receptor antagonist L741, 626: Binding, function, and SAR," Bioorganic & medicinal Chemistry Letters 17, 2007, pp. 745-749.
Gunaratne et al., "Characterization of N-myristoyltransferase from Plasmodium falciparum," Biochem. J., 2000, 348, pp. 459-463.
Herrera et al., "Validation of N-myristoyltransferase as Potential Chemotherapeutic Target in Mammal-Dwelling Stages of Trypanosoma cruzi," PLOS Neglected Tropical Diseases, 2016, DOI: 10.1371/journal.pntd.0004540, pp. 1-20.
Hutton et al., "Structure-Based Design of Potent and Selective Leishmania N-Myristoyltransferase Inhibitors," Journal of Medicinal Chemistry, 2014, 57, pp. 8664-8670.
International Search Report and Written Opinion issued in corresponding International Patent Application No. PCT/GB2023/052319 dated Jan. 4, 2024 (11 pages).
Johnson et al., "Genetic and Biochemical Studies of Protein N-Myristoylation," Annu. Rev. Biochem., 1994, 63, pp. 868-914.
Kawasaki et al., "Design and Synthesis of Novel Benzofurans as a New Class of Antifungal Agents Targeting Fungal N-Myristoyltransferase. Part 3," Bioorganic & Medicinal Chemistry Letters 13, 2003, pp. 87-91.
Khongorzul et al., "Antibody-Drug Conjugates: A Comprehensive Review", Molecular Cancer Research, vol. 18, No. 1, pp. 3-19.
Lee et al., "Synthesis and biological evaluation of 3,5-diaminoindazoles as cyclin-dependent kinase inhibitors," Bioorganic & Medicinal Chemistry Letters 18, 2008, pp. 2292-2295.

(56) References Cited

OTHER PUBLICATIONS

Liu et al., "Novel benzodithiazole derivatives with broad antifungal spectrum: design, synthesis and structure-activity relationships," Med. Chem. Commun., 2013, 4, pp. 1551-1651.
Lodge et al., "Comparison of Myristoyl-CoA: Protein N-Myristolytransferases from Three Pathogenic Fungi: Cryptococcus neoformans, Histoplasma capsulatum, and Candida albicans," the Journal of Biological Chemistry, 1994, vol. 269. No. 4, pp. 2996-3009.
Lueg et al., "N-myristoyltransferase inhibition is synthetic lethal in MYC-deregulated cancers," bioRxiv, Mar. 20, 2021, pp. 1-25.
Masubuchi et al., "Design and Synthesis of Novel Benzofurans as a New Class of Antifungal Agents Targeting Fungal N-Myrisyoyltransferase. Part 1," Bioorganic & Medicinal Chemistry Letters 11, 2001, pp. 1833-1837.
Masubuchi et al., "Synthesis and Biological Activities of Benzofuran Antifungal Agents Targeting Fungal N-Myristoyltransferase," Bioorganic and Medicinal Chemistry 11, 2003, pp. 463-4478.
McIlhinney et al., "Immunocytochemical Characterization and Subcellular Localization of Human Myristoyl-CoA: Protein N-Myristoyltransferase in Hela Cells," Experimental Cell Research, 1996, 223, pp. 348-356.
Mousnier et al., "Fragment-derived inhibitors of human N-myristoyltransferase block capsid assembly and replication of the common cold virus," Nature Chemistry, vol. 10, No. 6, May 14, 2018, 18 pages.
Music et al., "Synthesis of Benzylaminomethyl and aminomethyl substituted fused 1,2,4-triazoles," Synthetic Communications, 2001, 31(10), pp. 15111519.
Music et al., "Reaction of Acylglycines with Heteroarylhydrazines," heterocyclic Communications, 2005, vol. 11, Nos. 3-4, pp. 321-324.
Nagarajan et al., "Conformationally Constrained [p-(omega-Aminoalkyl)phenacetyl]-L-seryl-L-lysyl Dipeptide Amides as Potent Peptidomimietic Inhibitors of Candida albicans and Human Myristoyl-CoA:protein N-Myristoyl Transferase," J. Med. Chem., 1997, vol. 40, No. 10, pp. 1422-1438.
Olaleye et al., "Peptidomimetic inhibitors of N-myristoyltransferase from human malaria and leishmaniasis parasites," Organic & Biomolecular Chemistry, 2014, DOI: 10.1039/c4ob01669f, (6 pages).
Panethymitaki et al., "Characterization and selective inhibition of myristoyl-CoA:protein N-myristoyltransferase from Trypansoma brucei and Leishmania major," Biochem. J., 2006, 396, pp. 277-285.
Price et al., "Myristoyl-CoA: Protein N-Myristoyltransferase, an Essential Enzyme and Potential Drug Target in Kintoplastid Parasites," The Journal of Biological Chemistry, 2003, vol. 278, No. 9, pp. 7206-7214.

* cited by examiner

CYTOTOXIC IMIDAZO[1,2-A]PYRIDINE COMPOUNDS AND THEIR USE IN THERAPY

CROSS-REFERENCE TO RELATED APPLICATIONS

This application is a bypass Continuation Application under 35 U.S.C. § 111 of International Application No. PCT/GB2023/052319, filed Sep. 8, 2023, which claims priority to, and the benefit of, United Kingdom Application No. 2305546.0, filed Apr. 14, 2023, United Kingdom Application No. 2305541.1, filed Apr. 14, 2023, European Application No. 22194984.5, filed Sep. 9, 2022, and European Application No. 22194959.7, filed Sep. 9, 2022. The contents of each of these applications are incorporated herein by reference in their entireties.

DESCRIPTION OF THE XML SEQUENCE LISTING FILE SUBMITTED ELECTRONICALLY

The instant application contains a sequence listing, which has been submitted in XML format via EFS-Web. The contents of the XML copy named "MYX-P2921PCT—Sequence listing," which was created on Aug. 23, 2023 and is 12,288 bytes in size, the contents of which are incorporated herein by reference in their entirety.

FIELD OF INVENTION

This invention relates to novel cytotoxic compounds which are or are expected to be inhibitors of the human N-myristoyl transferases (human NMT). The invention also inter alia relates to such compounds for use as medicaments, in particular, in the treatment or prevention of hyperproliferative disorders such as cancer or other disease or disorder in which inhibition of human NMT provides a therapeutic or prophylactic effect.

BACKGROUND TO THE INVENTION

N-myristoyl transferase (NMT) is a monomeric enzyme, which is ubiquitous in eukaryotes. NMT catalyses an irreversible co-translational transfer of myristic acid (a saturated 14-carbon fatty acid) from myristoyl-Coenzyme A (myr-CoA) to a protein substrate containing an N-terminal glycine with formation of an amide bond (Farazi, T. A., G. Waksman, and J. I. Gordon, *J. Biol. Chem.*, 2001. 276(43): p. 39501-39504).

There are two types of human NMT, human NMT1 (HsNMT1) and human NMT2 (HsNMT2). Inhibition of human NMT has been suggested as a target for treating or preventing various diseases or disorders, for example hyperproliferative disorders (for example cancers, e.g. human colorectal cancer, gallbladder carcinoma, brain tumors, and lymphomas such as B-cell lymphoma) (Resh MD. 1993. Biochern. Biophys.Acta 1115, 307-22; Bertiaume L G, Beuachamp E, WO2017011907), and viral infections such as HIV (Gottlinger H G, Sodroski J G, Haseltine W A. 1989. Proc. Nat. Acad. Sci. USA 86:5781-85; Bryant M L, Ratner L. 1990. Proc. Natl. Acad. Sci. USA 87:523-27) and human rhinovirus (HRV) (Davis M P, Bottley, G, Beales L P, Killington, R A, Rowlands D J, Tuthill, T J, 2008 Journal of Virology 82 4169-4174; Mousnier A, Bell A S, Swieboda D P, Morales-Sanfrutos J, Perez-Dorado I, Brannigan J A, Newman J, Ritzefeld M, Hutton, J A, Guedan A, Asfor A S, Robinson, SW, Hopkins-Navratilova I, Wilkinson A J, Johnston S L, Leatherbarrow R J, Tuthill T J, Solari R, Tate E W 2018 Nature Chemistry 10 (6) 599-606), Corbic Ramijak I, Stanger J, Real-Hohn A. Dreier D, Wimmer L., RedTberger-Fritz M, Fischl W, Klingel K, Mihovilovic M D, Blaas D, Kowalski H, PLOS Pathogens 14(8): e1007203. As NMT plays a key role in protein trafficking, mediation of protein-protein interactions, stabilization of protein structures and signal transduction in living systems, inhibition of the HsNMT1 and/or HsNMT2 enzyme(s) has the potential to disrupt multi-protein pathways. Although it is expected that inhibitors of human NMT will inhibit both HsNMT1 and HsNMT2, their therapeutic and/or prophylactic activity is believed to primarily derive from inhibition of HsNMT1. The above characteristics are believed to be desirable to reduce the risk of the development of resistance in, for example, treatment or prevention of microbial infections and hyperproliferative disorders.

There are two binding pockets in NMT. One is the myr-CoA binding pocket and the other is the peptide binding pocket. Most NMT inhibitors reported to date target the peptide binding pocket.

Compounds active as inhibitors of NMT have previously been disclosed, see for example WO00/37464 (Roche), WO2010/026365 (University of Dundee), WO2013/083991 (Imperial Innovations Limited), WO2017/001812 (Imperial Innovations Limited), WO2020/128473 (Imperial College Innovations Limited), WO2020/128475 (Imperial College Innovations Limited) and WO2022/058745 (Imperial College Innovations Limited et al.). Particular uses of NMT inhibitors have been disclosed, see for example WO2022/090746 (Imperial College Innovations Limited et al.) and WO2022/082306 (Pacylex Pharmaceuticals Inc.).

However, there remains a need for further compounds having cytotoxic activity and inhibitors of human NMT, and in particular those that combine cytotoxic activity and very potent inhibition of human NMT with favourable pharmacokinetic properties e.g. cell permeability and/or metabolic stability and improved therapeutic window.

Surprisingly, the present inventors have now found that alcohol-substituted imidazo[1,2-a]pyridine compounds display particularly potent cytotoxic activity and/or are potent inhibitors of human NMT, and desirably may display other properties such as cell permeability and metabolic stability profiles which are suited for particular therapeutic purposes. These properties are expected to make the compounds of the invention especially suitable for use as medicaments for the treatment or prevention of hyperproliferative diseases such as cancers.

SUMMARY OF THE INVENTION

In a first aspect, the invention provides a compound of formula (I):

(I)

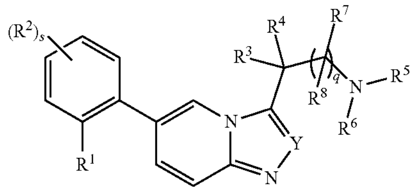

wherein:

$R^1$ is a group of formula O-L-A;

L is $-(CHR^{12})_m-$;

each $R^{12}$ is independently H or $C_{1-4}$ alkyl;

m is 1, 2 or 3;

A is:

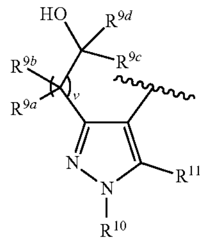

v is 0, 1 or 2;

$R^{9a}$ is H, $C_{1-4}$ alkyl or $C_{1-4}$ haloalkyl;

$R^{9b}$ is H, $C_{1-4}$ alkyl or $C_{1-4}$ haloalkyl;

$R^{9c}$ is $C_{1-4}$ alkyl or $C_{1-4}$ haloalkyl;

$R^{9d}$ is H, $C_{1-4}$ alkyl or $C_{1-4}$ haloalkyl;

$R^{10}$ is H, $C_{1-4}$ alkyl or $C_{1-4}$ haloalkyl;

$R^{11}$ is H, halo, CN, $C_{1-4}$ alkyl, $C_{1-4}$ haloalkyl, $C_{1-4}$alkoxy or $C_{1-4}$haloalkoxy;

s is 0, 1, 2 or 3;

each $R^2$ is independently F, Cl, Br, $OCH_3$, $OCF_3$ or $C_{1-4}$ alkyl optionally substituted by up to 3 halogen groups;

Y is CH or $C_{1-4}$ alkyl;

$R^3$ is H or $C_{1-4}$ alkyl;

$R^4$ is H or $C_{1-4}$ alkyl;

$R^5$ is H or $C_{1-4}$ alkyl;

$R^6$ is H or $C_{1-4}$ alkyl;

q is 0 or 1;

$R^7$ is H or methyl;

$R^8$ is H or methyl;

or $R^3$ and $R^5$ and the intervening atoms form a 3 to 7 membered non-aromatic heterocycle composed of the intervening atoms and bond, or the intervening atoms and $-(CHR^a)_r-$; or the $R^7$ group and the $R^5$ group and the intervening atoms form a 3 to 7 membered non-aromatic heterocycle composed of the intervening atoms and $-(CHR^a)_r-$;

r is 1, 2, 3, 4 or 5; and $R^a$ is hydrogen or methyl;

or a salt and/or solvate thereof.

A compound of formula (I) may be provided in the form of a salt and/or solvate. Suitably, the compound of formula (I) may be provided in the form of a pharmaceutically acceptable salt and/or solvate. Suitably, the compound of formula (I) may be provided in the form of the pharmaceutically acceptable solvate of the pharmaceutically acceptable salt. Suitably, the compound of formula (I) may be provided in the form of a pharmaceutically acceptable salt.

Suitably, the compound of formula (I) may be provided in the form of a pharmaceutically acceptable solvate. Suitably, the compound of formula (I) may be provided.

The invention further provides a pharmaceutical composition comprising a compound of formula (I), or a pharmaceutically acceptable salt and/or solvate thereof and a pharmaceutically acceptable carrier.

The invention also provides a compound of formula (I), or a pharmaceutically acceptable salt and/or solvate thereof for use as a medicament.

The invention also provides a compound of formula (I), or a pharmaceutically acceptable salt and/or solvate thereof, for use in the treatment or prevention of a hyperproliferative disorder (e.g. cancer).

The invention also provides the use of a compound of formula (I), or a pharmaceutically acceptable salt and/or solvate thereof, for the manufacture of a medicament for the treatment or prevention of a hyperproliferative disorder (e.g. cancer).

The invention also provides a method of treating or preventing a hyperproliferative disorder (e.g. cancer) in a subject, said method comprising administering a therapeutically effective amount of a compound of formula (I), or a pharmaceutically acceptable salt and/or solvate thereof.

The invention also provides a compound of formula (I) or a pharmaceutically acceptable salt and/or solvate thereof for use in the treatment or prevention of a disease or disorder in which inhibition of human NMT provides a therapeutic or prophylactic effect.

The invention also provides the use of a compound of formula (I), or a pharmaceutically acceptable salt and/or solvate thereof, for the manufacture of a medicament for the treatment or prevention of a disease or disorder in which inhibition of human NMT provides a therapeutic or prophylactic effect.

The invention also provides a method of treating or preventing a disease or disorder in which inhibition of human NMT provides a therapeutic or prophylactic effect in a subject, comprising administering a therapeutically effective amount of a compound of formula (I), or a pharmaceutically acceptable salt and/or solvate thereof.

The invention also provides a kit of parts comprising: (a) a first pharmaceutical composition comprising a compound of formula (I), or a pharmaceutically acceptable salt and/or solvate thereof and a pharmaceutically acceptable carrier; and (b) a second pharmaceutical composition comprising a further therapeutic agent, suitably a further compound of formula (I), or a pharmaceutically acceptable salt and/or solvate thereof and a pharmaceutically acceptable carrier.

SEQUENCE LISTINGS

Figure 1A:
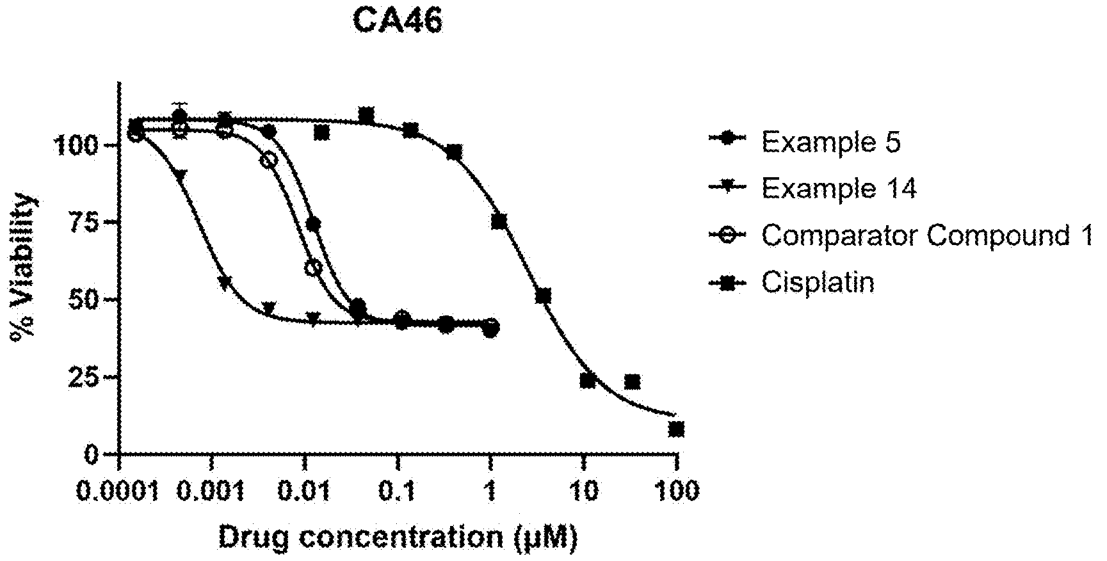
FIG. 1A: shows the effect of treatment of Examples 5 and 14 compared to Comparator Compound 1 and cis-platin on the percentage viability of CA46 cancer cells in vitro.
Figure 1B:
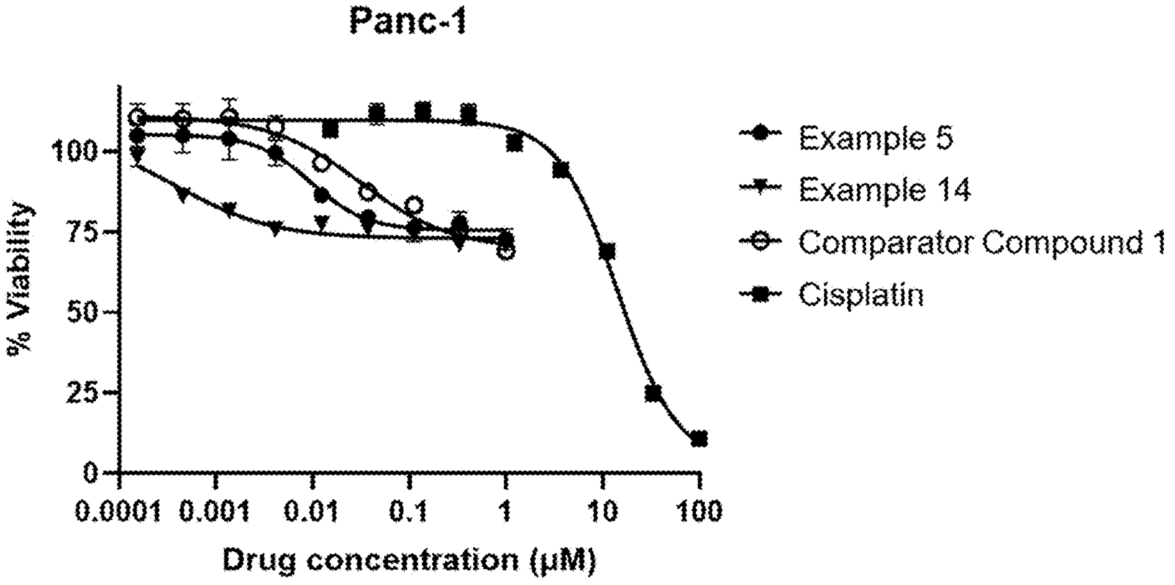
FIG. 1B: shows the effect of treatment of Examples 5 and 14 compared to Comparator Compound 1 and cis-platin on the percentage viability of Panc-1 cancer cells in vitro.
Figure 1C:
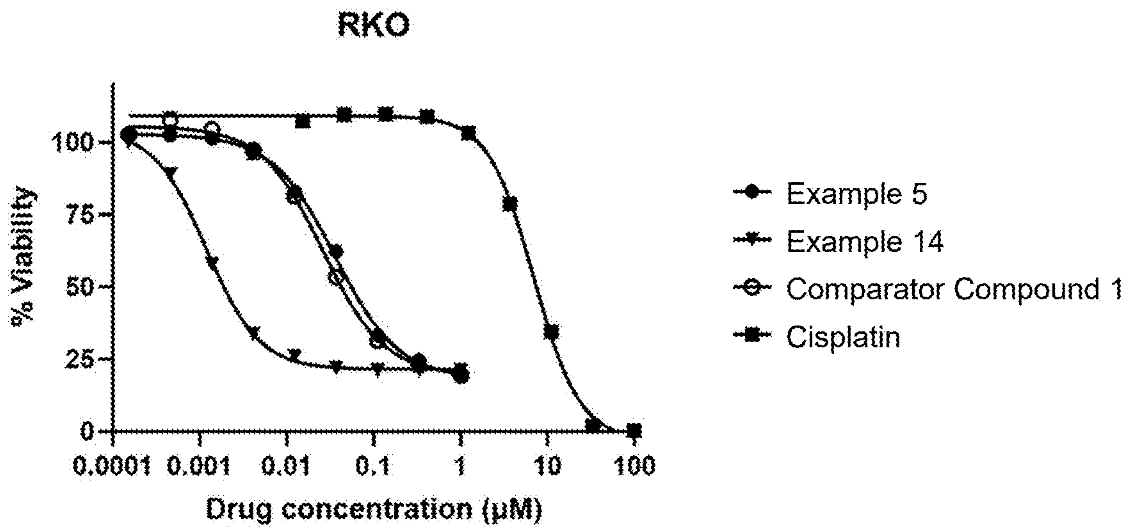
FIG. 1C: shows the effect of treatment of Examples 5 and 14 compared to Comparator Compound 1 and cis-platin on the percentage viability of RKO cancer cells in vitro.
Figure 1D:
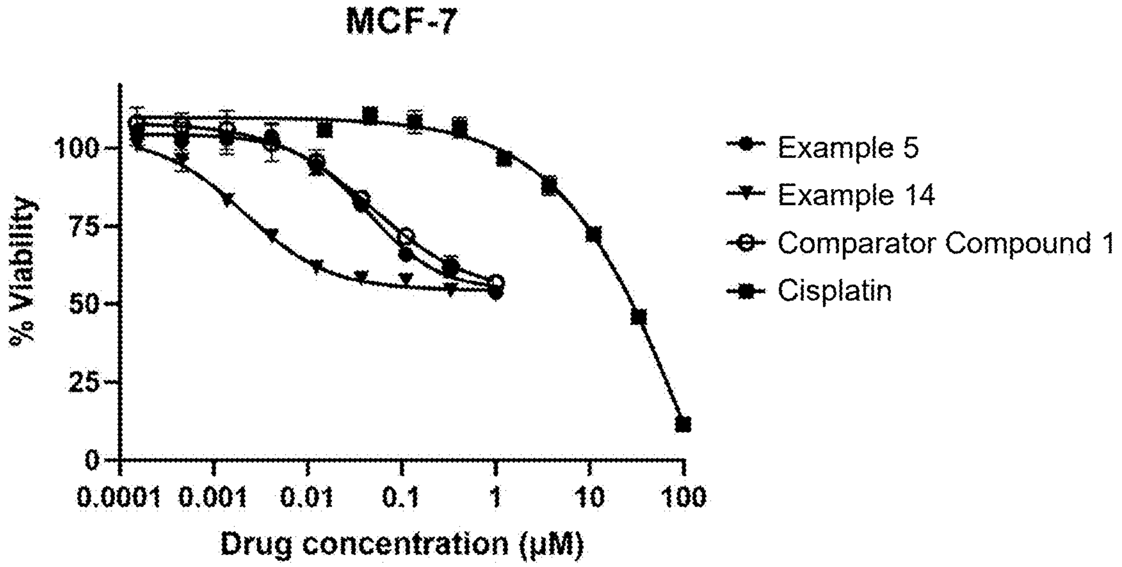
FIG. 1D: shows the effect of treatment of Examples 5 and 14 compared to Comparator Compound 1 and cis-platin on the percentage viability of MCF-7 cancer cells in vitro.
Figure 1E:
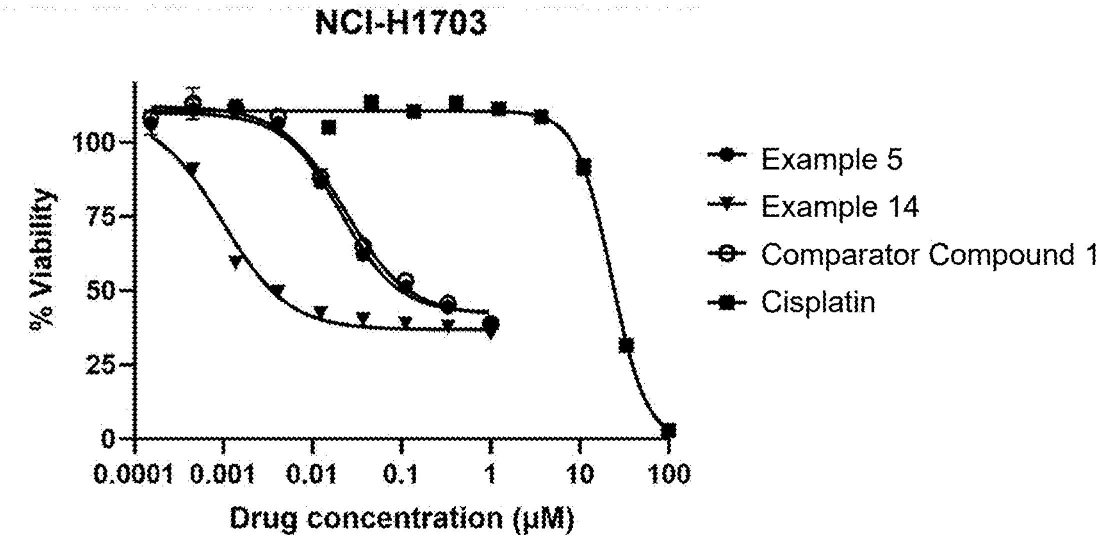
FIG. 1E: shows the effect of treatment of Examples 5 and 14 compared to Comparator Compound 1 and cis-platin on the percentage viability of NCI-H1703 cancer cells in vitro.
Figure 1F:
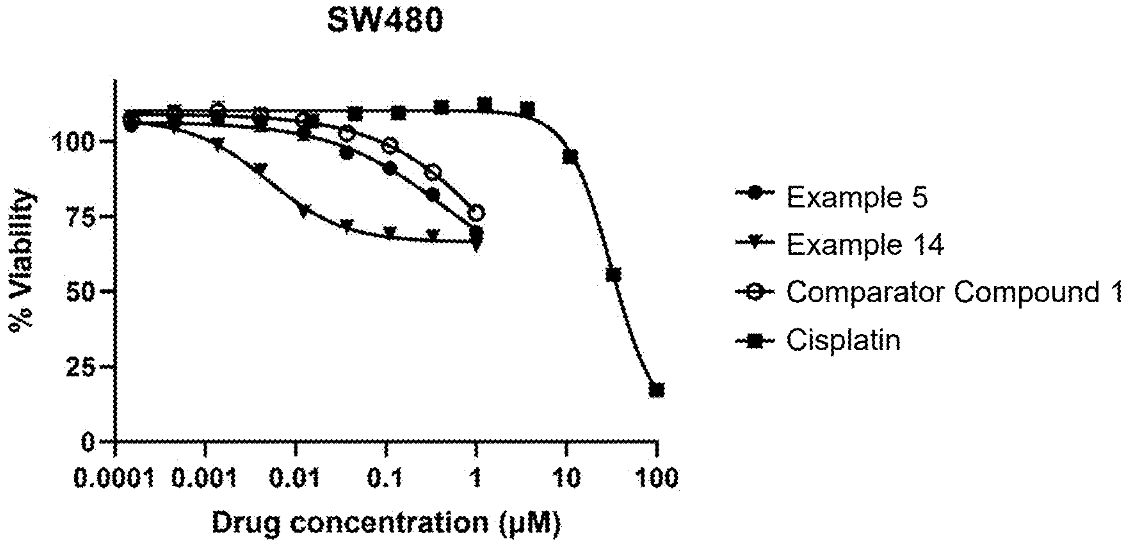
FIG. 1F: shows the effect of treatment of Examples 5 and 14 compared to Comparator Compound 1 and cis-platin on the percentage viability of SW480 cancer cells in vitro.
Figure 1G:
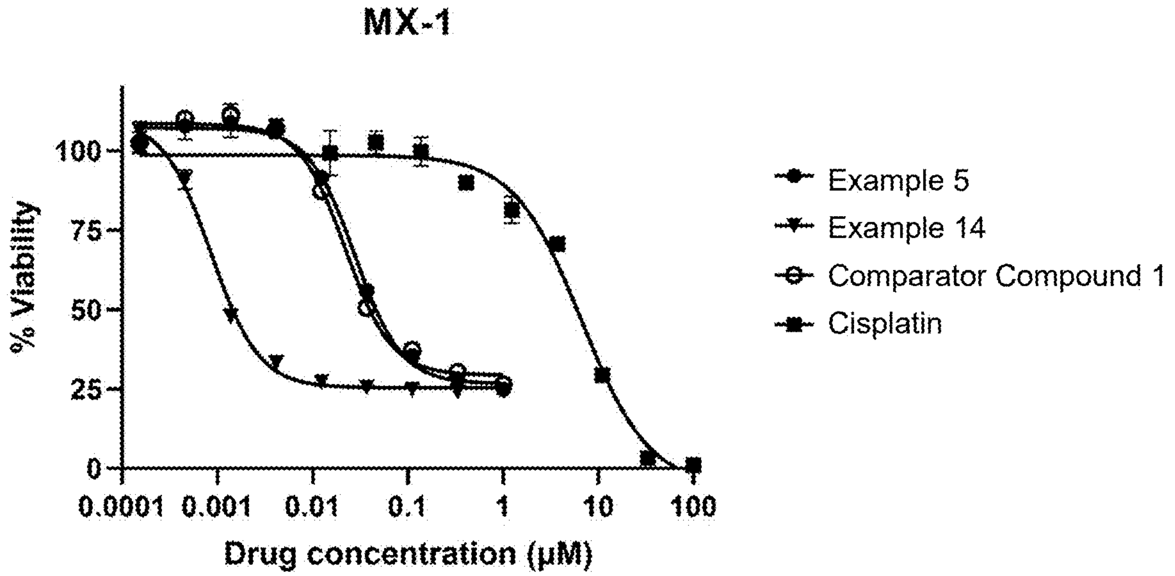
FIG. 1G: shows the effect of treatment of Examples 5 and 14 compared to Comparator Compound 1 and cis-platin on the percentage viability of MX-1 cancer cells in vitro.
Figure 1H:
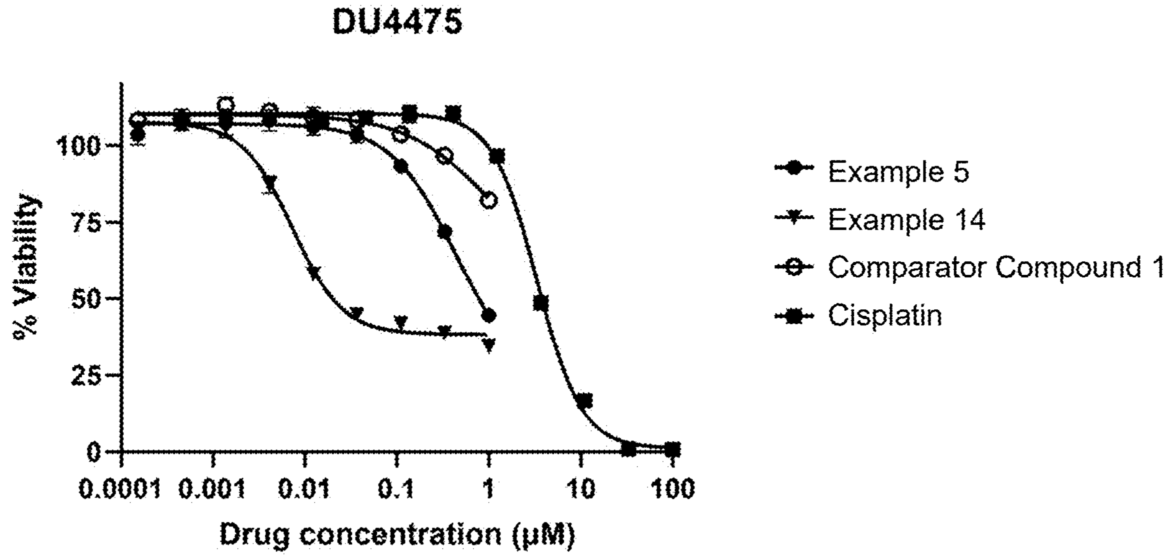
FIG. 1H: shows the effect of treatment of Examples 5 and 14 compared to Comparator Compound 1 and cis-platin on the percentage viability of DU4475 cancer cells in vitro.
Figure 1I:
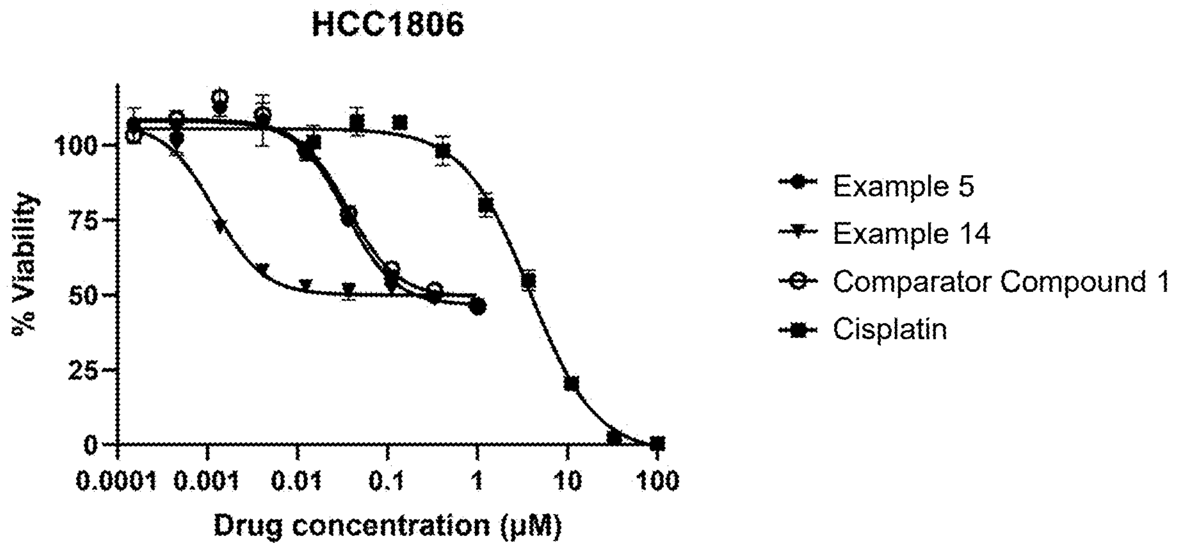
FIG. 1I: shows the effect of treatment of Examples 5 and 14 compared to Comparator Compound 1 and cis-platin on the percentage viability of HCC1806 cancer cells in vitro.
Figure 2A:
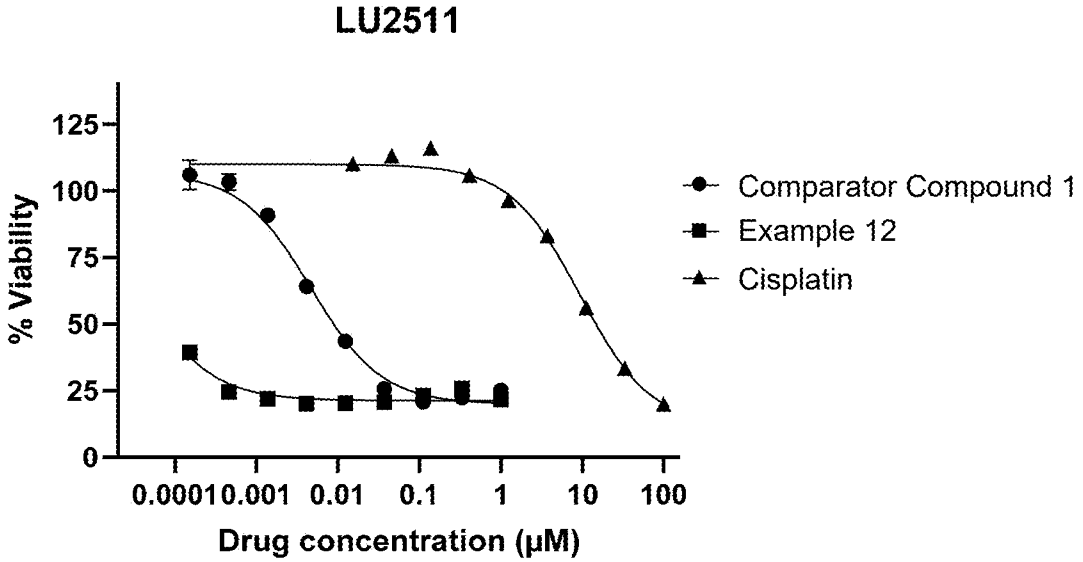
FIG. 2A: shows the effect of treatment of Example 12 compared to Comparator Compound 1 and cis-platin on the percentage viability of LU2511 cancer cells in vitro.
Figure 2B:
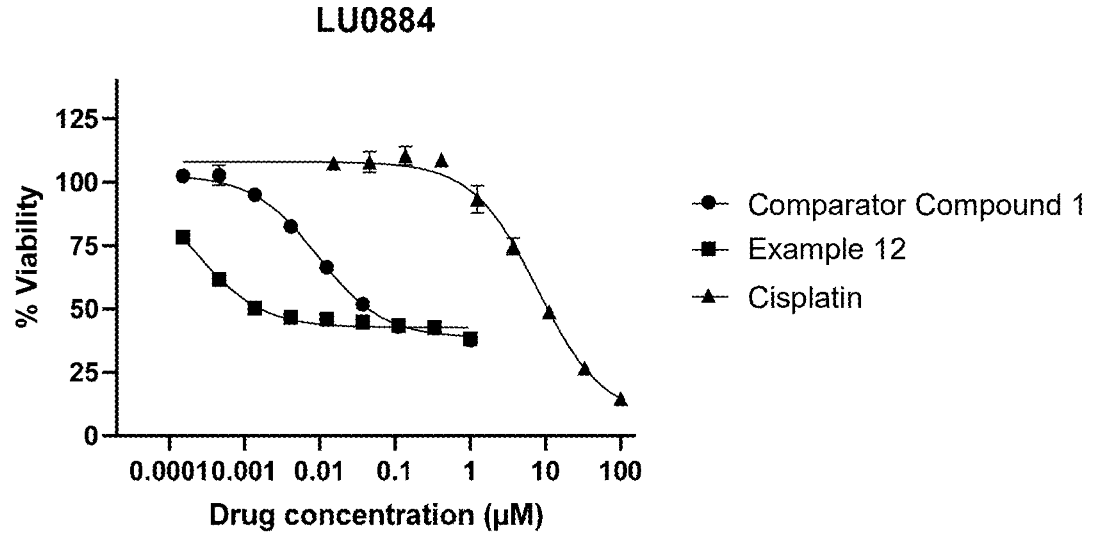
FIG. 2B: shows the effect of treatment of Example 12 compared to Comparator Compound 1 and cis-platin on the percentage viability of LU0884 cancer cells in vitro.

SEQ ID NO: 1—Amino acid sequence of the light chain of trastuzumab

SEQ ID NO: 2—Amino acid sequence of the heavy chain of trastuzumab

SEQ ID NO: 3—Amino acid sequence of the light chain of rituximab

SEQ ID NO: 4—Amino acid sequence of the heavy chain of rituximab

SEQ ID NO: 5—Amino acid sequence of the light chain of ifinatamab

SEQ ID NO: 6—Amino acid sequence of the heavy chain of ifinatamab

SEQ ID NO: 7—Amino acid sequence of the light chain of sacituzumab

SEQ ID NO: 8—Amino acid sequence of the heavy chain of sacituzumab

DETAILED DESCRIPTION OF THE INVENTION

The term "$C_{1-4}$ alkyl" as used herein refers to a straight alkyl chain or branched alkyl chain, whether alone or forming part of a large group e.g. $C_{1-4}$alkoxy. Examples of $C_{1-4}$ alkyl are methyl, ethyl, propyl and butyl. Reference to "propyl" includes n-propyl and iso-propyl, and reference to "butyl" includes n-butyl, iso-butyl, tert-butyl and sec-butyl. A particular group of exemplary $C_{1-4}$ alkyl groups are methyl, iso-propyl and tert-butyl. An example of $C_{1-4}$alkoxy is methoxy.

The term "$C_{1-4}$ haloalkyl" as used herein, includes straight chain or branched alkyl groups containing 1 to 4 carbon atoms substituted by one or more halo atoms, for example fluoromethyl, difluoromethyl and trifluoromethyl. A particular example of $C_{1-4}$ haloalkyl is trifluoromethyl.

The term "$C_{1-4}$haloalkoxy" as used herein, includes straight chain or branched alkoxy groups containing 1 to 4 carbon atoms substituted by one or more halo atoms, for example fluoromethyl, difluoromethyl and trifluoromethyl. Examples of $C_{1-4}$haloalkoxy are trifluoromethoxy and trifluoroethoxy.

The term heterocycle as used herein, such as in 3 to 7 membered non-aromatic heterocycle, is a fully or partially saturated hydrocarbon ring containing the specified number of carbon atoms and may include the carbon atom through which the cycloalkyl group is attached, wherein at least one of the carbon atoms in the ring is replaced by a heteroatom such as N, S or O. The heterocycloalkyl may be optionally by up to 3 substituents, such as 1 or 2 e.g. 1 substituent, independently selected from the group consisting of $C_{1-4}$ alkyl (e.g. Me), $C_{1-4}$ haloalkyl (e.g. $CF_3$), $C_{1-4}$alkoxy (e.g. Ome), $C_{1-4}$haloalkoxy (e.g. $OCF_3$), halo (e.g. Cl or F) and CN. In an embodiment, heterocycloalkyl is not substituted.

Examples of 3 to 7 membered non-aromatic heterocycle groups include pyrrolidine, tetrahydrofuan, tetrahydrothiophene, imidazolidine, pyrazolidine, oxazolidine, isoxazolidine, thiazolidine, isothiazolidine, dioxolane, dithiolane, piperidine, tetrahydropyran, thiane, diazinane, morpholine, thiomorpholine, dioxane, triazinane, trioxane, trithiane, azepane, oxepane and diazepane. An example of a substituted 3 to 7 membered non-aromatic heterocycle group is N-methylpiperazine.

The term "prophylaxis" is used herein to mean the provision in advance, and as such may involve preventing symptoms of a disease or disorder in a subject or preventing recurrence of symptoms of a disease or disorder in an afflicted subject and is not limited to complete prevention of an affliction.

The term "treatment" or "treating" as used herein includes the control, mitigation, reduction, or modulation of the disease state or its symptoms.

In one embodiment, at least one $R^{12}$ is H. Suitably, each $R^{12}$ is H. In a second embodiment, at least one $R^{12}$ is $C_{1-4}$ alkyl. Suitably, each $R^{12}$ is $C_{1-4}$ alkyl.

In one embodiment, m is 1. In a second embodiment, m is 2. In a third embodiment, m is 3. In one embodiment, v is 0. In one embodiment, v is 1. In one embodiment, v is 2.

In one embodiment, $R^{9a}$ is H. In a second embodiment, $R^{9a}$ is $C_{1-4}$ alkyl. In a third embodiment, $R^{9a}$ is $C_{1-4}$ haloalkyl. In one embodiment, $R^{9b}$ is H. In a second embodiment, $R^{9b}$ is $C_{1-4}$ alkyl. In a third embodiment, $R^{9b}$ is $C_{1-4}$ haloalkyl. In one embodiment, $R^{9c}$ is $C_{1-4}$ alkyl, such as methyl, ethyl, n-propyl, iso-propyl, n-butyl or tert-butyl, for example methyl, iso-propyl or tert-butyl. Suitably, $R^{9c}$ is methyl. Suitably, $R^{9c}$ is iso-propyl. Suitably, $R^{9c}$ is tert-butyl. In a second embodiment, $R^{9c}$ is $C_{1-4}$ haloalkyl. In one embodiment, $R^{9d}$ is H. In a second embodiment, $R^{9d}$ is $C_{1-4}$ alkyl, such as methyl. In a third embodiment, $R^{9d}$ is $C_{1-4}$ haloalkyl. In one embodiment, $R^{9c}$ is tert-butyl and $R^{9d}$ is H. In a second embodiment, $R^{9c}$ is methyl and $R^{9d}$ is methyl. In one embodiment, $R^{10}$ is H. In a second embodiment, $R^{10}$ is $C_{1-4}$ alkyl, such as methyl. In a third embodiment, $R^{10}$ is $C_{1-4}$ haloalkyl. In one embodiment, $R^{11}$ is H. In a second embodiment, $R^{11}$ is halo. In a third embodiment, $R^{11}$ Is CN. In a fourth embodiment, $R^{11}$ is $C_{1-4}$ alkyl, such as methyl. In a fifth embodiment, $R^{11}$ is $C_{1-4}$ haloalkyl. In a sixth embodiment, $R^{11}$ is $C_{1-4}$alkoxy. In a seventh embodiment, $R^{11}$ is $C_{1-4}$haloalkoxy.

In one embodiment, s is 0. In a second embodiment, s is 1. In a third embodiment, s is 2. In a fourth embodiment, s is 3.

In one embodiment, at least one $R^2$ is F, Cl or Br, such as Cl or F, especially F. Suitably, each $R^2$ is F, Cl or Br, such as Cl or F, especially F. In a second embodiment, at least one $R^2$ is $C_{1-4}$ alkyl and suitably, each $R^2$ is $C_{1-4}$ alkyl. In a third embodiment, at least one $R^2$ is $OCH_3$ and suitably, each $R^2$ is $OCH_3$. In a fifth embodiment, at least one $R^2$ is $OCF_3$ and suitably, each $R^2$ is $OCF_3$.

In one embodiment, s is 1 and $R^2$ is F. In a second embodiment, s is 2 and each $R^2$ is F.

In one embodiment, Y is CH. In a second embodiment, Y is $C_{1-4}$ alkyl. In one embodiment, $R^3$ is H. In a second embodiment, $R^3$ is $C_{1-4}$ alkyl.

In one embodiment, $R^4$ is H. In a second embodiment, $R^4$ is $C_{1-4}$ alkyl.

In one embodiment, $R^5$ is H. In a second embodiment, $R^5$ is $C_{1-4}$ alkyl, such as methyl.

In one embodiment, $R^6$ is H. In a second embodiment, $R^6$ is $C_{1-4}$ alkyl, such as methyl. In one embodiment, $R^5$ is methyl and $R^6$ is H. In one embodiment, at least one of $R^5$ and $R^6$ is H.

In one embodiment, q is 0. In a second embodiment, q is 1.

In one embodiment, $R^7$ is H. In a second embodiment, $R^7$ is methyl. In one embodiment, $R^8$ is H. In a second embodiment, $R^8$ is methyl.

In one embodiment, $R^3$ and $R^5$ and the intervening atoms form a 3 to 7 membered non-aromatic heterocycle composed of the intervening atoms and bond, or the intervening atoms and $-(CHR^a)_r$. In a second embodiment, the $R^7$ group and the $R^5$ group and the intervening atoms form a 3 to 7 membered non-aromatic heterocycle composed of the intervening atoms and $-(CHR^a)_r-$.

In one embodiment, r is 1. In a second embodiment, r is 2. In a third embodiment, r is 3. In a fourth embodiment, r is 4. In a fifth embodiment, r is 5.

In one embodiment, $R^a$ is hydrogen. In a second embodiment, $R^a$ is methyl.

In one embodiment, there is provided a compound of formula (IA):

(IA)

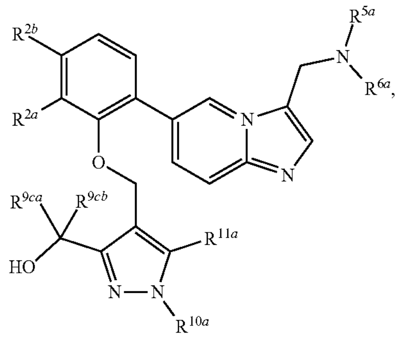

wherein:
$R^{2a}$ is H or F;
$R^{2b}$ is F;
$R^{5a}$ is H or methyl;
$R^{6a}$ is H or methyl;
$R^{9ca}$ is methyl, iso-propyl or tert-butyl;
$R^{9cb}$ is H or methyl;
$R^{10a}$ is methyl; and
$R^{11a}$ is methyl;
provided that when $R^{2a}$ is H, $R^{9cb}$ is H;
or a salt and/or solvate thereof.

It will be understood that references and preferences set out with respect to the compounds of formula (I), or salts and/or solvates thereof regarding pharmaceutical compositions, compounds for use, use and method aspects apply equally to the compound of formula (IA) or a salt and/or solvate thereof.

In one embodiment, $R^{2a}$ is H. In a second embodiment, $R^{2a}$ is H. In one embodiment, $R^{5a}$ is H. In a second embodiment, $R^{5a}$ is methyl. In one embodiment, $R^{6a}$ is H. In a second embodiment, $R^{6a}$ is methyl. In one embodiment, $R^{9ca}$ is methyl. In a second embodiment, $R^{9ca}$ is iso-propyl. In a third embodiment, $R^{9ca}$ is tert-butyl. In one embodiment, $R^{9c}$ b is H. In a second embodiment, $R^{9c}$ b is methyl. In one embodiment, $R^{9ca}$ is tert-butyl and $R^{9c}$ b is H. In a second embodiment, $R^{9ca}$ is methyl and $R^{9cb}$ is methyl.

In one embodiment, the compound of formula (I) is selected from the group consisting of:

1-{4-[2-(5-fluoro-2-{3-[(methylamino)methyl]imidazo[1,2-a]pyridin-6-yl}phenoxy)ethyl]-1,5-dimethyl-1H-pyrazol-3-yl}ethan-1-ol;

1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-ol;

(isomer 1) 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-ol;

(isomer 2) 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-ol;

1-{4-[2-(2,3-difluoro-6-{3-[(methylamino)methyl]imidazo[1,2-a]pyridin-6-yl}phenoxy)ethyl]-1,5-dimethyl-1H-pyrazol-3-yl}ethan-1-ol;

1-(4-(2-(6-(3-((dimethylamino)methyl)imidazo[1,2-a]pyridin-6-yl)-2,3-difluorophenoxy)ethyl)-1,5-dimethyl-1H-pyrazol-3-yl)ethan-1-ol;

1-(4-(2-(2-(3-(2-aminoethyl)imidazo[1,2-a]pyridin-6-yl)-5-fluorophenoxy)ethyl)-1,5-dimethyl-1H-pyrazol-3-yl) ethan-1-ol;

1-(4-(2-(5-fluoro-2-(3-((methylamino)methyl)imidazo[1,2-a]pyridin-6-yl)phenoxy)ethyl)-1,5-dimethyl-1H-pyrazol-3-yl)-2,2-dimethylpropan-1-ol;

(isomer 1) 1-(4-(2-(5-fluoro-2-(3-((methylamino)methyl)imidazo[1,2-a]pyridin-6-yl)phenoxy)ethyl)-1,5-dimethyl-1H-pyrazol-3-yl)-2,2-dimethylpropan-1-ol;

(isomer 2) 1-(4-(2-(5-fluoro-2-(3-((methylamino)methyl)imidazo[1,2-a]pyridin-6-yl)phenoxy)ethyl)-1,5-dimethyl-1H-pyrazol-3-yl)-2,2-dimethylpropan-1-ol;

1-(4-(2-(2-(3-((dimethylamino)methyl)imidazo[1,2-a]pyridin-6-yl)-5-fluorophenoxy)ethyl)-1,5-dimethyl-1H-pyrazol-3-yl)-2,2-dimethylpropan-1-ol;

1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol;

(isomer 1) 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol;

(isomer 2) 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol;

(isomer 1) 1-(4-(2-(6-(3-((dimethylamino)methyl)imidazo[1,2-a]pyridin-6-yl)-2,3-difluorophenoxy)ethyl)-1,5-dimethyl-1H-pyrazol-3-yl)-2,2-dimethylpropan-1-ol;

(isomer 2) 1-(4-(2-(6-(3-((dimethylamino)methyl)imidazo[1,2-a]pyridin-6-yl)-2,3-difluorophenoxy)ethyl)-1,5-dimethyl-1H-pyrazol-3-yl)-2,2-dimethylpropan-1-ol;

1-(4-(2-(6-(3-(aminomethyl)imidazo[1,2-a]pyridin-6-yl)-2,3-difluorophenoxy)ethyl)-1,5-dimethyl-1H-pyrazol-3-yl)-2,2-dimethylpropan-1-ol;

2-(4-(2-(5-fluoro-2-(3-((methylamino)methyl)imidazo[1,2-a]pyridin-6-yl)phenoxy)ethyl)-1,5-dimethyl-1H-pyrazol-3-yl) propan-2-ol;

2-(4-(2-(2-(3-((dimethylamino)methyl)imidazo[1,2-a]pyridin-6-yl)-5-fluorophenoxy)ethyl)-1,5-dimethyl-1H-pyrazol-3-yl) propan-2-ol;

2-[4-(2-{6-[3-(aminomethyl)imidazo[1,2-a]pyridin-6-yl]-2,3-difluorophenoxy}ethyl)-1,5-dimethyl-1H-pyrazol-3-yl] propan-2-ol;

2-(4-(2-(2,3-difluoro-6-(3-((methylamino)methyl)imidazo[1,2-a]pyridin-6-yl)phenoxy)ethyl)-1,5-dimethyl-1H-pyrazol-3-yl)propan-2-ol;

2-{4-[2-(2-{3-[(ethylamino)methyl]imidazo[1,2-a]pyridin-6-yl}-5-fluorophenoxy)ethyl]-1,5-dimethyl-1H-pyrazol-3-yl}propan-2-ol;

2-(4-(2-(2-(3-(2-aminoethyl)imidazo[1,2-a]pyridin-6-yl)-5-fluorophenoxy)ethyl)-1,5-dimethyl-1H-pyrazol-3-yl)propan-2-ol;

1-(4-(2-(2-(3-((dimethylamino)methyl)imidazo[1,2-a]pyridin-6-yl)-5-fluorophenoxy)ethyl)-1,5-dimethyl-1H-pyrazol-3-yl)-2-methylpropan-1-ol; and 1-{4-[2-(2,3-difluoro-6-{3-[(methylamino)methyl]imidazo[1,2-a]pyridin-6-yl}phenoxy)ethyl]-1,5-dimethyl-1H-pyrazol-3-yl}-2-methylpropan-1-ol.

Salts and/or solvates thereof (e.g. pharmaceutically acceptable salts thereof) are also provided.

In one embodiment, the invention provides 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol, or a salt and/or solvate thereof. In one embodiment, the invention provides a pharmaceutically acceptable solvate of the pharmaceutically acceptable salt of 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol. In one embodiment, the invention provides a pharmaceutically acceptable salt of 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol. In one embodiment, the invention provides a pharmaceutically acceptable solvate of 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol. In one embodiment, the invention provides 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol.

In one embodiment, the invention provides (isomer 1) 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol, or a salt and/or solvate thereof. In one embodiment, the invention provides a pharmaceutically acceptable solvate of the pharmaceutically acceptable salt of (isomer 1) 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol. In one embodiment, the invention provides a pharmaceutically acceptable salt of (isomer 1) 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol. In one embodiment, the invention provides a pharmaceutically acceptable solvate of (isomer 1) 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol.

In one embodiment, the invention provides (isomer 1) 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol.

In one embodiment, the invention provides (isomer 2) 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol, or a salt and/or solvate thereof. In one embodiment, the invention provides a pharmaceutically acceptable solvate of the pharmaceutically acceptable salt of (isomer 2) 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol. In one embodiment, the invention provides a pharmaceutically acceptable salt of (isomer 2) 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol. In one embodiment, the invention provides a pharmaceutically acceptable solvate of (isomer 2) 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol. In one embodiment, the invention provides (isomer 2) 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol.

In one embodiment, the invention provides 2-(4-(2-(2,3-difluoro-6-(3-((methylamino)methyl)imidazo[1,2-a]pyridin-6-yl)phenoxy)ethyl)-1,5-dimethyl-1H-pyrazol-3-yl)propan-2-ol, or a salt and/or solvate thereof. In one embodiment, the invention provides a pharmaceutically acceptable solvate of the pharmaceutically acceptable salt of 2-(4-(2-(2,3-difluoro-6-(3-((methylamino)methyl)imidazo[1,2-a]pyridin-6-yl)phenoxy)ethyl)-1,5-dimethyl-1H-pyrazol-3-yl)propan-2-ol. In one embodiment, the invention provides a pharmaceutically acceptable salt of 2-(4-(2-(2,3-difluoro-6-(3-((methylamino)methyl)imidazo[1,2-a]pyridin-6-yl)phenoxy)ethyl)-1,5-dimethyl-1H-pyrazol-3-yl)propan-2-ol. In one embodiment, the invention provides a pharmaceutically acceptable solvate of 2-(4-(2-(2,3-difluoro-6-(3-((methylamino)methyl)imidazo[1,2-a]pyridin-6-yl)phenoxy)ethyl)-1,5-dimethyl-1H-pyrazol-3-yl)propan-2-ol. In one embodiment, the invention provides 2-(4-(2-(2,3-difluoro-6-(3-((methylamino)methyl)imidazo[1,2-a]pyridin-6-yl)phenoxy)ethyl)-1,5-dimethyl-1H-pyrazol-3-yl)propan-2-ol.

In one embodiment, $R^{9d}$ is H and $R^{9c}$ and the alcohol has the following stereochemical arrangement:

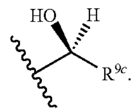

In one embodiment, $R^{9d}$ is H and $R^{9c}$ and the alcohol have the following stereochemical arrangement:

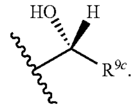

It will be appreciated that for use in medicine the salts of the compounds of formula (I) should be pharmaceutically acceptable. Non-pharmaceutically acceptable salts of the compounds of formula (I) may be of use in other contexts such as during preparation of the compounds of formula (I). Suitable pharmaceutically acceptable salts will be apparent to those skilled in the art. Pharmaceutically acceptable salts include those described by Berge et al. (1977). Such pharmaceutically acceptable salts include acid and base addition salts. Pharmaceutically acceptable acid additional salts may be formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain of the compounds of formula (I) may form acid addition salts with one or more equivalents of the acid. The present invention includes within its scope all possible stoichiometric and non-stoichiometric forms. The compounds of formula (I) may be prepared in crystalline or non-crystalline form and, if crystalline, may optionally be solvated, e.g. as the hydrate. His invention includes within its scope stoichiometric solvates (e.g. hydrates) as well as compounds containing variable amounts of solvent (e.g. water). It is to be understood that the present invention encompasses all isomers of formula (I), including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The present disclosure includes all isotopic forms of the compounds of formula (I) provided herein, or salts and/or solvates thereof whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exist as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound of formula (I), or salts and/or solvates thereof may thus contain one or more artificial or uncommon isotopes such as deuterium ($^{2}H$ or D), carbon-11 ($^{11}C$), carbon-13 ($^{13}C$), carbon-14 ($^{14}C$), nitrogen-13 ($^{13}N$), nitrogen-15 ($^{15}N$), oxygen-15 ($^{15}O$), oxygen-17 ($^{17}O$), oxygen-18 ($^{18}O$), phosphorus-32 ($^{32}P$), sulphur-35 ($^{35}S$), chlorine-36 ($^{36}Cl$), chlorine-37 ($^{37}Cl$), fluorine-18 ($^{18}F$) iodine-123 ($^{123}I$), iodine-125 ($^{125}I$) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Unnatural variant isotopic forms which incorporate deuterium i.e. $^2H$ or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}C$, $^{18}F$, $^{15}O$ and $^{13}N$, and would be useful in Positron Emission Topography (PET) studies for examining substrate receptor occupancy. In one embodiment, a compound of formula (I), or a salt and/or solvate thereof is provided in a natural isotopic form.

In one embodiment, a compound of formula (I), or a salt and/or solvate thereof is provided in an unnatural variant isotopic form. In a specific embodiment, the unnatural variant isotopic form is a form in which deuterium (i.e. $^2H$ or D) is incorporated where hydrogen is specified in the chemical structure in one or more atoms of a compound of formula (I), or a salt and/or solvate thereof. In one embodiment, the atoms of a compound of formula (I), or a salt and/or solvate thereof are in an isotopic form which is not radioactive. In one embodiment, one or more atoms of a compound of formula (I), or a salt and/or solvate thereof are in an isotopic form which is radioactive. Suitably radioactive isotopes are stable isotopes. Suitably the unnatural variant isotopic form is a pharmaceutically acceptable form.

In one embodiment, a compound of formula (I), or a salt and/or solvate thereof is provided whereby a single atom of the compound exists in an unnatural variant isotopic form. In another embodiment, a compound of formula (I), or a salt and/or solvate thereof is provided whereby two or more atoms exist in an unnatural variant isotopic form.

Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labelled) reagents in place of the normal reagents employed in the Examples. Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

In general, the compounds of formula (I), or salts and/or solvates thereof may be made according to the organic synthesis techniques known to those skilled in this field, as well as by the representative methods set forth below, those in the Examples and modifications thereof.

Patent applications WO2017/001812, WO2020/128473 and WO2020/128475, each incorporated herein by reference in their entirety, provide methods for the synthesis of intermediates which may be of use in the production of compounds of the present invention.

General Synthesis Schemes

Synthesis of Compounds of the Invention

Numerous synthetic routes to the compounds of the invention can be devised by a person skilled in the art and the exemplified synthetic routes described below do not limit the invention. Many methods exist in the literature for the synthesis of heterocycles, for example: Joule, J. A.; Mills, K., Heterocyclic Chemistry, 2010, 5th Edition, Pub. Wiley. A number of possible synthetic routes are exemplified below. Where appropriate, any initially produced compound according to the invention can be converted into another compound according to the invention by known methods. In the following description, the groups L, A, $R^1$, $R^2$, s, q, v, $R^3$, $R^4$, $R^5$, $R^6$, $R^7$, $R^8$, $R^{9a}$, $R^{9b}$, $R^{9c}$, $R^{9d}$, $R^{10}$, $R^{11}$ and $R^{12}$ are as defined above for the compound of formula (I), unless otherwise stated.

Scheme 1

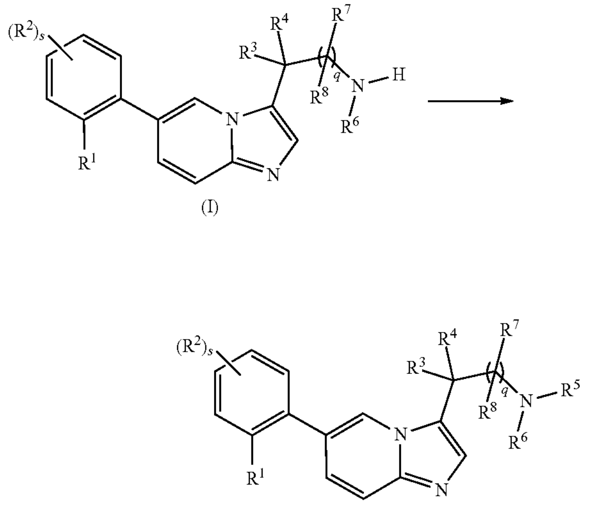

(I)

(I)

Compounds of formula (I), wherein $R^4$ and $R^5$ are both methyl, can be obtained by reductive amination. In this reaction, another compound of formula (I), wherein one of $R^5$ and $R^6$ is methyl and the other is H, is reacted with formaldehyde in the presence of a metal hydride reducing agent, such as $NaBH_3CN$ (sodium cyanoborohydride), in a suitable solvent, such as methanol, at 0° C.

Scheme 2

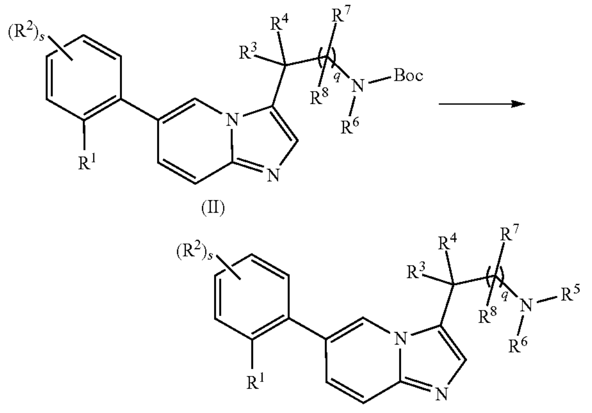

(II)

(I)

Compounds of formula (I), wherein one of $R^5$ and $R^6$ is H and the other is methyl, or wherein $R^5$ and $R^6$ are both H, can be obtained by reacting a compound of formula (II) with an acid, such as 2M HCl in diethyl ether ($Et_2O$).

Scheme 3

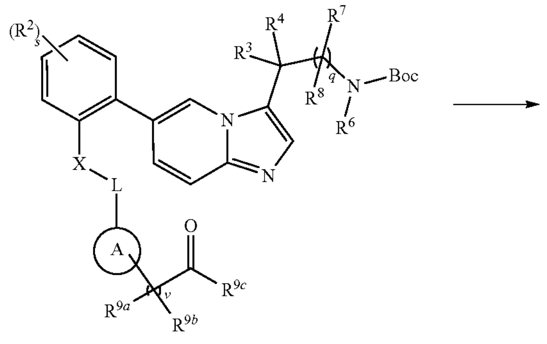

(III)

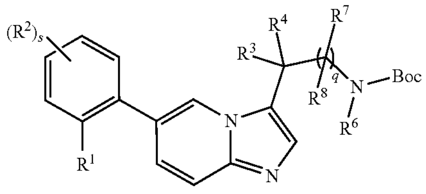

(II)

Compounds of formula (II) wherein $R^{9d}$ is H may be prepared by reacting a compound of formula (III) with a reducing agent, such as $NaBH_4$ in a solvent such as methanol.

Scheme 4

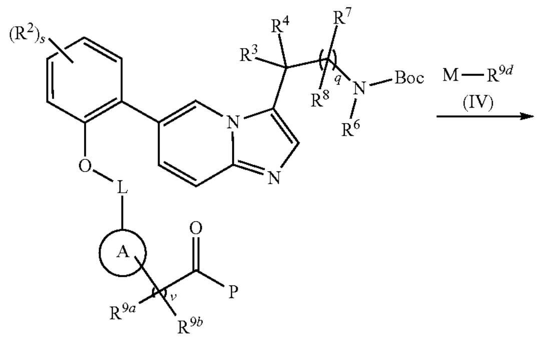

(III)

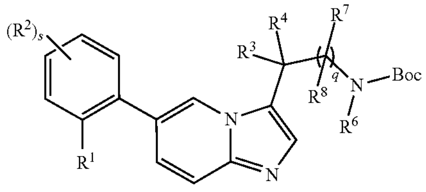

(II)

Compounds of formula (II) wherein $R^{9d}$ is $C_{1-4}$ alkyl or $C_{1-4}$ haloalkyl may be prepared by reacting a compound of formula (IV), wherein M is a metal ion e.g. Mg or Li in a suitable solvent, such as such as diethyl ether ($Et_2O$) or tetrahydrofuran (THF), with a compound of formula (III), wherein P is $C_{1-4}$ alkyl or $C_{1-4}$alkoxy.

Scheme 5a

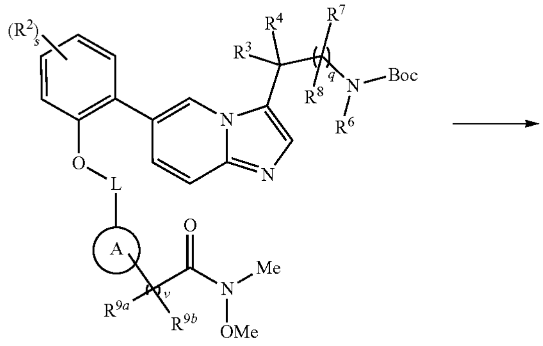

(IV)

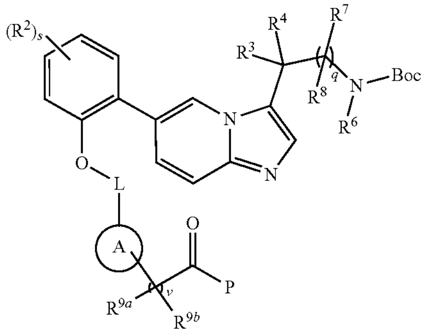

(III)

Compounds of formula (III) wherein P is $C_{1-4}$ alkyl may be obtained by reacting a compound of formula (V) with an organometallic reagent, such as an organomagnesium or organolithium compound, for example methylmagnesium bromide, iso-propylmagnesium bromide or tert-butyllithium, in a suitable solvent, such as diethyl ether ($Et_2O$) or tetrahydrofuran (THF).

Scheme 5b

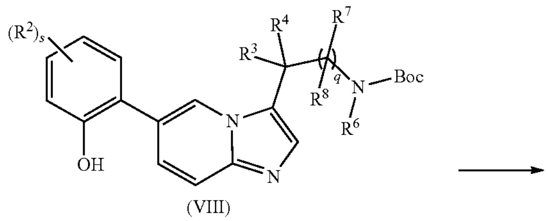

(VIII)

+

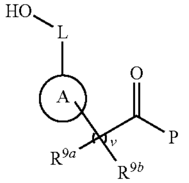

(IX)

-continued

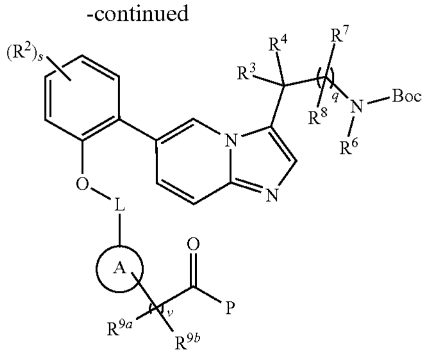

(III)

Compounds of formula (III) wherein P is $C_{1-4}$alkoxy may be obtained by reacting a compound of formula (VIII) with a compound of formula (IX), wherein P is $C_{1-4}$alkoxy, in the presence of a phosphine reagent, such as (tributylphosphoranylidene)acetonitrile, in a suitable solvent, such as toluene.

Scheme 6

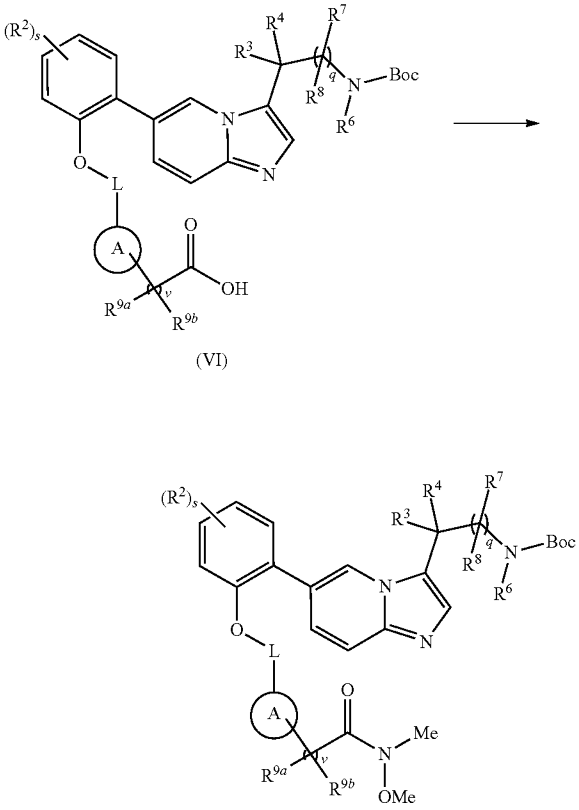

(VI)

(V)

Compounds of formula (V) may be obtained by reacting a compound of formula (VI) with an amine, such as N,O-Dimethylhydroxylamine hydrochloride, in the presence of a base, such as triethylamine ($Et_3N$), a carbodiimide, such as N-(3-dimethylaminopropyl)-N'-ethylcarbodiimide hydrochloride (EDC HCl) and hydroxybenzotriazole (HOBt), in a suitable solvent, such as tetrahydrofuran (THF).

Scheme 7

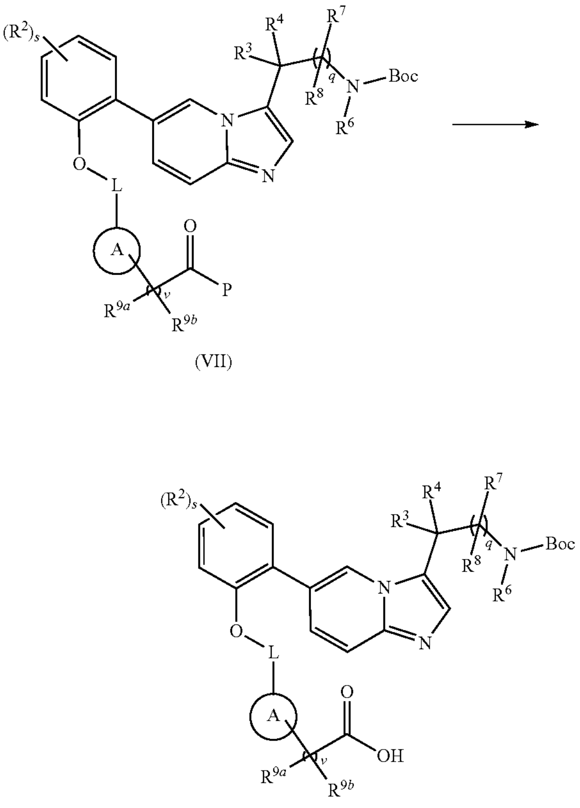

(VII)

(VI)

Compounds of formula (VI) may be obtained by reacting a compound of formula (VII), wherein P is $C_{1-4}$alkoxy, with a metal hydroxide, such as lithium hydroxide monohydrate (LiOH $H_2O$), in a suitable solvent, such as methanol.

Scheme 8

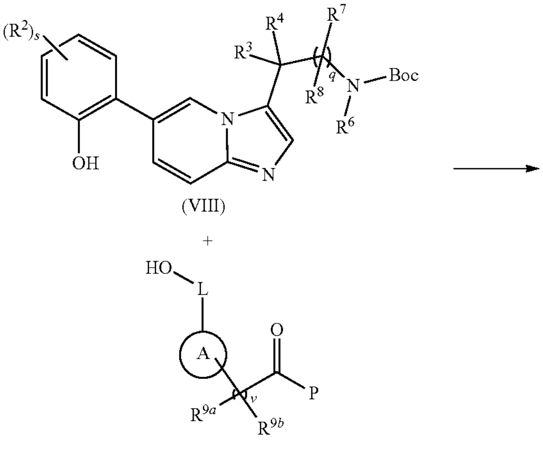

(VIII)

+

(IX)

-continued

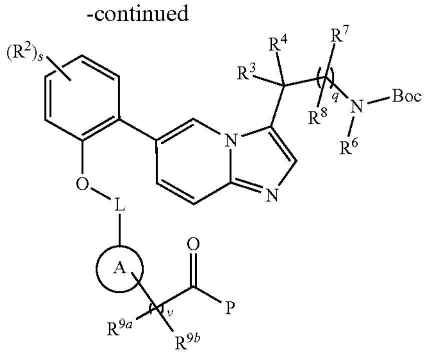

(VII)

Compounds of formula (VII), wherein P is $C_{1-4}$alkoxy, may be obtained by reacting a compound of formula (VIII) with a compound of formula (IX), wherein P is $C_{1-4}$alkoxy, in the presence of a phosphine reagent, such as (tributylphosphoranylidene)acetonitrile, in a suitable solvent, such as toluene.

The compound of formula (IX) may be a compound of formula (IXA):

(IXA)

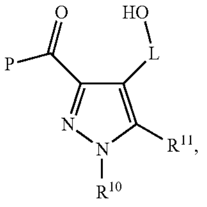

wherein P is $C_{1-4}$alkoxy.

Compounds of formula (IXA) can be prepared by methods described in WO2017/001812.

Intermediates of the Invention

The present invention also relates to novel intermediates in the synthesis of compounds of formula (I), such as compounds of formulae (II) to (VII). Particular intermediates of interest are those of the following general formulae, wherein the variable groups and associated preferences are as defined previously for compounds of formula (I):

a compound of formula (II):

(II)

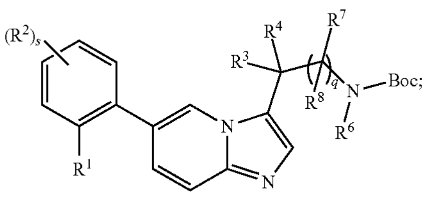

a compound of formula (III):

(III)

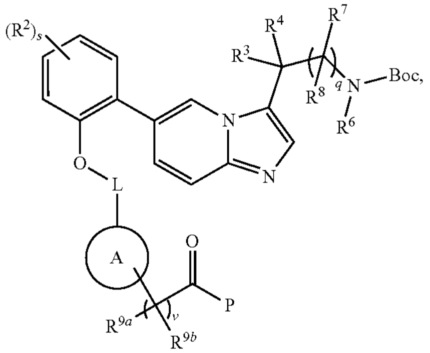

wherein P is $C_{1-4}$ alkyl or $C_{1-4}$alkoxy;

a compound of formula (V):

(V)

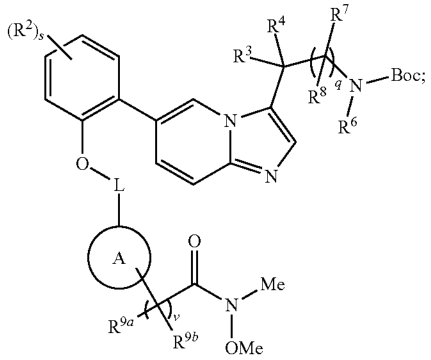

a compound of formula (VII)

(VI)

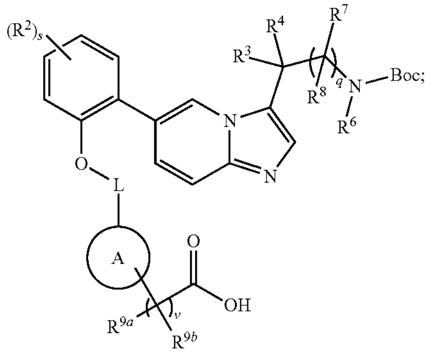

(VII)

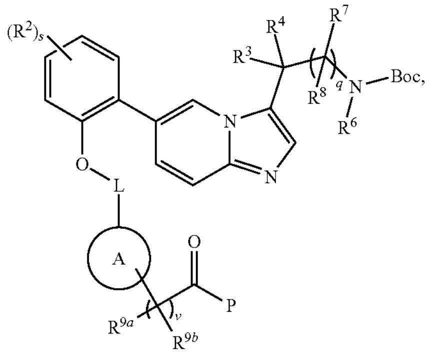

wherein P is $C_{1-4}$alkoxy.

Included as an aspect of the invention are salts, such as pharmaceutically acceptable salts of any one of the intermediates disclosed herein, such as any one of compounds of formulae (II) to (VII).

Uses of Compounds and ADCs of the Invention

In any one of the below medical use embodiments, the same use may be applied to an ADC of the invention, or a pharmaceutically acceptable salt thereof, since the ADC of the invention comprises a compound of formula (I), or a pharmaceutically acceptable salt and/or solvate.

Hyperproliferative Disorders

As the compounds of formula (I) have cytotoxic activity, the compounds of formula (I), or pharmaceutically acceptable salts and/or solvates thereof are expected to be useful in the treatment or prevention of a hyperproliferative disorder. Therefore, in one embodiment of the invention, the compounds of formula (I), or pharmaceutically acceptable salts and/or solvates thereof for use in the treatment or prevention of a hyperproliferative disorder. In one especially suitable embodiment, the compounds of formula (I), or pharmaceutically acceptable salts and/or solvates thereof are for use in the treatment of a hyperproliferative disorder.

As the ADCs of the invention have cytotoxic activity, the ADCs of the invention or pharmaceutically acceptable salts thereof are expected to be useful in the treatment or prevention of a hyperproliferative disorder.

Therefore, the invention provides an ADC of the invention or a pharmaceutically acceptable salt thereof for use in the treatment or prevention of a hyperproliferative disorder. In one especially suitable embodiment, the ADCs of the invention, or pharmaceutically acceptable salts thereof are for use in the treatment of a hyperproliferative disorder.

In one embodiment, the invention provides the use of the compounds of formula (I), or a pharmaceutically acceptable salt and/or solvate thereof for the manufacture of a medicament for the treatment or prevention of a hyperproliferative disorder. In one especially suitable embodiment, the invention provides the use of compounds of formula (I) or pharmaceutically acceptable salts and/or solvates thereof for the manufacture of a medicament for the treatment of a hyperproliferative disorder.

In one embodiment, the invention provides a method of treating or preventing a hyperproliferative disorder in a subject, said method comprising administering a therapeutically effective amount of a compound of formula (I), or a pharmaceutically acceptable salt and/or solvate thereof. In one especially suitable embodiment, the invention provides a method of treating a hyperproliferative disorder in a subject, said method comprising administering a therapeutically effective amount of a compound of formula (I), or a pharmaceutically acceptable salt and/or solvate thereof.

In one embodiment, the hyperproliferative disorder is a cancer.

In one embodiment, the cancer is a haematologic malignancy selected from the group consisting of lymphoma (for example B-cell lymphoma, and in particular a lymphoma selected from the group consisting high grade mantle zone lymphoma, follicular lymphoma, plasmablastic lymphoma, diffuse large B-cell lymphoma and Burkitt's lymphoma), myeloma (for example multiple myeloma), leukaemia (for example a leukaemia selected from the group consisting chronic lymphocytic leukaemia, AML and B-acute lymphocytic leukaemia), and melanoma (for example a melanoma selected from the group consisting of superficial spreading melanoma, nodular melanoma, lentigo maligna melanoma, amelanotic melanoma, and acral lentiginous melanoma).

The cancer may additionally, or alternatively, be a solid tumour selected from the group consisting of brain, lung, breast (e.g. triple negative breast cancer or a breast invasive carcinoma), prostate, ovary, colorectal (e.g. colon), gallbladder, kidney and liver cancer. For example, the cancer may be ovarian serous cystadenocarcinoma, esophageal carcinoma, lung squamous cell carcinoma, lung adenocarcinoma, bladder urothelial carcinoma, uterine carcinosarcoma, stomach cancer (herein referred to as "gastric cancer") such as stomach adenocarcinoma, breast invasive carcinoma or liver hepatocellular carcinoma. In one suitable embodiment, the cancer is breast cancer, for example triple negative breast cancer or a breast invasive carcinoma. In one suitable embodiment, the cancer is brain, breast, prostate, colon, gallbladder or kidney cancer. In certain embodiments, the cancer is breast, colon or gallbladder cancer. In another embodiment, the cancer is gastric cancer.

The cancer may also additionally, or alternatively, be a blastoma, and in particular a neuroblastoma, for example a retinoblastoma, a glioblastoma, a small cell lung carcinoma or an astrocytoma.

In an especially suitable embodiment, the cancer may be selected from the group consisting of a haematologic malignancy (such as a lymphoma, and in particular a B-cell lymphoma (e.g. high grade mantle zone lymphoma, follicular lymphoma, plasmablastic lymphoma, diffuse large B-cell lymphoma and Burkitt's lymphoma), a myeloma (e.g multiple myeloma) or a leukaemia (e.g. chronic lymphocytic leukaemia, AML and B-acute lymphocytic leukaemia)), a solid-tumour (such as brain, lung, breast (e.g. triple negative breast cancer or a breast invasive carcinoma), prostate, ovary, colorectal (e.g. colon), gallbladder, kidney or liver cancer, or a neuroblastoma (for example a retinoblastoma, a glioblastoma, a small cell lung carcinoma or an astrocytoma)), and a melanoma (such as superficial spreading melanoma, nodular melanoma, lentigo maligna melanoma, amelanotic melanoma, or acral lentiginous melanoma).

In a suitable embodiment, the cancer may be selected from the group consisting of diffuse large B-cell lymphoma, Burkitt's lymphoma, multiple myeloma, neuroblastoma, AML, and B-acute lymphocytic leukaemia. In a suitable embodiment, the cancer may be selected from the group consisting of diffuse large B-cell lymphoma, Burkitt's lymphoma, neuroblastoma, AML, B-acute lymphocytic leukaemia and breast cancer. In a suitable embodiment, the cancer may be selected from the group consisting of diffuse large B-cell lymphoma, neuroblastoma, B-acute lymphocytic leukaemia and triple negative breast cancer. In a suitable embodiment, the cancer may be selected from the group consisting of diffuse large B-cell lymphoma, Burkitt's lymphoma, multiple myeloma, neuroblastoma, AML, B-acute lymphocytic leukaemia and triple negative breast cancer. In a suitable embodiment, the cancer may be selected from the group consisting of multiple myeloma, neuroblastoma, AML, B-acute lymphocytic leukaemia and triple negative breast cancer. In a suitable embodiment, the cancer may be selected from the group consisting of multiple myeloma, neuroblastoma and triple negative breast cancer.

In one embodiment, the cancer is a MYC addicted cancer as described in WO2020/128475, the entire contents of which are incorporated by reference for the purpose of defining the MYC addicted cancer.

Inhibition of Human NMT

Inhibition of human NMT has been suggested as a target for treating or preventing various diseases or disorders, as described above. The present invention provides compounds which are or are expected to be human NMT inhibitors. The present invention also provides ADCs which comprise human NMT inhibitors. The term "human NMT inhibitor" as used herein is intended to cover any moiety which binds to human NMT. Human NMT is suitably HsNMT1. The inhibitor may act as a competitive inhibitor, or a partial competitive inhibitor. The inhibitor may bind to human NMT at the myr-CoA binding pocket or at the peptide binding pocket (or inhibit human NMT through another mechanism). As the compounds of formula (I), or pharmaceutically acceptable salts and/or solvates thereof are or are expected to be human NMT inhibitors, it is expected that the compound of the invention suitably binds and inhibits human NMT through the peptide binding pocket. Furthermore, as the ADCs of the present invention or pharmaceutically acceptable salts thereof comprise NMT inhibitors which are human NMT inhibitors, it is expected that after intracellular release of the NMT inhibitor from the ADCs of the invention, the NMT inhibitor suitably binds and inhibits human NMT through the peptide binding pocket.

As the compounds of formula (I), or pharmaceutically acceptable salts and/or solvates thereof are or are expected to be human NMT inhibitors, the compounds of formula (I), or pharmaceutically acceptable salts and/or solvates thereof are expected to be useful in the treatment or prevention of diseases or disorders associated with human NMT activity or are expected to be useful in the treatment or prevention of a disease or disorder by targeting human NMT activity for example, in addition to hyperproliferative diseases such as cancer, viral infections (such as picornaviral infections)). Accordingly, the present invention provides a compound of formula (I), or a pharmaceutically acceptable salt and/or solvate thereof for use as a medicament. The present invention also provides an ADC of the invention, or a pharmaceutically acceptable salt thereof for use as a medicament.

There is also provided a compound of formula (I), or a pharmaceutically acceptable salt and/or solvate thereof for use in the treatment or prevention of a disease or disorder in which inhibition of human NMT provides a therapeutic or prophylactic effect. In one embodiment there is provided a compound of formula (I), or a pharmaceutically acceptable salt and/or solvate thereof for use in the treatment of a disease or disorder in which inhibition of human NMT provides a therapeutic effect. In one embodiment there is provided a compound of formula (I), or a pharmaceutically acceptable salt and/or solvate thereof for use in the prevention of a disease or disorder in which inhibition of human NMT provides a prophylactic effect.

The invention also provides a method for the treatment or prevention of a disease or disorder in a subject in which inhibition of human NMT provides a therapeutic or prophylactic effect in a subject (e.g. a mammal, for example a human), which comprises administering to the subject a therapeutically effective amount of a compound according to formula (I), or a pharmaceutically acceptable salt and/or solvate thereof and a pharmaceutically acceptable carrier. The invention also provides a method for the treatment of a disease or disorder in a subject in which inhibition of human NMT provides a therapeutic effect in a subject (e.g. a mammal, for example a human), which comprises administering to the subject a therapeutically effective amount of a compound according to formula (I), or a pharmaceutically acceptable salt and/or solvate thereof and a pharmaceutically acceptable carrier. The invention also provides a method for the prevention of a disease or disorder in a subject in which inhibition of human NMT provides a prophylactic effect in a subject (e.g. a mammal, for example a human), which comprises administering to the subject a therapeutically effective amount of a compound according to formula (I), or a pharmaceutically acceptable salt and/or solvate thereof and a pharmaceutically acceptable carrier.

The invention also provides the use of a compound of formula (I), or a pharmaceutically acceptable salt and/or solvate thereof, for the manufacture of a medicament for the treatment or prevention of a disease or disorder in which inhibition of human NMT provides a therapeutic or prophylactic effect. The invention also provides the use of a compound of formula (I), or a pharmaceutically acceptable salt and/or solvate thereof, for the manufacture of a medicament for the treatment of a disease or disorder in which inhibition of human NMT provides a therapeutic effect. The invention also provides the use of a compound of formula (I), or a pharmaceutically acceptable salt and/or solvate thereof, for the manufacture of a medicament for the prevention of a disease or disorder in which inhibition of human NMT provides a prophylactic effect.

Diseases and disorders in which inhibition of human NMT provides a therapeutic or prophylactic effect include: hyperproliferative disorders such as cancer, viral infections (e.g. human immunodeficiency virus (HIV) or human rhinovirus (HRV)), neurological diseases, ischemia, osteoporosis, diabetes, autoimmune diseases and inflammatory diseases. Therefore, in a suitable embodiment, compounds of formula (I) or pharmaceutically acceptable salts and/or solvates thereof find use the treatment or prevention of those disorders/diseases.

In another especially suitable embodiment, a compound of formula (I) or a pharmaceutically acceptable salt and/or solvate thereof is for use in the treatment or prevention of a viral infection, and in particular an enteroviral infection, a retroviral infection, a poxviral infection, an arenaviral infection, a flaviviral infection, an alpha herpes viral infection, a varicella infection or a beta herpes viral infection. In another especially suitable embodiment, a compound of formula (I) or a pharmaceutically acceptable salt and/or solvate thereof is for use in the treatment of a viral infection, and in particular an enteroviral infection, a retroviral infection, a poxviral infection, an arenaviral infection, a flaviviral infection, an alpha herpes viral infection, a varicella infection or a beta herpes viral infection. In another especially suitable embodiment, a compound of formula (I) or a pharmaceutically acceptable salt and/or solvate thereof is for use in the prevention of a viral infection, and in particular an enteroviral infection, a retroviral infection, a poxviral infection, an arenaviral infection, a flaviviral infection, an alpha herpes viral infection, a varicella infection or a beta herpes viral infection. In an even more suitable embodiment, the enteroviral infection may be a picornaviral infection (for example a rhinovirus, poliovirus, foot-and-mouth disease virus, coxsackievirus, hepatitis A virus or enterovirus 71 infection); the retroviral infection may be a lentiviral infection (for example an HIV infection)).

In an even more suitable embodiment, the viral infection may be selected from the group consisting of a rhinovirus infection (HRV, also known as the common cold), lentivirus infection (for example HIV infection), poliovirus infection, foot-and-mouth disease virus infection, coxsackievirus infection, hepatitis A virus infection and enterovirus 71 infection. In one especially suitable embodiment, the compound of formula (I), or a pharmaceutically acceptable salt and/or solvate thereof, is for use in the treatment or prevention of a viral infection, wherein the viral infection is a picornaviral infection, and even more especially it is a rhinovirus infection (HRV, also known as the common cold).

The above-mentioned viral infections cause many types of diseases. For example: rhinovirus infection causes the common cold; various picornaviral infections, in particular coxsackievirus and enterovirus 71, cause hand, foot and mouth disease and polio-like syndrome; coxsackieviruses can also cause a flaccid paralysis, herpangina, acute hemorrhagic conjunctivitis, nonspecific febrile illnesses, rashes, upper respiratory tract disease, enterovirus 71 can also cause severe neurological diseases in children; foot-and-mouth disease virus causes foot-and-mouth disease; hepatitis A virus causes hepatitis A; HIV infection can cause acquired immunodeficiency syndrome (AIDS); poxviruses can cause small pox; areanaviruses can cause Lassa fever; Flaviruses can cause Dengue Fever; alpha herpes viruses can cause a simplex infection, a varicella infection, Marek's disease or laryngotracheitis; and betaherpesvirinae can cause congenital CMV infection, HHV-6 and HHV-7.

Therefore, in an especially suitable embodiment, a compound of formula (I) or a pharmaceutically acceptable salt and/or solvate thereof is for use in the treatment or prevention of the above-mentioned diseases caused by the viral infections mentioned above. In an especially suitable embodiment, a compound of formula (I) is for use in the treatment of the above-mentioned diseases caused by the viral infections mentioned above. In an especially suitable embodiment, a compound of formula (I) is for use in the prevention of the above-mentioned diseases caused by the viral infections mentioned above. Suitably, a compound of formula (I) may be used in the treatment or prevention (e.g. treatment) of other diseases and conditions caused by an enteroviral infection, a retroviral infection, a poxviral infection, an arenaviral infection, a flaviviral infection, an alpha herpes viral infection, a varicella infection or a beta herpes viral infection.

Combination therapies Whilst a compound of formula (I) or a pharmaceutically acceptable salt and/or solvate thereof may be used as the sole active ingredient in a medicament, it is also possible for a compound of formula (I) or a pharmaceutically acceptable salt and/or solvate thereof to be used in combination with one or more further therapeutic agents. Accordingly, the present invention also provides a compound of formula (I), or a pharmaceutically acceptable salt and/or solvate thereof together with a further therapeutic agent. The further therapeutic ingredient may be for simultaneous, sequential or separate administration. The invention also provides a kit of parts comprising: (a) a first pharmaceutical composition comprising a compound of formula (I) or a pharmaceutically acceptable salt and/or solvate thereof and a pharmaceutically acceptable carrier; and (b) a second pharmaceutical composition comprising a further therapeutic agent, and a pharmaceutically acceptable carrier. Such further therapeutic agents may be further compounds of formula (I), or a pharmaceutically acceptable salt and/or solvate thereof.

The compounds of formula (I), or pharmaceutically acceptable salts and/or solvates thereof can be used in combination with one or more further therapeutic agents useful for the treatment or prevention of hyperproliferative disorders such as cancer or another disease or disorder in which inhibition of human NMT provides a therapeutic or prophylactic effect (for example agents useful for the treatment or prevention of hyperproliferative disorders, viral infections, neurological diseases, ischemia, osteoporosis, diabetes, autoimmune diseases and inflammatory diseases, and in particular hyperproliferative disorders (e.g. cancer) and viral infections (e.g. HRV or HIV infection)). The individual components of such combinations can be administered separately at different times during the course of therapy or concurrently in divided or single combination forms. The present invention is therefore to be understood as embracing all such regimes of simultaneous or alternating treatment and the term "administering" is to be interpreted accordingly. It will be understood that the scope of combinations of the compound of the invention with other therapeutic agents useful for treating or prevention of a disease or disorder in which inhibition of human NMT provides a therapeutic or prophylactic effect includes in principle any combination with any pharmaceutical composition useful for treating or prevention of a disease or disorder in which inhibition of human NMT provides a therapeutic or prophylactic effect.

A further therapeutic agent, when employed in combination with a compound of formula (I), or a pharmaceutically acceptable salt and/or solvate thereof may be used, for example, in those amounts indicated in the Physicians' Desk Reference (PDR) for that agent, or as otherwise determined by one of ordinary skill in the art. Where a compound of formula (I) or a pharmaceutically acceptable salt and/or solvate thereof is utilized in combination with one or more further therapeutic agent(s), either concurrently or sequentially, the following combination ratios and dosage ranges are suitable: when combined with a further therapeutic agent, a compound of formula (I) or a pharmaceutically acceptable salt and/or solvate thereof may for example be employed in a weight ratio to the further therapeutic agent within the range from about 10:1 to about 1:10.

In one embodiment, where a compound of formula (I) or a pharmaceutically acceptable salt and/or solvate thereof is for the treatment or prevention of cancer, the compound of formula (I) or a pharmaceutically acceptable salt and/or solvate thereof may be utilized in combination with one or more further therapeutic agent(s), either concurrently or sequentially, for the treatment or prevention of cancer. More suitably, where a compound of formula (I) or a pharmaceutically acceptable salt and/or solvate thereof is for the treatment of cancer, the compound of formula (I) or a pharmaceutically acceptable salt and/or solvate thereof may be utilized in combination with one or more further therapeutic agent(s), either concurrently or sequentially, for the treatment of cancer.

Such conjoint treatment may be achieved by way of the simultaneous, sequential or separate dosing of the compound of formula (I) or a pharmaceutically acceptable salt and/or solvate thereof, and the one or more other therapeutic agents of the treatment. Such combination products may employ the NMT inhibitors of this invention within any suitable dosage range, such as, for example, the dosage range described hereinabove, and the other pharmaceutically-active agent may be within its approved dosage range Suitable, but non-limiting, examples of other therapeutic agents which may be administered in combination with the NMT inhibitor include one or more other chemotherapeutic agents.

In one embodiment, where the compound of formula (I) or a pharmaceutically acceptable salt and/or solvate thereof is for the treatment or prevention of rhinovirus (HRV, also known as the common cold), the compound of formula (I) or a pharmaceutically acceptable salt and/or solvate thereof may be utilized in combination with one or more further therapeutic agent(s), either concurrently or sequentially, for the treatment or prevention of HRV and/or for the treatment or prevention of asthma and/or for the treatment or prevention of chronic obstructive pulmonary disease (COPD). For example, the further therapeutic agent(s) may be selected from the group consisting of: pleconaril, pirodavir, vapendavir BTA-798, V-073, rupintrivir, enviroxime, IFN-β (SNG001); corticosteroids (inhaled and oral, for example beclomethasone, fluticasone, budesonide, ciclesonide), beta agonists (for example salbutamol, levosalbutamol, terbutaline, pirbuterol, procaterol, clenbuterol, metaproterenol, fenoterol, bitolterol mesylate, ritodrine, isoprenaline, salmeterol, formoterol, bambuterol, clenbuterol, olodaterol and indacaterol) muscarinic antagonists (for example ipratropium and diphenhydramine), leukotriene receptor antagonists (for example montelukast, zafirlukast, zileuton), cromylins, PDE4 inhibitors (for example ibudilast), and anti-cytokine antibodies, such as anti-IgE (for example omalizumab), anti-IL5 (for example mepolizumab, reslizumab and benralizumab) anti-IL4 (for example dupilumab and pitrakinra).

ADCs of the Invention

Payloads

The compounds of formula (I) are expected to be useful as payloads for an antibody drug conjugate (ADC). A payload is a drug which is tethered to an antibody in an ADC and is released at the site of action (targeted by the antibody, typically a cancerous cell e.g. a tumour cell expressing an antigen to which the antibody may bind) after administration, for example as described in Coats et al., Clin Cancer Res 2019; 25:5441-8. For example, the cancerous cell may express HER2 and the antibody may be trastuzumab or the cancerous cell may express CD20 and the antibody may be rituximab. Alternatively, the cancerous cell may express CD276/B7-H3 and the antibody may be ifinatamab. Alternatively, the cancerous cell may express Trop-2 and the antibody may be sacituzumab.

In one embodiment, the antibody binds to HER2. In one embodiment, the antibody is trastuzumab, pertuzumab, margetuximab, ertumaxomab, MM-111, HER2Bi-aATCs, MCLA-128, ZW25, MDX-210 ado-trastuzumab and fam-trastuzumab. Suitably, the antibody is trastuzumab. In one embodiment, the antibody is an antibody that has the 6 CODRs of trastuzumab. Trastuzumab comprises the heavy chain of SEQ ID NO: 2 and light chain of SEQ ID NO: 1.

In one embodiment, the antibody binds to 0020. Suitably, the antibody is rituximab. In one embodiment, the antibody is an antibody that has the 6 CORs of rituximab. Rituximab comprises the heavy chain of SEQ ID NO: 4 and light chain of SEQ ID NO: 3.

In one embodiment, the antibody binds to Trop-2. An ADC comprising said antibody may be for use in the treatment of Metastatic triple-negative breast cancer and metastatic urothelial cancer. In this embodiment, suitably the antibody is sacituzumab. In one embodiment, the cancer expresses Trop-2. Sacituzumab comprises the heavy chain of SEQ ID NO: 8 and light chain of SEQ ID NO: 7.

In one embodiment, the antibody binds to CD276 (B7-H3). An ADC comprising said antibody may be for use in the treatment of prostate cancer. In this embodiment, suitably the antibody is ifinatamab. In one embodiment, the cancer expresses CD276 (B7-H3). Ifinatamab comprises the heavy chain of SEQ ID NO: 6 and light chain of SEQ ID NO: 5.

Means of tethering drugs to antibodies in ADCs are described e.g. in WO2007/011968, WO2015/057699, WO2015/095755, WO20108/031690, WO2018/075600, WO2018/160683, WO2018/175994, WO2018/201087 and WO2019/923654, each of which documents is incorporated by reference herein.

The antibody may for example be tethered to a payload, such as the compounds of formula (I) via a linker (a bifunctional group which is capable of forming covalent bonds with the antibody and the compounds of formula (I) e.g. a glucuronide linker as described in WO2007/011968.

In order for the antibody to be tethered to the compounds of formula (I) via a linker, the antibody has a functional group that can form a bond with a functional group of the linker e.g. a functional group of an amino side chain of the antibody. Useful functional groups that can be present on the antibody, either naturally or via chemical manipulation include, but are not limited to, sulfhydryl (—SH), amino, hydroxyl, carboxy, the anomeric hydroxyl group of a carbohydrate, and carboxyl. In some embodiments, the antibody functional groups are sulfhydryl and/or amino, especially sulfhydryl. Sulfhydryl groups can be generated by reduction of an intramolecular disulfide bond of an antibody. Sulfhydryl groups also can be generated by reaction of an amino group of a lysine moiety of an antibody using 2-iminothiolane (Traut's reagent) or another sulfhydryl generating reagent.

In one embodiment, the linker forms a bond with a sulfur atom of an antibody. The sulfur atom can be derived from a sulfhydryl group of an antibody.

The linker may be tethered to a compound of formula (I) by forming a covalent bond to a functional group of the compound of formula (I). For example, the linker may comprise a carbonyl group which may form a covalent bond to an amino functional group of a compound of formula (I), for example, group $NR^5R^6$. When the linker forms a covalent bond to a compound of formula (I), such as between a carbonyl group in the linker and an amino functional group in the compounds of formula (I), the compound of formula (I) must have a suitable functional group for reaction with a suitable functional group on the linker to form a covalent bond. For example, an amino group in the compounds of formula (I) must have an available hydrogen atom (for example, $R^5$ or $R^6$ is H), in order to permit reaction with the corresponding functional group (e.g. carbonyl group) of the linker i.e. the amino group in the compounds of formula (I) cannot be tertiary.

The linker may be bound to the compound of formula (I) via a cleavable linkage (e.g. a carbamate derived from the nitrogen atom bearing the $R^5$ and $R^6$ groups and a carboxylic acid group on the linker), which when cleaved provides a compound of formula (I) in which $R^5$ is H.

The drug loading (referred to as variable "p") is the average number of NMT inhibitors per antibody. Where the compounds of the invention are bound to cysteine residues, drug loading may range from 1 to 10 NMT inhibitors per antibody, i.e. where 1, 2, 3, 4, 5, 6, 7, 8, 9 or 10 NMT inhibitors are covalently attached to the antibody. Compositions of conjugates include collections of antibodies, conjugated with a range of NMT inhibitors from 1 to 10. Suitably p is between 1 to 10, for example p is between 2 and 6, 4 and 6, 8 and 10, or 6 and 8. Most suitably, p is around e.g. is 5.

Therefore, in one embodiment the invention provides the use of a compound of formula (I), or a salt and/or solvate thereof as a payload for an antibody drug conjugate. In one embodiment the invention provides an antibody drug conjugate comprising as payload a compound of formula (I), or a salt and/or solvate thereof. In one embodiment, the antibody drug conjugate or a salt thereof further comprises a linker.

In one embodiment, the linker has the formula (LI):

(LI)

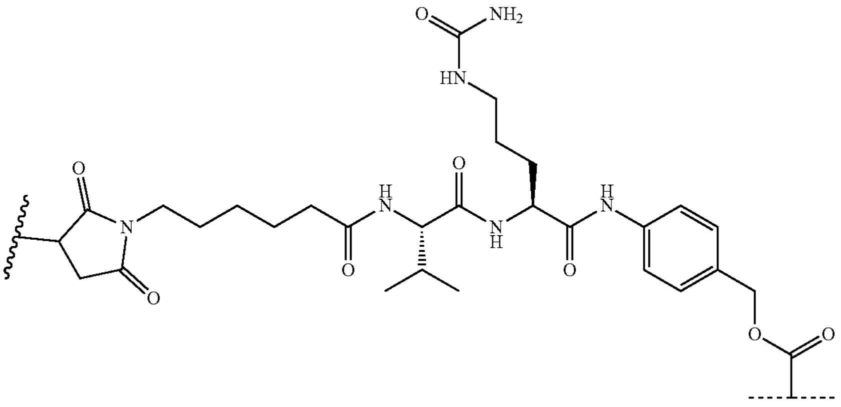

wherein denotes the point of attachment to a chain terminus (such as a N-terminus) or a functional group on an amino acid side chain of the antibody; and denotes the point of attachment to a functional group of the compound of formula (I).

In one embodiment, the linker has the formula (LII):

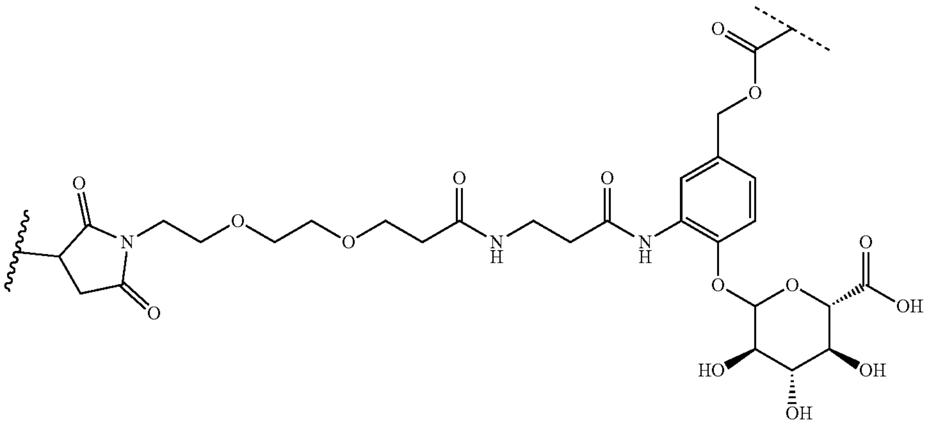

wherein denotes the point of attachment to a chain terminus (such as a N-terminus) or a functional group on an amino acid side chain of the antibody; and denotes the point of attachment to a functional group of the compound of formula (I).

In one embodiment, the linker has the formula (LIII):

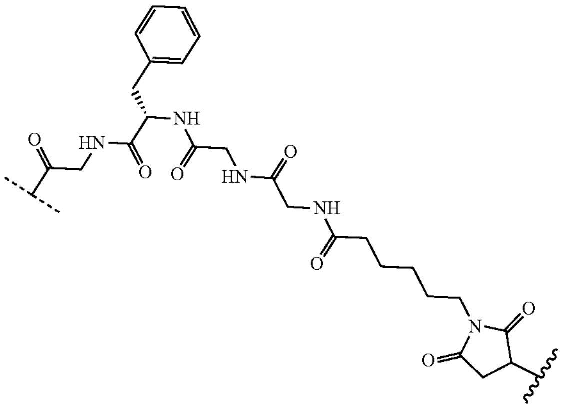

wherein  denotes the point of attachment to a chain terminus (such as a N-terminus) or a functional group on an amino acid side chain of the antibody; and

 denotes the point of attachment to a functional group of the NMT inhibitor.

In one embodiment, the linker has the formula (LIV):

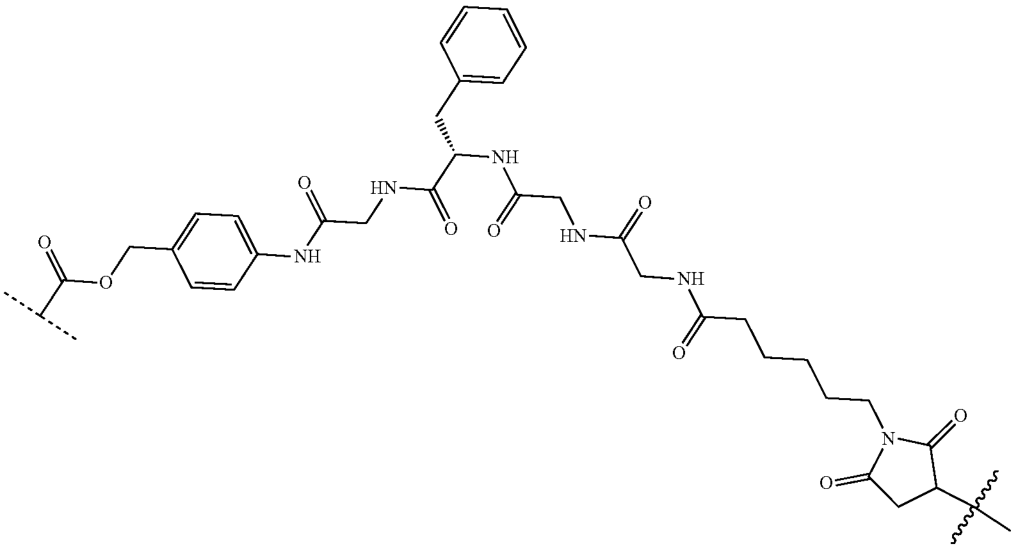

wherein  denotes the point of attachment to a chain terminus (such as a N-terminus) or a functional group on an amino acid side chain of the antibody; and

 denotes the point of attachment to a functional group of the NMT inhibitor.

The ADCs of the invention may be prepared using a drug conjugate or salt and/or solvate thereof which is later covalently bonded to the antibody. Therefore, in one embodiment there is provided a drug conjugate or a salt and/or solvate thereof, which comprises a group capable of forming a covalent bond to a chain terminus (such as a N-terminus) or a functional group on an amino acid side chain of an antibody e.g. a sulfhydryl group.

In one embodiment the drug conjugate has the formula (DC-1):

(DC-1)

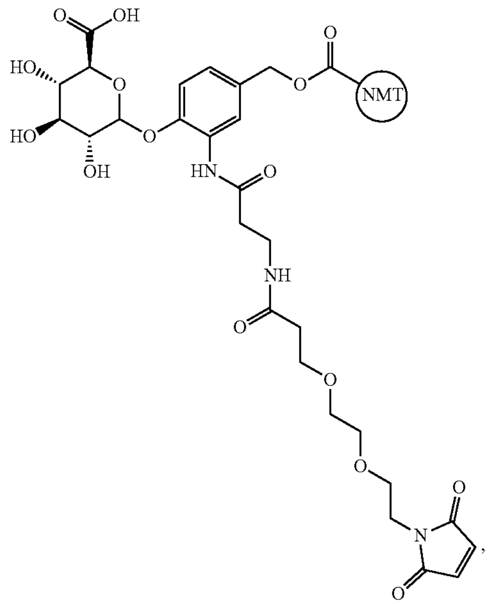

or a salt and/or solvate thereof, wherein

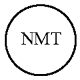

is a compound of formula (I) or a salt and/or solvate thereof.

In one embodiment, the drug conjugate is a compound of formula (DC-2):

(DC-2)

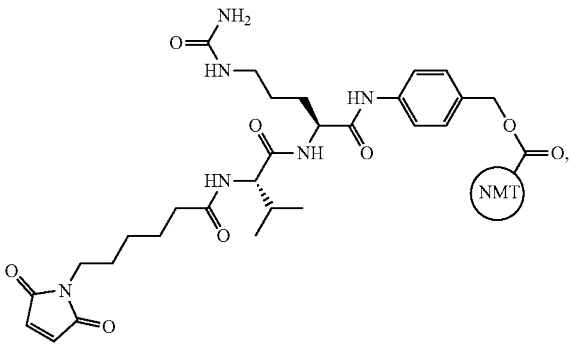

or a salt and/or solvate thereof, wherein

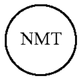

is a compound of formula (I) or a salt and/or solvate thereof.

In one embodiment, the drug conjugate is a compound of formula (DC-3):

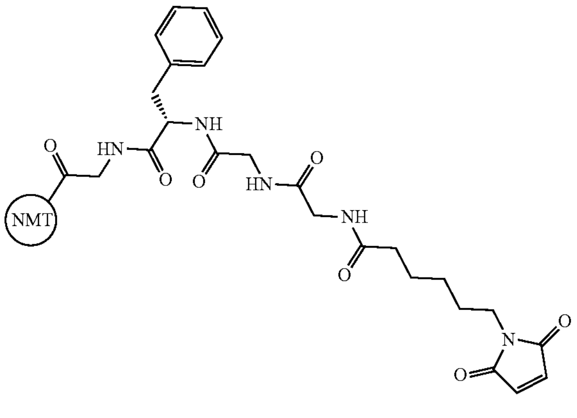

or a salt and/or solvate thereof, wherein

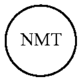

is a compound of formula (I) or a salt and/or solvate thereof.

In one embodiment, the drug conjugate is a compound of formula (DC-4):

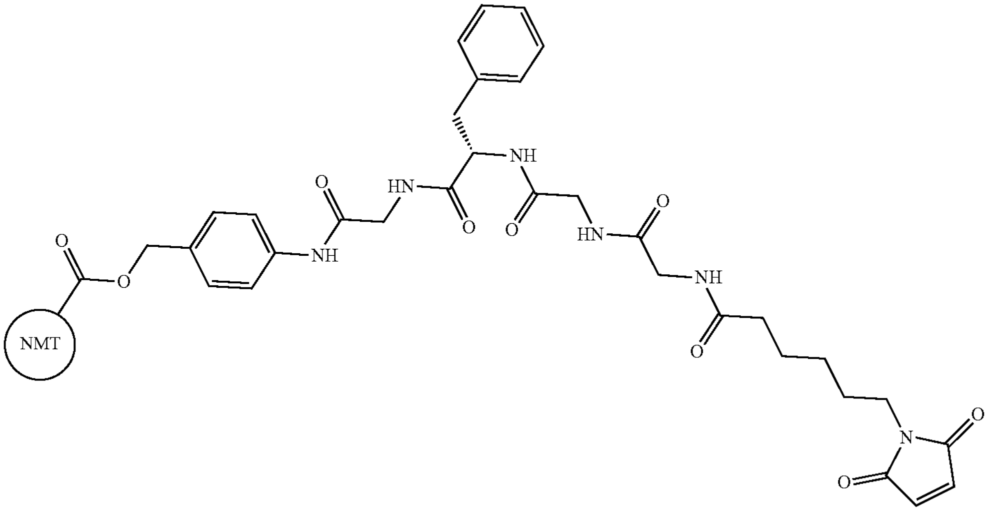 [SMILES: CC(=O)OCc1ccc(NC(=O)CNC(=O)[C@H](Cc2ccccc2)NC(=O)CNC(=O)CNC(=O)CCCCCN2C(=O)C=CC2=O)cc1]

or a salt and/or solvate thereof, wherein

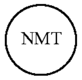

is a compound of formula (I) or a salt and/or solvate thereof.

The phrase "

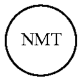

is a compound of formula (I)" as used herein would be understood by the skilled person to be the moiety which remains after an NMT inhibitor, such as an NMT inhibitor comprising a suitable functional group for attachment to a linker, such as an amino group (which comprises a hydrogen atom) or an alcohol (—OH), reacts with a suitable functional group on the linker, for example a carbonyl group, thus forming the linker-compound of formula (I) covalent bond.

Suitably, the drug conjugate is (1S,2R,3S,4R,5R)-5-(4-{[({[6-(3,4-difluoro-2-{2-[3-(1-hydroxy-2,2-dimethylpropyl)-1,5-dimethyl-1H-pyrazol-4-yl]ethoxy}phenyl)imidazo[1,2-a]pyridin-3yl]methyl}(methyl)carbamoyl)oxy]methyl}-2-[3-(3-{2-[2-(2,5-dioxo-2,5-dihydro-1H-pyrrol-1-yl)ethoxy]ethoxy}propanamido)propanamido]phenoxy)-3,4-dihydroxy-2-methylcyclohexane-1-carboxylic acid:

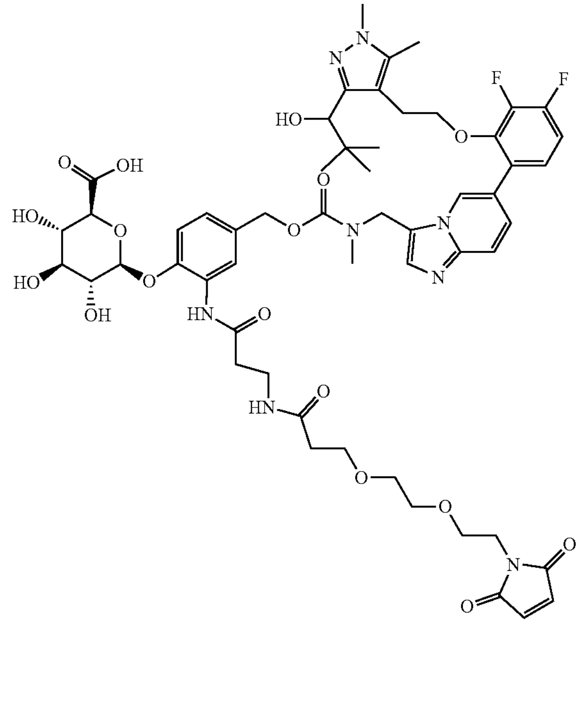 [SMILES: Cc1c(CCOc2c(-c3ccc4ncc(CN(C)C(=O)OCc5ccc(O[C@@H]6O[C@H](C(=O)O)[C@@H](O)[C@H](O)[C@H]6O)c(NC(=O)CCNC(=O)CCOCCOCCN6C(=O)C=CC6=O)c5)n4c3)ccc(F)c2F)c(C(O)C(C)(C)C)nn1C]

or a salt and/or solvate thereof.

In one embodiment, the ADC of the invention comprises the following formula:

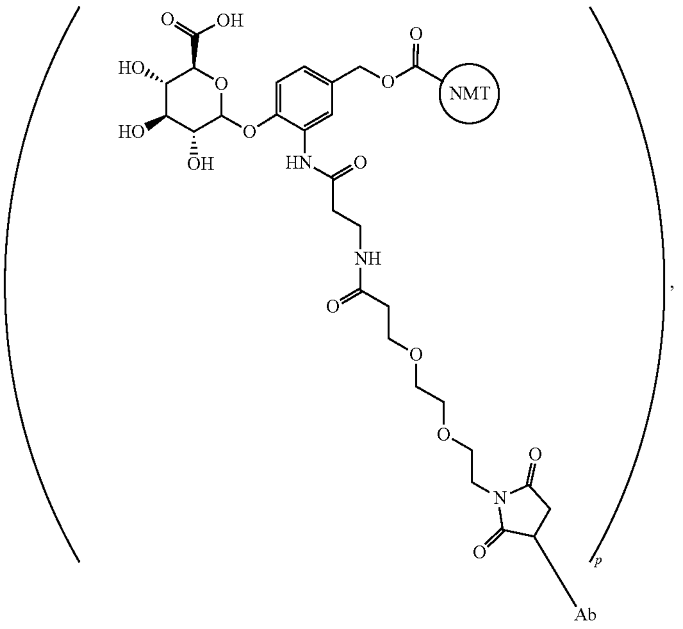

wherein Ab is an antibody as defined herein and

represents an NMT inhibitor such as a compound of formula (I) or a pharmaceutically acceptable salt thereof. Suitably, the ADC of the invention, or a salt thereof is bound to the antibody via a sulfhydryl group on the side chain of a cysteine amino acid on the antibody. Suitably, the antibody is trastuzumab or rituximab, especially trastuzumab. Alternatively, the antibody is sacituzumab. Alternatively, the antibody is ifinatamab. Suitably p is between 1 to 10, for example p is between 2 and 6, 4 and 6, 8 and 10, or 6 and 8. Most suitably, p is around e.g. is 5.

In one embodiment, the ADC of the invention comprises the following formula:

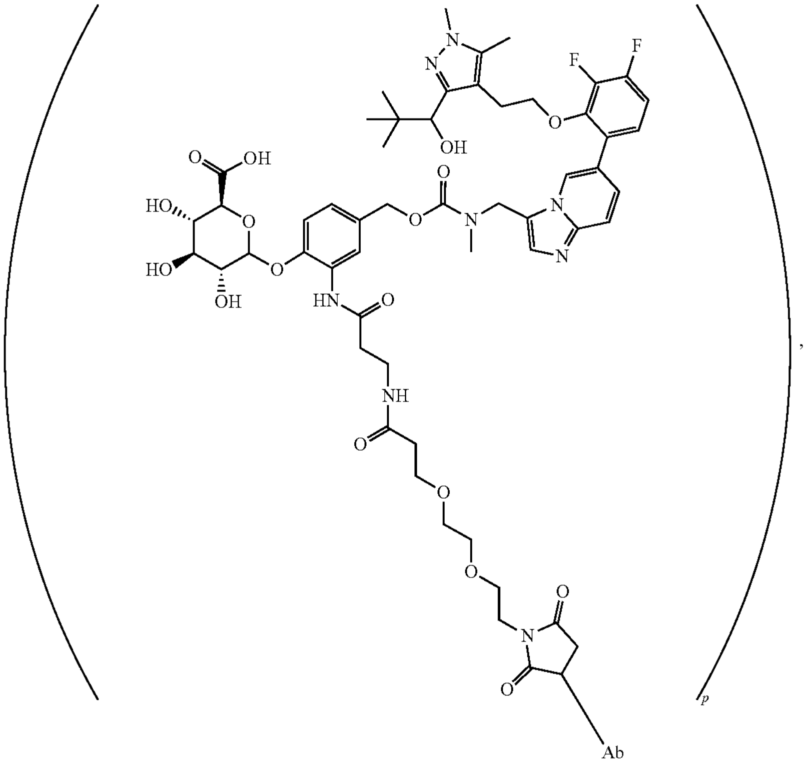

wherein Ab is an antibody as defined herein. Suitably, the ADC of the invention, or a salt thereof is bound to the antibody via a sulfhydryl group on the side chain of a cysteine amino acid on the antibody. Suitably, the antibody is trastuzumab or rituximab, especially trastuzumab. Alternatively, the antibody is sacituzumab. Alternatively, the antibody is ifinatamab. Suitably p is between 1 to 10, for example p is between 2 and 6, 4 and 6, 8 and 10, or 6 and 8. Most suitably, p is around e.g. is 5.

Doses and Formulations

The amount of active ingredient which is required to achieve a therapeutic effect will, of course, vary with the particular compound, the route of administration, the subject under treatment or prophylaxis, including the type, species, age, weight, sex, and medical condition of the subject and the renal and hepatic function of the subject, and the particular disorder or disease being treated or prevented, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, suitably 0.01 mg per kg of body weight per day (mg/kg/day) to 10 mg/kg/day, and most suitably 0.1 to 5.0 mg/kg/day, for adult humans. For oral administration, the compositions are suitably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated.

A medicament typically contains from about 0.01 mg to about 500 mg of the active ingredient, suitably from about 1 mg to about 100 mg of active ingredient. Intravenously, the most suitable doses will range from about 0.1 to about 10 mg/kg/minute during a constant rate infusion.

Advantageously, compounds of formula (I), or pharmaceutically acceptable salts and/or solvates thereof may be administered in a single daily dose, or the total daily dosage may be administered in divided doses of two, three or four times daily. Furthermore, suitably compounds of formula (I), or pharmaceutically acceptable salts and/or solvates thereof can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The dose provided to a subject will typically be a safe and effective dose, i.e. an amount providing an acceptable balance of desired benefits and undesired side effects. A “safe and effective amount” is intended to include an amount of a compound that is effective to achieve a desirable effect in treatment and/or prophylaxis of a disease-state. A desirable effect is typically clinically significant and/or measurable, for instance in the context of (a) preventing the disease-state from occurring in a mammal, in particular, when such mammal is predisposed to the disease-state but has not yet been diagnosed as having it; (b) inhibiting the disease-state, i.e., slowing or arresting its development; and/or (c) relieving the disease-state, i.e., causing regression of the disease state or a reduction in associated symptoms. The safe and effective amount may be one that is sufficient to achieve the desirable effect either when the compound is administered alone, or alternatively when it is administered in combination with one or more further APIs, which either are further compounds for use of the invention or are different from the compounds for use of the invention.

For avoidance of doubt, a "safe and effective amount" as recited herein can be achieved by any suitable dosage regimen, including but not limited to exemplary dosage regimens described elsewhere herein. Hence, for example, references herein to administering a safe and effective amount of a compound, such as by a particular administration route, include achieving the safe and effective amount via a single dose or by plural doses, such as administered by the specified administration route. For instance, orally administering a safe and effective amount includes both orally administering a single dose and orally administering any plural number of doses, provided that a safe and effective amount is thereby achieved by oral administration.

While it is possible for the active ingredient to be administered alone, it is preferable for it to be present in a pharmaceutical formulation or composition. Accordingly, the invention provides a pharmaceutical formulation or composition comprising a compound according to formula (I) or a pharmaceutically acceptable salt and/or solvate thereof, and a pharmaceutically acceptable diluent, excipient or carrier (collectively referred to herein as "carrier" materials). Pharmaceutical compositions of the invention may take the form of a pharmaceutical formulation as described below.

Therefore, in one embodiment the invention provides a pharmaceutical composition comprising a compound of formula (I), or a pharmaceutically acceptable salt and/or solvate thereof and a pharmaceutically acceptable carrier. The invention also provides a pharmaceutical composition comprising an ADC of the invention or a pharmaceutically acceptable salt thereof and a pharmaceutically acceptable carrier. The following uses of the pharmaceutical composition are equally applicable to a pharmaceutical composition comprising the ADC of the invention or a pharmaceutically acceptable salt thereof.

In one embodiment, there is provided a pharmaceutical composition comprising a compound of formula (I), or a pharmaceutically acceptable salt and/or solvate (e.g. pharmaceutically acceptable salt) thereof, for use in the treatment or prophylaxis of a disease or disorder as described herein. In one embodiment, there is provided a pharmaceutical composition comprising a compound of formula (I), or a pharmaceutically acceptable salt and/or solvate (e.g. pharmaceutically acceptable salt) thereof, for use in the treatment of a disease or disorder as described herein. In one embodiment, there is provided a pharmaceutical composition comprising a compound of formula (I), or a pharmaceutically acceptable salt and/or solvate (e.g. pharmaceutically acceptable salt) thereof, for use in the prophylaxis of a disease or disorder as described herein.

In a further embodiment, there is provided a method for the treatment or prophylaxis of a disease or disorder as described herein, which comprises administering to a subject in need thereof an effective amount of a pharmaceutical composition comprising a compound of formula (I) or a pharmaceutically acceptable salt and/or solvate (e.g. pharmaceutically acceptable salt) thereof. In a further embodiment, there is provided a method for the treatment of a disease or disorder as described herein, which comprises administering to a subject in need thereof an effective amount of a pharmaceutical composition comprising a compound of formula (I) or a pharmaceutically acceptable salt and/or solvate (e.g. pharmaceutically acceptable salt) thereof. In a further embodiment, there is provided a method for the prophylaxis of a disease or disorder as described herein, which comprises administering to a subject in need thereof an effective amount of a pharmaceutical composition comprising a compound of formula (I) or a pharmaceutically acceptable salt and/or solvate (e.g. pharmaceutically acceptable salt) thereof. Pharmaceutical compositions of the invention may take the form of a pharmaceutical formulation as described below.

The invention also provides the use of a pharmaceutical composition comprising a compound of formula (I), or a pharmaceutically acceptable salt and/or solvate thereof (e.g. pharmaceutically acceptable salt) thereof, in the manufacture of a medicament for the treatment or prophylaxis of a disease or disorder as described herein. The invention also provides the use of a pharmaceutical composition comprising a compound of formula (I), or a pharmaceutically acceptable salt and/or solvate thereof (e.g. pharmaceutically acceptable salt) thereof, in the manufacture of a medicament for the treatment of a disease or disorder as described herein. The invention also provides the use of a pharmaceutical composition comprising a compound of formula (I), or a pharmaceutically acceptable salt and/or solvate thereof (e.g. pharmaceutically acceptable salt) thereof, in the manufacture of a medicament for the prophylaxis of a disease or disorder as described herein.

The pharmaceutical formulations according to the invention include those suitable for oral, parenteral (including subcutaneous, intradermal, intramuscular, intravenous [bolus or infusion], and intraarticular), intranasal (also known as nasal administration), inhalation (including fine particle dusts or mists which may be generated by means of various types of metered dose pressurized aerosols, nebulizers or insufflators) insufflation, rectal, intraperitoneal and topical (including dermal, buccal, sublingual, and intraocular) administration, although the most suitable route may depend upon, for example, the condition and disorder of the recipient.

Suitable pharmaceutical formulations according to the invention are those suitable for oral and parenteral administration; and more suitably are those suitable for oral administration. Such embodiments are especially suitable for, for example, the treatment or prevention of a hyperproliferative disorder, and in particular a cancer.

In another suitable embodiment a compound according to formula (I) or a pharmaceutically acceptable salt and/or solvate thereof is administered by intranasal, inhalation (including fine particle dusts or mists which may be generated by means of various types of metered dose pressurized aerosols, nebulizers or insufflators) or insufflation administration. Such embodiments are especially suitable for, for example, the treatment or prevention of a picornaviral infection, such as human rhinovirus infection. Such a method of administration allows for low doses of the compound of the invention to be administered, which can lead to a reduction in side-effects. For example, a daily dose of 10 to 0.01 μg, suitably 1 to 0.01 μg, and more suitably in the region of as low as 0.1 μg (100 ng) of compound of the invention may be used.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

The compounds of formula (I) or pharmaceutically acceptable salts and/or solvates thereof can, for example, be administered in a form suitable for immediate release or extended release.

Immediate release or extended release can be achieved by the use of suitable pharmaceutical compositions comprising a compound of formula (I) or pharmaceutically acceptable salts and/or solvates thereof, or, particularly in the case of extended release, by the use of devices such as subcutaneous implants or osmotic pumps. The compounds of formula (I), or pharmaceutically acceptable salts and/or solvates thereof may also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, poly-ethylene glycol, waxes and the like. Disintegrators include without limitation starch, methylcellulose, agar, bentonite, xanthan gum and the like. The compounds of formula (I), or pharmaceutically acceptable salts and/or solvates thereof can also be delivered through the oral cavity by sublingual and/or buccal administration. Molded tablets, compressed tablets or freeze-dried tablets are exemplary forms which may be used. Exemplary compositions include those formulating a compound of the present invention with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

The compounds of formula (I), or pharmaceutically acceptable salts and/or solvates thereof can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), or phosphatidylcholine (lecithin).

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for intranasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Suitable unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of formula (I) or pharmaceutically acceptable salts and/or solvates thereof are expected to display one of more of the following advantageous properties:

- inhibition of human NMT e.g. as demonstrated in the HsNMT1 sensitive fluorescence-base assay of Biological Example 1;
- cytotoxic activity e.g. as demonstrated in the cell line assay of Biological Examples 2 and 3;
- in vivo cytotoxic activity e.g. as demonstrated in the mouse xenograft model of Biological Example 4.

The compounds of formula (I) or pharmaceutically acceptable salts and/or solvates thereof may also display one or more of the following advantageous properties:

- cellular permeability e.g. as demonstrated in the Caco-2 cell permeability assay of Biological Example 5;
- relatively low metabolic stability which is desirable for certain therapeutic applications (e.g. as a payload for an antibody drug conjugate) as demonstrated in the mouse and rat hepatocyte assay of Biological Example 6 and the in vivo mouse xenograft study of Biological Example 7.

The ADCs or pharmaceutically acceptable salts and/or solvates thereof may also display one or more of the following advantageous properties:

- in vivo cytotoxic activity e.g. as demonstrated in the mouse xenograft model of Biological Examples 7, 8, 9, 10 and 11; and
- in vivo tolerability e.g. as demonstrated in the mouse xenograft model of Biological Examples 7, 8, 9, 10 and 11.

Said properties are expected to make the compounds of formula (I) or pharmaceutically acceptable salts and/or solvates thereof or the ADCs of the invention or pharmaceutically acceptable salts thereof suitable for use in the treatment or prevention (e.g. treatment) of hyperproliferative disorders such as cancer or other disease or disorder in which inhibition of human NMT provides a therapeutic or prophylactic effect.

| Abbreviations | |
|---|---|
| ALT | alanine transaminase |
| AST | aspartate transaminase |
| ALP | alkaline phosphatase |
| GGT | gamma-glutamyl transferase |
| CK | creatine kinase |
| LDH | lactate dehydrogenase |
| TP | total protein |
| ALB | Albumin |
| GLO | Globulin |
| A/G | Albumin/Globulin ratio |
| TBIL | total bilirubin |
| BU | blood urea nitrogen |
| CRE | creatinine |
| BUN/C | Blood urea nitrogen/creatinine |
| GLU | Glucose |
| CHO | cholesterol |
| TG | triglycerides |
| Na | sodium |
| K | potassium |
| Cl | chloride |
| Ca | calcium |
| P | phosphate |
| WBC | white blood cells |
| ABNEUT | neutrophils |
| ABLYMP | lymphocytes |
| ABMONO | monocytes |
| ABBASO | basophils |
| ABEOS | eosinophils |
| PLT | platelets |
| MPV | mean platelet volume |
| RBC | red blood cell |
| HCT | haematocrit |
| HGB | haemoglobin |
| MCV | mean corpuscular volume |

-continued

| Abbreviations | |
|---|---|
| MCH | mean corpuscular hemoglobin |
| MCHC | Mean Corpuscular Haemoglobin Concentration |
| ABRETIC | reticulocytes |
| QW | once a week |

EXAMPLES

Synthesis of Example Compounds

General Experimental Details

LCMS Method Formic acid buffer 3 min run

Column—YMC Triart C18 (33×2.1 mm, 3 u), (mobile phase: 98% [0.05% HCOOH in water] and 2% [0.05% HCOOH in can:Water (90:10)] held for 0.75 min, then to 90% [0.05% HCOOH in water] and 10% [0.05% HCOOH canACN:Water (90:10)] in 1.0 min, further to 2% [0.05% HCOOH in water] and 98% [0.05% HCOcanin ACN:Water (90:10)] in 2.0 min, held this mobile phase composition up to 2.25 min and finally back to initial condition in 3.0 min). Flow=1.0 ml/min.

LCMS Method Ammonium acetate buffer 3 min run

Column—Xbridge C18 (50×3.0 mm, 3.5 u), (mobile phase: 95% [5 mM NH4Oac in water] and 5% [5 mM NcanAc in ACN:water 90:10] held for 0.75 min, then to 70% [5 mM NH4Oac in water] and 30% [5mcanH4Oac in ACN:water 90:10] in 1.00 min, further to 2% [5 mM NH4Oac in water] and 98% canM NH4Oac in ACN:water 90:10] in 2.0 min, held this mobile phase up to 2.25 min back to initial condition in 2.75 min, held this mobile phase up to 3.0 min). Flow=1.2 ml/min.

LCMS Method Ammonium acetate buffer 5 min run

Column—Xbridge C18 (50×3.0 mm, 3.5 u), (mobile phase: 95% [5 mM NH4Oac in water] and 5% [5 mM NH4Oac in ACN:water 90:10] held for 0.75 min, then to 85% [5 mM NH4Oac in water] and 15% [5 mM NH4Oac in ACN:water 90:10] in 1.25 min, further to 30% [5 mM NH4Oac in water] and 70% [5 mM NH4Oac in ACN:water 90:10] in 2.5 min, again 2% [0.05% HCOOH in water] and 98% [5 mM NH4Oac in ACN:water 90:10] in 3.75 min held this mobile phase composition up to 4.25 min and finally back to initial condition in 4.50 min and held the initial condition up to 5.10 min). Flow=1.2 ml/min.

HPLC

The purity of certain Examples was determined by TyeEclipse Extend or XDB 5 μm C18 (150×4.6 mm), Xbridge 5 μm C18 (100×4.6 mm), Zorbax Extend 5 μm C18 (150×4.6 mm), or Shimadzu L Column 2 ODS 5 μm C18 (150×4.6 mm) column using gradient elution of acetonitrile in water containing 10 mM ammonium acetate over 15 mins (HPLC B) 17 mins (B1) and 18 mins (B3).

The purity of certain Examples was determined by analytical HPLC using a Poroshell 120 2.7 μm EC18 (100×4.6 mm), Luna Omega Polar 3 μm C18 (100×4.6 mm), Xbridge 5 μm C18 (150×4.6 mm) or Sunfire 5 μm C18 (100×4.6 mm) using gradient elution of acetonitrile in water containing 0.05% trifluoroacetic acid over 12 mins (HPLC A), 14 mins (A1) or 17 mins (A2) and 16 mins (A4).

The purity of certain Examples was determined by analytical HPLC using a Gemini NX 3 μm $C_{18}$ (100×4.6 mm) column using gradient elution of acetonitrile in water containing 0.05% formic acid over 16 mins (A6).

NMR

$^1$H NMR and $^{13}$C spectra were recorded on 400 MHz and 101 MHz respectively instruments at room temperature unless specified otherwise were referenced to residual solvent signals. Data are presented as follows: chemical shift in ppm, integration, multiplicity (br=broad, s=singlet, d=doublet, t=triplet, q=quartet, p=pentet, m=multiplet) and coupling constants in Hz.

ADC Testing Methods

SEC-HPLC

Column: TOSOH TSKgel G3000SWXL 7.8 mm×30 cm 5 μm particle (MERCK808541) combined with a security guard column (MERCK 822858) with a GFC3000 4×3 mm cartridge (Phenomenex); Buffer: 0.2M Phosphate 0.25M KCl 10% IPA; Gradient: Isocratic @0.5 ml/min at 25° C. Sample load was approximately 10 μg with monomer and concentration determined from 214 nm signal. Monomer reported based on peak integration and [ADC] mg/mL based on a calibration curve of antibody.

RP-HPLC for residual NMT inhibitor

Column: Kinetex® 2.6 μm C8 100 Å, LC Column 50×4.6 mm, (Phenomex 00B-4497-EO); Mobile Phase A 0.05% TFA in water; Mobile Phase B 0.05% TFA in CAN; Gradient at 60° C. at 2 ml/min:

| TIME | % B |
|---|---|
| 0.00 | 5 |
| 8.00 | 95 |
| 8.10 | 100 |
| 9.00 | 100 |
| 9.10 | 5 |
| 10.00 | 5 |

50 μl sample (ADC or PBS/PS20 matrix)+2 μl 5M NaCl+150 μl cold MeOH (from −20 C freezer). Incubate at −20° C. for 30 minutes. Centrifuge at 21,000 g at 4° C. for 30 minutes. 125 μl of supernatant was extracted and mixed with 125 μl WFI. 100 μl of this was injected onto the Kinetex column. Data was analysed at 214 nm and the residual NMT inhibitor in the sample estimated from an external calibration curve of the relevant NMT inhibitor-linker. The result is expressed as the percentage free relative to free and bound using the ADC concentration and calculated DAR to determine the amount of bound NMT inhibitor.

HIC-HPLC for Average DAR (drug antibody ratio) calculations

This method can be used as an alternative to PLRP-HPLC methods for determining average DAR.

Column: TOSOH Butyl-NPR 4.6 mm×3.5 cm, 2.5 μm particle size (Merck 822855); Mobile phase A: 1.5 M (NH4)2SO4, 25 mM NaPi, pH 6.95±0.05; Mobile phase B: 25 mM NaH2PO4 pH 6.95±0.05±25% IPA; Gradient at 25° C. 0.8 ml/min:

| Time | % B |
|---|---|
| 0 | 0 |
| 12 | 100 |
| 12.1 | 0 |
| 18 | 0 |

Load cartridge. 10 μg and report result/analysed at 214 nm.

RP-HPLC for Average DAR Calculations

Column—PLRP-S 2.1 mm×5 cm, 5 μm (Agilent PL1912-1502); Mobile Phase A: 0.1% TFA in Water; Mobile Phase B: 0.1% TFA in Acetonitrile; Gradient at 80° C., 1 mL/min:

| Time | % B |
|---|---|
| 0 | 22.5 |
| 2 | 22.5 |
| 21.5 | 49.5 |
| 22.5 | 90.0 |
| 26.5 | 90.0 |
| 27.5 | 22.5 |
| 32.0 | 22.5 |

~10 ug of sample (ADC)+5 μl 0.1M DTT made up to 50 μL with 0.5M Tris, pH 8.0 incubated at 37° C. for 15 minutes. Sample then diluted 1:1 (+50 μL) with 49% Water, 49% Acetonitrile, 2% Formic Acid. 20 μL of this solution then injected onto the RP-HPLC column. Data was analysed at 214 nm and average DAR calculated.

Endotoxin Kinetic Chromogenic Assay

Endotoxin was determined by kinetic chromogenic LAL assay using an Endosafe PTS endotoxin system. The ADCs were diluted 10-fold in LAL reagent water. All samples were analysed on 0.01-1 EU/mL cartridges. The EU/mL value was converted to EU/mg by dividing by the ADC [P] mg/mL.

Preparation of Comparator Compound 1

Comparator Compound 1 is the compound 4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide:

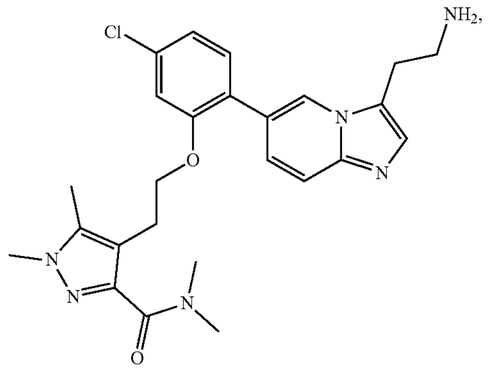 [SMILES: Cc1c(CCOc2cc(Cl)ccc2-c2ccc3ncc(CCN)n3c2)c(C(=O)N(C)C)nn1C]

and was prepared according to the methods described in WO2020/128473.

Preparation of Example Compounds 1 to 25

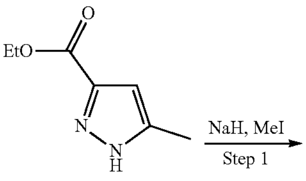

1

-continued

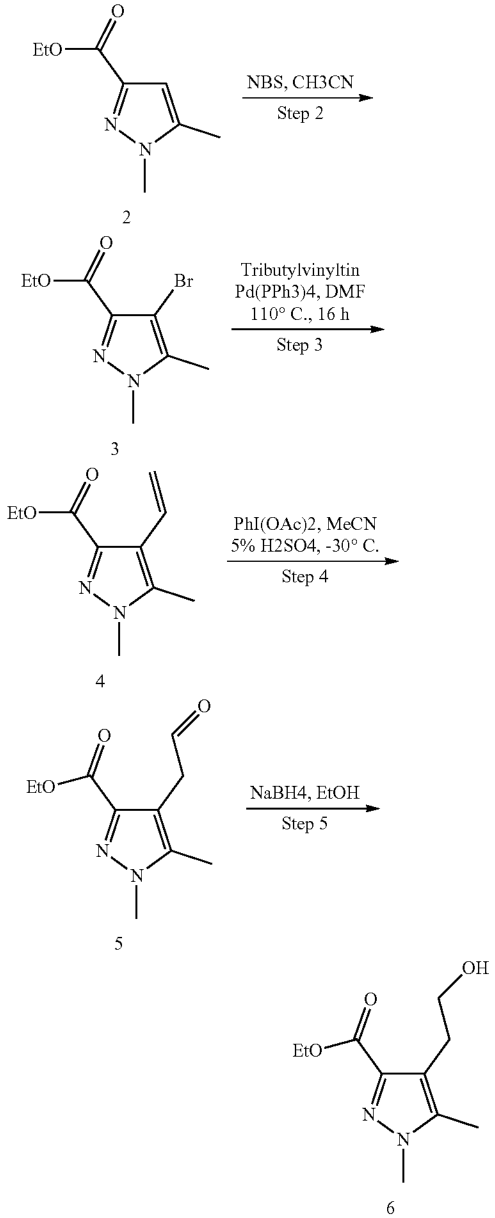

2

3

4

5

6

Step 1—Intermediate (2): 1,5-dimethyl-1H-pyrazole-3-carboxylic acid ethyl ester

Procedure: To a stirred solution of sodium hydride (60% in mineral oil, 31.17 g, 779.221 mmol) in THF (700 ml) at 0° C., was added a solution of 5-methyl-1H-pyrazole-3-carboxylic acid ethyl ester (100 g, 649.351 mmol) in THF (300 ml) slowly. The reaction mixture was stirred at 0° C. for 30 min. Then methyl iodide (48.19 ml, 779.221 mmol) was added drop wise at 0° C. and the reaction mixture was stirred at RT for 2 h. TLC showed formation of the product with complete consumption of starting material. The reaction mixture was diluted with water and extracted with ethyl acetate. Organic layer was washed with water and brine, dried over sodium sulphate and concentrated under reduced pressure to afford 1,5-dimethyl-1H-pyrazole-3-carboxylic acid ethyl ester (2) (109 g, 99.8%) as brown gum. LC-MS $MH^+$ 169, FA:ACN, $R_t$=1.35 min, 3 min run; $^1$H NMR (400 MHz, CDCl3) δ 6.52 (s, 1H), 4.34 (q, 2H), 3.81 (s, 3H), 2.26 (s, 3H), 1.34 (t, 3H).

Step 2—Intermediate (3): 4-bromo-1,5-dimethyl-1H-pyrazole-3-carboxylic acid ethyl ester Procedure: To a stirred solution of 1,5-Dimethyl-1H-pyrazole-3-carboxylic acid ethyl ester (intermediate (2)) (109 g, 648.81 mmol) in acetonitrile (990 ml) was added N-bromosuccinimide (120.58 g, 681.25 mmol) portion wise at 0° C. The resulting mixture was stirred at RT for 16 h. TLC showed formation of the product with complete consumption of starting material. The solvent was evaporated, diluted with water and extracted with ethyl acetate. Organic layer was washed with water and brine, dried over sodium sulphate and concentrated under reduced pressure. Crude compound was purified by column chromatography (silica gel, 100-200 mesh) eluted with 20% ethyl acetate and hexane to afford 4-bromo-1,5-dimethyl-1H-pyrazole-3-carboxylic acid ethyl ester (3) (140 g, 87.33%) as brown solid. LC-MS $MH^+$ 247 & 249, NH4Oac:ACN, $R_t$=3.32 min, 6 min run; $^1$H NMR (400 MHz, CDCl3) δ 4.37 (q, 2H), 3.85 (s, 3H), 2.26 (s, 3H), 1.36 (t, 3H).

Step 3—Intermediate (4): 1,5-Dimethyl-4-vinyl-1H-pyrazole-3-carboxylic acid ethyl ester Procedure: To a solution of 4-bromo-1,5-dimethyl-1H-pyrazole-3-carboxylic acid ethyl ester (intermediate (3)) (50 g, 202.429 mmol) in DMF (250 ml) was added tributylvinyltin (118.286 ml, 404.858 mmol). The solution was degassed with argon for 20 min and Pd(PPh3)4 (11.69 g, 10.121 mmol) was added under argon. The reaction mixture was stirred at 110° C. for 16 h. TLC showed formation of the product with complete consumption of starting material. The reaction mixture was cooled to RT, quenched with water and extracted with ethyl acetate. Organic layer was washed with saturated KF solution, precipitate was filtered through a celite pad and filtrate was washed with water and finally with brine. Organic layer was dried over anhydrous sodium sulphate, filtered and evaporated under vacuum. The crude product was purified by column chromatography (silica gel, 100-200 mesh) eluted with 20%-30% ethyl acetate and hexane to afford of 1,5-dimethyl-4-vinyl-1H-pyrazole-3-carboxylic acid ethyl ester (4) (30 g, 76.3%) as brown gum. LC-MS MH+ 195, FA:ACN, $R_t$=1.59 min, 3 min run; $^1$H NMR (400 MHz, CDCl3) δ 6.96 (dd, 1H), 5.39 (d, 1H), 5.27 (d, 1H), 4.24 (q, 2H), 3.81 (s, 3H), 2.33 (s, 3H), 1.26 (t, 3H).

Step 4—Intermediate (5): 1,5-dimethyl-4-(2-oxo-ethyl)-1H-pyrazole-3-carboxylic acid ethyl ester Procedure: To a stirred solution of 1,5-dimethyl-4-vinyl-1H-pyrazole-3-carboxylic acid ethyl ester (intermediate (4)) (35 g, 180.412 mmol) in acetonitrile (700 ml), was added (diacetoxyiodo)benzene (61 g, 189.433 mmol) at −10° C. Then 5% sulphuric acid (70 ml) was added drop wise and stirred at RT for 1 h. The solvent was evaporated under reduced pressure, diluted with water and extracted with ethyl acetate and finally extracted with 20% MeOH-DCM. Organic layer was dried over anhydrous sodium sulphate, filtered and evaporated the under vacuum to afford of 1,5-dimethyl-4-(2-oxo-ethyl)-1H-pyrazole-3-carboxylic acid ethyl ester (5) (32 g, 84.37%) as brown gum. Crude product was taken to next step without purification. LC-MS $MH^+$ 211, FA:ACN, $R_t$=1.32 min, 3 min run; $^1H$ NMR (400 MHz, CDCl3) δ 9.56 (s, 1H), 4.19 (q, 2H), 3.80 (s, 3H), 3.74 (s, 2H), 2.17 (s, 3H), 1.23 (t, 3H).

Step 5—Intermediate (6): 4-(2-hydroxy-ethyl)-1,5-dimethyl-1H-pyrazole-3-carboxylic acid ethyl ester Procedure: To a stirred solution of 1,5-dimethyl-4-(2-oxo-ethyl)-1H-pyrazole-3-carboxylic acid ethyl ester (intermediate (5)) (25 g, 119.048 mmol) in ethanol (450 ml) at 0° C. was added NaBH4 (9.7 g, 261.905 mmol) portion wise. The reaction mixture was stirred at RT for 1 h.

Then the solvent was evaporated under reduced pressure, diluted with saturated sodium bicarbonate solution, extracted with ethyl acetate, finally with 20% MeOH-DCM. Organic layer was dried over anhydrous sodium sulphate, filtered and evaporated the under vacuum. Crude compound was purified by column chromatography (silica gel, 100-200 mesh) eluted with 80% ethyl acetate and hexane to afford 4-(2-hydroxy-ethyl)-1,5-dimethyl-1H-pyrazole-3-carboxylic acid ethyl ester (6) (13 g, 51.45%) as light brown gum. LC-MS $MH^+$ 213, FA:ACN, $R_t$=1.27 min, 3 min run. $^1H$ NMR (400 MHz, CDCl3) δ 4.50 (t, 1H), 4.21 (q, 2H), 3.75 (s, 3H), 3.42 (q, 2H), 2.73 (t, 2H), 2.18 (s, 3H), 1.25 (t, 3H).

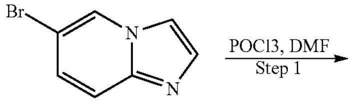

7

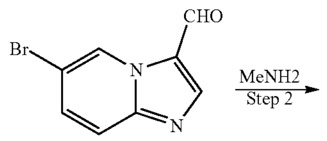

8

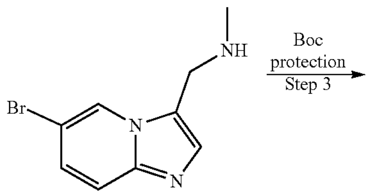

9

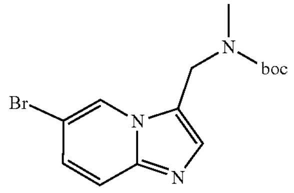

10

Step 1—Intermediate (8): 6-bromoimidazo[1,2-a]pyridine-3-carbaldehyde

Procedure: phosphorous oxychloride (6.102 ml, 65.469 mmol) was added dropwise to dry DMF (50 ml) at 0° C. and stirred for 1 h at that temperature. A solution of 6-bromo-imidazo[1,2-a]pyridine (5 g, 25.376 mmol) in DMF (10 ml) was added at 0° C. The reaction mixture was heated to 100° C. for 5 h and was stirred for 16 h at RT. The reaction mixture was quenched with cold sat sodium bicarbonate solution and extracted with ethyl acetate, washed with water and brine. The organic layer was dried over sodium sulphate and concentrated under reduced pressure to afford 6-bromo-imidazo[1,2-a]pyridine-3-carbaldehyde (8) (3.2 g, 56.04%) as brown solid. $^1H$ NMR (d6-DMSO, 400 MHz) δ 9.95 (s, 1H), 9.49 (s, 1H), 8.54 (s, 1H), 7.89-7.81 (m, 2H).

Step 2—Intermediate (9): 1-(6-bromoimidazo[1,2-a]pyridin-3-yl)-N-methylmethanamine Procedure: To a stirred solution of 6-bromoimidazo[1,2-a]pyridine-3-carbaldehyde (intermediate (8) (4.5 g, 20.089 mmol) in methanol (10 ml) was added methylamine solution (6.15 ml, 60.267 mmol) and stirred at RT for 16 h. To the reaction mixture $NaBH_4$ (1.56 g, 40.179 mmol) was added at 0° C. and stirred for 2 h. The reaction mixture was quenched with sat sodium bicarbonate solution and extracted with DCM, washed with water and brine. The organic layer was dried over sodium sulphate and concentrated under reduced pressure to get crude compound which was purified by column chromatography to afford 1-(6-bromoimidazo[1,2-a]pyridin-3-yl)-N-methylmethanamine (9) (1.6 g, 33.17%). LC-MS $MH^+$ 240, NH4Oac:ACN, $R_t$=1.46 min, 5 min run; $^1H$ NMR (d6-DMSO, 400 MHz) δ 8.69 (s, 1H), 7.54 (d, 1H), 7.50 (s, 1H), 7.36-7.29 (m, 1H), 3.98 (s, 2H), 2.24 (s, 3H).

Step 3—Intermediate (10): tert-butyl ((6-bromoimidazo[1,2-a]pyridin-3-yl)methyl)(methyl)carbamate Procedure: To a stirred solution of 1-(6-bromoimidazo[1,2-a]pyridin-3-yl)-N-methylmethanamine (intermediate (9) (4.9 g, 20.248 mmol) in DCM (50 ml) were added triethylamine (5.644 ml, 40.496 mmol) and Boc anhydride (5.576 ml, 24.298 mmol) at 0° C. and stirred at RT for 16 h. The reaction mixture was diluted with water and extracted with DCM, washed with water and brine. The organic layer was dried over sodium sulphate and concentrated under reduced pressure to get crude compound which was purified by column chromatography to afford tert-butyl ((6-bromoimidazo[1,2-a]pyridin-3-yl)methyl)(methyl)carbamate (10) (5.6 g, 81.29%). LC-MS $MH^+$ 340, NH4Oac:ACN, $R_t$=3.36 min, 5 min run. $^1H$ NMR (d6-DMSO, 400 MHz) δ 8.70 (bs, 1H), 7.62 (s, 1H), 7.59 (d, 1H), 7.38 (d, 1H), 4.75 (s, 2H), 2.67 (s, 3H), 1.46 (s, 9H).

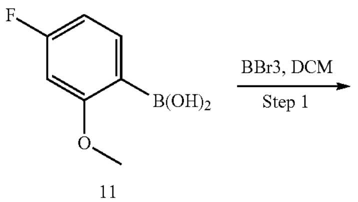

11

-continued

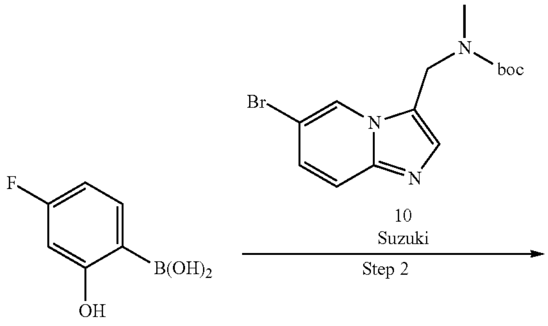

12

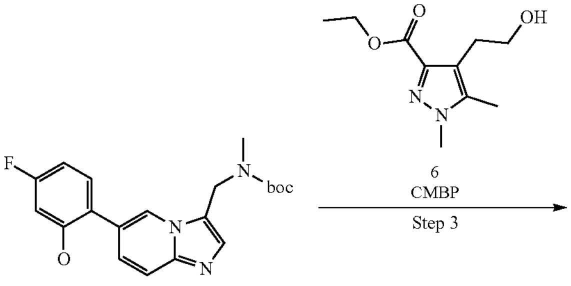

13

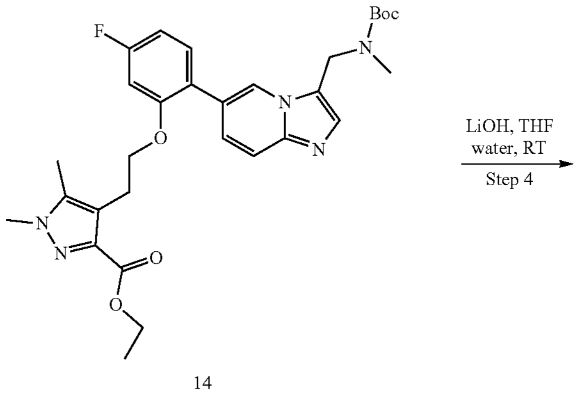

14

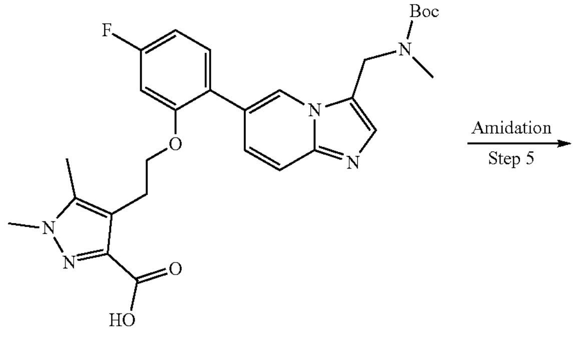

15

-continued

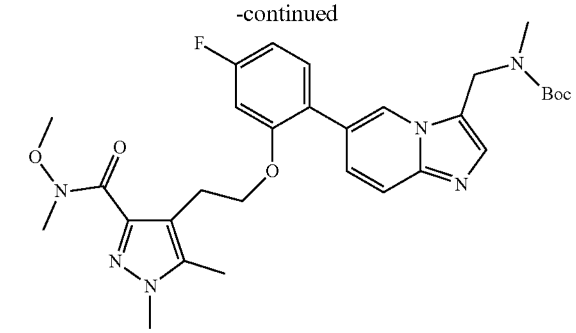

16

Step 1—Intermediate (12): 4-fluoro-2-hydroxyphenyl)boronic acid

Procedure: To a stirred solution of (4-fluoro-2-methoxyphenyl)boronic acid (11.0 g, 64.706 mmol) in dichloromethane (130.0 ml) was added $BBr_3$ (1M DCM) (129.0 ml, 129.41 mmol) at 0° C. Reaction mixture was stirred at RT for 1 h. After complete consumption of starting material reaction mixture was cooled to 0° C. and quenched with ice water. Resulting reaction mixture was diluted with dichloromethane, organic layer was separated and dried over anhydrous sodium sulphate, concentrated under vacuum to get (4-fluoro-2-hydroxyphenyl)boronic acid (12) (10 g, 99.12%). LC-MS MH-155, NH4Oac:ACN, Rt=2.73 min, 5 min run.

Step 2—Intermediate (13): tert-butyl ((6-(4-fluoro-2-hydroxyphenyl)imidazo[1,2-a]pyridine-3-yl) methyl)(methyl)carbamate Procedure: To a stirred solution of (4-fluoro-2-hydroxyphenyl)boronic acid (intermediate (12)) (6.8 g, 20.0 mmol) in 1,4-dioxane (75.0 ml) was added tert-butyl ((6-bromoimidazo[1,2-a]pyridine-3-yl)methyl)(methyl)carbamate (intermediate (10)) (6.2 g, 40.0 mmol) followed by addition of solution potassium phosphate (12.72 g 60.0 mmol) in water (15.0 ml). The reaction mixture was degassed under argon balloon for 30 min then tetrakis(triphenylphosphine) palladium(0) (2.31 g, 2.0 mmol) was added and reaction mixture was heated under reflux for 2 h. Reaction mixture was cooled to room temperature and evaporated under reduced pressure. The residue was partitioned between ethyl acetate and water. The organic phase was dried over sodium sulphate, concentrated under reduced pressure and the crude product was purified by flash column chromatography by elution with 3% MeOH in DCM to get tert-butyl ((6-(4-fluoro-2-hydroxyphenyl)imidazo[1,2-a]pyridine-3-yl) methyl)(methyl)carbamate (13) (5.0 g, 67.31%). $^1H$ NMR (d6-DMSO, 400 MHz) δ 10.2 (s, 1H), 8.53-8.51 (bs, 1H), 7.73-7.71 (m, 2H), 7.59-7.57 (m, 1H), 7.32-7.30 (m, 1H), 6.76-6.74 (m, 2H), 4.78 (s, 2H), 2.67 (s, 3H), 9.36 (s, 9H); LC-MS MH+ 372, NH4Oac:ACN, Rt=1.48 min, 5 min run.

Step 3—Intermediate (14): ethyl 4-(2-(2-(3-(((tert-butoxycarbonyl)(methyl)amino)methyl)imidazo[1,2-a]pyridin-6-yl)-5-fluorophenoxy)ethyl)-1,5-dimethyl-1H-pyrazole-3-carboxylate Procedure: To a stirred solution of tert-butyl ((6-(4-fluoro-2-hydroxyphenyl)imidazo[1,2-a]pyridin-3-yl)methyl) (methyl)carbamate (intermediate (13)) (1.5 g, 4.041 mmol)

and ethyl 4-(2-hydroxyethyl)-1,5-dimethyl-1H-pyrazole-3-carboxylate (intermediate (6)) (1.714 g, 8.081 mmol) in toluene (15.0 ml) was added cyanomethyltributylphosphorane (CMBP) (2.118 ml, 8.081 mmol) at room temperature and the reaction mixture was stirred at 110° C. for 16 h. TLC and LCMS showed formation of product. The reaction mixture was diluted with ethyl acetate and washed with water, brine, dried over anhydrous sodium sulphate and concentrated under reduced pressure. The crude was purified by column chromatography (silica gel, 100-200 mesh) using 5% MeOH-DCM to afford ethyl 4-(2-(2-(3-(((tert-butoxycarbonyl)(methyl)amino)methyl) imidazo[1,2-a]pyridin-6-yl)-5-fluorophenoxy)ethyl)-1,5-dimethyl-1H-pyrazole-3-carboxylate (14) (1.5 g, 65.63%) as a brown solid. $^{1}$H NMR (d6-DMSO, 400 MHz) δ 8.46-8.25 (m, 1H), 7.63 (s, 1H), 7.56 (d, 1H), 7.32 (bs, 1H), 7.24 (d, 1H), 7.08 (d, 1H), 6.85-6.83 (m, 1H), 4.76 (s, 2H), 4.20 (q, 2H), 4.11 (t, 2H), 3.66 (s, 3H), 2.99-2.97 (m, 2H), 2.66 (s, 3H), 1.88-1.86 (m, 3H), 1.31 (s, 9H), 1.20 (t, 3H); LC-MS MH+ 566, NH4Oac: ACN, Rt=3.41 min, 5 min run.

Step 4—Intermediate (15): 4-(2-(2-(3-(((tert-butoxycarbonyl)(methyl)amino)methyl)imidazo[1,2-a]pyridin-6-yl)-5-fluorophenoxy)ethyl)-1,5-dimethyl-1H-pyrazole-3-carboxylic acid Procedure: To a stirred solution of ethyl 4-(2-(2-(3-(((tert-butoxycarbonyl)(methyl)amino) methyl)imidazo[1,2-a]pyridin-6-yl)-5-fluorophenoxy)ethyl)-1,5-dimethyl-1H-pyrazole-3-carboxylate (intermediate (14)) (1.5 g, 2.655 mmol) in THF:water (4:1) (15.0 ml) were added ethanol (0.2 ml), LiOH·H2O (0.223 g, 5.31 mmol) at room temperature. The resulting reaction mixture was stirred at room temperature for 16 h. LCMS was checked which showed formation of the product. The reaction mixture was cooled at 0° C., acidified with citric acid solution (pH-2) and extracted with DCM. The organic layer was dried over anhydrous sodium sulphate and concentrated to afford 4-(2-(2-(3-(((tert-butoxycarbonyl)(methyl)amino)methyl)imidazo[1,2-a]pyridin-6-yl)-5-fluorophenoxy)ethyl)-1,5-dimethyl-1H-pyrazole-3-carboxylic acid (15) (1.3 g, 91.19%). $^{1}$H NMR (d6-DMSO, 400 MHz) b 8.56 (s, 1H), 7.62 (s, 1H), 7.56 (d, 1H), 7.28 (bs, 1H), 7.26 (d, 1H), 7.13 (d, 1H), 6.88-6.86 (m, 1H), 4.76 (s, 2H), 4.11 (t, 2H), 3.42 (s, 3H), 2.99-2.97 (m, 2H), 2.67 (s, 3H), 1.88-1.86 (m, 3H), 1.32 (s, 9H); LC-MS MH+538, FA:ACN, Rt=1.53 min, 3 min run.

Step 5—Intermediate (16): tert-butyl ((6-(4-fluoro-2-(2-(3-(methoxy(methyl)carbamoyl)-1,5-dimethyl-1H-pyrazol-4-yl)ethoxy)phenyl)imidazo[1,2-a]pyridin-3-yl)methyl)(methyl)carbamate Procedure: To a stirred solution of 4-(2-(2-(3-(((tert-butoxycarbonyl)(methyl)amino)methyl) imidazo[1,2-a]pyridin-6-yl)-5-fluorophenoxy)ethyl)-5-methyl-1H-pyrazole-3-carboxylic acid (intermediate (15)) (1.3 g, 2.421 mmol) in tetrahydrofuran (15.0 ml) was added N,O-dimethylhydroxylamine hydrochloride (0.354 g, 3.631 mmol). To the reaction mixture triethylamine (1.687 ml, 12.104 mmol), 1-(3-Dimethylaminopropyl)-3-ethylcarbodiimide hydrochloride (0.696 g, 3.631 mmol) and 1-Hydroxybenzotriazole (0.491 g, 3.631 mmol) were added and the reaction mixture was stirred at room temperature for 16 h. TLC was checked which showed formation of product. The reaction was washed with sodium bicarbonate solution and extracted with ethyl acetate. The organic layer was washed with water, brine, dried over anhydrous sodium sulphate and concentrated under reduced pressure. The crude was purified by combiflash using 5% MeOH in DCM to afford tert-butyl ((6-(4-fluoro-2-(2-(3-(methoxy(methyl)carbamoyl)-1,5-dimethyl-1H-pyrazol-4-yl)ethoxy)phenyl)imidazo[1,2-a]pyridin-3-yl)methyl)(methyl)carbamate (16) (1.2 g, 85.37%). $^{1}$H NMR (d6-DMSO, 400 MHz) b 8.46 (bs, 1H), 7.61 (s, 1H), 7.56 (d, 1H), 7.33 (bs, 1H), 7.26 (d, 1H), 7.06 (d, 1H), 6.84-6.82 (m, 1H), 4.77 (t, 2H), 4.09 (t, 2H), 3.65 (s, 6H), 3.25 (s, 3H), 2.88-2.86 (m, 2H), 2.67 (s, 3H), 1.90-1.88 (m, 3H), 1.32 (s, 9H); LC-MS MH+ 581, NH4Oac:ACN, Rt=3.33 min, 5 min run.

Example 8: 1-(4-(2-(5-fluoro-2-(3-((methylamino) methyl)imidazo[1,2-a]pyridin-6-yl)phenoxy)ethyl)-1,5-dimethyl-1H-pyrazol-3-yl)-2,2-dimethylpropan-1-ol

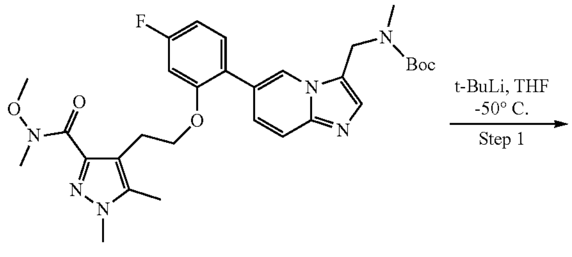

16

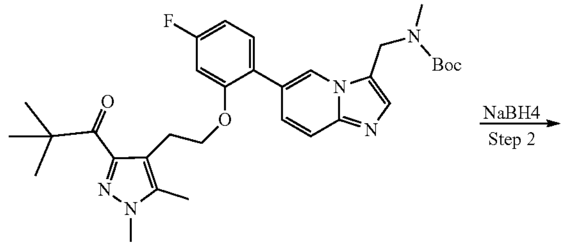

17

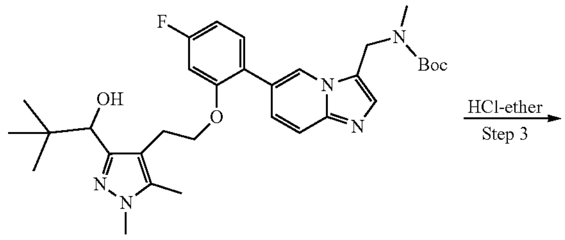

18

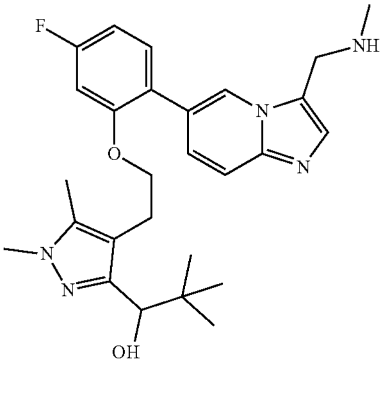

Step 1—Intermediate (17): tert-butyl ((6-(2-(2-(1,5-dimethyl-3-pivaloyl-1H-pyrazol-4-yl)ethoxy)-4-fluorophenyl)imidazo[1,2-a]pyridin-3-yl)methyl)(methyl)carbamate Procedure: A stirred solution of tert-butyl ((6-(4-fluoro-2-(2-(3-(methoxy(methyl)carbamoyl)-1,5-dimethyl-1H-pyrazol-4-yl)ethoxy)phenyl)imidazo[1,2-a]pyridin-3-yl)methyl)(methyl)carbamate (intermediate (16)) (500 mg, 0.862 mmol) in THF was cooled to −50° C. and t-butyl-lithium (1.26 ml, 2.155 mmol) was added at −50° C. Then the reaction mixture was stirred at −50° C. for 2 hrs. TLC was checked which showed formation of product and the reaction mixture was quenched with sat·$NH_4Cl$ solution. The reaction mixture was diluted with ethyl acetate, dried over sodium sulphate and concentrated. The crude product was purified by combi flash column chromatography using MeOH in DCM to afford tert-butyl ((6-(2-(2-(1,5-dimethyl-3-pivaloyl-1H-pyrazol-4-yl)ethoxy)-4-fluorophenyl)imidazo[1,2-a]pyridin-3-yl)methyl)(methyl)carbamate intermediate (17) (200 mg, 40.18%). LC-MS $MH^+$ 578, NH4Oac: ACN, $R_t$=4.14 min, 5 min run; $^1$H NMR (d6-DMSO, 400 MHz) δ 8.44 (bs, 1H), 7.61 (s, 1H), 7.56 (d, 1H), 7.33 (bs, 1H), 7.25 (d, 1H), 7.09-7.07 (m, 1H), 6.84-6.80 (m, 1H), 4.76 (t, 2H), 4.07 (t, 2H), 3.72 (s, 3H), 2.96-2.94 (d, 3H), 2.67 (s, 3H), 1.84-1.77 (m, 3H), 1.31-1.28 (m, 18H).

Step 2—Intermediate (18): tert-butyl ((6-(4-fluoro-2-(2-(3-(1-hydroxy-2,2-dimethylpropyl)-1,5-dimethyl-1H-pyrazol-4-yl)ethoxy)phenyl)imidazo[1,2-a]pyridin-3-yl)methyl)(methyl)carbamate Procedure: To a stirred solution of tert-butyl ((6-(2-(2-(1,5-dimethyl-3-pivaloyl-1H-pyrazol-4-yl)ethoxy)-4-fluorophenyl)imidazo[1,2-a]pyridin-3-yl)methyl)(methyl)carbamate (intermediate (17)) (250 mg, 0.433 mmol) in methanol (2 ml) was added sodium borohydride (50.602 mg, 1.3 mmol) at 0° C. Then reaction mixture was stirred at ambient temperature for 2 h. Upon completion of the reaction, the reaction mixture was concentrated in vacuo. The crude was diluted with ethyl acetate and washed with sat. sodium bicarbonate solution then water and then brine. Organic layer was separated, dried over sodium sulphate and evaporated under vacuum. Crude product was purified by combiflash using 3% MeOH in DCM to afford tert-butyl ((6-(4-fluoro-2-(2-(3-(1-hydroxy-2,2-dimethylpropyl)-1,5-dimethyl-1H-pyrazol-4-yl)ethoxy)phenyl)imidazo[1,2-a]pyridin-3-yl)methyl)(methyl)carbamate (18) (190 mg, 75.65%). LC-MS $MH^+$ 580.4, NH4Oac:ACN, $R_t$=3.73 min, 5 min run; $^1$H NMR (d6-DMSO, 400 MHz) b 8.50 (bs, 1H), 7.66-7.53 (m, 2H), 7.36 (d, 2H), 7.07 (d, 1H), 6.84 (bs, 1H), 4.87-4.72 (m, 3H), 4.21 (d, 1H), 4.13-3.83 (m, 2H), 3.56 (s, 3H), 3.02-2.72 (m, 2H), 2.68 (s, 3H), 1.89 (s, 3H), 1.33 (s, 9H), 0.86 (s, 9H).

Step 3—Example 8: 1-(4-(2-(5-fluoro-2-(3-((methylamino)methyl)imidazo[1,2-a]pyridin-6-yl)phenoxy)ethyl)-1,5-dimethyl-1H-pyrazol-3-yl)-2,2-dimethylpropan-1-ol Procedure: To a stirred solution of tert-butyl ((6-(4-fluoro-2-(2-(3-(1-hydroxy-2,2-dimethylpropyl)-1,5-dimethyl-1H-pyrazol-4-yl)ethoxy)phenyl)imidazo[1,2-a]pyridin-3-yl)methyl)(methyl)carbamate (intermediate (18)) (480 mg, 0.829 mmol) in diethyl ether (5 ml) was added 2M HCl in diethyl ether (25 ml) at 0° C. Reaction mixture was stirred for 2 h at RT. After complete consumption of SM, reaction mixture was evaporated under vacuum, triturated with diethyl ether and lyophilize to afford Example 8 1-(4-(2-(5-fluoro-2-(3-((methylamino)methyl)imidazo[1,2-a]pyridin-6-yl)phenoxy)ethyl)-1,5-dimethyl-1H-pyrazol-3-yl)-2,2-dimethylpropan-1-ol (423 mg, 98.94%) as light brown solid. LCMS (HCOOH:ACN): M+H=480.2, $R_t$=1.52 min in 3 mins run; $^1$H NMR (400 MHz, DMSO-$d_6$) d 10.06-9.65 (m, 2H), 9.20 (s, 1H), 8.42 (s, 1H), 8.17 (d, 1H), 8.01 (d, 1H), 7.75 (t, 1H), 7.17 (d, 1H), 6.99 (t, 1H), 4.88 (s, 2H), 4.26 (s, 1H), 4.18-4.04 (m, 2H), 3.69 (s, 3H), 3.01-2.91 (m, 1H), 2.83-2.72 (m, 1H), 2.62 (s, 3H), 2.07 (s, 3H), 0.86 (s, 9H); HPLC RT (A) 5.22 min.

Example 11: 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)-2,2-dimethylpropan-1-ol

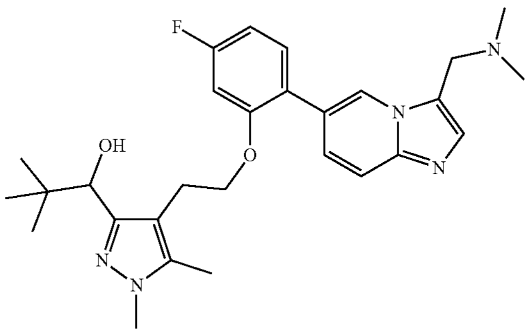 [SMILES: Cc1c(CCOc2cc(F)ccc2-c2ccc3ncc(CN(C)C)n3c2)c(C(O)C(C)(C)C)nn1C]

Procedure: To a stirred solution of 1-(4-(2-(5-fluoro-2-(3-((methylamino)methyl)imidazo[1,2-a]pyridin-6-yl)phenoxy)ethyl)-1,5-dimethyl-1H-pyrazol-3-yl)-2,2-dimethylpropan-1-ol (Example 8) (120 mg, 0.233 mmol) in MeOH (4 ml) was added HCHO solution (37%) (0.25 ml, 2.33 mmol) and stirred at RT for 1 h. Then $NaCNBH_3$ (43 mg, 0.699 mmol) was added at 0° C. and continue at RT for 16 h. The reaction mixture was evaporated under reduced pressure and diluted with DCM and washed with sat·$NaHCO_3$ solution, water and brine. Organic layer was separated and dried over anh. sodium sulphate and evaporated under reduce pressure to get crude. Crude was purified by prep TLC plate using 7% MeOH in DCM to afford Example 11 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)-2,2-dimethylpropan-1-ol (64 mg, 55.64%). LC-MS $MH^+$ 494.4, NH4Oac:ACN, $R_t$=3.36 min, 5 min run. $^1$H NMR (400 MHz, DMSO-$d_6$) d 8.50 (s, 1H), 7.57 (d, 1H), 7.50 (s, 1H), 7.43 (t, 1H), 7.34 (d, 1H), 7.05 (d, 1H), 6.88 (t, 1H), 4.85 (d, 1H), 4.22 (d, 1H), 4.13-3.98 (m, 2H), 3.73 (s, 2H), 3.56 (s, 3H), 3.01-2.89 (m, 1H), 2.77-2.67 (m, 1H), 2.15 (s, 6H), 1.90 (s, 3H), 0.87 (s, 9H). HPLC RT (A6) 5.07 min.

Example 19: 2-(4-(2-(2-(3-((dimethylamino)methyl)imidazo[1,2-a]pyridin-6-yl)-5-fluorophenoxy)ethyl)-1,5-dimethyl-1H-pyrazol-3-yl)propan-2-ol

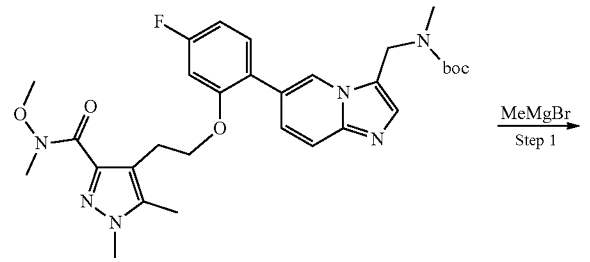

16

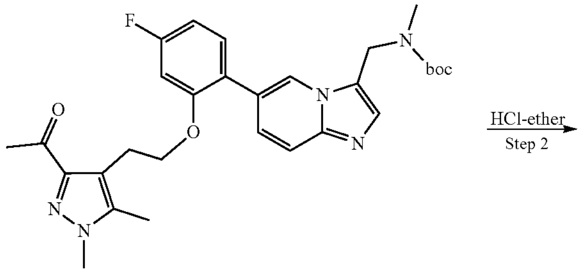

19

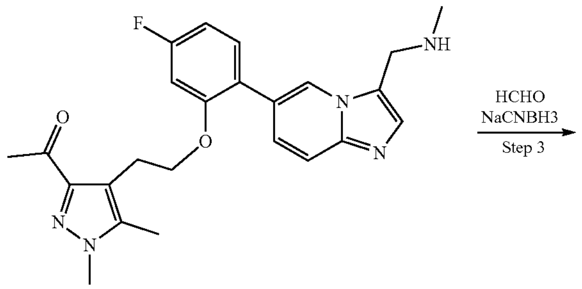

20

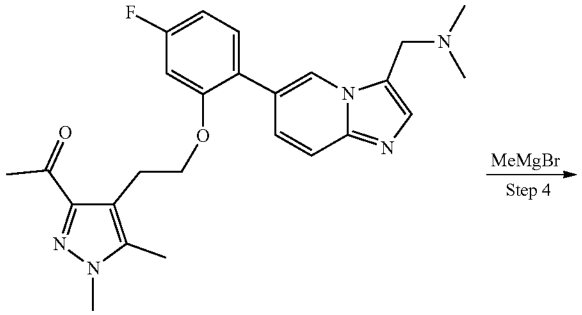

274

-continued

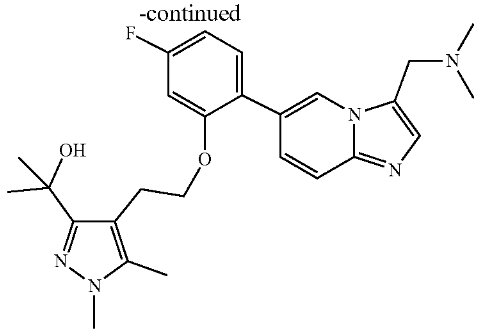

Step 1—Intermediate (19): tert-butyl ((6-(2-(2-(3-acetyl-1,5-dimethyl-1H-pyrazol-4-yl)ethoxy)-4-fluorophenyl)imidazo[1,2-a]pyridin-3-yl)methyl)(methyl)carbamate Procedure: A stirred solution of tert-butyl N-({6-[4-fluoro-2-(2-{3-[methoxy(methyl)carbamoyl]-1,5-dimethyl-1H-pyrazol-4-yl}ethoxy)phenyl]imidazo[1,2-a]pyridin-3-yl}methyl)-N-methylcarbamate (intermediate (16)) (1.0 g, 1.723 mmol) in tetrahydrofuran (17.0 mmol) was cooled at 0° C. and Methyl magnesium bromide (3M in ether) (2.9 ml, 8.615 mmol) was added at 0° C. The reaction mixture was stirred at room temperature for 1 h. TLC and LCMS was checked which showed formation of product and the reaction mixture was quenched with saturated solution of $NH_4Cl$. The reaction mixture was then extracted with ethyl acetate, dried over anhydrous sodium sulphate and concentrated to get crude product which was purified by combiflash column chromatography using MeOH in DCM to afford tert-butyl ((6-(2-(2-(3-acetyl-1,5-dimethyl-1H-pyrazol-4-yl)ethoxy)-4-fluorophenyl)imidazo[1,2-a]pyridin-3-yl)methyl)(methyl)carbamate (19) (700. g, 75.84 mmol). $^{1}$H NMR (d6-DMSO, 400 MHz) δ 8.44-8.26 (brs, 1H), 7.62 (s, 1H), 7.56 (d, 1H), 7.35-7.25 (brs, 1H), 7.24 (d, 1H), 7.10 (d, 1H), 6.85-6.78 (brs, 1H), 4.76 (s, 2H), 4.08 (t, 2H), 3.68 (s, 3H), 2.98 (s, 2H), 2.66 (s, 3H), 2.37 (s, 3H), 1.93-1.78 (brs, 3H) 1.31 (s, 9H); LC-MS MH+536, NH4Oac:ACN, Rt=3.54 min, 5 min run.

Step 2—Intermediate (20): 1-(4-(2-(5-fluoro-2-(3-((methylamino)methyl)imidazo[1,2-a]pyridin-6-yl)phenoxy)ethyl)-1,5-dimethyl-1H-pyrazol-3-yl)ethan-1-one Procedure: To a stirred solution of tert-butyl ((6-(2-(2-(3-acetyl-1,5-dimethyl-1H-pyrazol-4-yl)ethoxy)-4-fluorophenyl)imidazo[1,2-a]pyridin-3-yl)methyl)(methyl)carbamate (intermediate (19) (850.0 mg, 1.588 mmol) in diethyl ether (5.0 ml) was added 2M HCl in diethyl ether (40.0 ml) at 0° C. Reaction mixture was stirred at room temperature for 3 h. TLC and LCMS showed consumption of starting material. Reaction mixture was evaporated under reduced pressure to get crude. Crude was triturated with diethyl ether to afford 1-(4-(2-(5-fluoro-2-(3-((methylamino)methyl)imidazo[1,2-a]pyridin-6-yl)phenoxy)ethyl)-1,5-dimethyl-1H-pyrazol-3-yl)ethan-1-one (20) (650.0 mg, 94.05%) as HCl salt compound. $^{1}$H NMR (d6-DMSO, 400 MHz) b 9.70 (brs, 2H), 9.19 (s, 1H), 8.41 (s, 1H), 8.07 (d, 1H), 8.00 (d, 1H), 7.71 (t, 1H), 7.20 (d, 1H), 6.98 (t, 1H), 4.74 (t, 2H), 4.11 (t, 2H), 3.77 (s, 3H), 3.02 (t, 2H), 2.61 (t, 3H), 2.38 (s, 3H), 2.04 (s, 3H); LC-MS MH+ 436, NH4Oac:ACN, Rt=2.76 min, 5 min run.

Step 3—Intermediate 274: 1-(4-(2-(2-(3-((dimethylamino)methyl)imidazo[1,2-a]pyridine-6-yl)-5-fluorophenoxy)ethyl)-1,5-dimethyl-1H-pyrazol-3-yl)ethan-1-one Procedure: To a stirred solution of 1-(4-(2-(5-fluoro-2-(3-((methylamino)methyl)imidazo[1,2-a]pyridine-6-yl)phenoxy)ethyl)-1,5-dimethyl-1H-pyrazol-3-yl)ethan-1-one (intermediate (20)) (700.0 mg, 1.608 mmol) in methanol (10.0 ml) was added HCHO solution (~37%) (801.24 ml, 8.042 mmol) and the mixture was stirred at room temperature for 1 h. Then $NaCNBH_3$ (300.81 mg, 4.825 mmol) was added at 0° C. and the reaction was stirred at room temperature for 16 h. The reaction mixture was quenched with sodium bicarbonate solution and extracted with dichloromethane. The organic layer was dried over anhydrous sodium sulphate and concentrated under reduced pressure. The crude was purified by combiflash column chromatography (12 g silica column, 2% MeOH-DCM) to afford 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-one (274) (350.0 mg, 48.41%) as white solid. $^1$H NMR (d6-DMSO, 400 MHz) δ 8.44 (s, 1H), 7.54 (d, 1H), 7.50 (s, 1H), 7.40 (t, 1H), 7.25 (d, 1H), 7.09 (d, 1H), 6.87 (t, 1H), 4.08 (t, 2H), 3.72-3.69 (m, 5H), 3.00 (t, 2H), 2.39 (s, 3H), 2.13 (s, 6H), 1.86 (s, 3H); LC-MS MH+ 450, HCOOH:ACN, Rt=1.31 min, 3 min run; HPLC RT (A1) 6.054 min.

Step 4—Example 19: 2-(4-(2-(2-(3-((dimethylamino)methyl)imidazo[1,2-a]pyridin-6-yl)-5-fluorophenoxy)ethyl)-1,5-dimethyl-1H-pyrazol-3-yl)propan-2-ol Procedure: To a solution 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-one (274) (90.0 mg, 0.2 mmol) in tetrahydrofuran (5.0 ml) was cooled at 0° C. and Methyl magnesium bromide (3M in diethyl ether) (0.133 ml, 0.4 mmol) was added at 0° C. The reaction mixture was stirred at room temperature for 1 h. TLC and LCMS was checked which showed formation of product and the reaction mixture was quenched with saturated solution of NH4Cl. The reaction mixture was then extracted with ethyl acetate, dried over anhydrous sodium sulphate and concentrated to get crude product which was purified by combiflash column chromatography using MeOH in DCM to afford Example 19 2-(4-(2-(2-(3-((dimethylamino)methyl)imidazo[1,2-a]pyridin-6-yl)-5-fluorophenoxy)ethyl)-1,5-dimethyl-1H-pyrazol-3-yl)propan-2-ol (25.0 mg, 26.82%). $^1$H NMR (d6-DMSO, 400 MHz) δ 8.49 (s, 1H), 7.56 (d, 1H), 7.50 (s, 1H), 7.42 (t, 1H), 7.33 (d, 1H), 7.04 (d, 1H), 6.88 (t, 1H), 4.80 (s, 1H), 4.10 (t, 2H), 3.73 (s, 2H), 3.53 (s, 3H), 2.94 (t, 2H), 2.15 (s, 6H), 1.87 (s, 3H), 1.39 (s, 6H); LC-MS MH+ 466, NH4Oac:ACN, Rt=2.95 min, 5 min run; HPLC RT (B3) 8.587 min.

Example 2: 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-ol

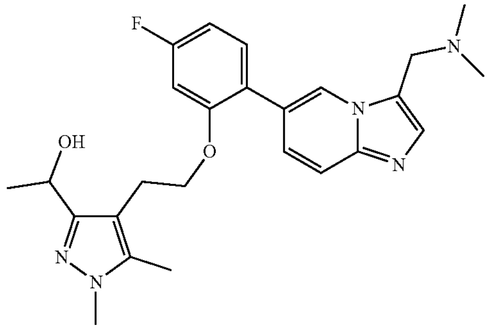 [SMILES: Cc1c(CCOc2cc(F)ccc2-c2ccc3ncc(CN(C)C)n3c2)c(C(C)O)nn1C]

Procedure: To a stirred solution of 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-one (274) (200.0 mg, 0.445 mmol) in MeOH (4.0 ml) was added NaBH4 (34.554 mg, 0.89 mmol) at 0° C. and stirred at room temperature for 3 h. TLC showed ~50% unreacted staring material. Again 18 mg of $NaBH_4$ was added and stirred at RT for additional 2 h. The reaction mixture was quenched with sodium bicarbonate solution and extracted with DCM. The organic layer was dried over sodium sulphate and concentrated under reduced pressure. Crude was purified over prep TLC (7% MeOH-DCM) to afford Example 2 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-ol (100.0 mg, 49.77%); $^1$H NMR (d6-DMSO, 400 MHz) δ 8.48 (s, 1H), 7.56 (d, 1H), 7.50 (s, 1H), 7.42 (t, 1H), 7.32 (d, 1H), 7.03 (d, 1H), 6.88 (t, 1H), 4.84 (d, 1H), 4.66 (t, 1H), 4.08 (t, 2H), 3.72 (s, 2H), 3.54 (s, 3H), 2.89-2.79 (m, 2H), 2.14 (s, 6H), 1.87 (s, 3H), 1.29 (d, 3H); LC-MS MH+ 452, NH4Oac:ACN, Rt=3.13 min, 5 min run.

Example 1: 1-{4-[2-(5-fluoro-2-{3-[(methylamino)methyl]imidazo[1,2-a]pyridin-6-yl}phenoxy)ethyl]-1,5-dimethyl-1H-pyrazol-3-yl}ethan-1-ol

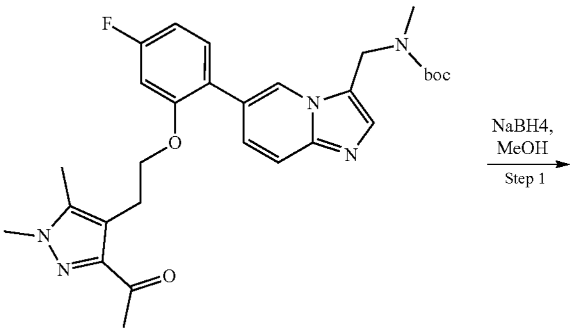

19

-continued

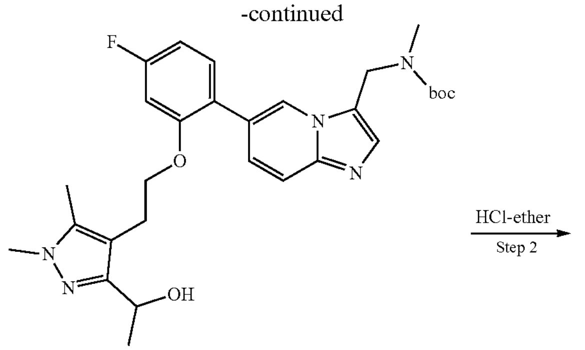

21

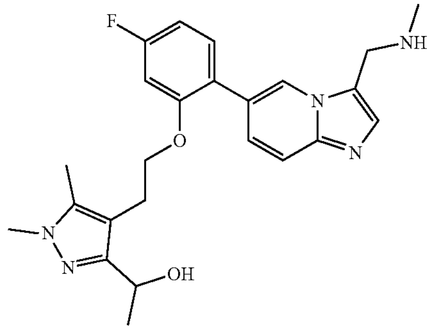

Step 1—Intermediate (21): tert-butyl ((6-(4-fluoro-2-(2-(3-(1-hydroxyethyl)-1,5-dimethyl-1H-pyrazol-4-yl)ethoxy)phenyl)imidazo[1,2-a]pyridin-3-yl)methyl)(methyl)carbamate Procedure: A stirred solution of tert-butyl ((6-(2-(2-(3-acetyl-1,5-dimethyl-1H-pyrazol-4-yl)ethoxy)-4-fluorophenyl)imidazo[1,2-a]pyridin-3-yl)methyl)-12-azanecarboxylate (intermediate (19)) (50.0 mg, 0.093 mmol) in methanol (1.0 ml) was cooled at 0° C. and $NaBH_4$ (5.447 mg, 0.14 mmol) was added at 0° C. Then the reaction mixture was stirred at RT for 1 h.

TLC was checked which showed formation of product. The reaction mixture was quenched with saturated sodium bicarbonate solution. The reaction mixture was then filtered through celite bed and washed with Ethyl acetate. The filtrated was dried over sodium sulphate and concentrated. The Crude was purified over prep TLC (5% MeOH in DCM) to afford tert-butyl((6-(4-fluoro-2-(2-(3-(1-hydroxyethyl)-1,5-dimethyl-1H-pyrazol-4-yl)ethoxy)phenyl)imidazo[1,2-a]pyridin-3-yl)methyl)(methyl)carbamate (21) (35.0 mg, 69.79%). $^1$H NMR (d6-DMSO, 400 MHz) δ 8.48 (brs, 1H), 7.61.7.57 (m, 2H), 7.36-7.33 (m, 2H), 7.04 (d, 1H), 6.83 (brs, 1H), 4.81-4.77 (m, 3H), 4.66 (brs, 1H), 4.08 (t, 2H), 3.54 (s, 3H), 2.85-2.80 (m, 2H), 2.67 (s, 3H), 1.87 (brs, 3H), 1.33-1.23 (m, 12H); LC-MS MH+ 538, NH4Oac:ACN, Rt=3.13 min, 5 min run.

Step 2—Example 1: 1-(4-(2-(5-fluoro-2-(3-((methylamino)methyl)imidazo[1,2-a]pyridin-6-yl)phenoxy)ethyl)-1,5-dimethyl-1H-pyrazol-3-yl)ethan-1-ol Procedure: A solution of tert-butyl ((6-(4-fluoro-2-(2-(3-(1-hydroxyethyl)-1,5-dimethyl-1H-pyrazol-4-yl)ethoxy)phenyl)imidazo[1,2-a]pyridin-3-yl)methyl)(methyl)carbamate (intermediate (21)) (35.0 mg, 0.065 mmol) in diethyl ether (2.0 ml), 2M HCl in diethyl ether (5.0 ml) was added at 0° C. Reaction mixture was stirred for 2 h at rt. After complete consumption of starting material reaction mixture was evaporated under vacuum, triturated with diethyl ether and lyophilized to produce Example 1 1-(4-(2-(5-fluoro-2-(3-((methylamino)methyl)imidazo[1,2-a]pyridin-6-yl)phenoxy)ethyl)-1,5-dimethyl-1H-pyrazol-3-yl)ethan-1-ol (22.0 mg, 77.15%). $^1$H NMR (d6-DMSO, 400 MHz) δ 9.54 (s, 2H), 9.16 (s, 1H), 8.37 (s, 1H), 8.11 (d, 1H), 7.98 (d, 1H), 7.69 (t, 1H), 7.15 (d, 1H), 6.99 (t, 1H), 4.73 (t, 2H), 4.68-4.62 (m, 2H), 4.13 (t, 3H), 3.61 (s, 3H), 2.87-2.82 (m, 2H), 2.64 (t, 2H), 2.01 (s, 3H), 1.29 (d, 3H); LC-MS MH+ 438, NH4Oac:ACN, Rt=2.98 min, 5 min run; HPLC RT (B3) 6.945 min.

Chiral Separation of racemic 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-ol to Produce Example 3 (isomer 1), 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-ol

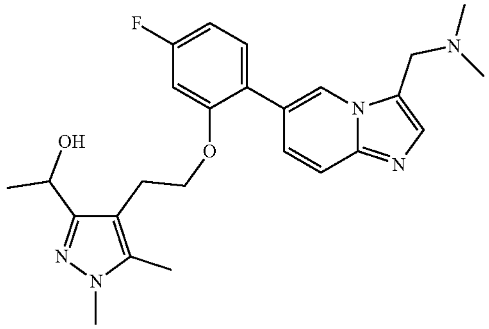 [SMILES: Cc1c(CCOc2cc(F)ccc2-c2ccc3ncc(CN(C)C)n3c2)c(C(C)O)nn1C]

and Example 4 (isomer 2) 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-ol

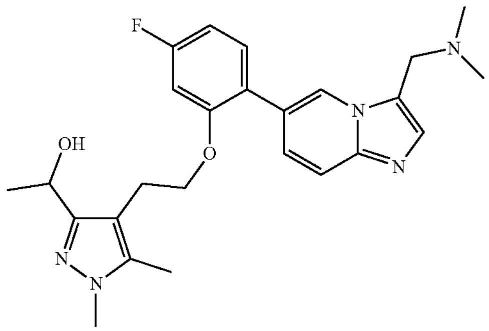 [SMILES: Cc1c(CCOc2cc(F)ccc2-c2ccc3ncc(CN(C)C)n3c2)c(C(C)O)nn1C]

Procedure: 100 mg of Example 2, racemic 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-ol was separated in chiral prep HPLC [COLUMN NAME: CHIRALPAK IC (21×250 mm, 5 i) FLOW RATE: 21.0 ml/min MOBILE PHASE: HEX/ETOH/EA/DEA: 70/15/15/

0.1 SOLUBILTY: MEOH] to afford (Peak-1) Example 3 (isomer 1, Rt 11.84 mins) 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-ol (16.0 mg, 16.0%) & (peak-2, Rt 13.60 mins) Example 4 (isomer 2) 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)ethan-1-ol (15.0 mg, 15.0%). Example 3 (isomer 1): LC-MS MH+452, NH4Oac:ACN, $R_t$=2.78 min, 5 min run; Example 4 (isomer 2): LC-MS MH+ 452, NH4Oac:ACN, Rt=2.78 min, 5 min run.

Examples 9 (Isomer 1) and 10 (Isomer 2): tert-butyl-((6-(4-fluoro-2-(2-(3-(1-hydroxy-2,2-dimethylpropyl)-1,5-dimethyl-1H-pyrazol-4-yl)ethoxy)phenyl)imidazo[1,2-a]pyridin-3-yl)methyl)(methyl) carbamate

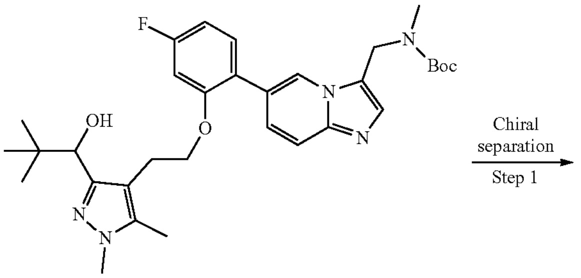

18

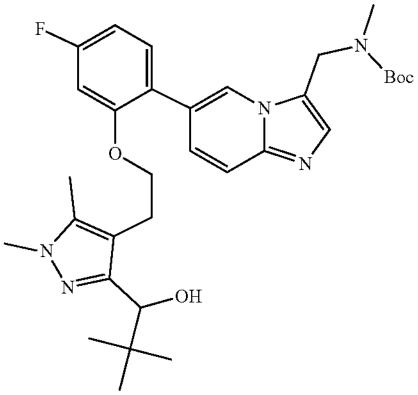

18a

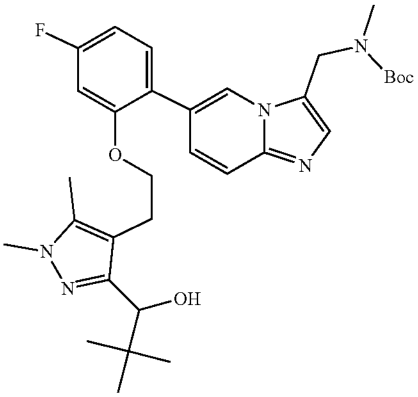

18b

-continued

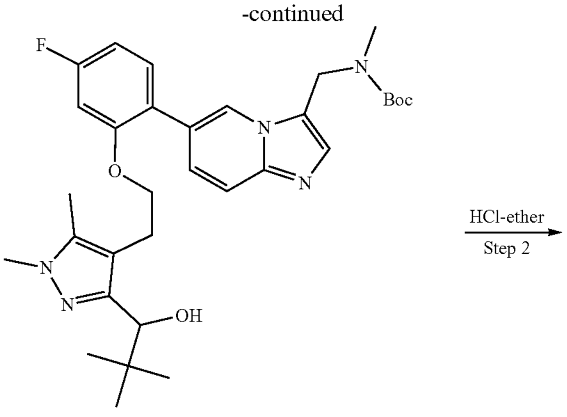

18a

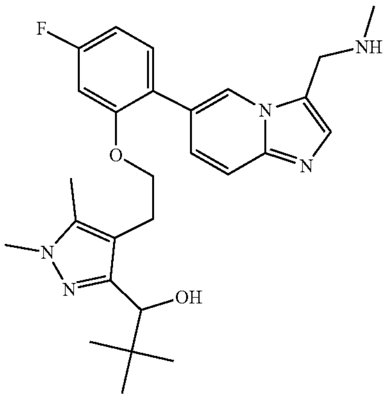

Step 1—Chiral separation of tert-butyl ((6-(4-fluoro-2-(2-(3-(1-hydroxy-2,2-dimethylpropyl)-1,5-dimethyl-1H-pyrazol-4-yl)ethoxy)phenyl)imidazo[1,2-a]pyridine-3-yl)methyl)(methyl)carbamate Procedure: racemic tert-butyl ((6-(4-fluoro-2-(2-(3-(1-hydroxy-2,2-dimethylpropyl)-1,5-dimethyl-1H-pyrazol-4-yl)ethoxy)phenyl)imidazo[1,2-a]pyridine-3-yl)methyl)(methyl)carbamate (intermediate (18)) (190 mg, 0.328 mmol) was separated by chiral prep SFC [Chiralpak IG, 0.3% Ipamine in MEOH Instrument Method (M-2-25F), Inj. Vol. (10), Column(IG), Well location (21B), Temperature (35.3), Flow(2), % Modifier(25), Pressure (100)]. After evaporation of prep fractions, we got 45 mg of Intermediate 18a (isomer 1) tert-butyl ((6-(4-fluoro-2-(2-(3-(1-hydroxy-2,2-dimethylpropyl)-1,5-dimethyl-1H-pyrazol-4-yl)ethoxy)phenyl)imidazo[1,2-a]pyridine-3-yl)methyl)(methyl)carbamate and 28 mg of Intermediate 18b (isomer 2) tert-butyl ((6-(4-fluoro-2-(2-(3-(1-hydroxy-2,2-dimethylpropyl)-1,5-dimethyl-1H-pyrazol-4-yl)ethoxy)phenyl)imidazo[1,2-a]pyridin-3-yl)methyl)(methyl)carbamate.

Intermediate 18a (isomer 1) tert-butyl-((6-(4-fluoro-2-(2-(3-(1-hydroxy-2,2-dimethylpropyl)-1,5-dimethyl-1H-pyrazol-4-yl)ethoxy)phenyl)imidazo[1,2-a]pyridin-3-yl)methyl)(methyl)carbamate: LCMS (HCOOH:ACN): M+H=580.6, $R_t$=2.41 min in 5 mins run; $^1$H NMR (d6-DMSO, 400 MHz) δ 8.50 (bs, 1H), 7.66-7.53 (m, 2H), 7.36 (d, 2H), 7.07 (d, 1H), 6.84 (bs, 1H), 4.87-4.72 (m, 3H), 4.21 (d, 1H), 4.13-3.83 (m, 2H), 3.56 (s, 3H), 3.02-2.72 (m, 2H), 2.68 (s, 3H), 1.89 (s, 3H), 1.33 (s, 9H), 0.86 (s, 9H).

Intermediate 18b (isomer 2) tert-butyl-((6-(4-fluoro-2-(2-(3-(1-hydroxy-2,2-dimethylpropyl)-1,5-dimethyl-1H-pyrazol-4-yl)ethoxy)phenyl)imidazo[1,2-a]pyridine-3-yl)methyl)(methyl)carbamate: LCMS (HCOOH:ACN):

M+H=580.6, Rt=2.39 min in 5 mins run; $^1$H NMR (d6-DMSO, 400 MHz) δ 8.50 (bs, 1H), 7.66-7.53 (m, 2H), 7.36 (d, 2H), 7.07 (d, 1H), 6.84 (bs, 1H), 4.87-4.72 (m, 3H), 4.21 (d, 1H), 4.13-3.83 (m, 2H), 3.56 (s, 3H), 3.02-2.72 (m, 2H), 2.68 (s, 3H), 1.89 (s, 3H), 1.33 (s, 9H), 0.86 (s, 9H).

Example 9 (isomer 1)-1-(4-(2-(5-fluoro-2-(3-((methylamino)methyl)imidazo[1,2-a]pyridin-6-yl)phenoxy)ethyl)-1,5-dimethyl-1H-pyrazol-3-yl)-2,2-dimethylpropan-1-ol

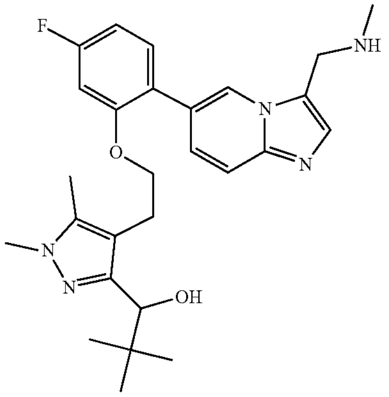

Procedure: To a stirred solution of intermediate 18a (45 mg, 0.078 mmol) in diethyl ether (2 ml) was added 2M HCl in diethyl ether (8 ml) at 0° C. Reaction mixture was stirred at RT for 2 h. After complete consumption of SM, reaction mixture was evaporated under vacuum, triturated with diethyl ether and lyophilized to afford Example 9 (isomer 1) 1-(4-(2-(5-fluoro-2-(3-((methylamino)methyl)imidazo[1,2-a]pyridin-6-yl)phenoxy)ethyl)-1,5-dimethyl-1H-pyrazol-3-yl)-2,2-dimethylpropan-1-ol (31 mg, 77.36%) as HCl salt. LC-MS MH$^+$ 480.5, NH4Oac:ACN, $R_t$=1.57 min, 3 min run; $^1$H NMR (400 MHz, DMSO-$d_6$) d 9.79 (bs, 2H), 9.20 (s, 1H), 8.41 (s, 1H), 8.17 (d, 1H), 8.01 (d, 1H), 7.74 (t, 1H), 7.19-7.14 (m, 1H), 7.02-6.94 (m, 1H), 4.74 (bs, 2H), 4.25 (s, 1H), 4.18-4.07 (m, 2H), 3.68 (s, 3H), 2.99-2.89 (m, 1H), 2.81-2.71 (m, 1H), 2.62 (t, 3H), 2.06 (s, 3H), 0.85 (s, 9H); HPLC RT (A6) 4.96 min.

Example 10 (isomer 2)-1-(4-(2-(5-fluoro-2-(3-((methylamino)methyl)imidazo[1,2-a]pyridin-6-yl)phenoxy)ethyl)-1,5-dimethyl-1H-pyrazol-3-yl)-2,2-dimethylpropan-1-ol

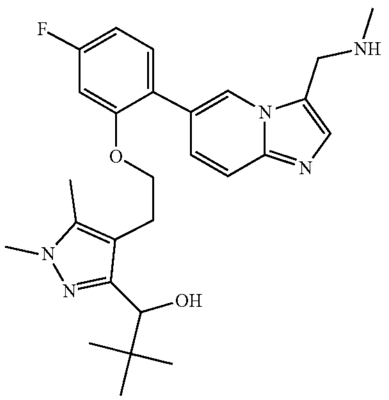

Procedure: To a stirred solution of intermediate 18b (isomer 2) (22_Peak 2) (28 mg, 0.048 mmol) in diethyl ether (2 ml) was added 2M HCl in diethyl ether (6 ml) at 0° C. Reaction mixture was stirred at rt for 2 h. After complete consumption of SM, reaction mixture was evaporated under vacuum, triturated with diethyl ether and lyophilized to afford Example 10 (isomer 2) 1-(4-(2-(5-fluoro-2-(3-((methylamino)methyl)imidazo[1,2-a]pyridin-6-yl)phenoxy)ethyl)-1,5-dimethyl-1H-pyrazol-3-yl)-2,2-dimethylpropan-1-ol (18.5 mg, 74.15%) as HCl salt. LC-MS MH+480.2, NH4Oac:ACN, $R_t$=1.37 min, 3 min run; $^1$H NMR (400 MHz, DMSO-$d_6$) d 9.67 (bs, 2H), 9.18 (s, 1H), 8.39 (s, 1H), 8.16 (d, 1H), 8.00 (d, 1H), 7.72 (t, 1H), 7.22-7.15 (m, 1H), 7.02-6.96 (m, 1H), 4.73 (t, 2H), 4.22 (s, 1H), 4.17-4.03 (m, 3H), 3.65 (s, 3H), 2.96-2.89 (m, 1H), 2.76-2.69 (m, 1H), 2.62 (t, 3H), 2.05 (s, 3H), 0.85 (s, 9H); HPLC RT (A6) 4.96 min.

Example 18: 2-(4-(2-(5-fluoro-2-(3-((methylamino)methyl)imidazo[1,2-a]pyridin-6-yl)phenoxy)ethyl)-1,5-dimethyl-1H-pyrazol-3-yl)propan-2-ol

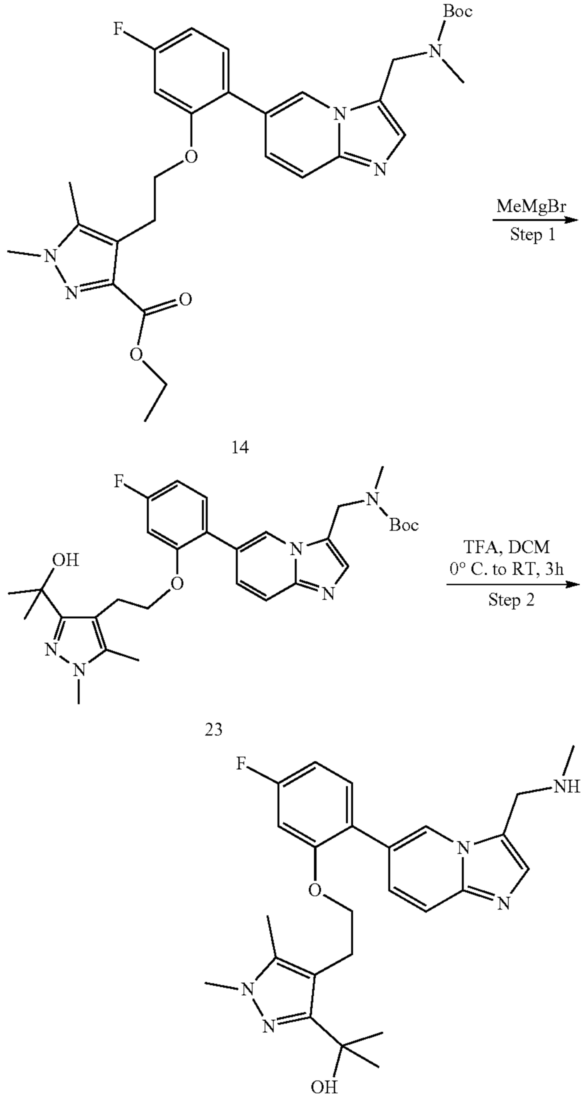

Step 1—Intermediate (23): tert-butyl ((6-(4-fluoro-2-(2-(3-(2-hydroxypropan-2-yl)-1,5-dimethyl-1H-pyrazol-4-yl)ethoxy)phenyl)imidazo[1,2-a]pyridin-3-yl)methyl)(methyl)carbamate Procedure: A stirred solution of ethyl 4-(2-(2-(3-(((tert-butoxycarbonyl)(methyl)amino)methyl)imidazo[1,2-a]pyridin-6-yl)-5-fluorophenoxy)ethyl)-1,5-dimethyl-1H-pyrazole-3-carboxylate (intermediate (14)) (2.0 g, 3.538 mmol) in THF (30.0 ml) was cooled at 0° C. and Methylmagnesiumbromide solution (3M in diethyl ether) (4.717 ml, 14.152 mmol) was added at 0° C. Then the reaction mixture was stirred at RT for 2 h. TLC was checked which showed formation of product. The reaction mixture was quenched with sat·$NH_4Cl$ solution. The reaction mixture was then extracted with ethyl acetate, dried over anhydrous sodium sulphate and concentrated to get crude product which was purified by combiflash using 5% MeOH in DCM to afford tert-butyl ((6-(4-fluoro-2-(2-(3-(2-hydroxypropan-2-yl)-1,5-dimethyl-1H-pyrazol-4-yl)ethoxy)phenyl)imidazo[1,2-a]pyridin-3-yl)methyl)(methyl)carbamate (23) (1.3 g, 66.6%) as off white sticky solid. $^1H$ NMR (d6-DMSO, 400 MHz) δ 8.50-8.45 (brs, 1H), 7.65-7.57 (m, 2H), 7.33 (d, 2H), 7.06 (d, 1H), 6.83 (t, 1H), 4.78 (s, 3H), 4.10 (t, 2H), 3.52 (s, 2H), 2.95-2.88 (brs, 2H), 2.68 (s, 3H), 1.86 (s, 3H), 1.38 (s, 6H), 1.33 (s, 9H); LC-MS MH+ 552, NH4Oac:ACN, Rt=1.32 min, 5 min run.

Step 2—Example 18: 2-(4-(2-(5-fluoro-2-(3-((methylamino)methyl)imidazo[1,2-a]pyridin-6-yl)phenoxy)ethyl)-1,5-dimethyl-1H-pyrazol-3-yl)propan-2-ol Procedure: To a solution of tert-butyl ((6-(4-fluoro-2-(2-(3-(2-hydroxypropan-2-yl)-1,5-dimethyl-1H-pyrazol-4-yl)ethoxy)phenyl)imidazo[1,2-a]pyridin-3-yl)methyl)(methyl)carbamate (intermediate (23)) (1.3 g, 2.358 mmol) in dichloromethane (25.0 ml), Trifluoroacetic acid (1.804 ml, 23.581 mmol) was added at 0° C. Reaction mixture was stirred at room temperature for 3 h. After complete consumption of starting material, reaction mixture was quenched with sodium bicarbonate solution at 0° C. and diluted with dichloromethane and organic layer was separated, evaporated to get compound which was purified by combi flash column chromatography using 5% MeOH in DCM to afford Example 18 2-(4-(2-(5-fluoro-2-(3-((methylamino)methyl)imidazo[1,2-a]pyridin-6-yl)phenoxy)ethyl)-1,5-dimethyl-1H-pyrazol-3-yl)propan-2-ol (650.0 mg, 61.05%). $^1H$ NMR (d6-DMSO, 400 MHz) δ 8.51 (s, 1H), 7.54 (d, 1H), 7.47 (s, 1H), 7.43 (t, 1H), 7.32 (d, 1H) 7.04 (d, 1H), 6.87 (t, 1H), 4.80 (s, 1H), 4.11 (t, 2H), 3.98 (s, 2H), 3.54 (s, 3H), 2.94 (t, 2H), 2.25 (s, 3H), 1.87 (s, 3H), 1.40 (s, 6H); LC-MS MH+452, NH4Oac:ACN, $R_t$=1.52 min, 3 min run; HPLC RT (A6) 5.247 min.

Intermediate (28): (3,4-difluoro-2-hydroxyphenyl)boronic acid

28

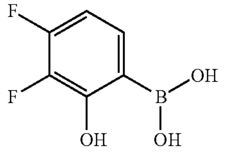

Intermediate (28) was prepared according to methods disclosed in WO2017/001812.

Intermediate (29): tert-butyl ((6-(3,4-difluoro-2-hydroxyphenyl)imidazo[1,2-a]pyridin-3-yl)methyl)(methyl)carbamate

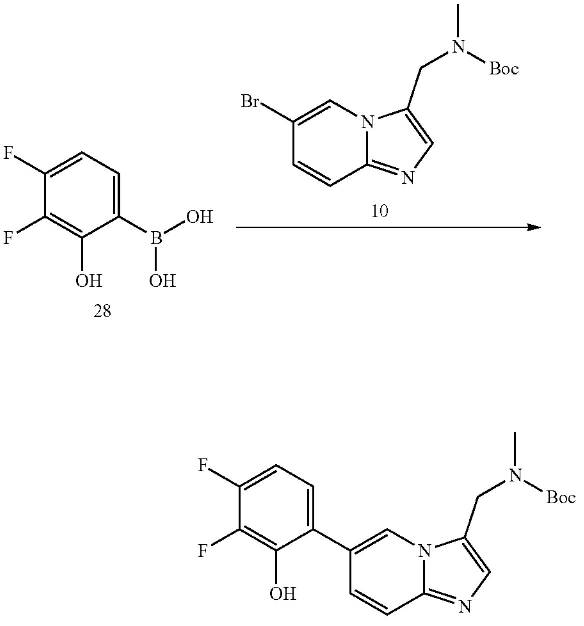
10
28
29

Procedure: Suzuki coupling of intermediates (28) and (10) using the procedure used for synthesis of intermediate (13). LCMS (HCOOH:ACN): M+H=390.3, $R_t$=1.54 min in 3 min run; $^1H$ NMR (400 MHz, DMSO-$d_6$) d 10.44 (s, 1H), 8.50 (bs, 1H), 7.67-7.54 (m, 2H), 7.41 (d, 1H), 7.12 (bs, 1H), 6.95 (d, 1H), 4.77 (s, 2H), 2.68 (s, 3H), 1.35 (s, 9H).

Example 5: 1-{4-[2-(2,3-difluoro-6-{3-[(methylamino)methyl]imidazo[1,2-a]pyridin-6-yl}phenoxy)ethyl]-1,5-dimethyl-1H-pyrazol-3-yl}ethan-1-ol

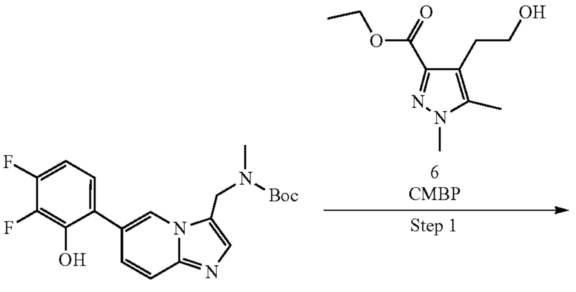

29

-continued

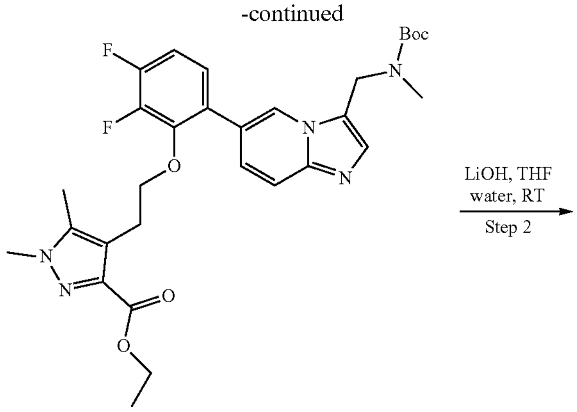

30

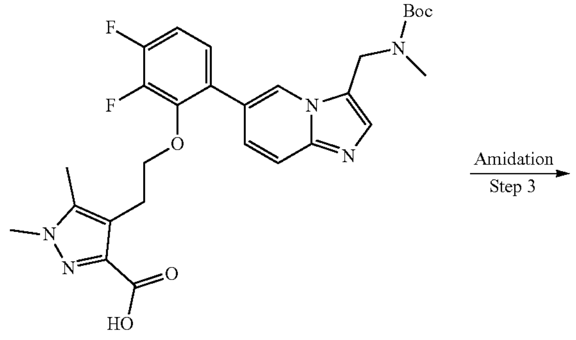

31

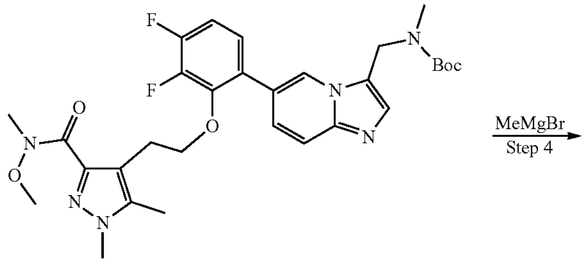

32

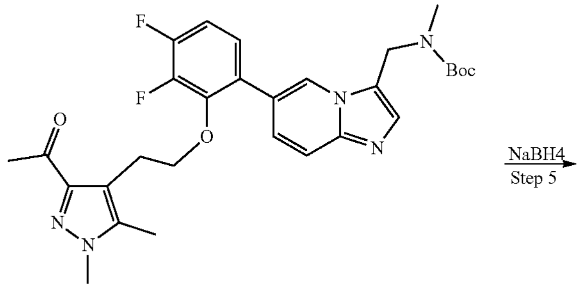

33

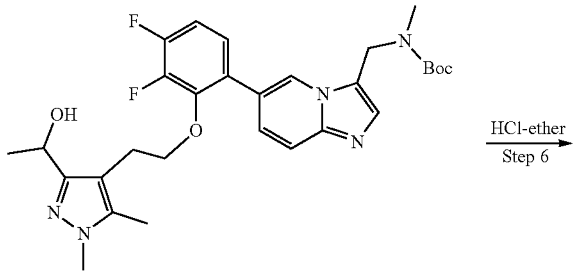

34

-continued

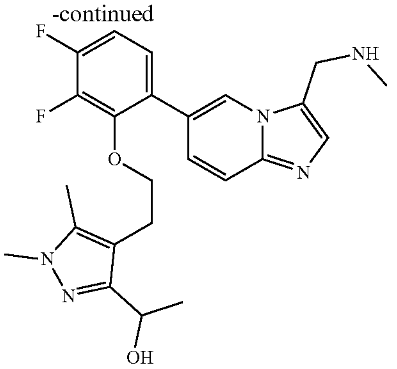

Step 1—Intermediate (30): ethyl 4-(2-(6-(3-(((tert-butoxycarbonyl)(methyl)amino)methyl)imidazo[1,2-a]pyridin-6-yl)-2,3-difluorophenoxy)ethyl)-1,5-dimethyl-1H-pyrazole-3-carboxylate Procedure: Coupling of intermediates (29) and (6) using the procedure as use for synthesis of intermediate (14). Yield—900 mg, 60.01%. $^{1}$H NMR (d6-DMSO, 400 MHz) δ 8.48-8.44 (brs, 1H), 7.63 (s, 1H), 7.56 (d, 1H), 7.27 (d, 3H), 4.76 (s, 2H), 4.12-4.07 (q, 2H), 3.95 (t, 2H), 3.63 (s, 3H), 2.84 (t, 2H), 2.66 (s, 3H), 1.85 (s, 3H), 1.32 (s, 9H) 1.14 (t, 3H); LC-MS MH$^{+}$ 584.1, NH4Oac:ACN, Rt=3.63 min, 5 min run.

Step 2—Intermediate (31): 4-(2-(6-(3-(((tert-butoxycarbonyl)(methyl)amino)methyl)imidazo[1,2-a]pyridin-6-yl)-2,3-difluorophenoxy)ethyl)-1,5-dimethyl-1H-pyrazole-3-carboxylic acid Procedure: Hydrolysis of intermediate (30) as used for synthesis of intermediate (15). Yield—2.3 g, 92.87%. $^{1}$H NMR (d6-DMSO, 400 MHz) δ 12.40-12.20 (brs, 1H), 8.50-8.42 (brs, 1H) 7.67 (s, 1H), 7.58 (d, 1H), 7.32 (d, 1H), 7.30-7.22 (brs, 2H) 4.77 (s, 2H), 4.05-3.98 (m, 2H), 3.61 (s, 3H), 2.84 (t, 2H), 2.78 (s, 3H), 1.83 (s, 3H), 1.32 (s, 9H). LC-MS MH$^{+}$ 556, NH4Oac:ACN, Rt=1.83 min, 3 min run.

Step 3—Intermediate (32): tert-butyl ((6-(3,4-difluoro-2-(2-(3-(methoxy(methyl)carbamoyl)-1,5-dimethyl-1H-pyrazol-4-yl)ethoxy)phenyl)imidazo[1,2-a]pyridin-3-yl)methyl)(methyl)carbamate Procedure: Amidation of intermediate (31) as used for synthesis of intermediate (16). Yield-2.0 g, 80.65%; $^{1}$H NMR (d6-DMSO, 400 MHz) δ 8.48-8.44 (brs, 1H), 7.63 (s, 1H), 7.55 (d, 1H), 7.27 (d, 3H), 4.77 (s, 2H), 3.95 (t, 2H), 3.61 (s, 3H), 3.59 (s, 3H), 3.16 (s, 3H), 2.71 (t, 2H), 2.68 (s, 3H), 1.84 (s, 3H), 1.33 (s, 9H); LC-MS MH$^{+}$ 599, NH4Oac:ACN, $R_t$=3.38 min, 5 min run.

Step 4—Intermediate (33): tert-butyl ((6-(2-(2-(3-acetyl-1,5-dimethyl-1H-pyrazol-4-yl)ethoxy)-3,4-difluorophenyl)imidazo[1,2-a]pyridin-3-yl)methyl)(methyl)carbamate)

Procedure: Addition of MeMgBr to intermediate (32) as used for synthesis of intermediate (19). Yield-600.0 mg, 64.84%$^{1}$H NMR (d6-DMSO, 400 MHz) δ 8.46-8.42 (brs, 1H), 7.65 (s, 1H), 7.55 (d, 1H), 7.27 (d, 3H), 4.76 (s, 2H), 3.95 (t, 2H), 3.66 (s, 3H), 2.82 (t, 2H), 2.67 (s, 3H), 2.26 (s, 3H), 1.89 (s, 3H), 1.32 (s, 9H). LC-MS $MH^+$ 554, NH4Oac: ACN, $R_t$=3.69 min, 5 min run.

Step 5—Intermediate (34): tert-butyl ((6-(3,4-difluoro-2-(2-(3-(1-hydroxyethyl)-1,5-dimethyl-1H-pyrazol-4-yl)ethoxy)phenyl)imidazo[1,2-a]pyridin-3-yl)methyl)(methyl)carbamate Procedure: reduction of intermediate (33) using procedure used for synthesis of intermediate (274). Yield—430.0 mg, 71.41%; $^1$H NMR (d6-DMSO, 400 MHz) δ 8.50-8.46 (brs, 1H), 7.63 (s, 1H), 7.58 (d, 1H), 7.33 (d, 1H), 7.30-7.18 (brs, 2H), 4.77 (s, 2H), 4.69 (d, 1H), 4.53 (t, 1H), 3.91 (t, 2H), 3.49 (s, 3H), 2.67 (s, 5H), 1.75 (s, 3H), 1.33 (s, 9H), 1.18 (d, 3H); LC-MS MH+556, HCOOH:ACN, $R_t$=1.87 min, 3 min run.

Step 6—Example 5, 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)ethan-1-01

Procedure: deprotection of Intermediate (34) as used for the synthesis of Intermediate (20). Yield—205.0 mg, 85.79%. $^1$H NMR (d6-DMSO, 400 MHz) δ 9.95-9.80 (brs, 2H), 9.22 (s, 1H), 8.42 (s, 1H), 8.00 (d, 1H), 7.92 (d, 1H), 7.62 (t, 1H), 7.44-7.37 (m, 1H), 4.72 (s, 2H), 4.57-4.51 (m, 2H), 4.03 (t, 2H), 3.60 (s, 3H), 2.75-2.66 (m, 2H), 2.61 (s, 3H), 2.00 (s, 3H), 1.19 (d, 3H); LC-MS $MH^+$ 456, HCOOH: ACN, $R_t$=1.35 min, 3 min run; HPLC RT (A5) 4.68 min.

Example 13: (isomer 1): 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol

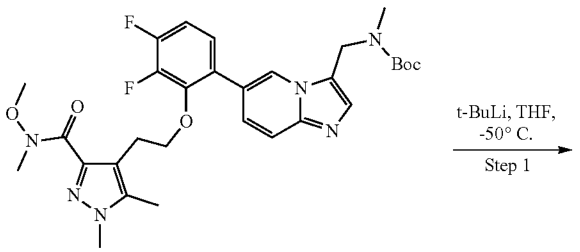

32

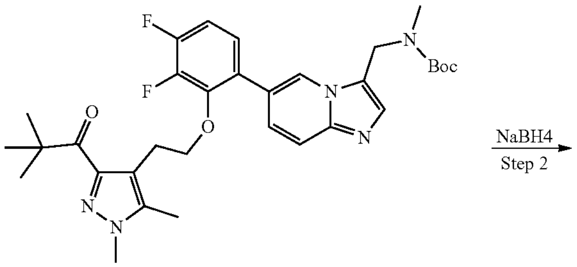

35

-continued

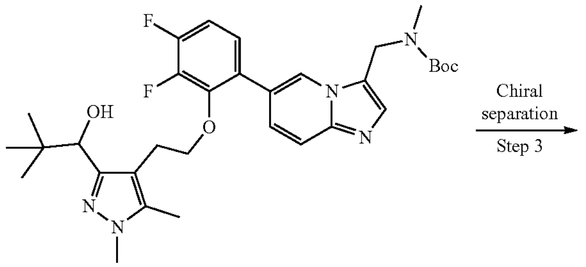

36

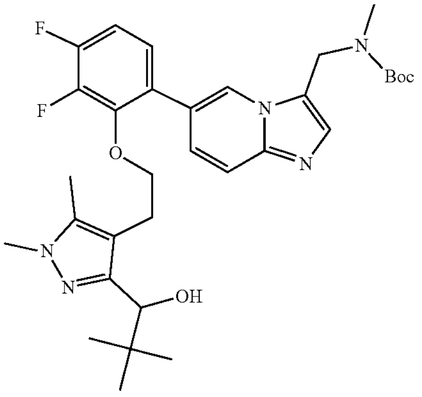

37a

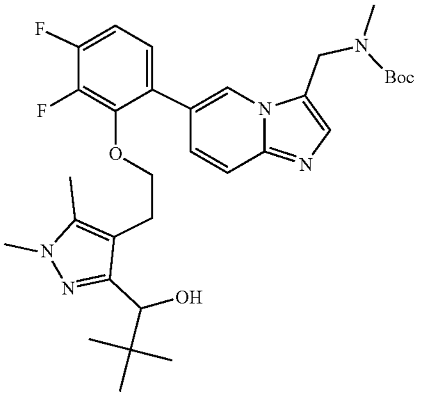

37b

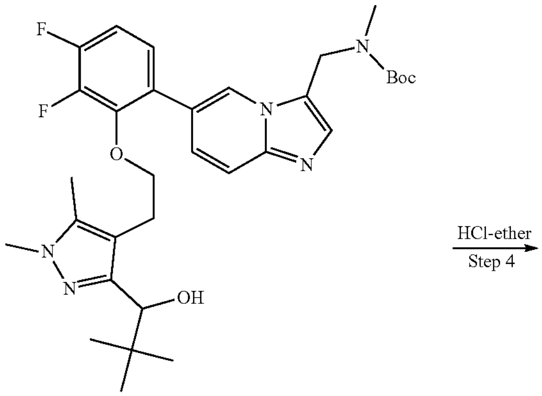

37a

-continued

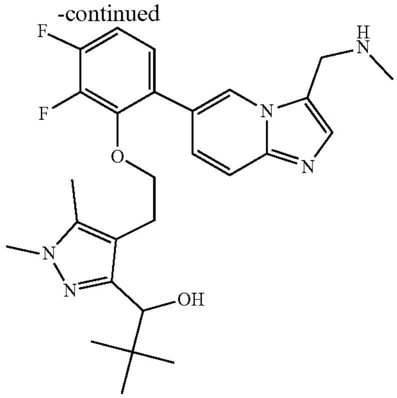

Step 1—Intermediate (35): tert-butyl ((6-(2-(2-(1,5-dimethyl-3-pivaloyl-1H-pyrazol-4-yl)ethoxy)-3,4-difluorophenyl)imidazo[1,2-a]pyridin-3-yl)methyl)(methyl)carbamate)

Procedure: addition of tBu group to intermediate (32) as used in synthesis of intermediate (17). Yield: 270 mg, 27.12%; LC-MS $MH^+$ 595.6, NH4Oac:ACN, $R_t$=4.48 min, 5 min run 1H NMR (400 MHz, DMSO-$d_6$) d 8.49 (bs, 1H), 7.63 (s, 1H), 7.55 (d, 1H), 7.31-7.13 (m, 3H), 4.76 (s, 2H), 3.93 (t, 2H), 3.67 (s, 3H), 2.81 (t, 2H), 2.67 (s, 3H), 1.87 (s, 3H), 1.32 (s, 9H), 1.19 (s, 9H).

Step 2—Intermediate (36): tert-butyl ((6-(3,4-difluoro-2-(2-(3-(1-hydroxy-2,2-dimethylpropyl)-1,5-dimethyl-1H-pyrazol-4-yl)ethoxy)phenyl)imidazo[1,2-a]pyridin-3-yl)methyl)(methyl)carbamate Procedure: reduction of intermediate 35 as used for synthesis of intermediate (18). Yield: 150 mg, (49.8%). LC-MS $MH^+$ 598.3, NH4Oac:ACN, $R_t$=3.77 min, 5 min run; $^1$H NMR (400 MHz, DMSO-$d_6$) d 8.52 (bs, 1H), 7.63 (s, 1H), 7.60 (d, 1H), 7.38 (d, 1H), 7.32-7.21 (m, 2H), 4.78 (s, 2H), 4.61 (d, 1H), 4.07 (d, 1H), 3.96-3.87 (m, 1H), 3.85-3.77 (m, 1H), 3.52 (s, 3H), 2.81-2.72 (m, 1H), 2.68 (s, 3H), 2.62-2.54 (m, 1H), 1.78 (s, 3H), 1.34 (s, 9H), 0.73 (s, 9H).

Step 3—Intermediate (37a) (isomer 1), tert-butyl-((6-(3,4-difluoro-2-(2-(3-(1-hydroxy-2,2-dimethylpropyl)-1,5-dimethyl-1H-pyrazol-4-yl)ethoxy)phenyl)imidazo[1,2-a]pyridin-3-yl)methyl)(methyl)carbamate) and Intermediate (37b) (isomer 2), tert-butyl-((6-(3,4-difluoro-2-(2-(3-(1-hydroxy-2,2-dimethylpropyl)-1,5-dimethyl-1H-pyrazol-4-yl)ethoxy)phenyl)imidazo[1,2-a]pyridin-3-yl)methyl)(methyl)carbamate Procedure: Intermediate (36) (150 mg, 0.251 mmol) was subjected to chiral separation by Chiral prep HPLC [COLUMN NAME: CHIRALPAK IC (250×20 mm, 5 i) FLOW RATE: 18.0 ml/min MOBILE PHASE: HEX/ETOH/IP-AMINE: 80/20/0.1 SOLUBILTY: MEOH]. Evaporation of prep fractions afforded 50 mg of Intermediate (37a) (isomer 1), tert-butyl-((6-(3,4-difluoro-2-(2-(3-(1-hydroxy-2,2-dimethylpropyl)-1,5-dimethyl-1H-pyrazol-4-yl)ethoxy)phenyl)imidazo[1,2-a]pyridine-3-yl)methyl)(methyl)carbamate and 45 mg of Intermediate (37b), (isomer 2), tert-butyl-((6-(3,4-difluoro-2-(2-(3-(1-hydroxy-2,2-dimethylpropyl)-1,5-dimethyl-1H-pyrazol-4-yl)ethoxy)phenyl)imidazo[1,2-a]pyridine-3-yl)methyl)(methyl)carbamate. (stereochemistry was assigned arbitrarily). Intermediate (37a) (isomer 1): LCMS (HCOOH:ACN): M+H=598.3, $R_t$=2.48 min in 5 mins run; Intermediate (37b) (isomer 2): LCMS (HCOOH:ACN): M+H=598.3, $R_t$=2.46 min in 5 mins run.

Example 13, (isomer 1): 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol

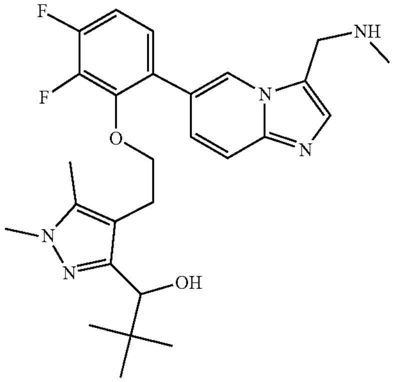

Procedure: deprotection of Intermediate (37a) (isomer 1) using the procedure used for Example 9 (isomer 1). Yield: 40 mg, 91.09%. LC-MS $MH^+$ 498.4, NH4Oac:ACN, $R_t$=3.15 min, 5 min run; $^1$H NMR (400 MHz, DMSO-$d_6$) d 9.83 (bs, 2H), 9.23 (s, 1H), 8.42 (s, 1H), 8.07 (d, 1H), 7.97 (d, 1H), 7.62 (t, 1H), 7.47-7.38 (m, 1H), 4.74 (s, 2H), 4.11 (s, 1H), 3.97 (t, 2H), 3.63 (s, 3H), 2.88-2.78 (m, 1H), 2.73-2.52 (m, 4H), 2.04 (s, 3H), 0.76 (s, 9H); HPLC RT (A4) 6.47 min.

Example 14 (isomer 2): 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol

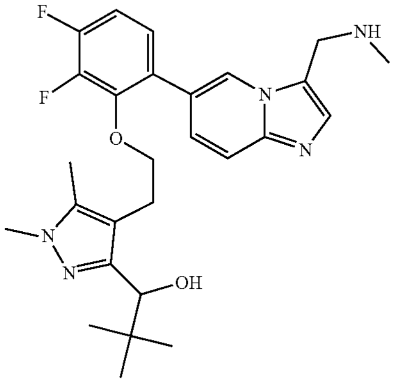

Procedure: deprotection of intermediate (37b) (isomer 2) using the procedure as in Example 10 (isomer 2) Yield: 394 mg, 95.93%; LCMS (HCOOH:ACN): M+H=498.33, $R_t$=1.53 min in 3 mins run; 1H NMR (400 MHz, DMSO-$d_6$) d 10.10-9.86 (m, 2H), 9.26 (s, 1H), 8.44 (s, 1H), 8.08 (d, 1H), 7.98 (d, 1H), 7.64 (t, 1H), 7.46-7.38 (m, 1H), 4.75 (s, 2H), 4.14 (s, 1H), 3.98 (t, 2H), 3.68 (s, 3H), 2.88-2.78 (m, 1H), 2.72-2.58 (m, 4H), 2.07 (s, 3H), 0.77 (s, 9H); HPLC RT (A4) 6.45 min.

Example 15—(isomer 1): 1-(4-(2-(6-(3-((dimethylamino)methyl)imidazo[1,2-a]pyridin-6-yl)-2,3-difluorophenoxy)ethyl)-1,5-dimethyl-1H-pyrazol-3-yl)-2,2-dimethylpropan-1-ol

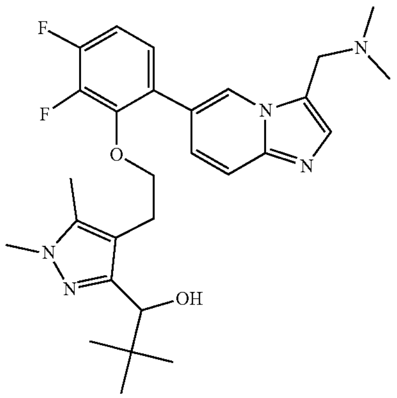

Procedure: reductive amination of Example 13 (isomer 1) using same procedure as used for Example 11 Yield: 22 mg, 53.46%. LCMS (HCOOH:ACN): M+H=512.29, $R_t$=1.48 min in 3 mins run; $^1$H NMR (400 MHz, DMSO-$d_6$) d 8.53 (s, 1H), 7.58 (s, 1H), 7.52 (s, 1H), 7.38 (d, 1H), 7.32-7.24 (m, 2H), 4.635 (d, 1H), 4.08 (d, 1H), 3.99-3.91 (m, 1H), 3.88-3.82 (m, 1H), 3.74 (s, 2H), 3.53 (s, 3H), 2.88-2.75 (m, 1H), 2.69-2.59 (m, 1H), 2.14 (s, 6H), 1.80 (s, 3H), 0.76 (s, 9H); HPLC RT (A4) 6.49 min.

Example 16, (isomer 2): 1-(4-(2-(6-(3-((dimethylamino)methyl)imidazo[1,2-a]pyridin-6-yl)-2,3-difluorophenoxy)ethyl)-1,5-dimethyl-1H-pyrazol-3-yl)-2,2-dimethylpropan-1-ol

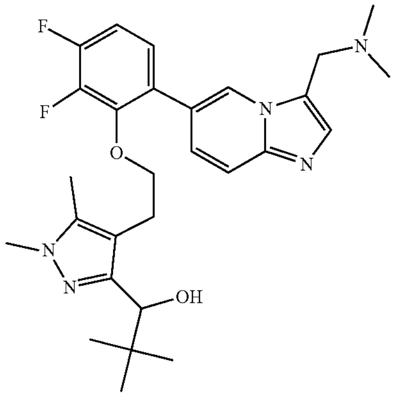

Procedure: reductive animation of Example 14 using the same procedure as used in the synthesis of Example 11. Yield: 16 mg, 51.84%; LCMS (HCOOH:ACN): M+H=512.29, $R_t$=1.48 min in 3 mins run. $^1$H NMR (400 MHz, DMSO-$d_6$) d 8.53 (s, 1H), 7.58 (s, 1H), 7.52 (s, 1H), 7.38 (d, 1H), 7.35-7.26 (m, 2H), 4.635 (d, 1H), 4.08 (d, 1H), 3.97-3.91 (m, 1H), 3.88-3.82 (m, 1H), 3.74 (s, 2H), 3.53 (s, 3H), 2.86-2.78 (m, 1H), 2.67-2.62 (m, 1H), 2.14 (s, 6H), 1.80 (s, 3H), 0.76 (s, 9H); HPLC RT (A3) 5.32 min.

Example 6: 1-(4-(2-(6-(3-((dimethylamino)methyl)imidazo[1,2-a]pyridin-6-yl)-2,3-difluorophenoxy)ethyl)-1,5-dimethyl-1H-pyrazol-3-yl)ethan-1-ol

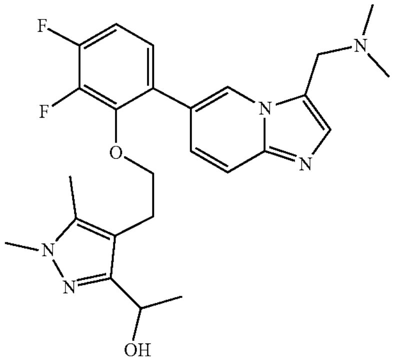

Procedure: Reductive amination of Example 5, using the same procedure used for synthesis of Example 11. Yield: 95.07 mg, 52.87%; LCMS (HCOOH:ACN): M+H=470.26, $R_t$=1.38 min in 3 mins run; $^1$H NMR (400 MHz, DMSO-$d_6$) d 8.49 (s, 1H), 7.56 (d, 1H), 7.52 (s, 1H), 7.37-7.25 (m, 3H), 4.77-4.67 (m, 1H), 4.61-4.51 (m, 1H), 3.95 (t, 2H), 3.73 (s, 2H), 3.51 (s, 3H), 2.73 (t, 2H), 2.14 (s, 6H), 1.79 (s, 3H), 1.21 (d, 3H); HPLC RT (A1) 5.85 min.

Example 21: 2-(4-(2-(2,3-difluoro-6-(3-((methylamino)methyl)imidazo[1,2-a]pyridin-6-yl)phenoxy)ethyl)-1,5-dimethyl-1H-pyrazol-3-yl)propan-2-ol

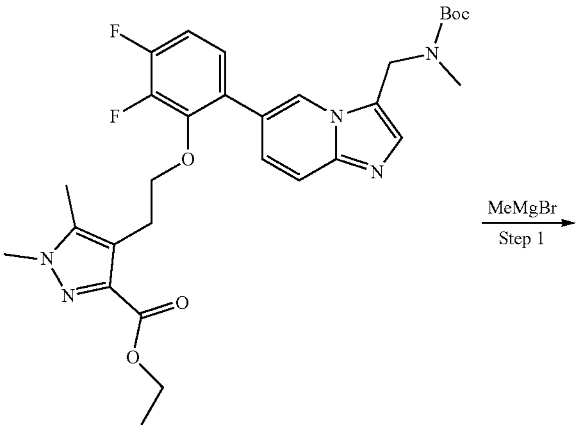

30

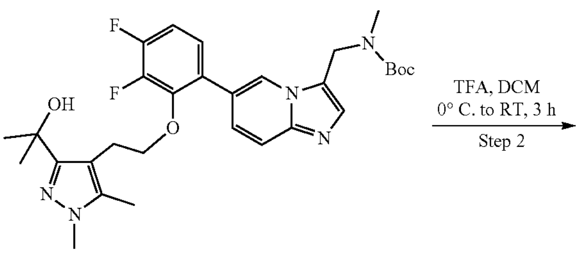

38

-continued

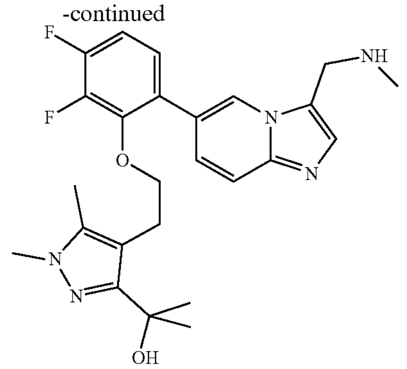

Step 1—Intermediate 38: tert-butyl ((6-(3,4-difluoro-2-(2-(3-(2-hydroxypropan-2-yl)-1,5-dimethyl-1H-pyrazol-4-yl)ethoxy)phenyl)imidazo[1,2-a]pyridin-3-yl)methyl)(methyl)carbamate Procedure: Conversion of ester intermediate (30) to corresponding gem dimethyl alcohol (38) using procedure used in synthesis of intermediate (23). Yield—340.0 mg, 39.79%; $^{1}H$ NMR (d6-DMSO, 400 MHz) δ 8.52-8.48 (brs, 1H), 7.63 (s, 1H), 7.58 (d, 1H), 7.36 (d, 1H), 7.32-7.20 (brs, 2H), 4.77 (s, 2H), 4.61 (s, 1H), 3.92 (t, 2H), 3.43 (s, 3H), 2.79 (t, 2H), 2.68 (s, 3H), 1.73 (s, 3H), 1.33 (s, 9H), 1.26 (s, 6H); LC-MS $MH^+$ 570, HCOOH:ACN, $R_t$=1.59 min, 3 min run.

Step 2—Example 21: 2-(4-(2-(2,3-difluoro-6-(3-((methylamino)methyl)imidazo[1,2-a]pyridin-6-yl)phenoxy)ethyl)-1,5-dimethyl-1H-pyrazol-3-yl)propan-2-ol Procedure: Deprotection of intermediate (38) using same conditions as used for synthesis of Example 18. Yield—160.0 mg, 57.03%; $^{1}H$ NMR (d6-DMSO, 400 MHz) δ 8.52 (s, 1H), 7.55 (d, 1H), 7.49 (s, 1H), 7.35-7.25 (m, 3H), 4.64 (s, 1H), 3.99 (s, 2H), 3.95 (d, 2H), 3.49 (s, 3H), 2.83 (t, 2H), 2.24 (s, 3H), 1.79 (s, 3H), 1.28 (s, 6H); LC-MS $MH^+$ 470, HCOOH:ACN, $R_t$=1.81 min, 3 min run; HPLC RT (A1) 5.818 min Intermediate (47): [2-(6-Bromo-imidazo[1,2-a]pyridine-3-yl)-ethyl]-carbamic acid tert-butyl ester

47

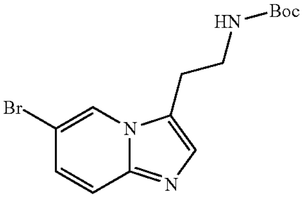

Procedure: Intermediate 47 was prepared according to methods disclosed in WO2020/128473.

Example 23: 2-(4-(2-(2-(3-(2-aminoethyl)imidazo[1,2-a]pyridin-6-yl)-5-fluorophenoxy)ethyl)-1,5-dimethyl-1H-pyrazol-3-yl)propan-2-ol

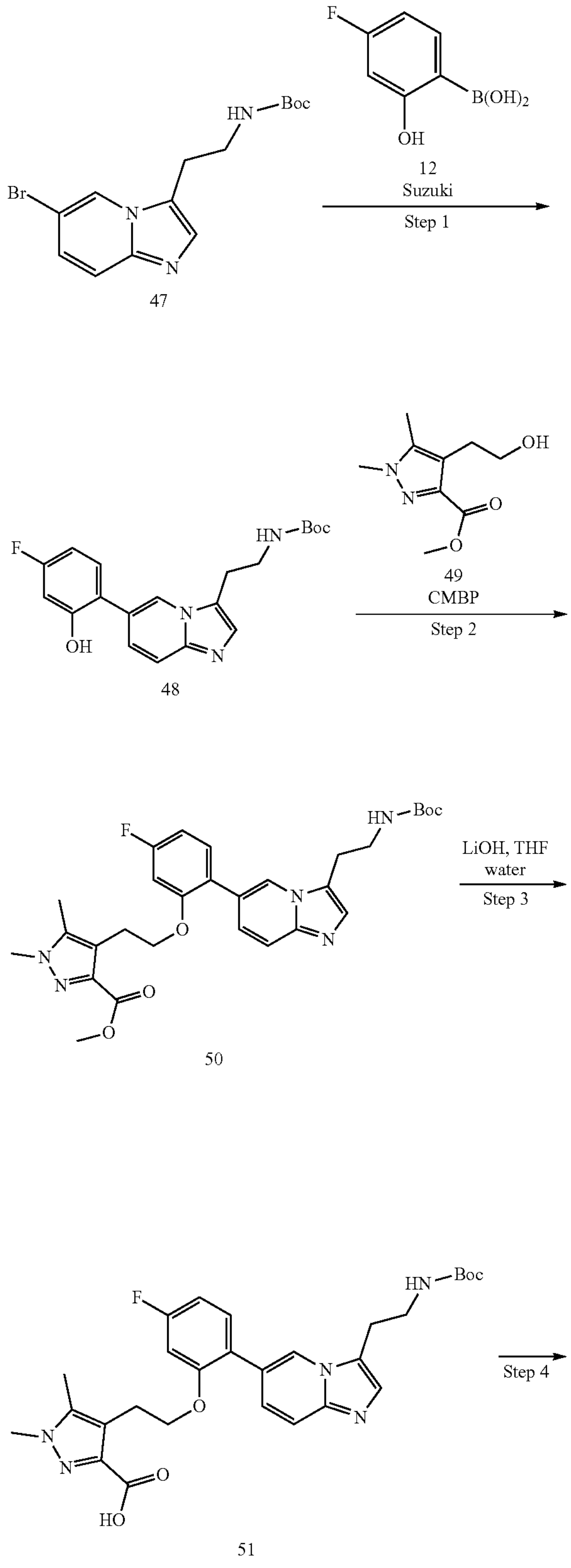

-continued

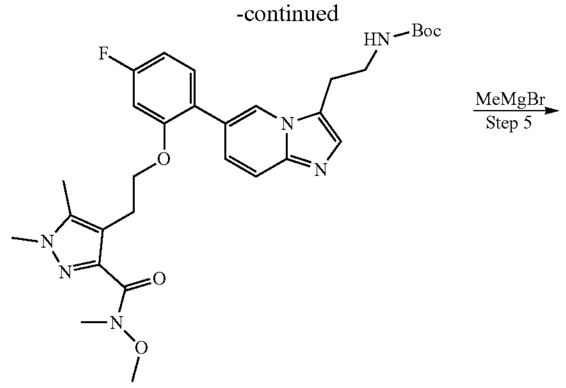

52

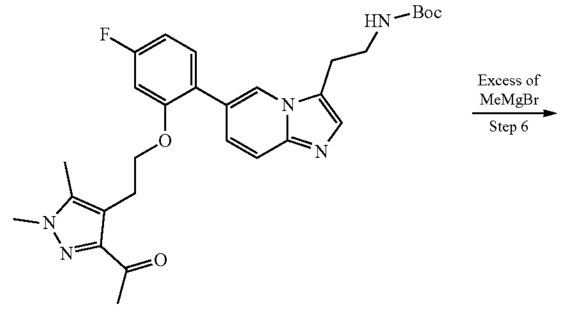

53

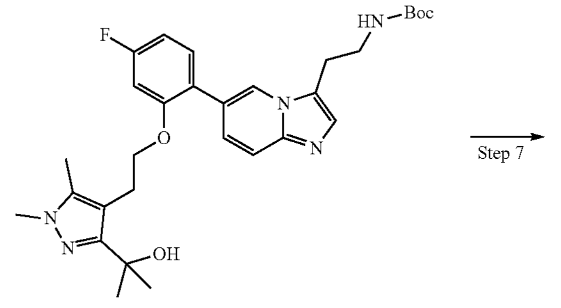

54

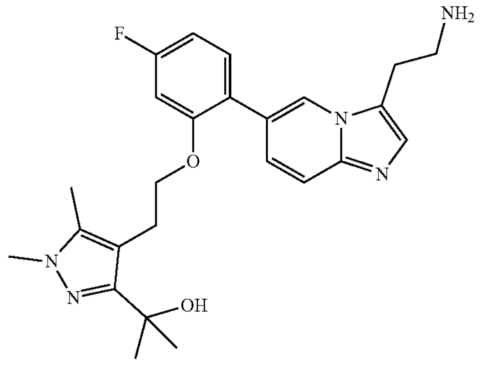

Step 1—Intermediate (48): tert-butyl (2-(6-(4-fluoro-2-hydroxyphenyl)imidazo[1,2-a]pyridin-3-yl) ethyl)carbamate Procedure: Intermediate (48) was prepared by coupling intermediates 47 and 12 using the procedure used for synthesis of intermediate (29)). Yield: 1.0 g, 76.29%; $^{1}$H NMR (d6-DMSO, 400 MHz) δ 10.27 (s, 1H), 8.36 (s, 1H), 7.70-7.62 (brs, 1H), 7.54 (d, 1H), 7.45-7.38 (m, 2H), 6.98 (t, 1H), 6.74 (d, 2H) 3.27 (t, 2H), 3.04 (t, 2H), 1.30 (s, 9H).

Step 2—Intermediate (50): methyl 4-(2-(2-(3-(2-((tert-butoxycarbonyl)amino)ethyl)imidazo[1,2-a] pyridin-6-yl)-5-fluorophenoxy)ethyl)-1,5-dimethyl-1H-pyrazole-3-carboxylate Procedure: Intermediate (50) was synthesized by coupling intermediates 48 and 49 using the same procedure as used to synthesize intermediate (30). Yield: 300.0 mg, 67.26%; $^{1}$H NMR (d6-DMSO, 400 MHz) δ 8.33 (s, 1H), 7.49 (d, 1H), 7.44 (d, 1H), 7.41 (s, 1H), 7.20 (d, 1H), 7.07 (d, 1H), 6.97 (t, 1H), 6.87 (t, 1H), 4.12 (t, 2H), 3.70 (s, 3H), 3.68 (s, 3H), 3.32-3.24 (m, 2H), 3.03-3.00 (m, 4H), 1.90 (s, 3H), 1.29 (s, 9H); LC-MS MH+ 552, NH4Oac:ACN, Rt=3.13 min, 5 min run.

Step 3—Intermediate (51): 4-(2-(2-(3-(2-((tert-butoxycarbonyl)amino)ethyl)imidazo[1,2-a]pyridin-6-yl)-5-fluorophenoxy)ethyl)-1,5-dimethyl-1H-pyrazole-3-carboxylic acid Procedure: Intermediate (51) was prepared by hydrolysis of intermediate (50) using the procedure used for intermediate (31). Yield: 290.0 mg, 99.08%; $^{1}$H NMR (CDCl3, 400 MHz) b 8.15 (s, 1H), 7.90-7.86 (m, 1H) 7.63-7.59 (m, 2H), 7.51-7.45 (m, 2H), 6.75-6.72 (m, 2H), 4.12-4.10 (m, 2H), 3.74 (s, 3H), 3.49-3.47 (m, 2H), 3.14-3.12 (m, 4H), 2.05 (s, 3H), 1.38 (s, 9H); LC-MS MH+ 538, NH4Oac:ACN, Rt=2.63 min, 5 min run.

Step 4—Intermediate (52): tert-butyl (2-(6-(4-fluoro-2-(2-(3-(methoxy(methyl)carbamoyl)-1,5-dimethyl-1H-pyrazol-4-yl)ethoxy)phenyl)imidazo[1,2-a]pyridin-3-yl)ethyl)carbamate Procedure: Intermediate (52) was prepared by amidation of intermediate 51 using the same procedure as used for synthesis of intermediate (32). Yield: 100.0 mg, 46.33%; $^{1}$H NMR (d6-DMSO, 400 MHz) δ 8.62 (s, 1H), 7.74-7.66 (m, 3H), 7.50 (t, 1H), 7.12-7.09 (m, 1H), 6.99 (t, 1H), 6.92 (t, 1H), 4.12 (t, 2H), 3.68 (s, 3H), 3.65 (s, 3H), 3.25 (s, 3H), 3.11-3.09 (m, 2H), 2.89 (t, 3H), 1.99 (s, 3H), 1.27 (s, 9H); LC-MS $MH^{+}$ 581, NH4Oac:ACN, $R_t$=3.04 min, 5 min run.

Step 5—Intermediate (53): tert-butyl (2-(6-(2-(2-(3-acetyl-1,5-dimethyl-1H-pyrazol-4-yl)ethoxy)-4-fluorophenyl)imidazo[1,2-a]pyridin-3-yl)ethyl)carbamate Procedure: Intermediate (53) was prepared from intermediate (52) by addition of MeMgBr using the same procedure used to prepare intermediate (33). Yield—20.0 mg, 21.69%. $^{1}$H NMR (d6-DMSO, 400 MHz) δ 8.36 (s, 1H), 7.50 (d, 1H), 7.45-7.41 (m, 2H), 7.21 (d, 1H), 7.09 (d, 1H), 6.97 (t, 1H), 6.87 (t, 1H), 4.10 (t, 1H), 3.70 (s, 3H), 3.29-3.26 (m, 2H), 3.03-2.97 (m, 4H), 2.32 (s, 3H), 1.90 (s, 3H), 1.30 (s, 9H); LC-MS MH+ 536, NH4Oac:ACN, Rt=3.43 min, 5 min run.

Step 6—Intermediate (54): tert-butyl (2-(6-(4-fluoro-2-(2-(3-(2-hydroxypropan-2-yl)-1,5-dimethyl-1H-pyrazol-4-yl)ethoxy)phenyl)imidazo[1,2-a]pyridin-3-yl)ethyl)carbamate Procedure: Intermediate (54) was prepared from intermediate (53) using the same procedure as used synthesis of Example 19. Yield: 35.0 mg, 56.78%; $^{1}$H NMR (d6-DMSO, 400 MHz) b 8.34 (s, 1H), 7.50 (d, 1H), 7.42 (t, 1H), 7.38 (s, 1H), 7.28 (d, 1H), 7.03 (d, 1H), 6.95 (s, 1H), 6.84 (t, 1H), 4.78 (s, 1H), 4.09 (t, 2H), 3.51 (s, 3H), 3.24 (d, 2H), 3.00 (t, 2H), 2.90 (t, 2H), 1.88 (s, 3H), 1.37 (s, 9H), 1.27 (s, 6H).

Step 7—Example 23: 2-(4-(2-(2-(3-(2-aminoethyl) imidazo[1,2-a]pyridine-6-yl)-5-fluorophenoxy) ethyl)-1,5-dimethyl-1H-pyrazol-3-yl)propan-2-ol Procedure: Example 23 was prepared from intermediate (54) using the same deprotection procedure as used for Example 18. Yield: 15.0 mg, 50.30%; $^{1}$H NMR (d6-DMSO, 400 MHz) b 8.41 (s, 1H), 7.52 (d, 1H), 7.44-7.41 (m, 2H), 7.28 (d, 1H), 7.06 (d, 1H), 6.86 (t, 1H), 4.89-4.85 (brs, 1H), 4.11 (t, 2H), 3.54 (s, 3H), 2.97-2.87 (m, 6H), 1.90 (s, 3H), 1.40 (s, 6H); HPLC RT (B1) 6.674 min.

Example 7: 1-(4-(2-(2-(3-(2-aminoethyl)imidazo[1,2-a]pyridin-6-yl)-5-fluorophenoxy)ethyl)-1,5-dimethyl-1H-pyrazol-3-yl)ethan-1-ol

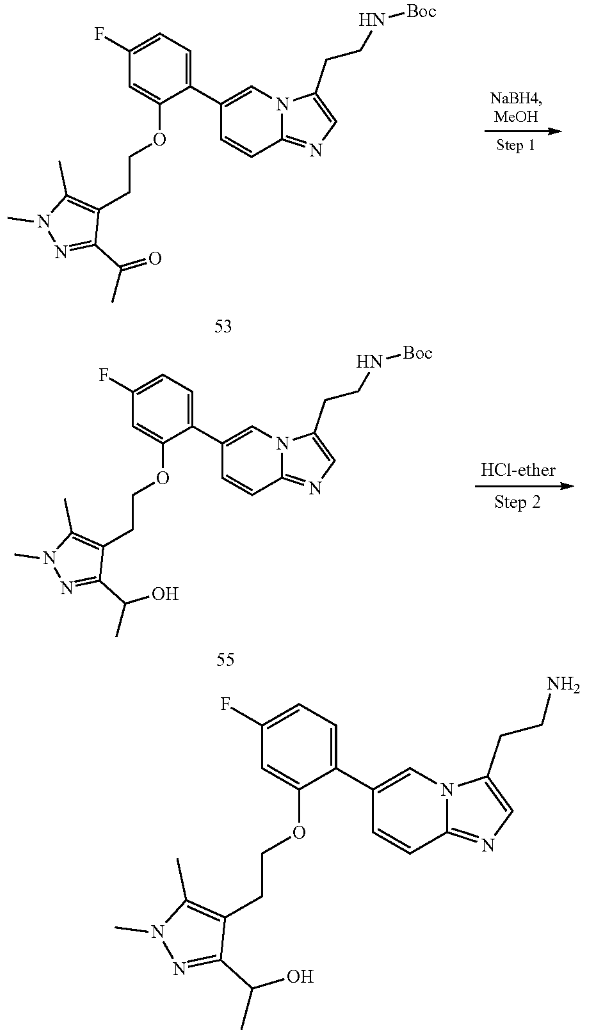

53

55

Step 1—Intermediate (55): tert-butyl (2-(6-(4-fluoro-2-(2-(3-(1-hydroxyethyl)-1,5-dimethyl-1H-pyrazol-4-yl)ethoxy)phenyl)imidazo[1,2-a]pyridine-3-yl)ethyl)carbamate Procedure: Intermediate (55) was prepared by reduction of intermediate (53) using the same procedure as intermediate (21). Yield: 35.0 mg, 58.16%; $^{1}$H NMR (d6-DMSO, 400 MHz) b 8.36 (s, 1H), 7.52 (d, 1H), 7.47-7.41 (m, 2H), 7.29 (d, 1H), 7.05-6.98 (m, 2H), 6.87 (t, 1H), 4.83 (d, 1H), 4.66 (t, 1H), 4.09 (t, 2H), 3.55 (s, 3H), 3.31 (t, 2H), 3.02 (t, 2H), 2.85-2.75 (m, 2H), 1.91 (s, 3H), 1.30-1.13 (m, 12H).

Step 2—Example 7 1-(4-(2-(2-(3-(2-aminoethyl) imidazo[1,2-a]pyridin-6-yl)-5-fluorophenoxy)ethyl)-1,5-dimethyl-1H-pyrazol-3-yl)ethan-1-ol Procedure: Example 7 was prepared by deprotection of intermediate (55) using the procedure as for Example 1. Yield: 35.0 mg, 98.00%. $^{1}$H NMR (d6-DMSO, 400 MHz) δ 8.95 (s, 1H), 8.19 (brs, 3H), 8.15 (s, 1H), 8.07 (d, 1H), 8.00 (d, 1H), 7.55 (t, 1H), 7.14 (d, 1H), 6.96 (t, 1H), 4.66 (s, 1H), 4.13 (t, 2H), 3.62 (s, 3H), 3.44 (t, 2H), 3.19 (s, 2H), 2.88-2.81 (m, 2H), 2.02 (s, 3H), 1.28 (d, 3H); LC-MS $MH^+$ 438, HCOOH:ACN, $R_t$=1.22 min, 3 min run; HPLC RT (A2) 6.53 min.

Example 24: 1-(4-(2-(2-(3-((dimethylamino)methyl) imidazo[1,2-a]pyridin-6-yl)-5-fluorophenoxy)ethyl)-1,5-dimethyl-1H-pyrazol-3-yl)-2-methylpropan-1-ol

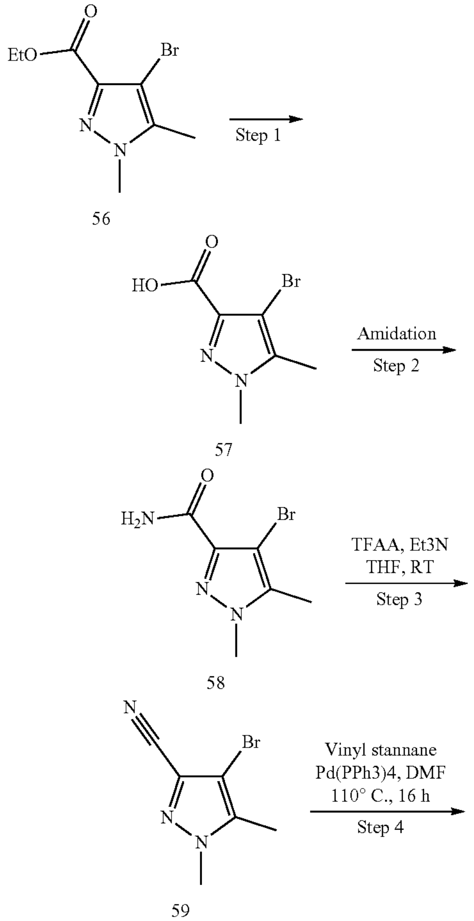

56

57

58

59

-continued

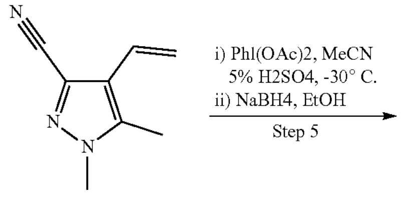

60

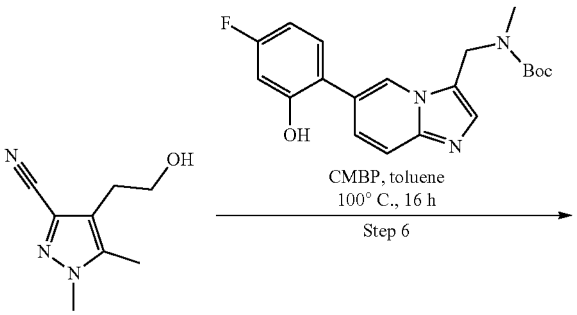

61

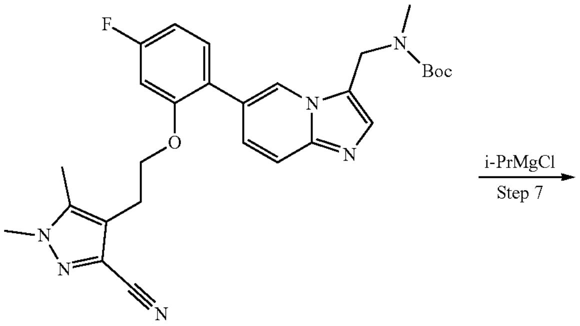

62

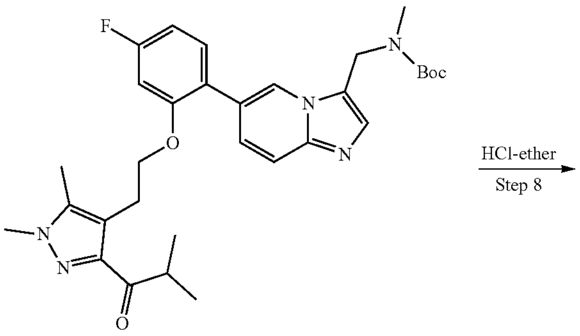

63

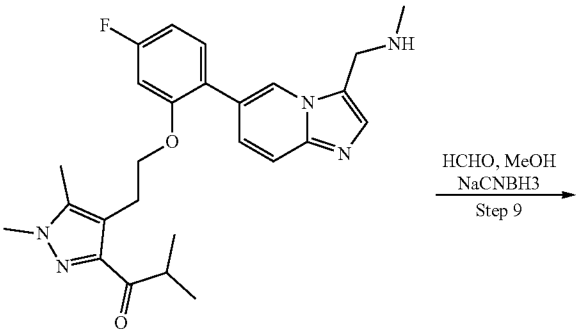

289

-continued

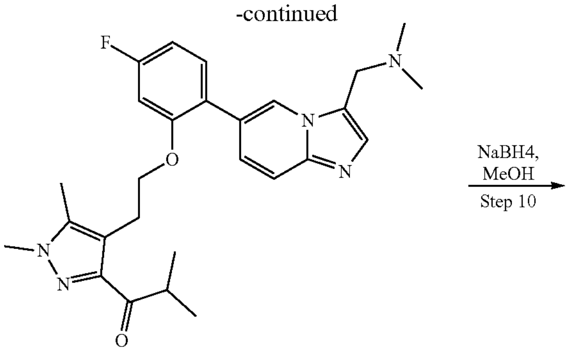

290

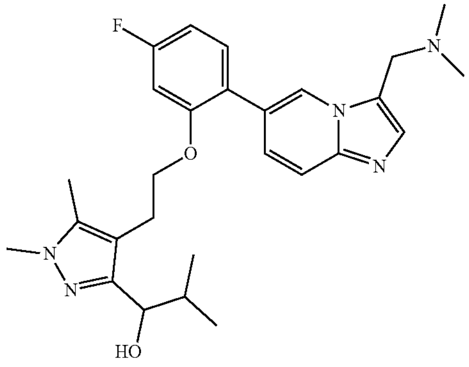

Step 1—Intermediate (57): 4-bromo-1,5-dimethyl-1H-pyrazole-3-carboxylic acid Procedure: To a stirred solution of ethyl 4-bromo-1,5-dimethyl-1H-pyrazole-3-carboxylate (intermediate (56)) (10.0 g, 40.486 mmol) in THF (112 ml) and water (28 ml) was added Ethanol (6 ml). Then at 0° C. $LiOH \cdot H_2O$ (3.401 g, 80.972 mmol) was added portion wise and the resulting mixture was stirred at RT for 16 h. After that TLC was checked, it showed formation of desired product. The reaction mixture was then distilled under vacuum. The crude reaction mixture was acidified by 6N HCl solution and extracted with 5% MeOH/DCM. The final organic layer was dried over sodium sulphate, concentrated to afford 4-bromo-1,5-dimethyl-1H-pyrazole-3-carboxylic acid (57) (8 g, 90.21%) as a light brown solid. $^1H$ NMR (400 MHz, DMSO-$d_6$) b 12.73 (bs, 1H), 3.84 (s, 3H), 2.26 (s, 3H).

Step 2—Intermediate (58)-4-bromo-1,5-dimethyl-1H-pyrazole-3-carboxamide

Procedure: To a stirred solution of 4-bromo-1,5-dimethyl-1H-pyrazole-3-carboxylic acid (intermediate (57)) (8 g, 36.53 mmol) in dry DCM (80 ml), oxalyl chloride (3.785 ml, 43.836 mmol) and catalytic amount of DMF (0.1 ml) was added at 0° C. and stirred the reaction at RT for 3 h. After that, the reaction mixture was evaporated under $N_2$ atmosphere. Then acid chloride was dissolved in THF and slowly added to the ammonia solution in THF at 0° C. Then the reaction mixture was stirred at RT for 16 h. Then reaction mixture was evaporated, extracted with 10% MeOH/DCM, and dried over sodium sulphate, and concentrated in vacuum to afford 4-bromo-1,5-dimethyl-1H-pyrazole-3-carboxamide (58) (7 g, 87.88%); LCMS (HCOOH:ACN):

M+H=218.2, $R_t$=1.45 min in 3 min run; $^1$H NMR (400 MHz, DMSO-$d_6$) b 7.38 (s, 1H), 7.22 (s, 1H), 3.81 (s, 3H), 2.24 (s, 3H).

Step 3—Intermediate (59): 4-bromo-1,5-dimethyl-1H-pyrazole-3-carbonitrile

Procedure: To a stirred solution of 4-bromo-1,5-dimethyl-1H-pyrazole-3-carboxamide (intermediate (58)) (7 g, 32.11 mmol) in THF (100 ml) was added TEA (22.522 ml, 160.55 mmol) at 0° C. and then slowly added TFAA (11.157 ml, 80.275 mmol) and stirred at RT for 2 h.

After that volatiles were evaporated under $N_2$ atmosphere then quenched with saturated sodium bicarbonate solution. The reaction mixture was diluted with ethyl acetate, the organic layer was washed with brine solution and separated, dried over sodium sulphate and concentrated in vacuum. Then the crude was purified by column chromatography by using 100-200 silica gel and eluted with 10% Ethylacetate/Hexane to afford 4-bromo-1,5-dimethyl-1H-pyrazole-3-carbonitrile (59) (5.5 g, 85.63%). $^1$H NMR (400 MHz, DMSO-$d_6$) b 3.89 (s, 3H), 2.29 (s, 3H).

Step 4—Intermediate (60): 1,5-dimethyl-4-vinyl-1H-pyrazole-3-carbonitrile

Procedure: To a solution of 4-bromo-1,5-dimethyl-1H-pyrazole-3-carbonitrile (intermediate (59)) (5.5 g, 27.5 mmol) in DMF (26 ml) was added Vinyl stannane (16.069 ml, 55 mmol). The solution was degassed with argon for 20 min and Pd(PPh3)$_4$ (1.588 g, 1.375 mmol) was added under argon. The reaction mixture was stirred at 110° C. for 16 h. TLC showed formation of the product with complete consumption of starting material. The reaction mixture was cooled to RT, quenched with water and extracted with ethyl acetate. Organic layer was washed with saturated KF solution, precipitate was filtered through the celite pad and filtrate was washed with water and finally with brine. Organic layer was dried over anhydrous sodium sulphate, filtered and evaporated the under vacuum. Crude compound purified by column chromatography (silica gel, 100-200 mesh) eluted with 30% ethyl acetate and hexane to afford 1,5-dimethyl-4-vinyl-1H-pyrazole-3-carbonitrile (60) (2.9 g, 71.65%). LC-MS $MH^+$ 147.93, FA:ACN, $R_t$=1.68 min, 3 min run; $^1$H NMR (400 MHz, CDCl3) δ 6.60 (dd, 1H), 5.73 (d, 1H), 5.35 (d, 1H), 3.82 (s, 3H), 2.31 (s, 3H).

Step 5—Intermediate (61): 4-(2-hydroxyethyl)-1,5-dimethyl-1H-pyrazole-3-carbonitrile Procedure: To a stirred solution of 1,5-dimethyl-4-vinyl-1H-pyrazole-3-carbonitrile (intermediate (60)) (2.9 g, 19.728 mmol) and (diacetoxyiodo)benzene (6.67 g, 20.714 mmol) in acetonitrile (56.0 ml) was added 5% sulfuric acid (5.8 ml) dropwise at −30° C. The mixture was stirred at −30° C. for 1 h. Upon the completion of the reaction, the residue was treated with ethyl acetate and washed with saturated sodium bicarbonate solution, water and brine solution. The aqueous layer was back-extracted with ethyl acetate and the combined organic layers were dried over anhydrous sodium sulphate, filtered and concentrated which was dissolve in ethanol (50.0 ml), sodium borohydride (1.448 g, 39.141 mmol) was added portion wise at ice cold condition. The reaction mixture was stirred at 0° C. for 30 min. Upon the completion of the reaction, the mixture was quenched with sodium bicarbonate solution and diluted with ethyl acetate, washed with water, brine concentrated in vacuum to get crude which was purified by combi flash column chromatography using 2% MeOH in DCM to give 4-(2-hydroxyethyl)-1,5-dimethyl-1H-pyrazole-3-carbonitrile (61) (2 g, 68.05%) as a colorless oil. LCMS (HCOOH:ACN): M+H=165.94, $R_t$=1.38 min in 3 mins run; $^1$H NMR (400 MHz, DMSO) δ 4.72 (bs, 1H), 3.79 (S, 3H) 3.47 (t, 2H) 2.58 (t, 2H), 2.22 (s, 3H).

Step 6—Intermediate (62) tert-butyl ((6-(2-(2-(3-cyano-1,5-dimethyl-1H-pyrazol-4-yl)ethoxy)-4-fluorophenyl)imidazo[1,2-a]pyridin-3-yl)methyl)(methyl)carbamate)

Procedure: Intermediate (62) was prepared by coupling intermediate 61 and 13 using the procedure used for intermediate (14). Yield: 260 mg, 37.3%; $^1$H NMR (d6-DMSO, 400 MHz) b 8.43 (bs, 1H), 7.61 (s, 1H), 7.53 (d, 1H), 7.34 (t, 1H), 7.20 (d, 1H), 7.13-7.07 (m, 1H), 6.86 (t, 1H), 4.75 (s, 2H), 4.15 (t, 2H), 3.68 (s, 3H), 2.93-2.82 (m, 2H), 2.66 (s, 3H), 1.93 (bs, 3H), 1.32 (s, 9H); LCMS (HCOOH:ACN): M+H=519.58, $R_t$=1.55 min in 3 mins run.

Step 7—Intermediate (63): tert-butyl ((6-(4-fluoro-2-(2-(3-isobutyryl-1,5-dimethyl-1H-pyrazol-4-yl)ethoxy)phenyl)imidazo[1,2-a]pyridin-3-yl)methyl)(methyl)carbamate Procedure: Intermediate (63) was prepared from intermediate (62) by addition of isopropyl Mg Br using same procedure as used for synthesis of intermediate (23). Yield: 450 mg, 75.19%.

Step 8—Intermediate (289): 1-(4-(2-(5-fluoro-2-(3-((methylamino)methyl)imidazo[1,2-a]p yridine-6-yl)phenoxy)ethyl)-1,5-dimethyl-1H-pyrazol-3-yl)-2-methylpropan-1-one Procedure: Intermediate 289 was synthesized by deprotection of intermediate (63), using procedure as for intermediate (20). Yield: 250 mg, 66.01%; $^1$H NMR (d6-DMSO, 400 MHz) b 9.23 (bs, 2H), 9.03 (s, 1H), 8.20 (s, 1H), 7.88 (s, 2H), 7.62 (t, 1H), 7.17 (d, 1H), 6.98 (t, 1H), 4.71 (s, 2H), 4.10 (t, 2H), 3.77 (s, 3H), 3.66-3.61 (m, 1H), 3.02 (t, 2H), 2.63 (s, 3H), 2.04 (s, 3H), 1.02 (d, 6H).

Step 9—Intermediate (290): 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)-2-methylpropan-1-one Procedure: Intermediate (290) was prepared by reductive amination of intermediate (289) using the procedure as for synthesis of (274). Yield: 7 mg, 3.65%; $^1$H NMR (d6-DMSO, 400 MHz) δ 8.42 (s, 1H), 7.51 (d, 1H), 7.47 (s, 1H), 7.38 (t, 1H), 7.22 (d, 1H), 7.07-7.01 (m, 1H), 6.88-6.81 (m, 1H), 4.05 (t, 2H), 3.75-3.58 (m, 6H), 2.98 (t, 2H), 2.11 (s, 6H), 1.84 (s, 3H), 1.01 (d, 6H).

Step 10—Example 24: 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)-2-methylpropan-1-ol

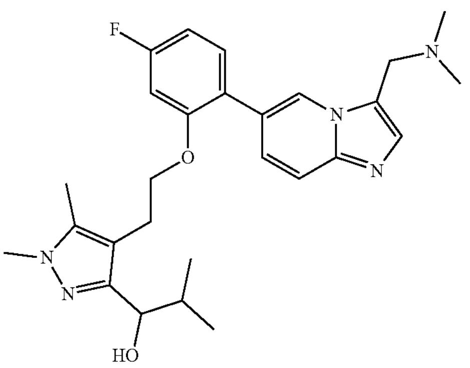

Procedure: 1-(4-(2-(2-(3-((dimethylamino)methyl)imidazo[1,2-a]pyridin-6-yl)-5-fluorophenoxy)ethyl)-1,5-dimethyl-1H-pyrazol-3-yl)-2-methylpropan-1-ol was prepared by reductive animation of intermediate (290) using procedure used for synthesis of Example 2. Yield: 13 mg, 32.37%; $^1$H NMR (d6-DMSO, 400 MHz) δ 8.46 (s, 1H), 7.53 (d, 1H), 7.47 (s, 1H), 7.40 (t, 1H), 7.30 (d, 1H), 7.01 (d, 1H), 6.85 (t, 1H), 4.82 (d, 1H), 4.11-3.94 (m, 3H), 3.70 (s, 2H), 3.53 (s, 3H), 2.88-2.71 (m, 2H), 2.12 (s, 6H), 1.98-1.81 (m, 4H), 0.91 (d, 3H), 0.63 (d, 3H).

Example 17: 1-(4-(2-(6-(3-(aminomethyl)imidazo[1,2-a]pyridin-6-yl)-2,3-difluorophenoxy)ethyl)-1,5-dimethyl-1H-pyrazol-3-yl)-2,2-dimethylpropan-1-ol

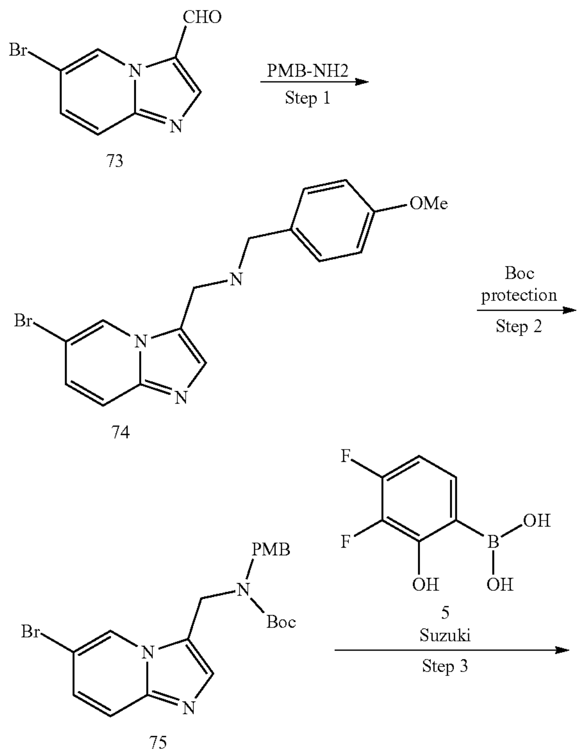

-continued

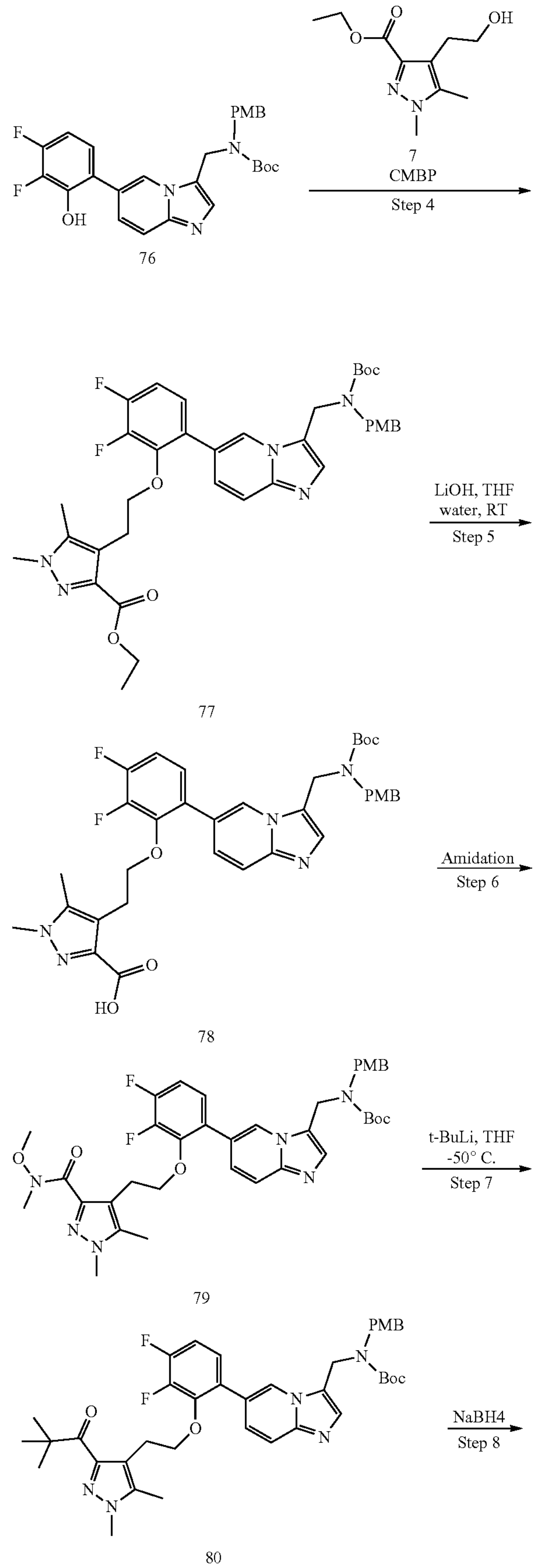

-continued

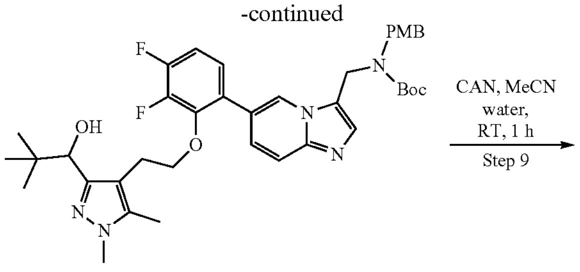

81

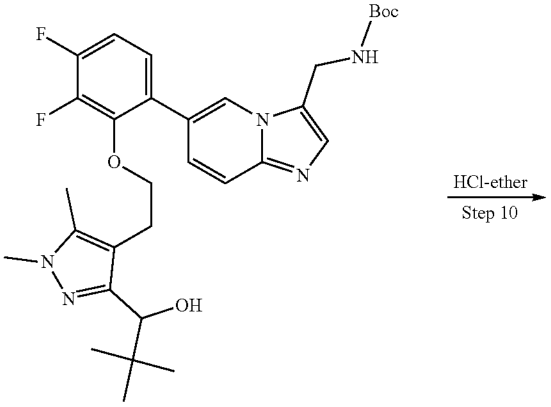

82

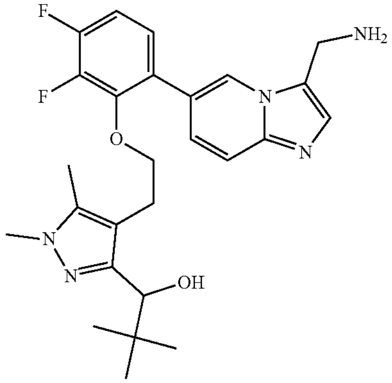

Step 1—Intermediate (74): 1-(6-bromoimidazo[1,2-a]pyridin-3-yl)-N-(4-methoxybenzyl)methanamine Procedure: To a stirred solution of 6-bromoimidazo[1,2-a]pyridine-3-carbaldehyde (intermediate (73)) (3 g, 13.333 mmol) in methanol (15 ml) was added 4-Methoxybenzylamine (2.613 ml, 20.0 mmol) and was stirred at RT for 16 h. To the reaction mixture $NaBH_4$ (1.035 g, 26.667 mmol) was added at 0° C. and was stirred at same temperature for 2 h. The reaction mixture was quenched with satsodium bicarbonate solution and extracted with DCM. Organic layer was washed with water and brine. The organic layer was dried over sodium sulphate and concentrated under reduced pressure to get crude compound which was purified by combi-flash column chromatography to afford 1-(6-bromoimidazo[1,2-a]pyridine-3-yl)-N-(4-methoxybenzyl)methanamine (74) (2.2 g, 47.66%). LC-MS $MH^+$ 345.6, NH4Oac:ACN, $R_t$=3.43 min, 5 min run.

Step 2—Intermediate (75) tert-butyl N-({6-bromo-imidazo[1,2-a]pyridin-3-yl}methyl)-N-[(4-methoxy-phenyl)methyl]carbamate Procedure: Intermediate (75) tert-butyl N-({6-bromoimidazo[1,2-a]pyridin-3-yl}methyl)-N-[(4-methoxyphenyl)methyl]carbamate was prepared by Boc protection of intermediate (74) using the procedure used for intermediate (10). Yield: 1.7 g, 59.94%; $^1H$ NMR (d6-DMSO, 400 MHz) δ 8.62 (bs, 1H), 7.63-7.47 (m, 2H), 7.35 (d, 1H), 7.03 (d, 2H), 6.79 (d, 2H), 4.72 (s, 2H), 4.20 (s, 2H), 3.70 (s, 3H), 1.46 (s, 9H). LCMS (HCOOH:ACN): M+H=446.33 & 448.28, $R_t$=1.73 min in 3 mins run.

Step 3—Intermediate (76): tert-butyl ((6-(3,4-difluoro-2-hydroxyphenyl)imidazo[1,2-a]pyridin-3-yl)methyl)(4-methoxybenzyl)carbamate Procedure: Intermediate (76) was prepared by coupling intermediates (74) and (5) of (using the procedure as used for intermediate (13). Yield: 1.4 g, 73.96%; LCMS (HCOOH:ACN): M+H=496.3, $R_t$=2.07 min in 3 mins run.

Step 4—Intermediate (77) ethyl 4-(2-(6-(3-(((tert-butoxycarbonyl)(4-methoxybenzyl)amino)methyl)imidazo[1,2-a]pyridin-6-yl)-2,3-difluorophenoxy)ethyl)-1,5-dimethyl-1H-pyrazole-3-carboxylate Procedure: Intermediate (77) was synthesized by coupling intermediates (76) and (7) using the procedure as used for Intermediate (14). Yield: 200 mg, 35.9%; LCMS (HCOOH:ACN): M+H=690.29, $R_t$=1.97 min in 3 mins run.

Step 5—Intermediate (78) 4-(2-(6-(3-(((tert-butoxycarbonyl)(4-methoxybenzyl)amino)methyl)imidazo[1,2-a]pyridin-6-yl)-2,3-difluorophenoxy)ethyl)-1,5-dimethyl-1H-pyrazole-3-carboxylic acid Procedure: Intermediate (78) was synthesized by hydrolysis of intermediate (77) using the procedure used for intermediate (15). Yield: 900 mg, 93.71%; LCMS (HCOOH:ACN): M+H=662.6, $R_t$=2.02 min in 3 mins run.

Step 6—Intermediate (79): tert-butyl ((6-(3,4-difluoro-2-(2-(3-(methoxy(methyl)carbamoyl)-1,5-dimethyl-1H-pyrazol-4-yl)ethoxy)phenyl)imidazo[1,2-a]pyridin-3-yl)methyl)(4-methoxybenzyl)carbamate Procedure: Intermediate (79) was synthesized by amidation of intermediate (78) using the same procedure as used for intermediate (16). Yield: 430 mg, 44.83%; $^1H$ NMR (d6-DMSO, 400 MHz) δ 8.42 (bs, 1H), 7.60 (bs, 1H), 7.53 (d, 1H), 7.27 (d, 2H), 7.17 (bs, 1H), 7.07 (d, 2H), 6.80 (d, 2H), 4.73 (s, 2H), 4.19 (s, 2H), 3.95 (t, 2H), 3.69 (s, 3H), 3.62 (s, 3H), 3.59 (s, 3H), 3.16 (s, 3H), 2.72 (t, 2H), 1.87 (s, 3H), 1.35 (s, 9H); LCMS (HCOOH:can): M+H=705.4, $R_t$=2.16 min in 3 mins run.

Step 7—Intermediate (80): tert-butyl ((6-(2-(2-(1,5-dimethyl-3-pivaloyl-1H-pyrazol-4-yl)ethoxy)-3,4-difluorophenyl)imidazo[1,2pyridinedin-3-yl)methyl)(4-methoxybenzyl)carbamate Procedure: Intermediate (8) was synthesized from intermediate (79) by addition of tBu using the same procedure as for intermediate (17). Yield: 200 mg, 46.66%. $^1H$ NMR (d6-DMSO, 400 MHz) δ 8.41 (bs, 1H), 7.60 (bs, 1H), 7.52 (d, 1H), 7.26 (d, 2H), 7.17 (bs, 1H), 7.06 (d, 2H), 6.80 (d, 2H), 4.72 (s, 2H), 4.18 (s, 2H), 3.93 (t, 2H), 3.69 (s, 3H), 3.67 (s, 3H), 2.81 (t, 2H), 1.89 (s, 3H), 1.34 (s, 9H), 1.20 (s, 9H); LCMS (HCOOH:ACN): M+H=702.78, $R_t$=1.87 min in 3 mins run.

Step 8—Intermediate (81): tert-butyl ((6-(3,4-difluoro-2-(2-(3-(1-hydroxy-2,2-dimethylpropyl)-1,5-dimethyl-1H-pyrazol-4-yl)ethoxy)phenyl)imidazo[1,2-a]pyridin-3-yl)methyl)(4-methoxybenzyl) carbamate Procedure: Intermediate (81) was synthesized by reduction of intermediate (80) using the same procedure as for intermediate (21). Yield: 140 mg, 69.75%; $^1$H NMR (d6-DMSO, 400 MHz) δ 8.44 (bs, 1H), 7.65-7.52 (m, 2H), 7.37 (d, 1H), 7.31-7.18 (m, 2H), 7.08 (d, 2H), 6.81 (d, 2H), 4.73 (s, 2H), 4.60 (d, 1H), 4.18 (s, 2H), 4.07 (d, 1H), 3.96-3.79 (m, 2H), 3.70 (s, 3H), 3.52 (s, 3H), 2.81-2.71 (m, 1H), 1.80 (s, 3H), 1.36 (s, 9H), 0.74 (s, 9H); LCMS (HCOOH:ACN): M+H=704.76, $R_t$=1.76 min in 3 mins run.

Step 9—Intermediate (82): tert-butyl ((6-(3,4-difluoro-2-(2-(3-(1-hydroxy-2,2-dimethylpropyl)-1,5-dimethyl-1H-pyrazol-4-yl)ethoxy)phenyl)imidazo[1,2-a]pyridine-3-yl)methyl)carbamate Procedure: To a stirred solution of intermediate (81) (130 mg, 0.185 mmol) in acetonitrile (2.7 ml) was added Cerium Ammonium Nitrate (202.573 mg, 0.37 mmol) dissolve in water (0.3 ml) at 0° C. Reaction mixture was stirred at same temperature for 1 h. Reaction mixture was checked by TLC and LCMS showed SM was consumed. Reaction mixture was quenched with sodium bicarbonate solution and extracted with Ethyl acetate. Organic layer was washed with saturated solution of sodium sulfite, water and brine. Organic layer was concentrated under vacuum to get crude. Crude was purified by prep TLC plate using 3% Methanol in DCM to afford tert-butyl ((6-(3,4-difluoro-2-(2-(3-(1-hydroxy-2,2-dimethylpropyl)-1,5-dimethyl-1H-pyrazol-4-yl)ethoxy)phenyl)imidazo[1,2-a]pyridine-3-yl)methyl)carbamate (82) (40 mg, 37.08%) as colorless sticky gum. LCMS (HCOOH:ACN): M+H=584.6, $R_t$=2.05 min in 3 mins run.

Step 10—Example 17: 1-(4-(2-(6-(3-(aminomethyl)imidazo[1,2-a]pyridin-6-yl)-2,3-difluorophenoxy)ethyl)-1,5-dimethyl-1H-pyrazol-3-yl)-2,2-dimethylpropan-1-ol Procedure: Example 17 was synthesized by deprotecting intermediate (82) using the same procedure as used for Example 9 (isomer 1). Yield: 22 mg, 66.31%; $^1$H NMR (d6-DMSO, 400 MHz) δ 9.18 (s, 1H), 8.95-8.77 (m, 3H), 8.35 (s, 1H), 8.08 (d, 1H), 7.97 (d, 1H), 7.58 (t, 1H), 7.48-7.35 (m, 1H), 4.77 (s, 2H), 4.12 (s, 1H), 4.03-3.94 (m, 2H), 3.63 (s, 3H), 2.91-2.78 (m, 1H), 2.72-2.61 (m, 1H), 2.03 (s, 3H), 0.77 (s, 9H); LCMS (HCOOH:ACN): M+H=484.38, $R_t$=1.51 min in 3 mins run; HPLC RT (A3) 3.84 min.

Example 12: 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol

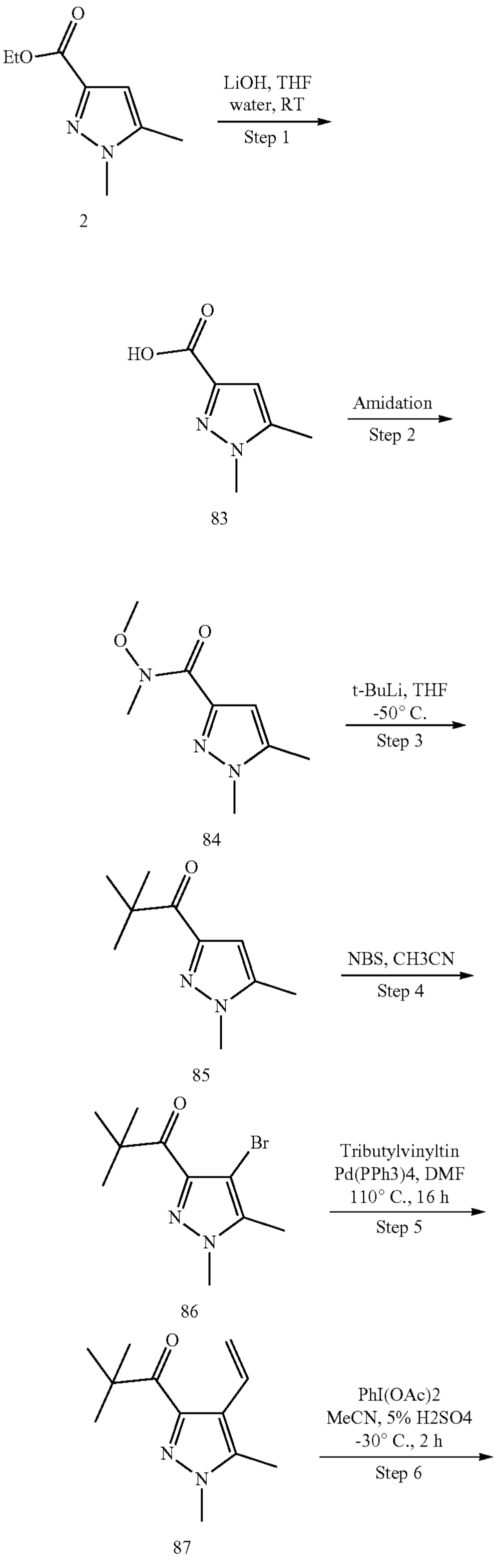

-continued

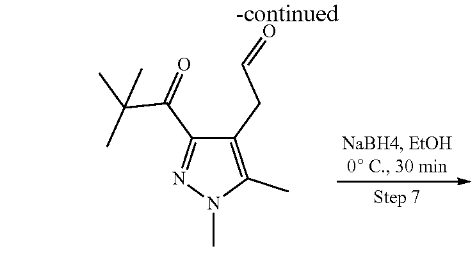

88

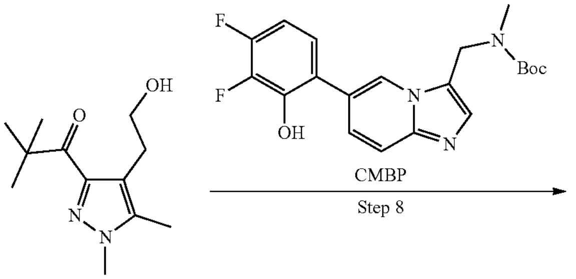

89

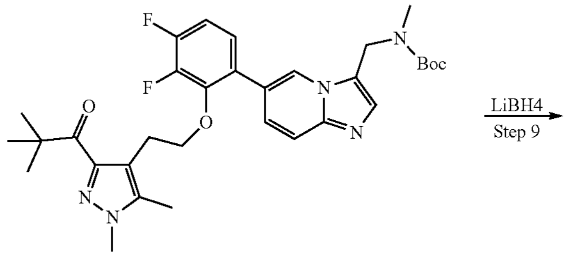

90

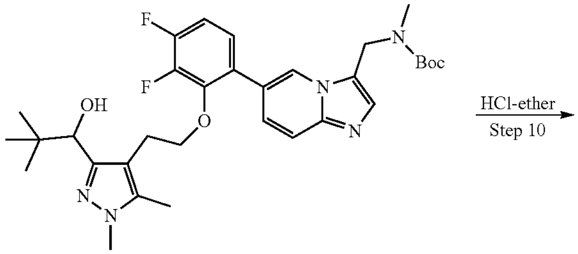

91

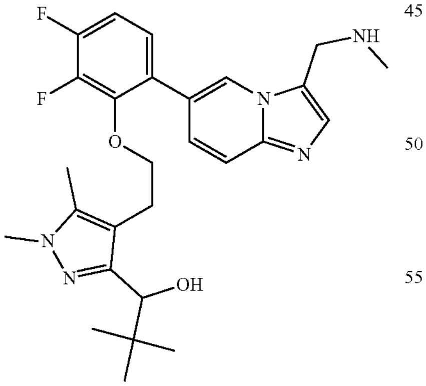

Step 1—Intermediate (83): 1,5-dimethyl-1H-pyrazole-3-carboxylic acid

Procedure: To a solution ethyl 1,5-dimethyl-1H-pyrazole-3-carboxylate (intermediate (2)) (20.0 g, 118.984 mmol) in THF:water (4:1) (280 ml, 70 ml) were added ethanol (0.4 ml) and $LiOH{\cdot}H_2O$ (9.985 g, 237.968 mmol) at room temperature. The resulting mixture was stirred at room temperature for 16 hrs. TLC/LCMS showed complete consumption of SM. The reaction mixture was acidified with 3N HCl solution (pH-2) at 0° C. and extracted with ethyl acetate. The organic layer was dried over anhydrous sodium sulphate and concentrated to get 1,5-dimethyl-1H-pyrazole-3-carboxylic acid (83) as light-yellow solid (16 g, 99%). $^1H$ NMR (400 MHz, DMSO) δ 12.42 (s, 1H), 6.45 (s, 1H), 3.77 (s, 3H), 2.25 (s, 3H).

Step 2—Intermediate (84): N-methoxy-N,1,5-trimethyl-1H-pyrazole-3-carboxamide

Procedure: To a stirred solution of 1,5-dimethyl-1H-pyrazole-3-carboxylic acid (intermediate (83)) (16.6 g, 118.571 mmol) in tetrahydrofuran (350.0 ml) was added N,O-Dimethylhydroxylamine hydrochloride (17.34 g, 177.857 mmol). Triethylamine (82.633 ml, 592.857 mmol), 1-(3-Dimethylaminopropyl)-3-ethylcarbodiimide hydrochloride (34.095 g, 177.857 mmol) and 1-Hydroxybenzotriazole (24.032 g, 177.857 mmol) were added and the reaction mixture was stirred at RT for 16 h. TLC was checked which showed formation of product. The reaction was washed with sodium bicarbonate solution and extracted with ethyl acetate. The organic layer was washed with water, brine, dried over anhydrous sodium sulphate and concentrated under reduced pressure. The crude was purified by combiflash using 5% MeOH in DCM to get N-methoxy-N,1,5-trimethyl-1H-pyrazole-3-carboxamide (84) as light-yellow solid (15.0 g, 69.05%). $^1H$ NMR (400 MHz, DMSO) δ 6.41 (s, 1H), 3.76 (s, 3H), 3.67 (s, 3H), 3.32 (s, 3H), 2.26 (s, 3H); LCMS (NH4Oac:ACN): M+H=184, $R_t$=2.17 min in 5 mins run.

Step 3—Intermediate (85): 1-(1,5-dimethyl-1H-pyrazol-3-yl)-2,2-dimethylpropan-1-one Procedure: A stirred solution of N-methoxy-N,1,5-trimethyl-1H-pyrazole-3-carboxamide (intermediate (84)) (15.0 g, 81.922 mmol) in tetrahydrofuran (150.0 ml) was cooled to −50° C. and t-butyllithium (1.7M in pentane) (96.379 ml, 163.844 mmol) was added at −50° C. Then the reaction mixture was stirred at −50° C. for 2 hrs. TLC was checked which showed formation of product and the reaction mixture was quenched with sat. NH4Cl solution. The reaction mixture was diluted with ethyl acetate and washed with water, brine solution. Organic layer was separated and dried over anhydeoua sodium sulphate and concentrated under reduced pressure. The crude was purified by combiflash chromatography using 5% MeOH in DCM to afford 1-(1,5-dimethyl-1H-pyrazol-3-yl)-2,2-dimethylpropan-1-one (85) as light yellow solid (6.0 g, 40.63%). $^1H$ NMR (400 MHz, DMSO) δ 6.45 (s, 1H), 3.79 (s, 3H), 2.25 (s, 3H), 1.31 (s, 9H); LCMS (HCOOH:ACN): M+H=181, $R_t$=1.86 min in 3 mins run.

Step 4—Intermediate (86): 1-(4-bromo-1,5-dimethyl-1H-pyrazol-3-yl)-2,2-dimethylpropan-1-one Procedure: To a solution of 1-(1,5-dimethyl-1H-pyrazol-3-yl)-2,2-dimethylpropan-1-one (intermediate (85)) (6.0 g, 33.309 mmol) in Acetonitrile (100.0 ml) was added N-bromosuccinimide (6.191 g, 34.975 mmol) portion wise at ice cold condition. The resulting reaction mixture was stirred at RT for 16 hrs. TLC and LCMS was checked which showed formation of the product. The reaction mixture was then diluted with ethyl acetate and washed with $Sat{\cdot}NaHCO_3$ solution, water and brine solution. The organic layer was dried over anhydrous sodium sulphate and concentrated under vacuum to afford 1-(4-bromo-1,5-dimethyl-1H-pyrazol-3-yl)-2,2-dimethylpropan-1-one (86) as yellow solid compound (8.0 g, 92.68%) which was used for next step without purification. $^1$H NMR (400 MHz, DMSO) δ 3.86 (s, 3H), 2.25 (s, 3H), 1.30 (s, 9H); LCMS (NH4Oac:ACN): M+H=259, $R_t$=3.59 min in 5 mins run.

Step 5—Intermediate (87): 1-(1,5-dimethyl-4-vinyl-1H-pyrazol-3-yl)-2,2-dimethylpropan-1-one Procedure: To a solution of 1-(1,5-dimethyl-4-vinyl-1H-pyrazol-3-yl)-2,2-dimethylpropan-1-one (intermediate (86)) (7.0 g, 27.129 mmol) in dry N,N-dimethylformamide (100.0 ml) was added Tributylvinyltin (17.2 ml, 54.257 mmol) at room temperature. Then argon was purged through the reaction mixture for 15 min and Pd(PPh3)4 (3.133 g, 2.713 mmol) was added. The reaction mixture was stirred at 110° C. for 16 hrs. TLC was checked which showed starting material was consumed and formation of the desired product. The reaction mixture was then diluted with ethyl acetate and washed with Potassium Fluoride solution the precipitate was filtered through cintre and washed with water and brine, dried over sodium sulphate and concentrated. The crude was purified by column chromatography (100-200) in 10% Ethyl acetate-Hexane to get 1-(1,5-dimethyl-4-vinyl-1H-pyrazol-3-yl)-2,2-dimethylpropan-1-one (87) (5.0 g, 89.35%). $^1$H NMR (400 MHz, DMSO) δ 6.96-6.89 (m, 1H), 5.29-5.20 (m, 2H), 3.82 (s, 3H), 2.31 (s, 3H), 1.30 (s, 9H); LCMS (HCOOH:ACN): M+H=207, $R_t$=2.19 min in 3 mins run.

Step 6—Intermediate (88): 2-(1,5-dimethyl-3-pivaloyl-1H-pyrazol-4-yl)acetaldehyde Procedure: To a solution of 1-(1,5-dimethyl-4-vinyl-1H-pyrazol-3-yl)-2,2-dimethylpropan-1-one (intermediate (87)) (4.1 g, 19.903 mmol) and (diacetoxyiodo)benzene (6.729 g, 20.898 mmol) in acetonitrile (60.0 ml) was added 5% sulfuric acid (3.525 ml) dropwise at −30° C. The mixture was stirred at −30° C. for 1 hour. Upon the completion of the reaction, the residue was treated with ethyl acetate and washed with saturated sodium bicarbonate solution, water and brine solution. The aqueous layer was back-extracted with ethyl acetate and the combined organic layers were dried over anhydrous sodium sulphate, filtered and concentrated in vacuum to get 2-(1,5-dimethyl-3-pivaloyl-1H-pyrazol-4-yl)acetaldehyde (88) (2.7 g, 61.03%). This fraction was then used for next step without purification. $^1$H NMR (400 MHz, DMSO) δ 9.49 (s, 1H), 3.82 (s, 3H), 3.65 (s, 2H), 2.17 (s, 3H), 1.30 (s, 9H); LCMS (NH4Oac:ACN): M+H=223, $R_t$=1.86 min in 3 mins run.

Step 7—Intermediate (89): 1-(4-(2-hydroxyethyl)-1,5-dimethyl-1H-pyrazol-3-yl)-2,2-dimethylpropan-1-one Procedure: To a solution of 2-(1,5-dimethyl-3-pivaloyl-1H-pyrazol-4-yl)acetaldehyde (intermediate (88)) (2.7 g, 12.162 mmol) in ethanol (60.0 ml), sodium borohydride (0.460 g, 12.162 mmol) was added portion wise at ice cold condition. The reaction mixture was stirred at 0° C. for 30 min. Upon the completion of the reaction, the mixture was quenched with sodium bicarbonate solution and diluted with ethyl acetate, washed with water, brine concentrated in vacuum to get crude. This batch was purified by combi flash using 2% MeOH in DCM to give 1-(4-(2-hydroxyethyl)-1,5-dimethyl-1H-pyrazol-3-yl)-2,2-dimethylpropan-1-one (89) (2.1 g, 76.98%) as a colorless oil. $^1$H NMR (400 MHz, DMSO) δ 4.46 (t, 1H), 3.77 (s, 3H) 3.36 (t, 2H), 2.69 (t, 2H), 2.17 (s, 3H), 1.30 (s, 9H); LCMS (HCOOH:ACN): M+H=225, Rt=1.81 min in 3 mins run.

Step 8—Intermediate (90): tert-butyl ((6-(2-(2-(1,5-dimethyl-3-pivaloyl-1H-pyrazol-4-yl)ethoxy)-3,4-difluorophenyl)imidazo[1,2-a]pyridin-3-yl)methyl)(methyl)carbamate Procedure: To a stirred solution of 1-(4-(2-hydroxyethyl)-1,5-dimethyl-1H-pyrazol-3-yl)-2,2-dimethylpropan-1-one (intermediate (89)) (2.3 g, 10.268 mmol) and tert-butyl ((6-(3,4-difluoro-2-hydroxyphenyl)imidazo[1,2-a]pyridin-3-yl)methyl)(methyl)carbamate (3.994 g, 10.268 mmol) in Toluene (40.0 ml) was added CMBP (5.382 ml, 20.536 mmol) at room temperature and the reaction mixture was stirred at 110° C. for 16 hrs. TLC and LCMS were showed formation of product and the reaction mixture was diluted with ethyl acetate and washed with water, brine, dried over anhydrous sodium sulphate and concentrated under reduced pressure. The Crude was purified by combiflash using 5% MeOH-DCM to afford tert-butyl ((6-(2-(2-(1,5-dimethyl-3-pivaloyl-1H-pyrazol-4-yl)ethoxy)-3,4-difluorophenyl)imidazo[1,2-a]pyridin-3-yl)methyl)(methyl)carbamate (90) as a brown sticky gum (3.0 g, 49.05%). $^1$H NMR (400 MHz, DMSO) δ 8.50-8.42 (brs, 1H), 7.62 (s, 1H), 7.53 (d, 1H), 7.30-7.15 (m, 3H), 4.76 (s, 2H), 3.92 (t, 2H), 3.67 (s, 3H), 2.81 (t, 2H), 2.67 (s, 3H), 1.86 (s, 3H), 1.32 (s, 9H), 1.19 (s, 9H); LCMS (HCOOH:ACN): M+H=596, Rt=1.75 min in 5 mins run.

Step 9—Intermediate (91): tert-butyl ((6-(3,4-difluoro-2-(2-(3-(1-hydroxy-2,2-dimethylpropyl)-1,5-dimethyl-1H-pyrazol-4-yl)ethoxy)phenyl)imidazo[1,2-a]pyridin-3-yl)methyl)(methyl)carbamate Procedure: To a solution of tert-butyl ((6-(2-(2-(1,5-dimethyl-3-pivaloyl-1H-pyrazol-4-yl)ethoxy)-3,4-difluorophenyl)imidazo[1,2-a]pyridin-3-yl)methyl)(methyl)carbamate (intermediate (90)) (2.5 g, 4.202 mmol) in methanol (25.0 ml) was added lithium borohydride (0.458 g, 21.008 mmol). The mixture was stirred at ambient temperature for 5 h. Upon the completion of the reaction, solvent was evaporated, diluted with DCM and washed with sodium bicarbonate solution, water, brine. Organic layer was dried over sodium sulphate and concentrated to get crude product. Crude product was purified by prep TLC using 5% MeOH in DCM to afford tert-butyl ((6-(3,4-difluoro-2-(2-(3-(1-hydroxy-2,2-dimethylpropyl)-1,5-dimethyl-1H-pyrazol-4-yl)ethoxy)phenyl)imidazo[1,2-a]pyridin-3-yl)methyl)(methyl)carbamate (91) (1.9 g, 75.66%). $^1$H NMR (400 MHz, DMSO) δ 8.55-8.45 (brs, 1H), 7.63 (s, 1H), 7.60 (d, 1H), 7.38 (d, 1H), 7.35-7.25 (brs, 2H), 4.78 (s, 2H), 4.60 (d, 1H), 4.07 (d, 1H), 3.92-3.88 (m, 1H), 3.84-3.78 (m, 1H), 3.52 (s, 3H), 2.80-2.70 (m, 1H), 2.68 (s, 3H), 2.60-2.52 (brs, 1H), 1.78 (s, 3H), 1.34 (s, 9H), 0.74 (s, 9H); LCMS (NH4OAc:ACN): M+H=598, Rt=3.75 min in 5 mins run.

Step 10—Example 12: 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol Procedure: To a solution of tert-butyl ((6-(3,4-difluoro-2-(2-(3-(1-hydroxy-2,2-dimethylpropyl)-1,5-dimethyl-1H-pyrazol-4-yl)ethoxy)phenyl)imidazo[1,2-a]pyridin-3-yl)methyl)(methyl)carbamate (91) (1.2 g, 2.009 mmol) in diethyl ether (10.0 ml) was added 2M HCl in diethyl ethyl ether (40.0 ml) at 0° C. Reaction mixture was stirred at rt for 3 h. TLC and LCMS showed starting material was consumed. Reaction mixture was evaporated under reduce pressure to get crude. Crude was triturated with diethyl ether and lyophilized to get 1-(4-(2-(2,3-difluoro-6-(3-((methylamino)methyl)imidazo[1,2-a]pyridin-6-yl)phenoxy)ethyl)-1,5-dimethyl-1H-pyrazol-3-yl)-2,2-dimethylpropan-1-ol as light yellow solid (HCl salt) (1.04 g, 96.93 mmol, 49%). $^{1}$H NMR (400 MHz, DMSO) δ 10.02-9.96 (brs, 2H), 9.26 (s, 1H), 8.44 (s, 1H) 8.08 (d, 1H), 7.98 (d, 1H), 7.64 (t, 1H), 7.46-7.40 (m, 1H), 4.75 (s, 3H), 4.16 (s, 1H), 3.97 (t, 2H), 3.71 (s, 3H), 2.87-2.80 (m, 1H), 2.72-2.65 (m, 1H), 2.60 (s, 3H), 2.09 (s, 3H), 0.76 (s, 9H); LCMS (HCOOH:ACN): M+H=498, Rt=2.54 min in 5 mins run; HPLC RT(B3) 8.739 min.

Example 20: 2-[4-(2-{6-[3-(aminomethyl)imidazo[1,2-a]pyridin-6-yl]-2,3-difluorophenoxy}ethyl)-1,5-dimethyl-1H-pyrazol-3-yl]propan-2-ol Example 20 was prepared via the same route as Example 21, starting with tert-butyl N-({6-bromoimidazo[1,2-a]pyridin-3-yl}methyl)-N-[(4-methoxyphenyl)methyl]carbamate to produce The two amine protecting groups were cleaved sequentially using the procedures as used for Example 17 to yield 60 mg (49%) of Example 20. $^{1}$H NMR (d6-DMSO, 400 MHz) δ 8.54 (s, 1H), 7.55 (d, 1H), 7.47 (s, 1H) 7.31 (m, 3H), 4.66 (brds, 1H) 4.07 (s, 2H), 3.95 (t, 2H), 2.83 (m, 2H), 2.40 (brds, 1H), 1.81 (s, 3H), 1.28 (s, 6H); LCMS (HCOOH:ACN): M+H=456.30, $R_t$=1.471 min in 3 mins run; HPLC RT (A4) 5.672 min.

Example 22: 2-{4-[2-(2-{3-[(ethylamino)methyl]imidazo[1,2-a]pyridin-6-yl}-5-fluorophenoxy)ethyl]-1,5-dimethyl-1H-pyrazol-3-yl}propan-2-ol Example 22 was prepared via the same route as Example 18, starting with the corresponding ({6-bromoimidazo[1,2-a]pyridin-3-yl}methyl)(ethyl)amine. The final deprotection step yielded (466 mg, 55%) of Example 22. $^{1}$H NMR (d6-DMSO, 400 MHz) δ 8.51 (s, 1H), 7.54 (d, 1H), 7.48 (s, 1H), 7.43 (t, 1H), 7.32 (d, 1H) 7.05 (d, 1H), 6.878 (t, 1H), 4.80 (s, 1H), 4.12 (t, 2H), 4.07 (s, 2H), 3.54 (s, 3H), 2.94 (t, 2H), 2.55 (q, 2H) 2.26 (s, 3H), 1.87 (s, 3H), 1.40 (s, 6H), 1.01 (t, 3H); LC-MS MH$^{+}$ 466, NH4Oac:ACN, Rt=1.61 min, 3 min run; HPLC RT (A6) 5.257 min.

Example 25: 1-{4-[2-(2,3-difluoro-6-{3-[(methylamino)methyl]imidazo[1,2-a]pyridin-6-yl}phenoxy)ethyl]-1,5-dimethyl-1H-pyrazol-3-yl}-2-methylpropan-1-ol Example 22 was prepared via the same route as Example 24, starting with intermediate (28). The final step deprotection yielded 38 mg, 66% of Example 25. $^{1}$H NMR (d6-DMSO, 400 MHz) δ 8.55 (s, 1H), 7.56 (d, 1H), 7.51 (s, 1H), 7.31 (m, 3H), 4.72 (s, 1H), 4.03 (s, 2H), 3.94 (m, 2H), 3.88 (m, 1H), 3.53 (s, 3H), 2.72 (t, 2H), 2.26 (s, 3H), 0.84 (d, 3H), 0.52 (d, 3H); LC-MS MH+484.36, FA:ACN, Rt=1.52 min, 3 min run; HPLC RT (B1) 9.062 min.

Synthesis of Antibody Drug Conjugate (ADC) Example 1—Trastuzumab-NMT Inhibitor ADC Synthesis of Drug Conjugate 1: (1S,2R,3S,4R,5R)-5-(4-{[({[6-(3,4-difluoro-2-{2-[3-(1-hydroxy-2,2-dimethylpropyl)-1,5-dimethyl-1H-pyrazol-4-yl]ethoxy}phenyl)imidazo[1,2-a]pyridin-3yl]methyl}(methyl)carbamoyl)oxy]methyl}-2-[3-(3-{2-[2-(2,5-dioxo-2,5-dihydro-1H-pyrrol-1-yl)ethoxy]ethoxy}propanamido)propanamido]phenoxy)-3,4-dihydroxy-2-methylcyclohexane-1-carboxylic acid (as hydrate)

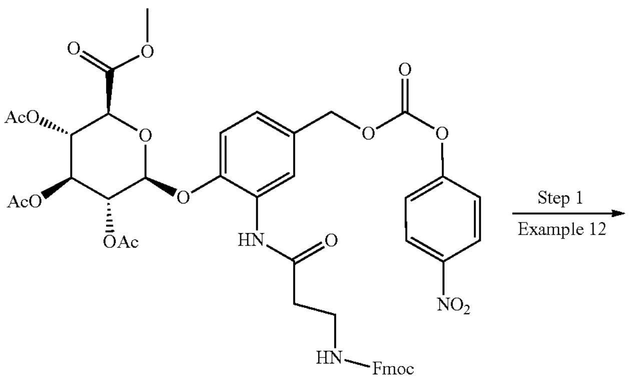

ADC Intermediate 1

-continued
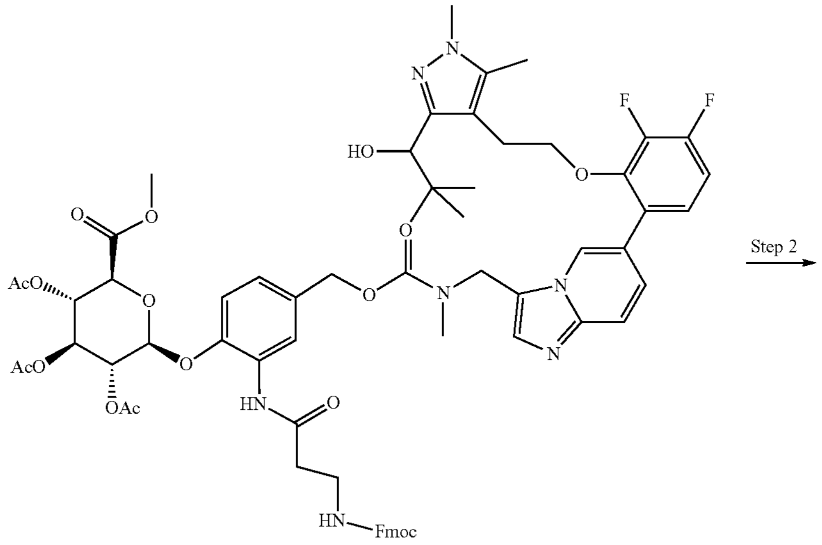
ADC Intermediate 2
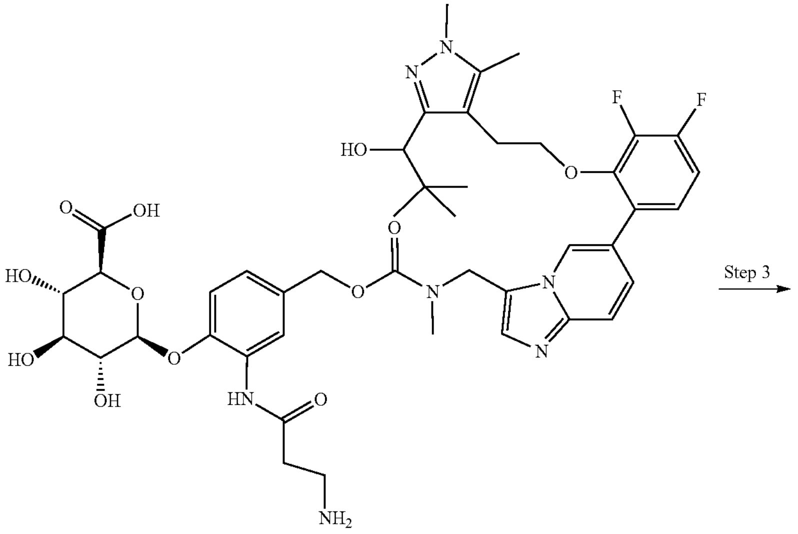
ADC Intermediate 3

-continued

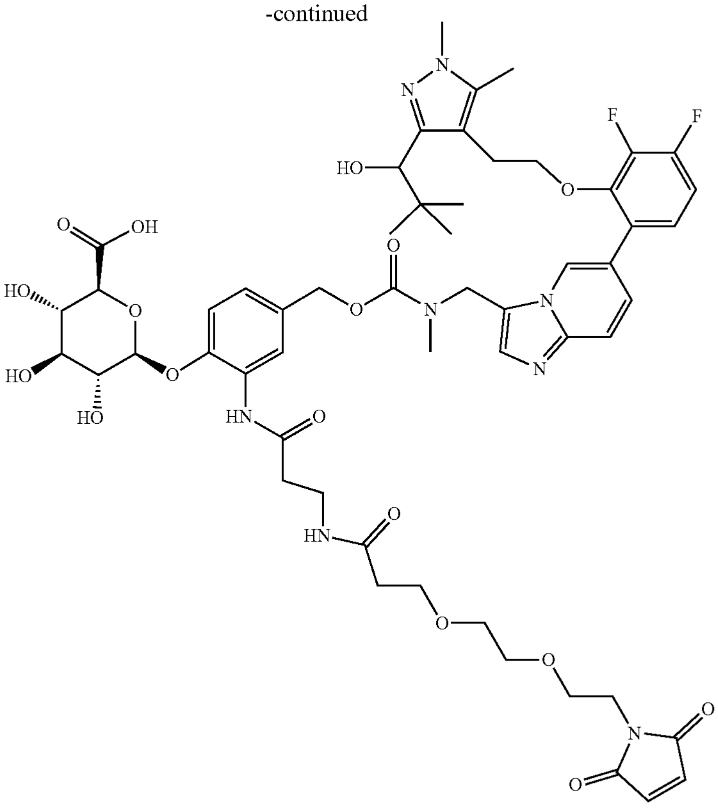

Drug Conjugate 1

Step 1: To a solution of (1S,2R,3S,4R,5R)-5-[2-(3-{[(9H-fluoren-9-yloxy)carbonyl]amino}propanamido)-4-({[(4-nitrophenoxy)carbonyl]oxy}methyl)phenoxy]-2,3,4-trihydroxycyclohexane-1-carboxylic acid (ADC Intermediate 1, 100 mg, 0.11 mmol) (Bioconjugate Chem., 2006, 17, 831-840) in anhydrous DMF (2 mL) was added Example 12 (50 mg), followed by DIEA (40 mL) and HOAt (3 mg), and the reaction was stirred at room temperature (22° C.). After 16 h, the mixture was purified directly by RP-HPLC to give (1S,2R,3S,4R,5R)-5-(4-{[({[6-(3,4-difluoro-2-{2-[3-(1-hydroxy-2,2-dimethylpropyl)-1,5-dimethyl-1H-pyrazol-4-yl]ethoxy}phenyl)imidazo[1,2-a]pyridin-3-yl]methyl}(methyl)carbamoyl)oxy]methyl}-2-(3-{[(9H-fluoren-9-yloxy)carbonyl]amino}propanamido)phenoxy)-2,3,4-trihydroxycyclohexane-1-carboxylic acid (ADC Intermediate 2) as a white solid after lyophilization (107 mg).

Step 2: (1S,2R,3S,4R,5R)-5-(4-{[({[6-(3,4-difluoro-2-{2-[3-(1-hydroxy-2,2-dimethylpropyl)-1,5-dimethyl-1H-pyrazol-4-yl]ethoxy}phenyl)imidazo[1,2-a]pyridin-3-yl]methyl}(methyl) carbamoyl)oxy]methyl}-2-(3-{[(9H-fluoren-9-yloxy)carbonyl]amino}propanamido)phenoxy)-2,3,4-trihydroxycyclohexane-1-carboxylic acid (ADC Intermediate 2, 105 mg) was dissolved in acetonitrile/water (6/4, v/v, 4 mL), and NaOH (1N, aq., 0.5 mL) was added dropwise at room temperature. The mixture was stirred at room temperature for 8 h. HCl (4 N in dioxane, 0.1 mL) was added, and the mixture was purified by RP-HPLC to give (1S,2R,3S,4R,5R)-5-[2-(3-aminopropanamido)-4-{[({[6-(3,4-difluoro-2-{2-[3-(1-hydroxy-2,2-dimethylpropyl)-1,5-dimethyl-1H-pyrazol-4-yl]ethoxy}phenyl)imidazo[1,2-a]pyridin-3-yl]methyl}(methyl)carbamoyl)oxy]methyl}phenoxy]-2,3,4-trihydroxycyclohexane-1-carboxylic acid (ADC Intermediate 3) as a white solid (TFA salt, 42 mg) after lyophilization.

Step 3: To a solution of (1S,2R,3S,4R,5R)-5-[2-(3-aminopropanamido)-4-{[({[6-(3,4-difluoro-2-{2-[3-(1-hydroxy-2,2-dimethylpropyl)-1,5-dimethyl-1H-pyrazol-4-yl]ethoxy}phenyl)imidazo [1,2-a]pyridin-3-yl]methyl}(methyl)carbamoyl)oxy]methyl}phenoxy]-2,3,4-trihydroxycyclohexane-1-carboxylic acid (ADC Intermediate 3, 40 mg) in acetonitrile/water (6/4, v/v, 2 mL) was added Mal-PEG2-Osu (15 mg), followed by DIEA (14 mL). The reaction mixture was stirred at room temperature for 1 h, and purified directly by RP-HPLC to give (1S,2R,3S,4R,5R)-5-(4-{[({[6-(3,4-difluoro-2-{2-[3-(1-hydroxy-2,2-dimethylpropyl)-1,5-dimethyl-1H-pyrazol-4-yl]ethoxy}phenyl) imidazo[1,2-a]pyridin-3-yl]methyl}(methyl)carbamoyl)oxy]methyl}-2-(3-{[(9H-fluoren-9-yloxy)carbonyl]amino}propanamido)phenoxy)-2,3,4-trihydroxycyclohexane-1-carboxylic acid hydrate (Drug Conjugate 1) as a white solid after lyophilization (36 mg).

Preparation of ADC Example 1—Trastuzumab-NMT inhibitor ADC (DAR 5)

Trastuzumab was purchased and reconstituted to yield a 25 mg/mL solution. 5% v/v of 500 mM Tris, 25 mM EDTA, pH 8.5 was added to adjust the pH prior to reduction and conjugation. 2.5 molar equivalents of TCEP (tris(2-carboxyethyl)phosphine) relative to antibody was added from a 10 mM stock in water and the antibody left to reduce for 90 minutes. 8 molar equivalents of Drug Conjugate 1 was added from a 10 mM stock in DMA (dimethylacetamide)

and the reduced antibody allowed to conjugate for 60 minutes. 8 molar equivalents of NAC (N-acetylcysteine) was added from a 10 mM stock in water to quench unreacted Drug Conjugate 1 and allowed to react for 20 minutes. The conjugate was purified by preparative SEC (size exclusion chromatography) using a Superdex 200PG column equilibrated in PBS. The protein containing fractions were pooled and terminally filtered through a suitably sized 0.2 µm PES filter (chromatography direct/FIL-S-PES-022-13-100-S) under grade A laminar flow. The final product was sampled for QC testing—monomer and [ADC] mg/ml by SEC HPLC, average DAR (drug antibody ratio) by PLRP-HPLC (polymeric reverse phase HPLC), Residual NMT inhibitor 1 by RP-HPLC, and endotoxin by Endosafe kinetic chromogenic assay.

ADC Example 3 was prepared using the same method as described for ADC Example 1 except sacituzumab was used as the antibody instead of trastuzumab.

ADC Example 4 was prepared using the same method as described for ADC Example 1 except ifinatamab was used as the antibody instead of trastuzumab.

Preparation of ADC Example 5

ADC Example 5 was prepared using Drug Conjugate 2. Drug Conjugate 2 was prepared using the same method as Drug Conjugate 1 except that NMT inhibitor 21 was used instead of NMT inhibitor 1:

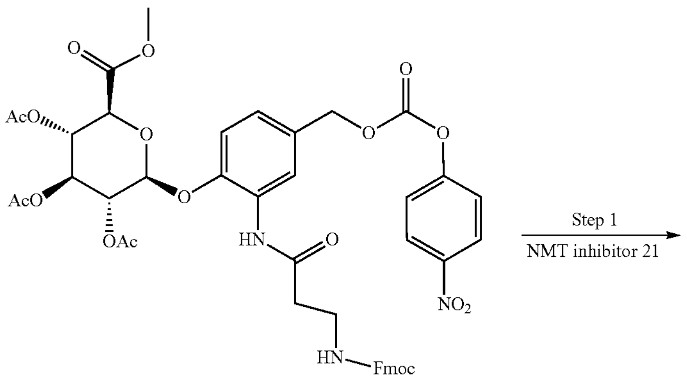

ADC Intermediate 1

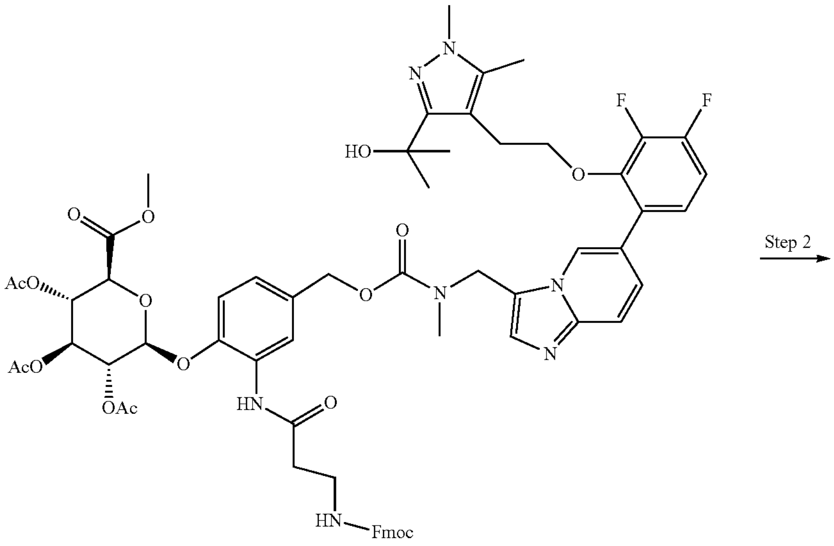

ADC Intermediate 4

-continued

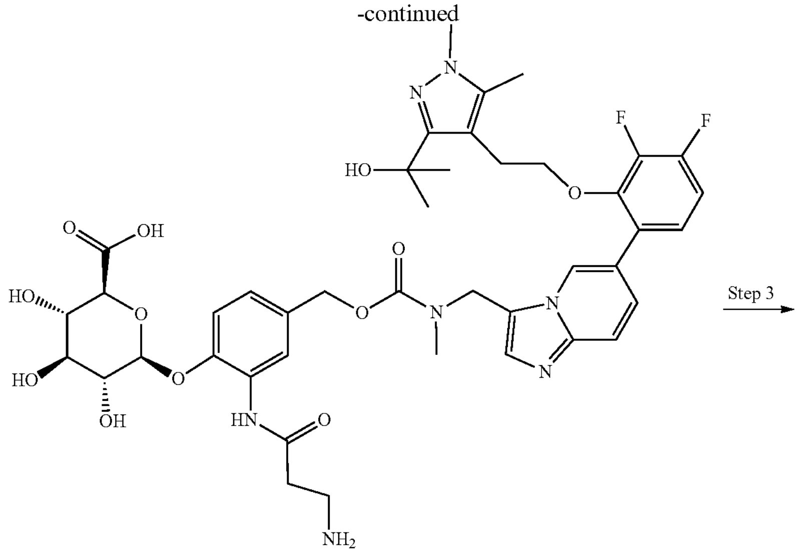

ADC Intermediate 5

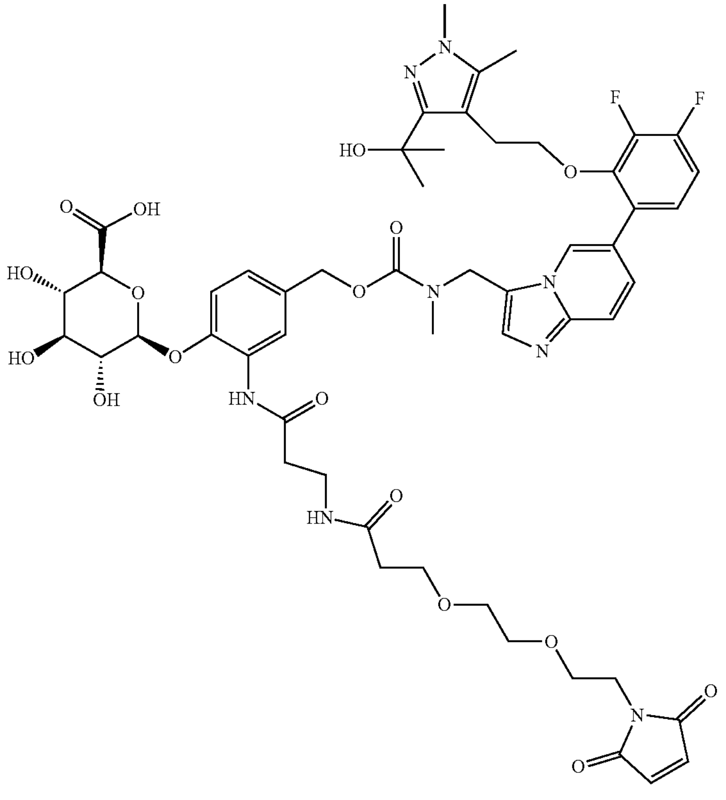

Drug Conjugate 2 wherein Steps 1 to 3 are as described for Drug Conjugate 1.

Herceptin (trastuzumab) was purchased and reconstituted to yield a 25.6 mg/mL solution. 5% v/v of 500 mM Tris, 25 mM EDTA, pH 8.5 was added to adjust the pH prior to reduction and conjugation. 2.55 molar equivalents of TCEP (tris(2-carboxyethyl)phosphine) relative to antibody was added from a 5 mM stock in water and the antibody was left to reduce for 120 minutes. The reduced mAb was diluted 1/3 with PBS prior to conjugation. 8 molar equivalents of Drug Conjugate 2 was added from a 10 mM stock in DMA (dimethylacetamide) and the reduced antibody was allowed to conjugate for 90 minutes. 8 molar equivalents of NAC (N-acetylcysteine) was added from a 100 mM stock in water to quench unreacted Drug Conjugate 2 and allowed to react for 20 minutes. The conjugate was buffer exchanged into PBS using G25 Resin (NAP25 columns) and then dosed with activated carbon at a 1 mg Carbon: 1 mg ADC ratio and allowed to incubate overnight on a roller mixer at 10 rpm at room temperature.

The conjugate was then spun down at 4000×G for 15 minutes to pellet the carbon and the supernatant (ADC) was removed and filtered through a 0.2 μM PES filter. The conjugate was then further purified and concentrated via diafiltration using Amicon15 devices where 6× Diafiltration Volumes (DV's) of PBS, pH 7.4 were used in the buffer exchange. The conjugate was then terminally filtered through a 13 mm 0.2 μm PES filter (chromatography direct/FIL-S-PES-022-13-100-S) under grade A laminar flow and then formulated to 0.02% PS80. The final product was sampled for QC testing—monomer and [ADC] mg/ml by SEC HPLC, average OAR by PLRP, Residual NMT inhibitor by RP-HPLC, and endotoxin by Endosafe.

Preparation of ADC Example 6

ADC Example 6 was prepared using the same method as described for ADC Example 1, except Drug Conjugate 3 was used wherein the linker used was GGFG.

Structure of Drug Conjugate 3:

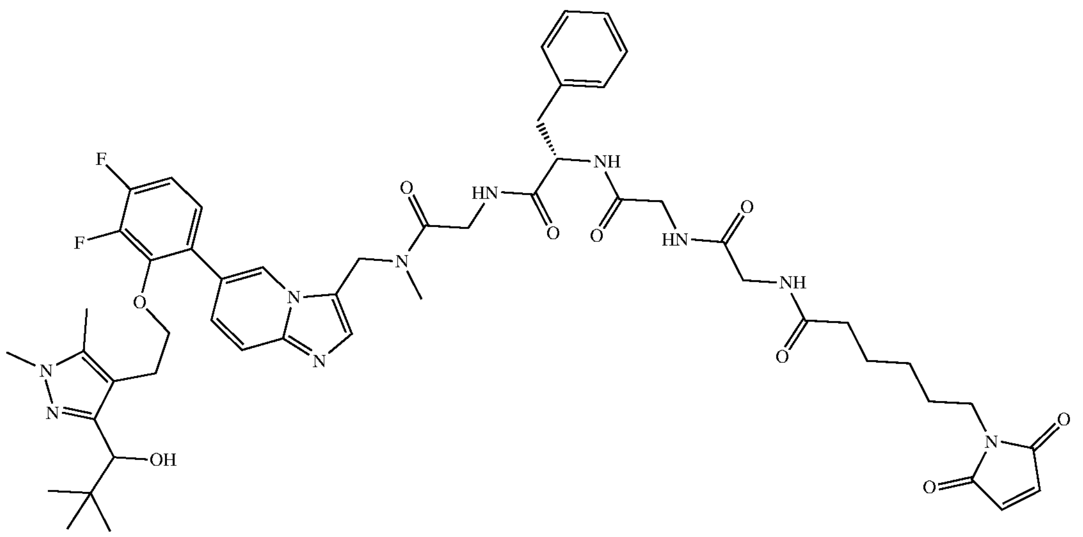 [SMILES: Cc1c(CCOc2c(-c3ccc4ncc(CN(C)C(=O)CNC(=O)[C@H](Cc5ccccc5)NC(=O)CNC(=O)CNC(=O)CCCCCN5C(=O)C=CC5=O)n4c3)ccc(F)c2F)c(C(O)C(C)(C)C)nn1C]

which may be prepared using the same method as Drug Conjugate 1.

BIOLOGICAL EXAMPLES

Biological Example 1: HsNMT1 $IC_{50}$

The $IC_{50}$ values for human NMT1 (HsNMT1) of certain Example compounds, and Comparator Compound 1, were measured using a sensitive fluorescence-based assay based on detection of CoA by 7-diethylamino-3-(4-maleimidophenyl)-4-methylcoumarin, as described in Goncalves, V., et al., Analytical Biochemistry, 2012, 421, 342-344 and Goncalves, V., et al., J. Med. Chem, 2012, 55, 3578.

Results: The HsNMT1 $IC_{50}$ values for certain Example compounds of the invention and Comparator Compound 1, are shown below in Table 1. The results indicate that the tested Example compounds of the invention are highly potent inhibitors of human NMT.

Biological Example 2: Cell Cytotoxicity in SU-DHL-10 Cell Line

Certain Example compounds of the invention and Comparator Compound 1 were tested in the SU-DHL-10 cell line (human B cell lymphoma). Compounds which show efficacy in this assay are expected to be useful as agents for treating or preventing hyperproliferative disorders such as cancer.

Cells were seeded in 96-well microplates and treated with compounds or cisplatin (as a positive control) at 9 increasing concentrations in technical triplicate. $IC_{50}$ of the tested compound and cisplatin were determined following 72 h treatment in each cell line.

1. On day 1, 90 μL of various cell suspensions with the number of cells ranging from 5000-8000 cells/well were seeded into wells of a 96-well plate (Corning). The number of cells to be seeded was previously determined.
2. All 96-wells plates with cells were placed in an incubator overnight at 37° C. with 5% $CO_2$.
3. On day 2, cells were observed under a microscope ensuring the cells treated with vehicle control were in good condition.
4. A dilution series of the test compounds and cisplatin were prepared at 10× the final concentrations required. 10 μL/well of 10× compound solution was added to the corresponding plates. The final volume was 100 μL/well for all the plates. Final DMSO concentration was 0.1%.
5. On day 5 (after 72 hours of incubation), 50 μL of CTG reagent was added to each well.
6. Contents were mixed for 5 minutes on an orbital shaker to facilitate cell lysis.
7. The plate was allowed to incubate at room temperature for 10 minutes to stabilize luminescent signals.

Luminescence was recorded using an EnVision Multi Label Reader. Data analysis was performed using GraphPad Prism 8.0.

To calculate $IC_{50}$, a concentration-response curve was generated using a nonlinear regression model with a sigmoidal concentration response. The formula for calculating the % of viable cells was shown below, and the $IC_{50}$s are automatically generated by GraphPad Prism 8.0.

$$\%\text{ viable cells} = \left(\frac{\textit{LumTest}\text{ article} - \textit{LumMedium}\text{ control}}{\textit{LumNone}\text{ treated} - \textit{LumMedium}\text{ control}}\right) \times 100\%$$

(LumTest article=luminescence in test article treated well; LumNone treated=luminescence in vehicle treated well; LumMedium control=luminescence in a well containing only medium and no cells; LumNone treated-LumMedium control was set as 100%)

Results: $IC_{50}$ values for certain Example compounds of the invention are provided in Table 1, below. Table 1 also shows an $IC_{50}$ value for Comparator Compound 1. The results indicate that the tested compounds of the invention display potent cytotoxic activity. Many of the Example compounds were significantly more potent than Comparator Compound 1.

TABLE 1

Results of Biological Examples 1 and 2

| Example | HsNMT1 $IC_{50}$ (nM) | SU-DHL-10 $IC_{50}$ (nM) |
|---|---|---|
| Comparator Compound 1 | 1.5 | 5.0 |
| 1 | 2.2 | 15.3 |
| 2 | — | — |
| 3 | — | 9.4 |
| 4 | — | 12 |
| 5 | 2.2 | 5.9 |
| 6 | — | 5.0 |
| 7 | 9 | — |
| 8 | — | 0.7 |
| 9 | — | 0.6 |
| 10 | — | 2.0 |
| 11 | — | 0.9 |
| 12 | 2.1 | 0.6 |
| 13 | — | 0.7 |
| 14 | — | 0.4 |
| 15 | — | 1.2 |
| 16 | — | 0.2 |
| 17 | 2.0 | 1.0 |
| 18 | 1.9 | 5.3 |
| 19 | — | — |
| 20 | 2.0 | 12.0 |
| 21 | — | 0.4 |
| 22 | 3.0 | 9 |
| 23 | — | — |
| 24 | — | 0.7 |
| 25 | 2.0 | 1.0 |

Biological Example 3: Cell Cytotoxicity in Additional Cell Lines

The effects of Comparator Compound 1 and certain Example compounds on the viability of various cell lines (LYXFDLBC2835, LYXFDLBC4009 and LYXFDLBC411 (patient-derived xenograft lymphoma), HT1080 (human fibrosarcoma), CA46 (human B cell lymphoma), RKO (human colon carcinoma), NCI-H1703 (human lung squamous cell carcinoma), MX-1 (human breast carcinoma), DU4475 (human breast carcinoma), LU2511 (human lung large cell undifferentiated carcinoma), LU0884 (human lung squamous cell carcinoma)), Panc-1 (human pancreatic carcinoma), MCF-7 (human breast cancer), SW480 (human colon adenocarcinoma) and HCC1806 (human breast ductal carcinoma) were performed using the standard CellTiter-Glo assay (CTG, Promega) as described in Biological Example 2. Compounds which show efficacy in these assays are expected to be useful as agents for treating or preventing hyperproliferative disorders such as cancer.

Results: $IC_{50}$ values for certain Example compounds of the invention are provided in Table 2 below. Table 2 also shows $IC_{50}$ values for Comparator Compound 1. FIGS. 1A to 2B show percentage inhibition values for certain Example compounds, Comparator Compound 1 and cisplatin (as control) which were tested in certain assays listed above. The results indicate that the tested compounds of the invention display potent cytotoxic activity across the different cell lines. The tested Example compounds were more potent than Comparator Compound 1 across the different cell lines.

TABLE 2

$IC_{50}$ values for Comparator Compound 1 and certain Example compounds

| Cell Line | Comparator Compound 1 $IC_{50}$ (nM) | Example 21 $IC_{50}$ (nM) | Example 12 $IC_{50}$ (nM) | Example 14 $IC_{50}$ (nM) |
|---|---|---|---|---|
| LYXFDLBC2835 | 130 | 54 | 10 | — |
| LYXFDLBC4009 | 1540 | 35 | 3 | — |
| LYXFDLBC4113 | 890 | 23 | 3 | — |
| HT1080 | 6.4 | — | — | 1 |
| CA46 | 613 | — | — | 2 |
| RKO | 96 | — | — | 2 |
| NCI-H1703 | 82 | — | — | 4 |
| MX-1 | 40 | — | — | 1.4 |
| DU4475 | >1000 | — | — | 20 |
| LU2511 | 9 | — | 0.07 | — |
| LU0884 | 44 | — | 3 | — |

Biological Example 4: Mouse Xenograft Model

The in vivo efficacy of certain Example compounds was assessed in a subcutaneous xenograft DOHH-2 Lymphoma Model using 10 female 6-8 week old CB17/SCID Mice. Each mouse was inoculated subcutaneously at the right front region with DOHH-2 tumor cells ($5\times10^6$) in 0.1 ml of PBS mixed with matrigel (1:1 PBS:matrigel) for tumor development. The test compound administration started once the mean tumor size reached approximately 100-150 $mm^3$.

Compounds were administered either IP (vehicle 10 mM sodium phosphate+0.2% Tween-80 (pH7.4) or orally (vehicle 15 $Na_2HPO_4$ buffer (10 mM) (pH 4.5)+0.2% tween 80). Tumor volumes were measured in two dimensions using a caliper, and the volume expressed in $mm^3$ using the formula: $V=(L\times W\times W)/2$, where V is tumor volume, L is tumor length (the longest tumor dimension) and W is tumor width (the longest tumor dimension perpendicular to L).

Figure 3:
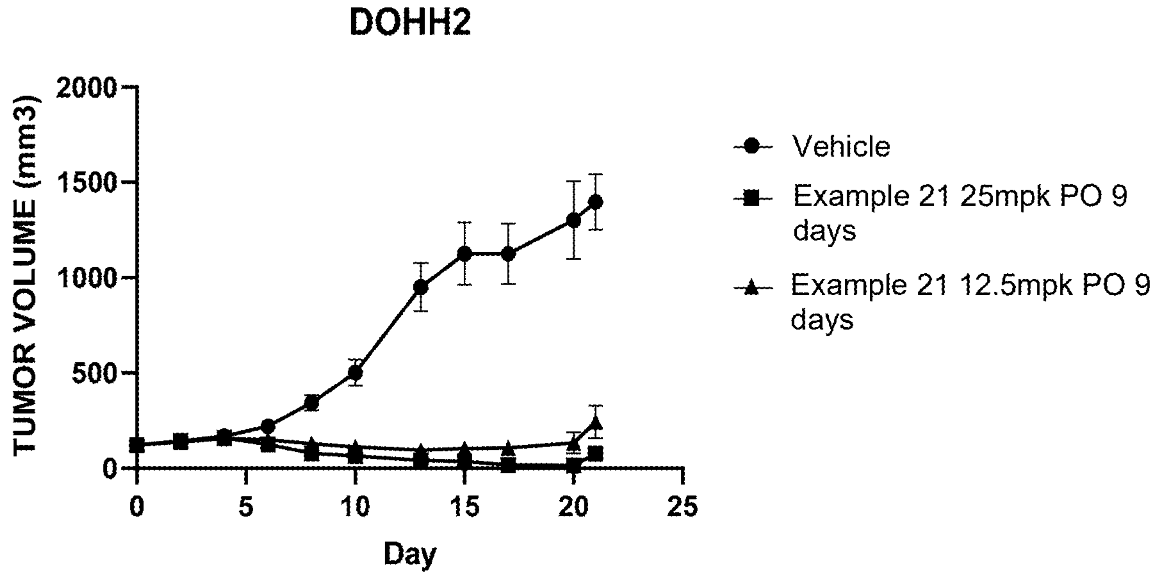
FIG. 3: shows the effect of treatment of Example 21 compared to vehicle on the tumour volume in a DOHH2 xenograft model.
Figure 4:
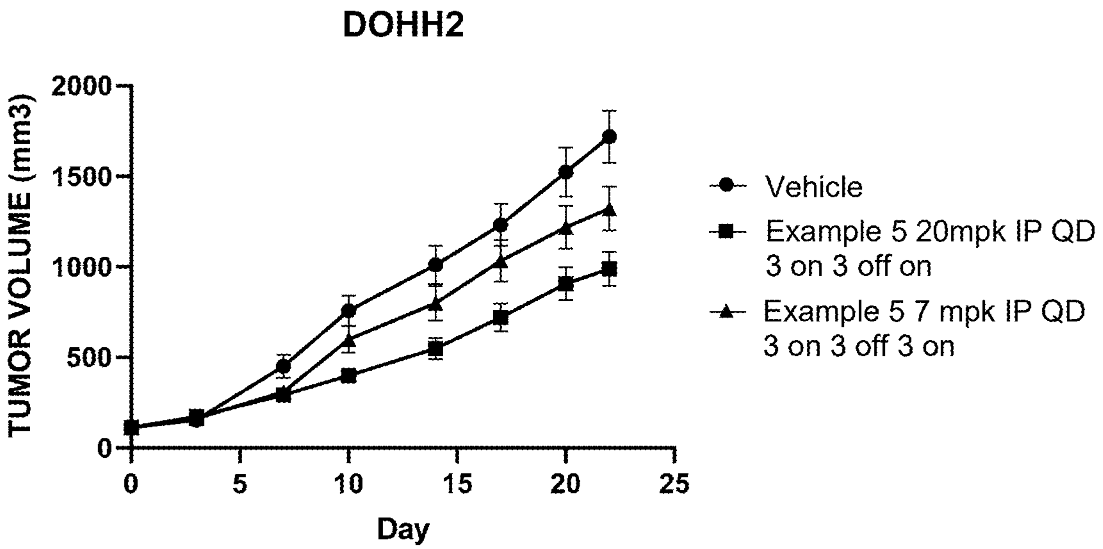
FIG. 4: shows the effect of treatment of Example 5 compared to vehicle on the tumour volume in a DOHH2 xenograft model.
Figure 5:
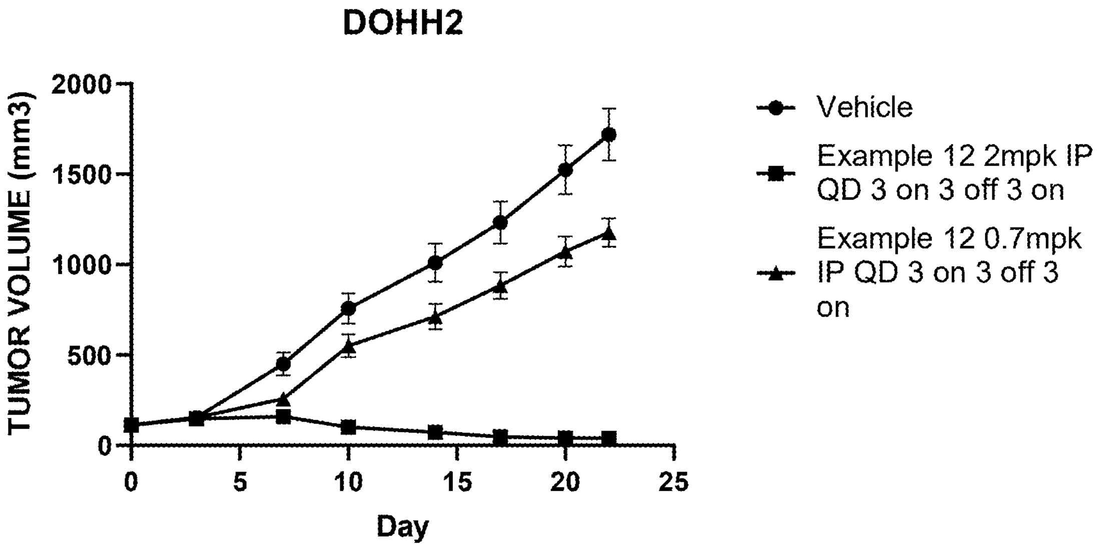
FIG. 5: shows the effect of treatment of Example 12 compared to vehicle on the tumour volume in a DOHH2 xenograft model.
Figure 6:
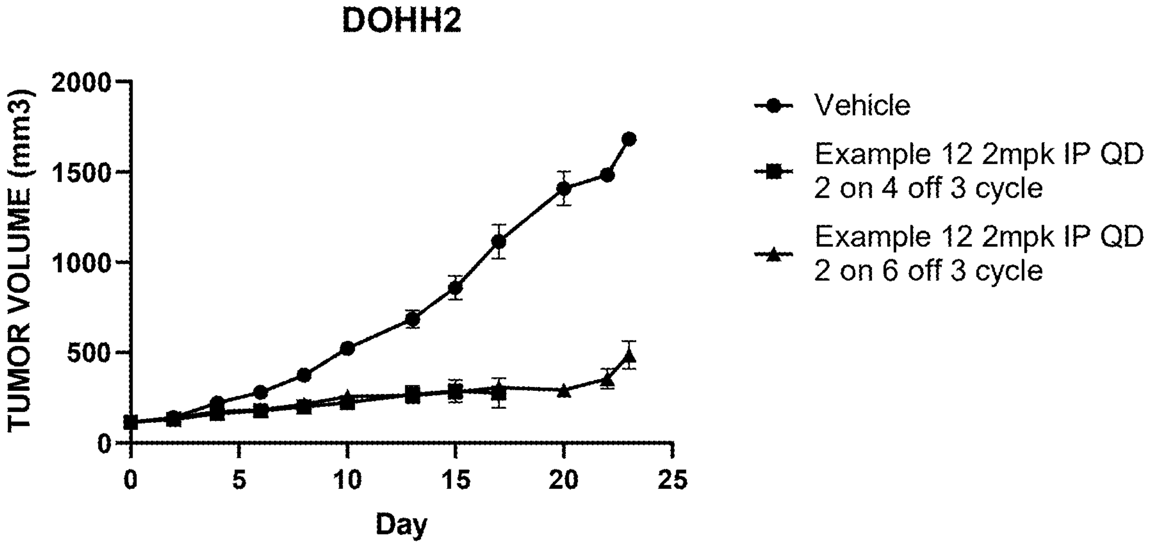
FIG. 6: shows the effect of treatment of Example 12 compared to vehicle on the tumour volume in a DOHH2 xenograft model.

Mice were dosed with Example 21 orally (12.5 or 25 mg/kg) once a day for 9 consecutive days (FIG. 3). Example 5 was dosed intraperitoneally (7 or 20 mg/kg) in a cycle consisting of administration QD for three days followed by a three day no-dosing period followed by QD dosing for a further three days (FIG. 4). Example 12 was dosed intraperitoneally (0.7 or 2 mg/kg) in a cycle consisting of administration QD for three days followed by a three day no-dosing period followed by QD dosing for a further three days (FIG. 5). In a separate study Example 12 was dosed at 2 mg/pk in a cycle consisting of administration QD for two days followed by either four or six day no-dosing period, and this cycle was repeated three times (FIG. 6).

The protocol and any amendment(s) or procedures involving the care and use of animals in this study were reviewed and approved by the Institutional Animal Care and Use Committee (IACUC) of CrownBio prior to execution. During the study, the care and use of animals was conducted in accordance with the regulations of the Association for Assessment and Accreditation of Laboratory Animal Care (AAALAC).

Results: FIGS. 3 to 6 show that intraperitoneal dosing of Examples 5 and 12 and oral dosing of Example 21 lead to a significant reduction in tumour volume or reduced growth in tumour volume when compared to vehicle. The results demonstrate that the high in vitro potency of the tested Example compounds in Biological Examples 2 and 3 (particularly Examples 12 and 21) translates into high in vivo potency.

As such it is expected that the tested Example compounds will be useful as medicaments, in particular the treatment of hyperproliferative disorders such as cancer.

Biological Example 5: Caco-2 Cell Permeability Assay

Certain Example compounds and Comparative Example 1 were tested for their apical to basal (AB) and basal to apical (BA) permeability in Caco-2 cells.

Cell Culture: Caco-2 cells were grown for 10 days in 96-well plates in HBSS buffer containing 10 mM HEPES. Both the apical and basal pH was buffered at pH 7.4. The apical/basal volumes were 75 μl and 250 μl respectively. The incubation time was 2.5 h at 37° C. (without shaking) under 5% $CO_2$ & 95% relative humidity.

Cell Seeding: Cells were seeded at a density of 18750 cells/well (membrane area=0.0804 $cm^2$) in a 96 well plate.

AB Assay: 75 μl of cell suspension was added at a density $2.5\times10^5$ cells/ml to the apical wells. 40 ml media was added to the feeder tray. The plates were placed in the incubator (37° C., 5% $CO_2$ and controlled humidity). The Caco-2 cells were grown for 10 days with a media change on every alternate day.

BA Assay: 25 μl of cell suspension was added at a density of $7.5\times10^5$ cells/ml to the bottom side (keeping the plate upside down) of apical wells. The plate (upside down position) was placed in the incubator (37° C., 5% $CO_2$ and 95% Relative humidity) for 2 h. The plate was turned right side up. 75 μl media was added to the apical wells and 40 ml media to the feeder tray.

Permeablity Assay: The apical and basal wells were washed with buffer (pH 7.4) and 250 μl buffer was added to the wells of the basal plate. 75 μl of compound solution (2 μM, dissolved in water with 1% DMSO) was transferred to the apical wells (n=2). The apical plate was placed onto the basal plate. The lid was placed on to prevent evaporation. The assembly was incubated at 37° C. for 2.5 h (without shaking) under 5% $CO_2$ and 95% relative humidity. After incubation the apical plate was separated from the basal plate. Aliquots were taken out from the acceptor and donor wells, diluted and quantified using LC-MS/MS along with initial donor samples.

Membrane Integrity Test: Solution in the apical wells was discarded by inverting the plate and soaking onto tissue paper. 250 μl buffer (pH 7.4) was added to each well of basal plate and 75 μl of Lucifer Yellow (LY; 0.1 mg/ml) in buffer (pH 7.4) to the wells of apical plate. The apical plate was placed onto the basal plate and the lid used to prevent evaporation. The assembly was incubated at 37° C. for 1 h (without shaking) under 5% $CO_2$ and 95% relative humidity. The apical plate was separated from the basal plate. Fluorescence (Ex: 432 nm, Em: 530 nm) of aliquots (100 ul) was measured from basal wells. Fluorescence of 100 μl buffer (pH 7.4) and 100 μl LY(0.1 mg/ml) was also measured. Wells having more than 1% fluorescence intensity with respect to 0.1 mg/ml LY were considered non-integrated membrane. Such wells, if any, were not considered for permeability calculation.

Calculation: Drug was detected and quantified by LC-MS/MS. Data generated took the form of an apparent permeability (Papp) value. Papp=[Va/(AreaxTime)]×(LC-MS Area of Acceptor sample×Sample dilution factor/LC-MS Area of Initial Donor). Va=Volume of Acceptor Well (in ml)=0.25, Vd=Volume of Donor Well (in ml)=0.075, Area=Surface area of the membrane (cm2)=0.0804, Time=Time of incubation (sec)=9000 Results: The results of the assay are shown in Table 3 below. The results indicate that many of the tested Example compounds are more permeable to cells than Comparator Compound 1 in this assay. Consequently, the tested Example compounds, or at least some of them, are expected to have superior bioavailability than Comparator Compound 1.

Biological Example 6: Rat hepatocyte half life Certain Example compounds and Comparator Compound 1 were tested for metabolic stability in a metabolic assay using mouse- and rat-derived hepatocytes. Compounds having good metabolic stability in the assay are expected to be especially useful as agents for preventing and/or treating cancer, by having a long half-life in human patients.

Frozen pooled rat and mouse hepatocytes obtained from LifeTechnologies were thawed and purified according to the manufacturer's instructions. The test compound (4 mM) in DMSO was diluted with acetonitrile to provide a 100 μM sub-stock then further diluted with pH 7.4 Krebs-Henseleit buffer (supplemented with $CaCl_2$, $NaHCO_3$, HEPES, fructose and glycine) to provide a 2 μM working solution. 25 μL of working solution was incubated at 37° C., treated with 25 μL of rat or mouse hepatocyte suspension (containing $1\times10^6$ cells/mL) and incubated at 37° C. with 5% $CO_2$ level at 95% relative humidity. Wells were incubated for an appropriate time (0, 15, 30, 45, 60 and 75 min) then quenched with 250 μL of acetonitrile containing reference standards diltiazem, 7-ethoxycoumarin and propranolol). The plates were shaken, sonicated for 5 min then cooled to 4° C. until all sampling was complete. All plates were centrifuged at 4000 rpm for 20 min to pellet the debris. 110 μL supernatant was diluted 110 μL water and quantitated using LC-MS/MS.

The results were used to calculate the % Remaining of the test compound at time point t=100×—[(AUC at time point t)/(AUC at T=0)]. A linear regression curve was fitted to a plot of natural logarithm (In) of AUC against time. The T-half (min)=0.693/slope Results: The results of Biological Example 6 are shown in Table 3 below. The results indicate that certain Example compounds exhibit lower metabolic stability than Comparator Compound 1. The combination of high in vitro and in vivo potency (as outlined in Biological Examples 2 to 4) and lower metabolic stability is expected to make the compounds of the invention, or at least some of them, more suitable than Comparator Compound 1 for certain applications, such as payloads for antibody drug conjugates.

TABLE 3

Results of Biological Examples 5 and 6

| Example | Caco-2 A-B ($10^{-6}$ cm/s) | Caco-2 B-A($10^{-6}$ cm/s) | mHeps $t^{1/2}$ (min) | rHeps $t^{1/2}$ (min) |
|---|---|---|---|---|
| Comparator Compound 1 | 0.0 | 9.1 | 127.68 | — |
| 1 | 0.1 | 14.1 | — | 68 |
| 3 | 1.2 | 22.6 | — | — |
| 4 | 1.3 | 24.9 | — | — |
| 5 | 0.195 | 16 | 51.17 | — |
| 6 | 3.04 | 22 | — | 15 |
| 9 | 0.26 | 8.02 | — | — |
| 10 | 0.305 | 8.89 | — | — |
| 11 | 15.9 | 78 | — | — |

TABLE 3-continued

| Results of Biological Examples 5 and 6 | | | | |
|---|---|---|---|---|
| Example | Caco-2 A-B ($10^{-6}$ cm/s) | Caco-2 B-A($10^{-6}$ cm/s) | mHeps $t^{1/2}$ (min) | rHeps $t^{1/2}$ (min) |
| 12 | 0.95 | not tested | — | — |
| 14 | 0.215 | 5.14 | 26.73 | 18 |
| 15 | 1.345 | 7.44 | — | — |
| 16 | 1.395 | 9.06 | — | — |
| 18 | 0.3 | 21.1 | — | — |
| 19 | 3.5 | 29.4 | — | — |
| 23 | 0 | 9.7 | — | — |

Biological Example 7: Orthotopic Breast Cancer Xenograft Model

NOD/SCID mice were implanted with estrogen pellets (17β-estradiol, 60 day release, 0.36 mg) subcutaneously in the right flank one day before the tumour inoculation. On day −8 each mouse was then injected in the right mammary fat pad with $1\times10^7$ viable BT474 breast cancer cells resuspended in 0.2 mL of Phosphate Buffered Saline mixed with matrigel (1:1). Mice were assigned to treatment groups when tumour volumes averaged 149.78 $mm^3$ on study day 0. Dosing commenced the following day, and all animals were dosed intravenously with trastuzumab, Example 12 or ADC Example 1. The study was terminated on Study Day 35.

Figure 7:
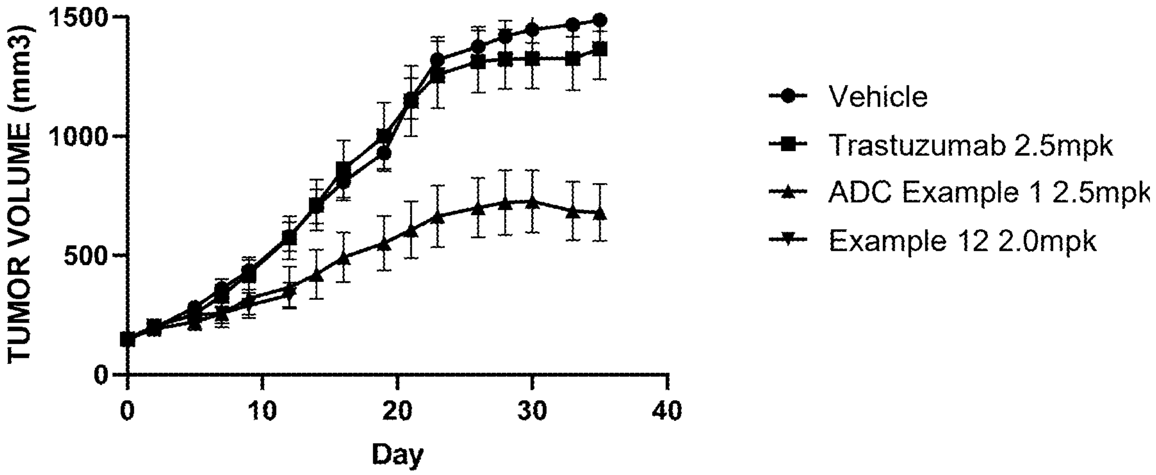
FIG. 7: Shows the effect of treatment with trastuzumab (2.5 mg/Ig), ADC Example 1 (2.5 mg/kg) or Example 12 (2 mg/kg) on tumour volume in a mouse xenograft study.
Figure 8:
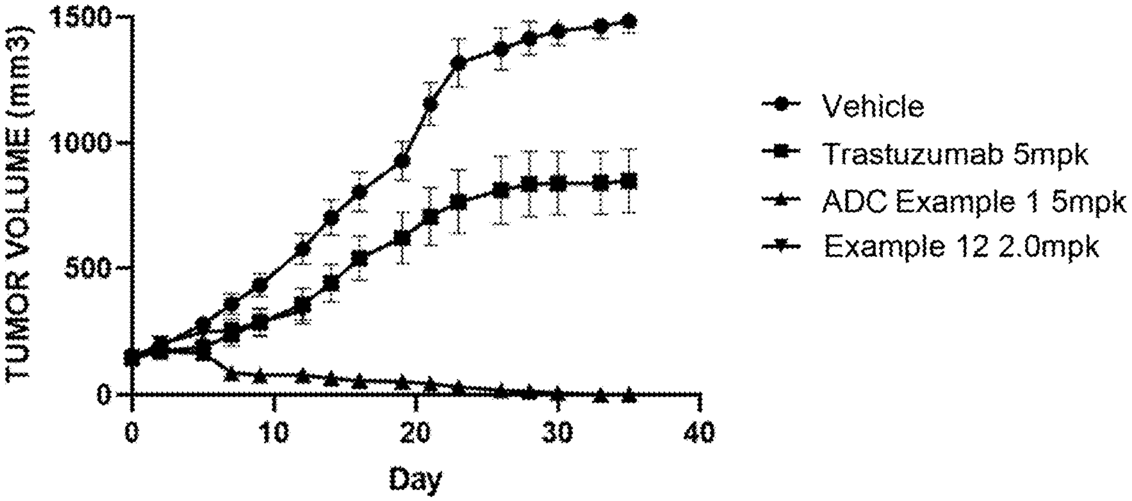
FIG. 8: Shows the effect of treatment with trastuzumab (5 mg/kg), ADC Example 1 (5 mg/kg) or Example 12 (2 mg/kg) on tumour volume in a mouse xenograft study.

Mice were dosed once per week for four weeks with either vehicle alone (Group 1), 2.5 mg/Kg trastuzumab (Group 2), 5 mg/Kg trastuzumab (Group 3), 2.5 mg/Kg ADC Example 1 (Group 4) or 5 mg/Kg ADC Example 1 (Group 5) or 2 mg/Kg Example 12 dosed for 2 days followed by a 5 day holiday (Group 6). Each group was comprised of 10 mice. Tumour volumes in mice were measured three times per week and tumour volume was calculated using the formula 0.5 ($L\times W^2$). The mean tumour volumes (+SEM) for each study group at each measurement are shown in FIGS. 7 and 8 plotted as Last Observation Carried Forward. Statistical analyses were carried out on tumour readings for Groups 1, 2, 3, 4 and 5 up to Study Day 23 (after this point >50% of the animals within one of the study groups were lost; Group 2) using two-way ANOVA, or a Mixed-Effects model was fitted when values were missing from groups (PRISM GraphPad Software Inc.). Statistical analysis of Group 6 was conducted until day 12 (at this point the study was terminated due to the significant loss of observed body weight). Using a ROUT outlier analysis in GraphPad Prism, one mouse in Group 5 was identified as an outlier across all timepoints (at the 5% confidence level) and has therefore been excluded from analysis.

Tumour Growth Inhibition, $\Delta TGI\ \%=((mean(C)-mean(CO))-(mean(T)-mean(TO)))/(mean(C)-mean(CO))\times 100\%$ where T is the mean tumour volume on the measurement day and TO is the mean tumour volume of the treated group on Study Day 0. C is the mean tumour volume of the control Group 1 mice on the measurement day and CO is the mean tumour volume on Study Day 0.

During the study, body weights were measured three times weekly for all animals. Animals were given Diet Gel for the entire duration on the study. The mean body weights for each group during the dosing phase are presented in FIGS. 9 and 10.

Results

The results of treatment with trastuzumab alone or ADC Example 1 on tumour size are depicted as percentage tumour growth inhibition in Table 4, and as tumour volume ($mm^3$) in FIGS. 7 and 8. FIGS. 7 and 8 also depict the tumour volume of mice treated with Example 12 alone, but this study was terminated early due to significant loss of body weight observed in the treatment group.

TABLE 4

| Tumour growth inhibition | | |
|---|---|---|
| Group | Treatment | Tumor growth inhibition % on day 23 |
| 1 | Vehicle | — |
| 2 | trastuzumab 2.5 mg/kg | 3.6% |
| 3 | trastuzumab 5 mg/kg | 46% |
| 4 | ADC Example 1 2.5 mg/kg | 55% |
| 5 | ADC Example 1 5 mg/kg | 110% |

Mice treated with ADC Example 1, 2.5 mg/kg (Group 4) had a significantly reduced tumour volume compared treated to animals receiving trastuzumab, 2.5 mg/kg (Group 2; $p<0.0001$) (FIG. 7). Furthermore, animals treated with ADC Example 1, 5.0 mg/kg (Group 5) had a significantly reduced tumour volume compared to animals treated with trastuzumab, 5 mg/kg (Group 3; $p<0.0001$) (FIG. 8). Mice treated with ADC Example 1, 5.0 mg/kg (Group 5) had a significantly reduced tumour volume compared to animals treated with ADC Example 1, 2.5 mg/kg (Group 4; $p<0.0001$) (see Table 4). Mice treated with ADC Example 1, 5.0 mg/kg (Group 5) had a significantly reduced tumour volume compared to mice treated with 2.0 mg/Kg of Example 12. Mice treated with Example 12, 2.0 mg/kg (Group 6) reduced tumour size (see FIGS. 7 and 8) but due to the significant loss in observed body weight in this study group, the study was stopped at day 13. ADC Example 1 dosed at 2.5 mg/kg was approximately equieffective at that time point compared to Example 12 (Group 4, see FIG. 7) although ADC Example 1 dosed at 5.0 mg/kg was more effective (FIG. 8). The dose of Example 12 delivered when administered as ADC Example 1 dosed at 2.5 mg/kg is approximately 100 fold lower than Example 12 dosed alone, meaning that ADC Example 1 is approximately 100 fold more potent in vivo than Example 12.

Figure 9:
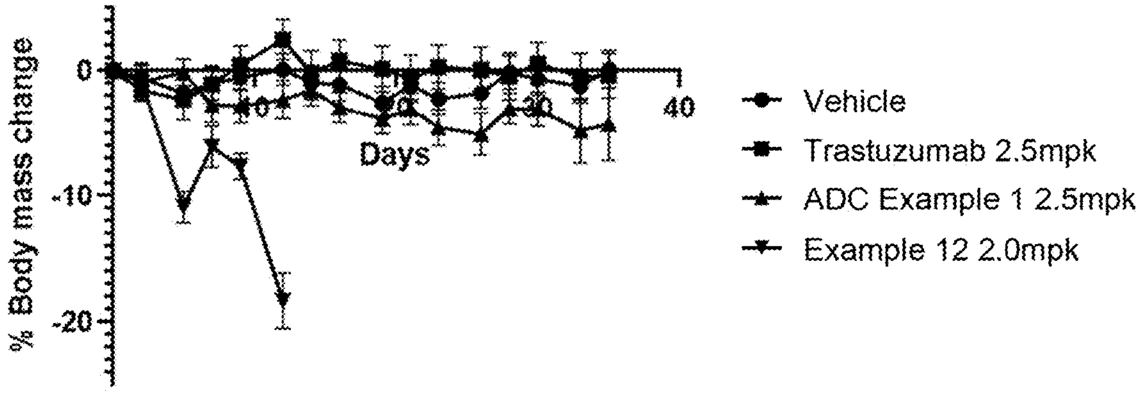
FIG. 9: Shows the effect of treatment with trastuzumab (2.5 mg/kg), ADC Example 1 (2.5 mg/kg) or Example 12 (2 mg/kg) on the body weight of mice in a mouse xenograft study.
Figure 10:
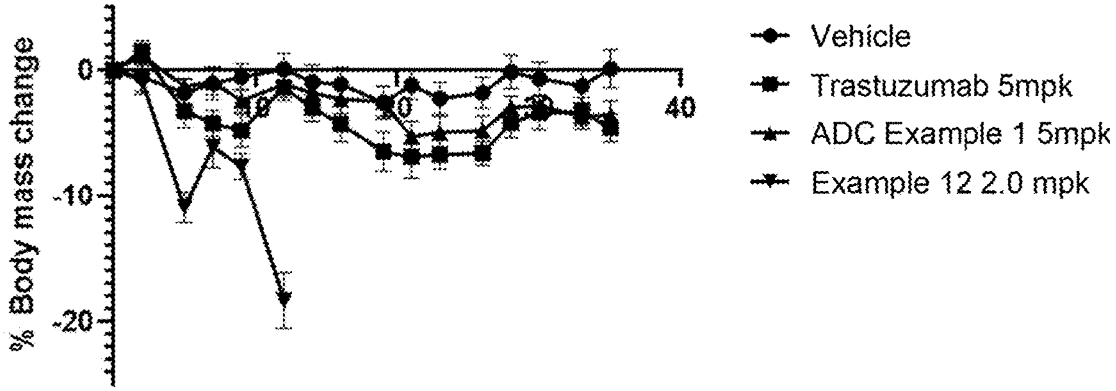
FIG. 10: Shows the effect of treatment with trastuzumab (5 mg/kg), ADC Example 1 (5 mg/kg) or Example 12 (2 mg/kg) on the body weight of mice in a mouse xenograft study.

The effect of treatment with trastuzumab alone, Example 12 alone or ADC Example 1 on the body weights of mice are shown in FIGS. 9 and 10. Mice treated with trastuzumab or ADC Example 1 did not differ significantly from the vehicle control, whilst body weights of mice in Group 6 (Example 12) decreased significantly (FIGS. 9 and 10) before this study was terminated early due to the significant loss in observed body weight.

Biological Example 8: Gastric Cancer Xenograft Model

The objective of this study was to evaluate preclinically the in vivo therapeutic efficacy of an antibody-drug conjugate (ADC Example 1) in the treatment of subcutaneous NCI-N87 human gastric xenograft model in female BALB/c nude mice.

In this study, 143 mice were inoculated subcutaneously in the right flank region with $1\times10^7$ viable NCI-N87 tumour cells resuspended in 0.1 mL of PBS mixed with Matrigel (1:1) for tumour development. 102 mice were assigned to 9 treatment groups on study day 0 when tumour volumes averaged 168.08 $mm^3$. Dosing commenced the following day, and animals were dosed intravenously with vehicle control, trastuzumab, ADC Example 1, trastuzumab deruxtecan and an isotype control antibody conjugated to NMT inhibitor 1 (Isotype control). The study was terminated on study Day 28. Mice were dosed once per week for two weeks with either vehicle control (Group 1), 2.5 mg/Kg trastuzumab (Group 2), 5 mg/Kg trastuzumab (Group 3), 2.5 mg/Kg ADC Example 1 (Group 4), 5 mg/Kg ADC Example 1 (Group 5), 2.5 mg/Kg trastuzumab deruxtecan (Group 6), 5 mg/Kg trastuzumab deruxtecan (Group 7) or 5 mg/Kg isotype control antibody (Group 8).

TABLE 5

Summary of dosing regimen study

| GROUP | TREATMENT | Dose mg/Kg | Schedule | TGI study day 28 |
|---|---|---|---|---|
| 1 | Vehicle | — | QW × 2 weeks | |
| 2 | trastuzumab | 2.5 | QW × 2 weeks | 123.08 |
| 3 | trastuzumab | 5 | QW × 2 weeks | 167.70 |
| 4 | ADC Example 1 | 2.5 | QW × 2 weeks | 153.55 |
| 5 | ADC Example 1 | 5 | QW × 2 weeks | 224.01 |
| 6 | trastuzumab-deruxtecan | 2.5 | QW × 2 weeks | 71.66 |
| 7 | trastuzumab-deruxtecan | 5 | QW × 2 weeks | 140.71 |
| 8 | Isotype control-ADC | 5 | QW × 2 weeks | — |

Figure 11:
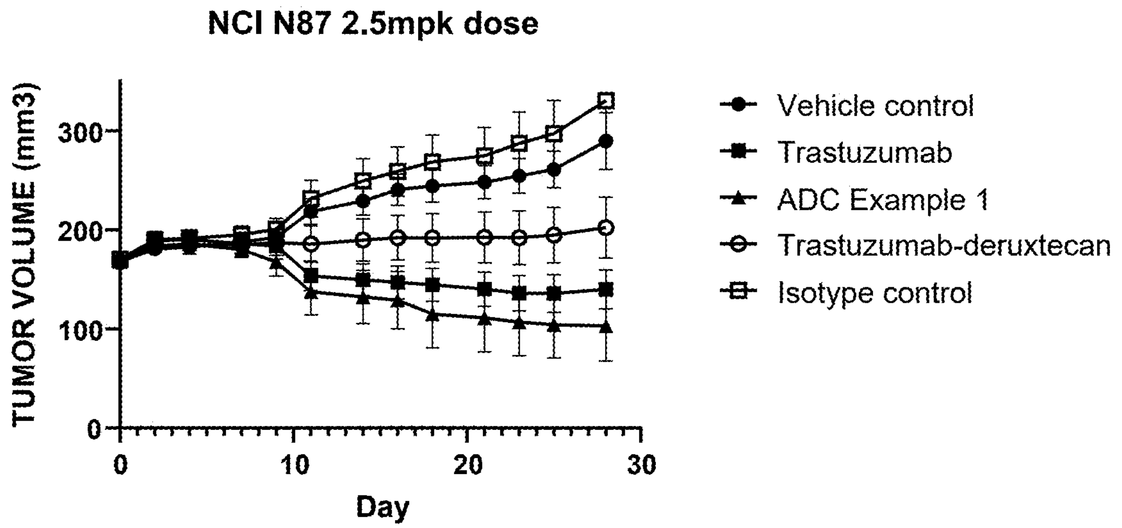
FIG. 11: Shows the effect of treatment with trastuzumab (2.5 mg/kg), ADC Example 1 (2.5 mg/kg), trastuzumab deruxtecan (2.5 mg/kg), and isotype control antibody (5 mg/kg) on tumour volume in a mouse gastric cancer xenograft Model.
Figure 12:
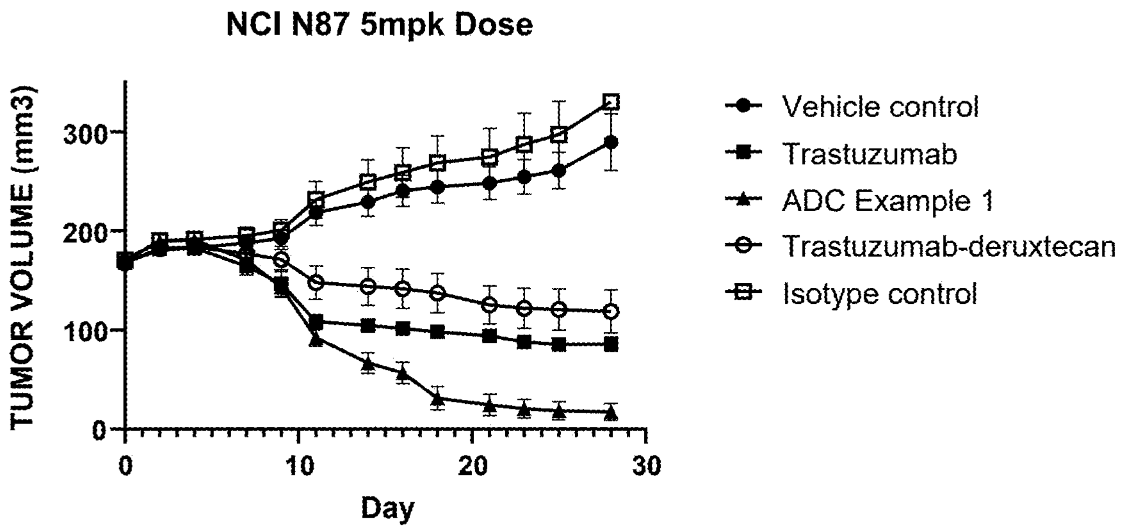
FIG. 12: Shows the effect of treatment with trastuzumab (5 mg/kg), ADC Example 1 (5 mg/kg), trastuzumab deruxtecan (5 mg/kg), and isotype control antibody (5 mg/kg) on tumour volume in a mouse gastric cancer xenograft Model.

Tumour volumes in mice were measured three times per week and tumour volume was calculated using the formula 0.5 (L×W2). The mean tumour volumes (+SEM) for each study group at each measurement are shown in FIGS. 11 and 12.

Tumour Growth Inhibition, ΔTGI %=((mean(C)−mean (CO))−(mean(T)−mean(TO)))/(mean(C)−mean(CO)) *100% where T is the mean tumour volume of the treated group on the measurement day and TO is the mean tumour volume on Study Day 0. C is the mean tumour volume of the control Group 1 mice on the measurement day and CO is the mean tumour volume on Study Day 0.

Figure 13A:
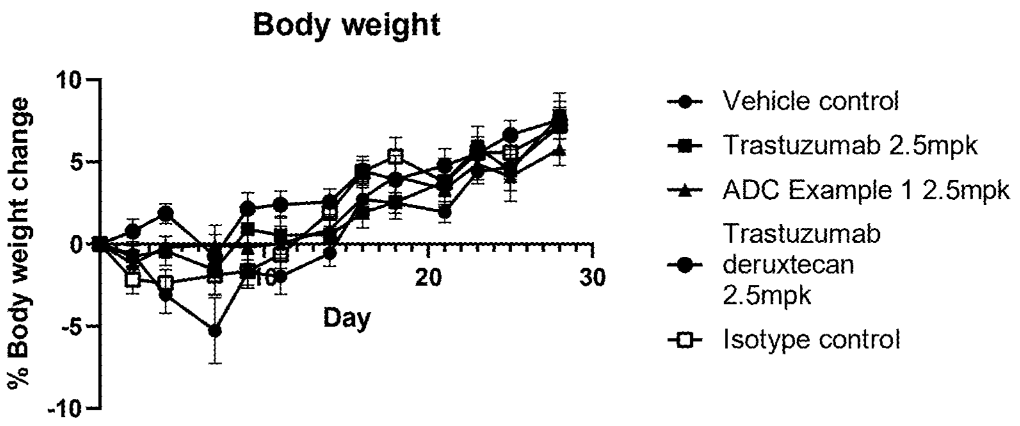
FIG. 13A: Shows the % body weight change of the mice following experiments described in Biological Example 8 (and FIG. 11, 2.5 mg/kg (mpk)).
Figure 13B:
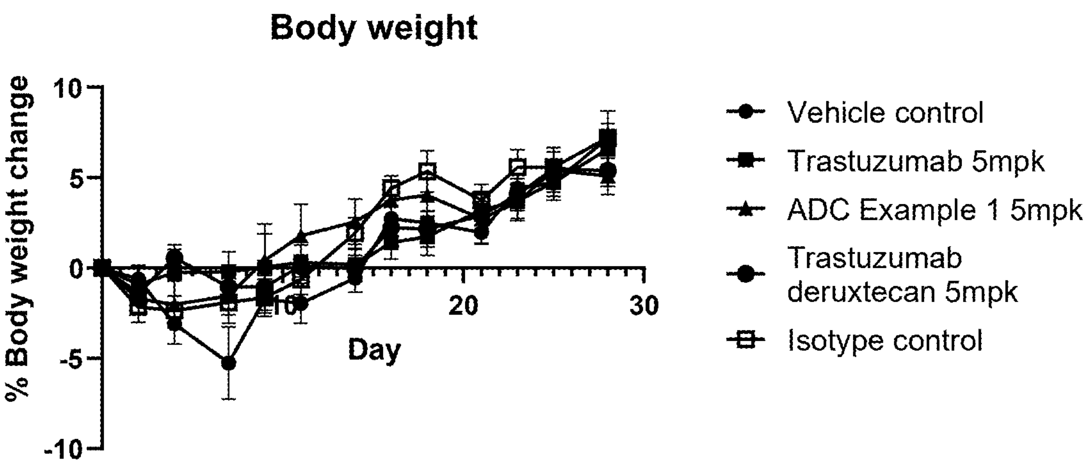
FIG. 13B: Show the % body weight change of the mice following experiments described in Biological Example 8 (and FIG. 12, 5 mg/kg (mpk)).

During the study, body weights were measured three times weekly for all animals. Animals were given Diet Gel for the entire duration on the study. The mean body weights for each group during the dosing phase are presented in FIGS. 13A (2.5 mg/kg) and 13B (5 mg/kg).

Results

Significant body weight loss (>10%) was observed for 3/10 animals in Group 1 (vehicle control); one animal in Group 2 (2.5 mg/Kg trastuzumab) and one animal in Group 3 (5 mg/Kg trastuzumab); all mice regained body weight by the next measurement. No significant body weight loss was observed in any of the other groups.

There was a significant decrease ($p<0.0001$) in the tumour volumes of mice treated with trastuzumab, ADC Example 1 and trastuzumab deruxtecan at all concentrations (2.5 mg/kg or 5 mg/kg), when compared to vehicle alone (Group 1). Isotype control ADC (Group 8; $p=0.7935$) showed no significant difference compared to vehicle alone (Group 1).

Mice treated with trastuzumab 5 mg/kg (Group 3; $p<0.0001$) and ADC Example 1 5 mg/kg (Group 5; $p<0.0001$), showed a significant decrease in tumour volume compared to those treated with trastuzumab 2.5 mg/kg (Group 2). Mice treated with trastuzumab deruxtecan 2.5 mg/kg (Group 6; $p<0.0001$) and Isotype control-ADC (Group 8; $p<0.0001$) showed significantly higher tumour volumes compared to Group 2 (trastuzumab 2.5 mg/kg). There was no significant difference between ADC Example 1 2.5 mg/kg (Group 4; $p=0.8757$) and trastuzumab deruxtecan 5 mg/kg (Group 7; $p=0.9965$) compared to trastuzumab 2.5 mg/kg (Group 2).

Mice treated with ADC Example 1 5 mg/kg (Group 5; $p<0.0001$) showed a significant decrease in tumour volume compared to trastuzumab 5 mg/kg (Group 3). There was no significant difference between Group 3 (trastuzumab 5 mg/Kg) and Group 4 (ADC Example 1 2.5 mg/kg). Otherwise all other groups (Groups 6-8) had significantly higher tumour volume compared to Group 3 (trastuzumab 5 mg/kg).

Mice treated with ADC Example 1 5 mg/kg (Group 5; $p<0.0001$) showed a significant decrease in tumour volume compared to ADC Example 1 2.5 mg/kg (Group 4). There was no significant difference between Group 4 and Group 7 (trastuzumab deruxtecan 5 mg/kg $p=0.9932$). Otherwise all other groups (Groups 6 and 8) had significantly higher tumour volume compared to Group 4 (ADC Example 1 2.5 mg/kg).

Group 5 mice treated with ADC Example 1 5 mg/kg had significantly lower tumour volume compared to all other groups ($p<0.0001$).

Mice treated with trastuzumab deruxtecan 5 mg/kg (Group 7 $p<0.0001$) showed a significant decrease in tumour volume compared to trastuzumab deruxtecan 2.5 mg/kg (Group 6). Group 8 showed significantly higher tumour volume ($p<0.0001$) compared to Group 6.

Mice treated with Isotype control-ADC (Group 8; $p<0.0001$) had significantly higher tumour volume compared to Group 7 (trastuzumab deruxtecan 5 mg/kg).

Increased tumour growth inhibition (TGI) compared to the vehicle group (Group 1) was apparent in all treatment groups other than Groups 8. Treatment with 5.0 mg/kg ADC Example 1 was the most efficacious when the tumour growth inhibition of all treatment groups was compared (Group 5; TGI=224.01%).

$$TGI = (\text{mean } \mathit{tumour} \text{ volume of vehicle group} - \text{mean } \mathit{tumour} \text{ volume of treatment group})/(\text{mean } \mathit{tumour} \text{ volume of vehicle group} - \text{mean initial } \mathit{tumour} \text{ volume}) \times 100$$

Biological Example 9: LNCaP Prostate Cancer Xenograft Model

The objective of the study was to evaluate the efficacy of ADC Example 4 in male NOD SCID mice bearing LNCaP tumours.

A total of 84 male NOD SCID mice aged 5-8 weeks and weighing 25-30 g were used for the study. $1\times10^7$ LNCaP tumour cells at 78% viability and approximately 70-80% confluency were implanted subcutaneously onto the flank of male NOD SCID mice. When tumours reached approximately 80-100 $mm^3$, animals were assigned to treatment groups as demonstrated below in Table 6, allocating 10 mice per group with a similar mean and distribution of tumour volumes to each group. Mice were treated with vehicle alone, unconjugated ifinatamab, ifinatamab-deruxtecan (ifinatamab-DXd) or ADC Example 4.

TABLE 6

| Dosing regimen for Biological Example 11 | | | | | |
|---|---|---|---|---|---|
| Group | n | Treatment | Dose | Route | Dosing frequency |
| 1 | 10 | Vehicle (PBS + 0.02% PS80) | — | IV | Q7D (three total doses) |
| 2 | 10 | ifinatamab | 10 mg/kg | IV | Q7D (three total doses) |
| 3 | 10 | ifinatamab | 5 mg/kg | IV | Q7D (three total doses) |
| 4 | 10 | ifinatamab-DXd | 10 mg/kg | IV | Q7D (three total doses) |
| 5 | 10 | ifinatamab-DXd | 5 mg/kg | IV | Q7D (three total doses) |
| 6 | 10 | ADC Example 4 | 10 mg/kg | IV | Q7D (three total doses) |
| 7 | 10 | ADC Example 4 | 5 mg/kg | IV | Q7D (three total doses) |

Duration of observation: 35 days.
Dosing volume: 5 mL/kg for all IV doses

Figure 15:
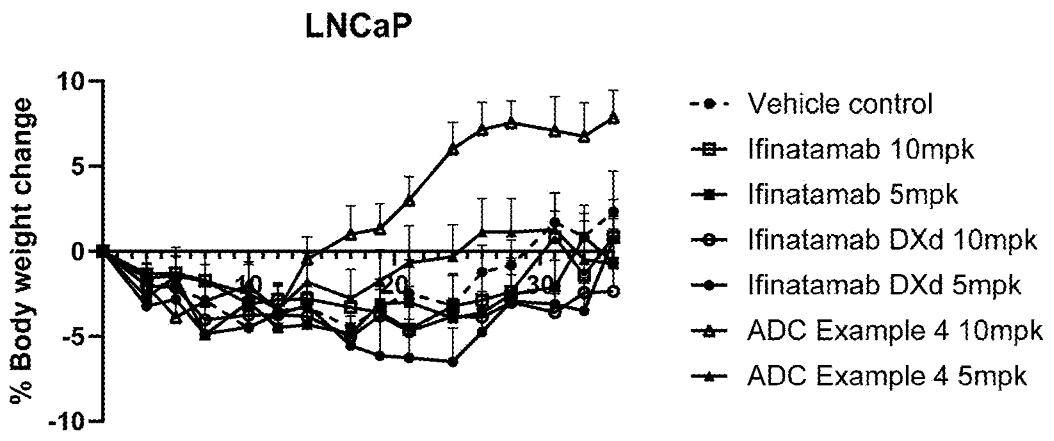
FIG. 15: Shows the effect of treatment with ifinatamab (5 mg/kg and 10 mg/kg), ifinatamab-DXd (5 mg/kg and 10 mg/kg), ADC Example 4 (5 mg/kg and 10 mg/kg) and vehicle control on body weight in a mouse LNCaP prostate cancer xenograft model.

During the course of the study, no adverse responses to any doses were observed and the mean bodyweight of each group remained within 10% of the pre-treatment level (FIG. 15).

Individual cases of bodyweight loss >10% were observed at various points in the study. Three weeks after the first animal entered treatment, DietGel was provided to all mice to ameliorate bodyweight loss. No animals were euthanised early due to the bodyweight loss and these instances of weight loss were likely to be associated with tumour burden.

Animals that received three Q7D doses of ADC Example 4 at 10 mg/kg showed a significantly higher mean bodyweight than those receiving vehicle control treatments on day 28 of the study (One way ANOVA, Dunnett's p=0.0046). At this timepoint, no other treatment groups significantly differed from the vehicle in bodyweight.

Two animals were terminated early due to welfare concerns. The first was euthanized on day 26 of treatment with 10 mg/kg ifinatamab, while the second was euthanized on day 33 of treatment with 5 mg/kg ifinatamab-DXd. Both animals were primarily euthanized due to gasping. Necropsies on each recorded large spontaneous thymic tumours.

Tumours in the vehicle treatment group grew steadily during the study, reaching a mean volume of 752±89.4 $mm^3$ by day 28 of the study.

Figure 14:
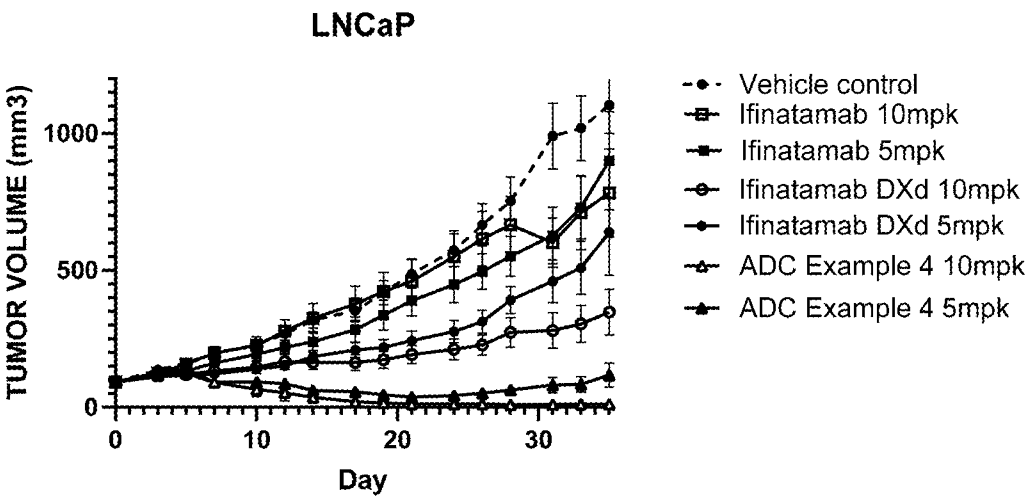
FIG. 14: Shows the effect of treatment with ifinatamab (5 mg/kg and 10 mg/kg), ifinatamab-DXd (5 mg/kg and 10 mg/kg), ADC Example 4 (5 mg/kg and 10 mg/kg) and vehicle control on tumour volume in a mouse LNCaP prostate cancer xenograft model.

Treatment with ifinatamab at either 10 mg/kg or 5 mg/kg had no significant effect on LNCaP tumour volume at day 28, and animals receiving this therapy showed a largely similar tumour growth curve to those treated with vehicle alone (FIG. 14, Table 7).

Treatment with ifinatamab-DXd at 10 mg/kg significantly reduced the mean volume of LNCaP tumours by day 28 compared to the vehicle control. Animals receiving this therapy largely showed a lower rate of tumour growth than control animals. At a dosage of 5 mg/kg ifinatamab-DXd slowed the growth of LNCaP tumours to a lesser extent (FIG. 14, Table 7).

All animals that were dosed with 10 mg/kg ADC Example 4 showed tumour regression within three weeks of starting treatment (FIG. 14, Table 7) this therapy produced a significant reduction in mean tumour volume (Mann-Whitney) from day 7 onwards compared to the vehicle. By day 28, each tumour had regressed to 525% of their volume at the start of treatment.

Likewise, animals receiving 5 mg/kg ADC Example 4 showed a significant reduction in tumour volume from days 7 to 28 compared to the control group (Mann-Whitney) (FIG. 14, Table 7). By day 28 all but one animal showed a lower tumour volume than recorded at the start of treatment.

TABLE 7

Tumour volume comparison of treatment groups. Adjusted p value calculated by Kruskal-Wallis test and Dunn's multiple comparisons relative to vehicle control.

| Treatment Group | Day 28 tumour volume ($mm^3$, mean ± SEM) | Adj p value vs. vehicle (TV) | Tumour growth inhibition (TGI, %) |
|---|---|---|---|
| G1: Vehicle | 752.4 ± 89.4 | — | — |
| G2: ifinatamab, 10 mg/kg, IV; Q7D (×3) | 666.56 ± 103.2 | >0.9999 (ns) | 13.0 |
| G3: ifinatamab, 5 mg/kg, IV; Q7D (×3) | 551.4 ± 73.1 | >0.9999 (ns) | 30.6 |
| G4: ifinatamab-DXd, 10 mg/kg, IV; Q7D (×3) | 259.5 ± 50.3 | 0.0251 (*) | 75.0 |
| G5: ifinatamab-DXd, 5 mg/kg, IV; Q7D (×3) | 364.6 ± 51.7 | 0.1836 (ns) | 58.8 |
| G6: ADC Example 4, 10 mg/kg, IV; Q7D (×3) | 10.1 ± 2.3 | <0.0001 (****) | 112.4 |
| G7: ADC Example 4, 5 mg/kg, IV; Q7D (×3) | 63.2 ± 16.4 | <0.0001 (****) | 104.4 |

Biological Example 10: VcaP Prostate Cancer Xenograft Model

The objective of this study was to evaluate preclinically the in vivo therapeutic efficacy of ADC Example 4 in the treatment of subcutaneous VcaP human prostate cancer xenograft model in non-castrated male CB17/SCID mice.

In this study, 144 mice were inoculated subcutaneously in the right front flank region with $1\times10^7$ viable VcaP tumour cells resuspended in 0.1 mL of PBS mixed with Matrigel (1:1) for tumour development on Study Day −20. 80 mice were assigned to 8 treatment groups when tumour volumes averaged ~162.16 $mm^3$ on Study Day 0. Dosing commenced the following day and all animals were dosed intravenously with ADC Example 4, ifinatamab-deruxtecan (ifinatamab-Dxd) or unconjugated ifinatamab. All mice received two doses of test agent, on Study Day 1 and Study Day 8. The study was terminated on Study Day 30.

The 8 groups were assigned as follows:

| | |
|---|---|
| Group 1 | Vehicle control |
| Group 2 | Unconjugated ifinatamab 5 mpk |
| Group 3 | Unconjugated ifinatamab 2.5 mpk |
| Group 4 | ifinatamab-deruxtecan 5 mpk |
| Group 5 | ifinatamab-deruxtecan 2.5 mpk |
| Group 6 | ADC Example 4 10 mpk |
| Group 7 | ADC Example 4 5 mpk |
| Group 8 | ADC Example 4 2.5 mpk |

Figure 17:
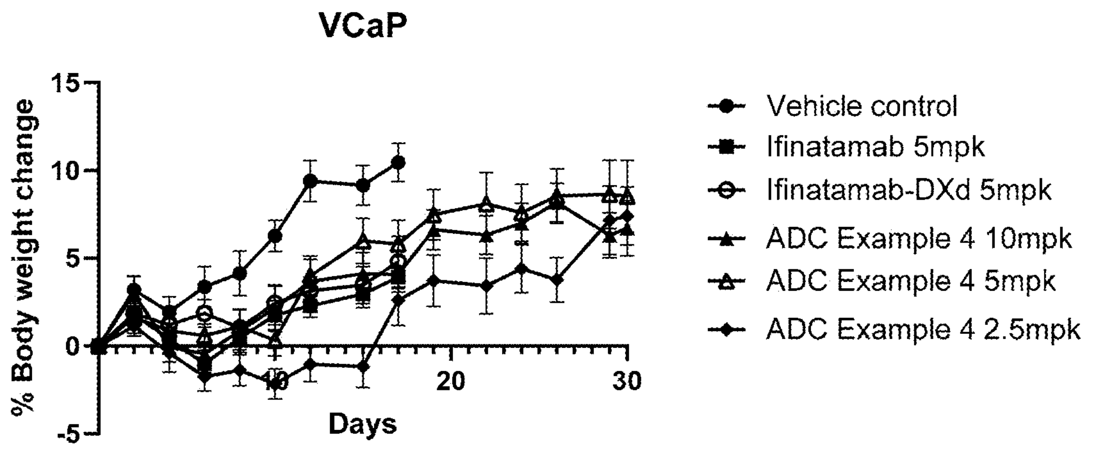
FIG. 17: Shows the effect of treatment with ifinatamab (5 mg/kg), ifinatamab-DXd (5 mg/kg), ADC Example 4 (2.5 mg/kg, 5 mg/kg and 10 mg/kg) and vehicle control on body weight in a mouse VCaP prostate cancer xenograft model.

No significant body weight loss was observed in any of the animals on study (FIG. 17).

Figure 16:
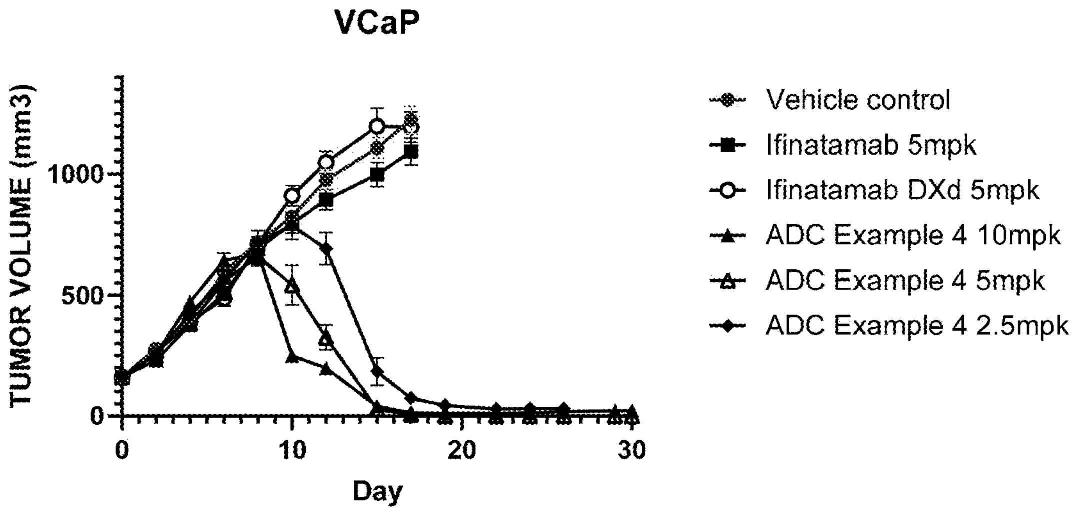
FIG. 16: Shows the effect of treatment with ifinatamab (5 mg/kg), ifinatamab-DXd (5 mg/kg), ADC Example 4 (2.5 mg/kg, 5 mg/kg and 10 mg/kg) and vehicle control on tumour volume in a mouse VCaP prostate cancer xenograft model.

There was a significant decrease ($p<0.0001$) in the tumour volumes of mice treated with ADC Example 4 at all concentrations (Group 8, 2.5 mg/kg; Group 7, 5 mg/kg and Group 6; 10 mg/kg), when compared to vehicle alone (Group 1). Ifinatamab-Dxd 5 mg/kg (Group 4; p=0.0078) showed a significantly higher tumour volume compared to vehicle alone (Group 1), while ifinatamab-Dxd 2.5 mg/kg (Group 5; p=0.8127) and unconjugated infinatamab at both concentrations (Group 2; p=0.1104 and Group 3; p=0.6703) showed no significant difference compared to vehicle alone (Group 1), see FIG. 16.

Mice treated with ADC Example 4 at all three concentrations (Group 6, 10 mg/kg; Group 7, 5 mg/kg and Group 8, 2.5 mg/kg) showed significant decreases in tumour volume compared to all other treatment groups (Groups 2-5; $p<0.0001$). There was also evidence of a dose response, with the greatest tumour volume reduction in Group 6 (10 mg/kg), then Group 7 (5 mg/kg), followed by Group 8 (2.5 mg/kg); significant differences were observed between each group ($p<0.0001$), see FIG. 16.

There was no significant difference in tumour volume between mice treated with ifinatamab-Dxd 2.5 mg/kg (Group 5) and Groups 2, 3 and 4 (unconjugated ifinatamab 5 mg/kg, unconjugated ifinatamab 2.5 mg/kg, ifinatamab-Dxd 5 mg/kg, respectively). Mice treated with ifinatamab-Dxd 5 mg/kg (Group 4) had significantly higher tumour volume compared to those treated with unconjugated ifinatamab 5 mg/kg (Group 2, p=0.0002) and unconjugated ifinatamab 2.5 mg/kg (Group 3, p=0.0216), see FIG. 16.

Increased tumour growth inhibition (ΔTGI) compared to the vehicle group (Group 1) was apparent in all treatment groups. Treatment with 10 mg/kg and 5 mg/kg ADC Example 4 were the most efficacious when the tumour growth inhibition of all treatment groups was compared (Group 6; ΔTGI=114.03% and Group 7; ΔTGI=114.69%), see Table 8.

TABLE 8

Dosing regimen for Biological Example 10 and Results

| Group | Treatment Description | Test Article Dose (mg/kg) | Schedule | ΔTGI (Study Day 17) |
|---|---|---|---|---|
| 1 | Vehicle - PBS + 0.02% PS80 pH 7.4 | — | QW × 2 weeks | — |
| 2 | Unconjugated ifinatamab | 5 | QW × 2 weeks | 12.44 |
| 3 | Unconjugated ifinatamab | 2.5 | QW × 2 weeks | 8.47 |
| 4 | ifinatamab-Dxd | 5 | QW × 2 weeks | 2.86 |
| 5 | ifinatamab-Dxd | 2.5 | QW × 2 weeks | 5.24 |
| 6 | ADC Example 4 | 10 | QW × 2 weeks | 114.03 |
| 7 | ADC Example 4 | 5 | QW × 2 weeks | 114.69 |
| 8 | ADC Example 4 | 2.5 | QW × 2 weeks | 108.31 |

Biological Example 11: JIMT-1 Breast Cancer Xenograft Model

The objective of this study was to evaluate preclinically the in vivo therapeutic efficacy of ADC Example 3 in the treatment of subcutaneous JIMT-1 human breast xenograft model in female NOD/SCID mice.

In this study, 128 mice were inoculated subcutaneously in the right front flank region with $5\times10^6$ viable JIMT-1 tumour cells resuspended in 0.1 mL of PBS for tumour development on Study Day −15. 80 mice were assigned to 8 treatment groups when tumour volumes averaged ~160.66 $mm^3$ on Study Day 0. Dosing commenced the following day and all animals were dosed intravenously with ADC Example 3, sacituzumab govitecan or unconjugated sacituzumab. The study was terminated on the Study Day 60. The 8 groups were assigned as follows:

| | |
|---|---|
| Group 1 | Vehicle control |
| Group 2 | Unconjugated sacituzumab 5 mpk |
| Group 3 | Unconjugated sacituzumab 2.5 mpk |
| Group 4 | sacituzumab govitecan 5 mpk (ADC Example 3, 5 mg/kg added on Days 27 and 34) |
| Group 5 | sacituzumab govitecan 2.5 mpk (ADC Example 3, 5 mg/kg added on Day 27) |
| Group 6 | ADC Example 3 10 mpk |
| Group 7 | ADC Example 3 5 mpk |
| Group 8 | ADC Example 3 2.5 mpk |

Figure 20:
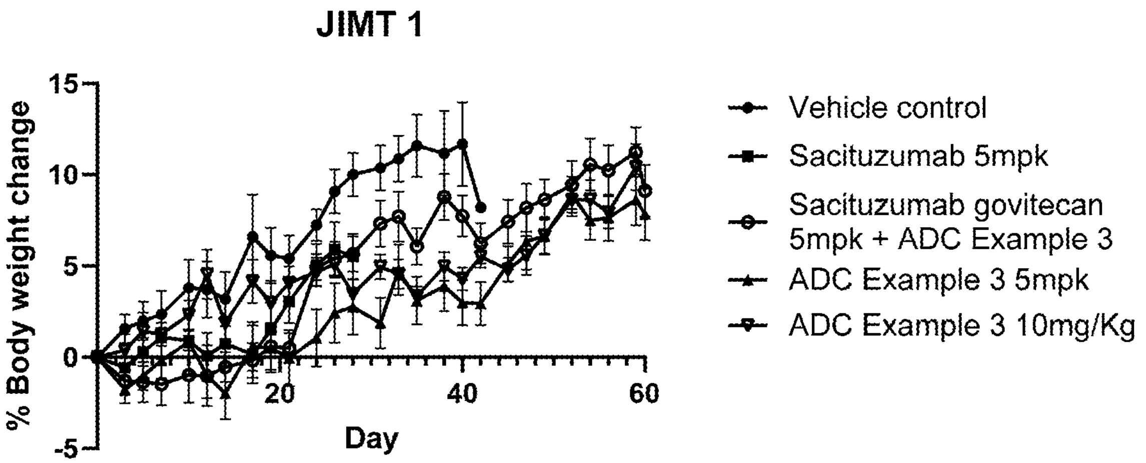
FIG. 20: Shows the effect of treatment with sacituzumab (5 mg/kg), sacituzumab govitecan (5 mg/kg) (plus ADC Example 3 5 mg/kg added on Study Days 27 and 34), and ADC Example 3 (5 mg/kg and 10 mg/kg) and vehicle control on body weight in a mouse JIMT-1 Breast cancer xenograft model.
Figure 21:
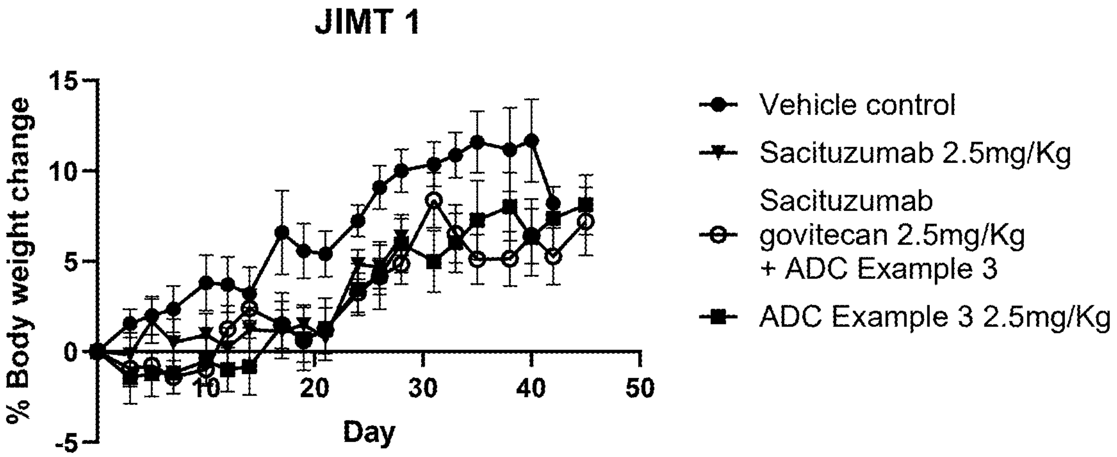
FIG. 21: Shows the effect of treatment with sacituzumab (2.5 mg/kg), sacituzumab govitecan (2.5 mg/kg plus ADC Example 3 5 mg/kg added on Study Day 27) and ADC Example 3 (2.5 mg/kg) and vehicle control on body weight in a mouse JIMT-1 Breast cancer xenograft model.

Significant body weight loss (>10%) was observed for one animal in Group 7. No significant body weight loss was observed in any of the other groups on study, see FIGS. 20 and 21. On Study Day 10, one animal in Group 2 was found dead.

Figure 18:
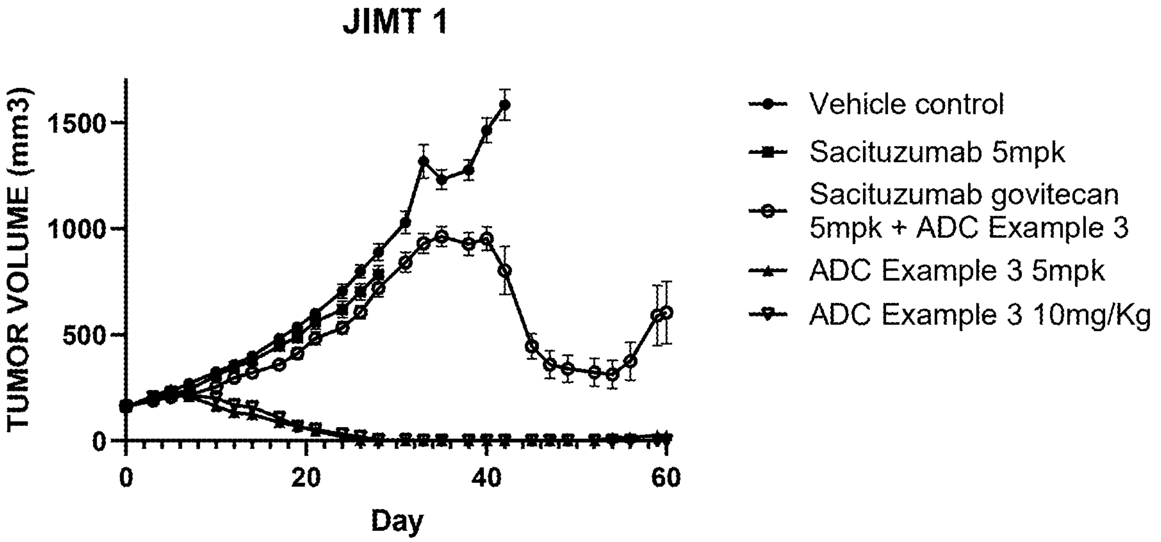
FIG. 18: Shows the effect of treatment with sacituzumab (5 mg/kg), sacituzumab govitecan (5 mg/kg) (plus ADC Example 3 5 mg/kg added on Study Days 27 and 34), and ADC Example 3 (5 mg/kg) and vehicle control on tumour volume in a mouse JIMT-1 Breast cancer xenograft model.
Figure 19:
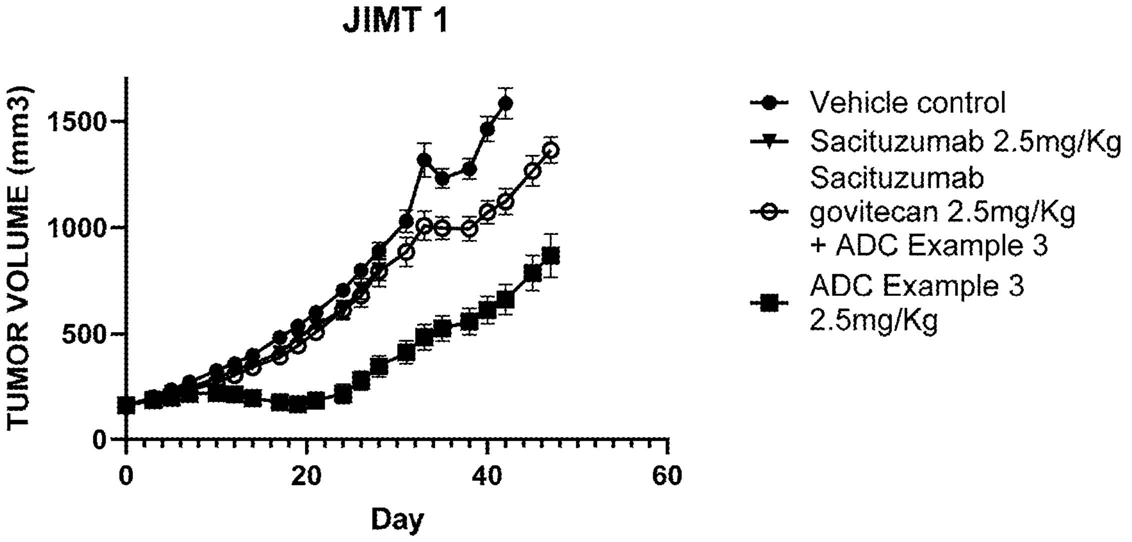
FIG. 19: Shows the effect of treatment with sacituzumab (2.5 mg/kg), sacituzumab govitecan (2.5 mg/kg plus ADC Example 3 5 mg/kg added on Study Day 27), and ADC Example 3 (2.5 mg/kg) and vehicle control on tumour volume in a mouse JIMT-1 Breast cancer xenograft model.

There was a significant decrease ($p<0.0001$) in the tumour volumes of mice treated with ADC Example 3 at all concentrations (Group 8, 2.5 mg/kg; Group 7, 5 mg/kg and Group 6 10 mg/kg) when compared to vehicle alone (Group 1). Sacituzumab govitecan at both concentrations (Group 4, 5 mg/kg, $p<0.0001$; Group 5 2.5 mg/kg, p=0.0348) showed a significant decrease in tumour volume compared to vehicle alone (Group 1). There was a significant decrease in tumour volume with unconjugated sacituzumab in Group 2 (5 mg/kg, p=0.0028), but there was no significant difference with Group 3 (2.5 mg/kg, p=0.0586) when compared to vehicle alone (Group 1). Data for 5 mg/kg and 10 mg/kg groups are shown in FIG. 18. Data for 2.5 mg/kg groups are shown in FIG. 19.

Mice treated with ADC Example 3 at all three concentrations (Group 6, 10 mg/kg; Group 7, 5 mg/kg and Group 8, 2.5 mg/kg) showed significant decreases in tumour volume compared to all other treatment groups (Groups 2-5; $p<0.0001$). There was also evidence of a dose response, with Groups 6 (10 mg/kg) and 7 (5 mg/kg), showing the greatest tumour volume reduction ($p<0.0001$), compared to Group 8 (2.5 mg/kg).

While Group 4 sacituzumab govitecan, 5 mg/kg showed a significant decrease in tumour volume compared to unconjugated sacituzumab Group 2 (5 mg/kg, p=0.0097) and Group 3 (2.5 mg/kg, p=0.0499), there was no significant difference between Group 5 (sacituzumab govitecan, 2.5 mg/kg) and Groups 2 (p=0.8424) and 3 (p=0.9995). There was also no significant difference between the two concentrations of unconjugated sacituzumab Group 2 (5 mg/kg) and Group 3 (2.5 mg/kg), p=0.9837. However, there was a significant difference between the two concentrations of sacituzumab govitecan, Group 4 (5 mg/kg) and Group 5 (2.5 mg/kg), p=0.3802.

Increased tumour growth inhibition (ΔTGI) compared to the vehicle group (Group 1) was apparent in all treatment groups. Treatment with 10 mg/kg and 5 mg/kg ADC Example 3 were the most efficacious when the tumour growth inhibition of all treatment groups was compared (Group 6; ΔTGI=121.55% and Group 7; ΔTGI=122.04%).

Since treatment with sacituzumab govitecan was only partially efficacious in Group 4, additional doses of ADC Example 3 were administered IV at 5 mpk on Study Days 27 and 34. This resulted in a significant reduction in tumour volume compared with vehicle control (see FIG. 18). Group 5 also received a dose of ADC Example 3 (IV at 5 mpk) on Study Day 27 (see FIG. 19) although no significant response was observed.

TABLE 9

Dosing regimen for Biological Example 11 and Results

| Group | Treatment Description | Test Article Dose (mg/kg) | Schedule | ΔTGI (Study Day 28) |
|---|---|---|---|---|
| 1 | Vehicle (PBS + 0.02% polysorbate 80, pH 7.4) | — | QW × 2 weeks | — |
| 2 | Unconjugated sacituzumab | 5 | QW × 2 weeks | 14.44 |
| 3 | Unconjugated sacituzumab | 2.5 | QW × 2 weeks | 12.11 |
| 4 | sacituzumab govitecan | 5 | QW × 2 weeks | 23.39 |
| 5 | sacituzumab govitecan | 2.5 | QW × 2 weeks | 13.13 |
| 6 | ADC Example 3 | 10 | QW × 2 weeks | 121.55 |
| 7 | ADC Example 3 | 5 | QW × 2 weeks | 122.04 |
| 8 | ADC Example 3 | 2.5 | QW × 2 weeks | 74.76 |

QW = once a week

Conclusion: The results of Biological Examples 1 and 2 demonstrate that the tested compounds of the invention are highly potent inhibitors of human NMT1 and display potent cytotoxic activity in a cancer cell line. Biological Example 3 demonstrates that the tested compounds of the invention display potent activity in a range of diverse cancer cell lines. The results of Biological Example 4 demonstrate that the tested compounds of the invention reduce the increase in tumour volume, or significantly decrease tumour volume when compared to vehicle. Biological Example 5 demonstrates that the tested compounds of the invention show improved cell permeability compared to Comparator Compound 1. Biological Example 6 demonstrates that the tested compounds of the invention have better metabolic stability profiles for certain purposes than Comparator Compound 1. Biological Example 7 demonstrates that the tested Example compound is an effective payload for an ADC, and as an ADC reduces tumour growth in a breast cancer xenograft model in vivo without adverse effect on body weight. The results of Biological Example 8 further demonstrate that the tested Example compound is an effective payload for an ADC, and as an ADC reduces tumour growth in a gastric cancer xenograft model in vivo without adverse effect on body weight.

The results of Biological Example 9 indicate that ADC Example 4 is well tolerated in mice at both 5 mg/kg and 10 mg/kg doses in a LNCaP prostate cancer xenograft model. Animals receiving these doses of ADC Example 4 showed a significant reduction in tumour volume, unlike treatment with ifinatamab alone which had no significant effect on tumour volume. ADC Example 4 also performed better than ifinatamab-DXd at both doses.

The results from Biological Example 10 indicate that ADC Example 4 is well tolerated in mice at 2.5 mg/kg, 5 mg/kg and 10 mg/kg doses in a VcaP human prostate cancer xenograft model.

ADC Example 4 reduced tumour volumes more than ifinatamab-Dxd and unconjugated Infinatamab. Indeed using unconjugated infinatamab showed no significant difference compared to vehicle alone. ADC Example 4 resulted in the most increased tumour growth inhibition compared with the controls, see Table 8.

The results from Biological Example 11 indicate that ADC Example 3 is well tolerated in mice at 2.5 mg/kg, 5 mg/kg and 10 mg/kg doses in a JIMT-1 human breast xenograft model. Mice treated with ADC Example 3 at all three concentrations showed significant decreases in tumour volume compared to all other treatment groups, also shown by the ΔTGI results in Table 9 wherein ADC Example 3 resulted in the most increased tumour growth inhibition.

Therefore, the compounds of the invention are expected to be useful pharmaceuticals particularly for the treatment or prevention of hyperproliferative disorders such as cancer.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference—in their entirety.

What is claimed is:

1. A drug conjugate having the following formula:

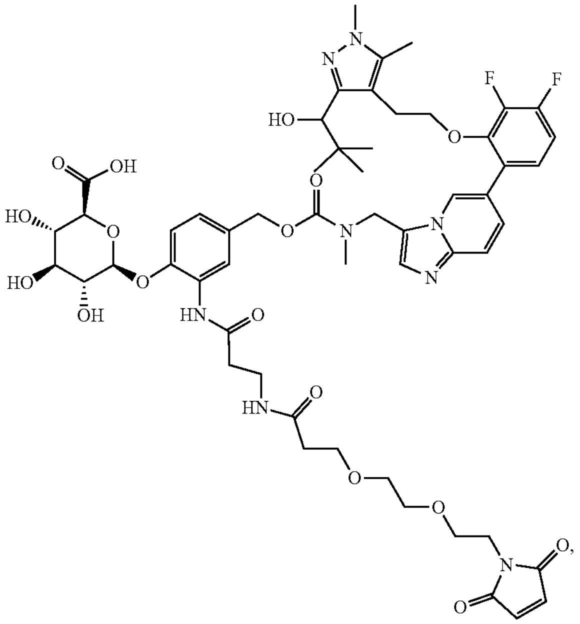 [SMILES: Cc1c(CCOc2c(-c3ccc4ncc(CN(C)C(=O)OCc5ccc(O[C@@H]6O[C@H](C(=O)O)[C@@H](O)[C@H](O)[C@H]6O)c(NC(=O)CCNC(=O)CCOCCOCCN6C(=O)C=CC6=O)c5)n4c3)ccc(F)c2F)c(C(O)C(C)(C)C)nn1C]

or a salt thereof.

2. The drug conjugate according to claim 1, wherein the drug conjugate is conjugated to a functional group on an amino acid side chain.

3. The drug conjugate according to claim 1, wherein the drug conjugate is conjugated to a chain terminus.

4. The drug conjugate according to claim 1, wherein the drug conjugate is conjugated to a N-terminus.

5. The drug conjugate according to claim 1, wherein the drug conjugate, or salt thereof, is conjugated to a chain terminus or a functional group on an amino acid side chain at a functional group of the linker, wherein the functional group of the linker is maleimide.

6. A pharmaceutical composition comprising the drug conjugate or salt thereof according to claim 5, and a pharmaceutically acceptable carrier.

7. A method for the treatment of cancer, which comprises administering to the subject a therapeutically effective amount of the drug conjugate or salt thereof according to claim 5.

8. The method according to claim 7, wherein the cancer is breast cancer, bladder cancer, lung cancer, prostate cancer, kidney cancer, esophageal carcinoma, colorectal cancer, gallbladder carcinoma, brain tumor, lymphoma, leukemia or neuroblastoma.

9. A drug conjugate having the following formula:

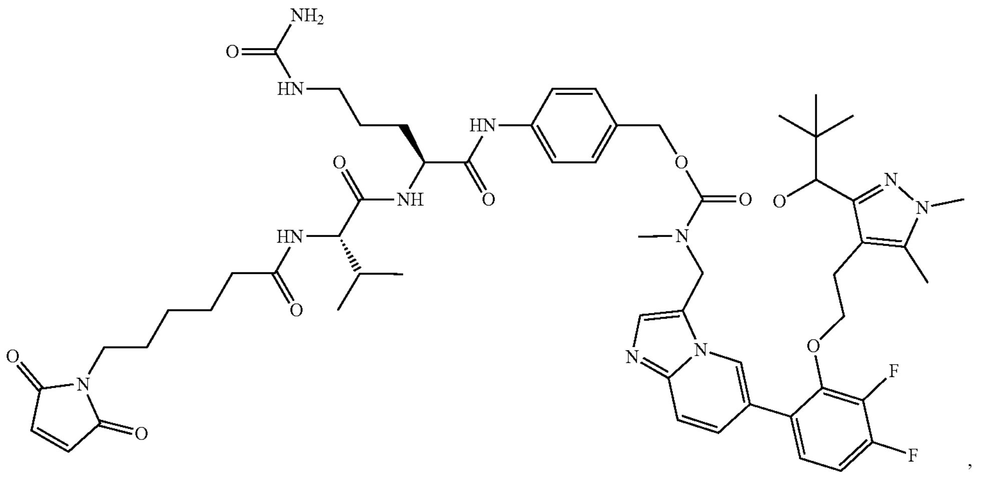

or a salt thereof.

10. The drug conjugate according to claim 9, wherein the drug conjugate is conjugated to a functional group on an amino acid side chain.

11. The drug conjugate according to claim 9, wherein the drug conjugate is conjugated to a chain terminus.

12. The drug conjugate according to claim 9, wherein the drug conjugate is conjugated to a N-terminus.

13. The drug conjugate according to claim 9, wherein the drug conjugate, or salt thereof, is conjugated to a chain terminus or a functional group on an amino acid side chain at a functional group of the linker, wherein the functional group of the linker is maleimide.

14. A method for the treatment of cancer, which comprises administering to the subject a therapeutically effective amount of the drug conjugate or salt thereof according to claim 13.

15. The method according to claim 14, wherein the cancer is breast cancer, bladder cancer, lung cancer, prostate cancer, kidney cancer, esophageal carcinoma, colorectal cancer, gallbladder carcinoma, brain tumor, lymphoma, leukemia or neuroblastoma.

16. A drug conjugate having the following formula:

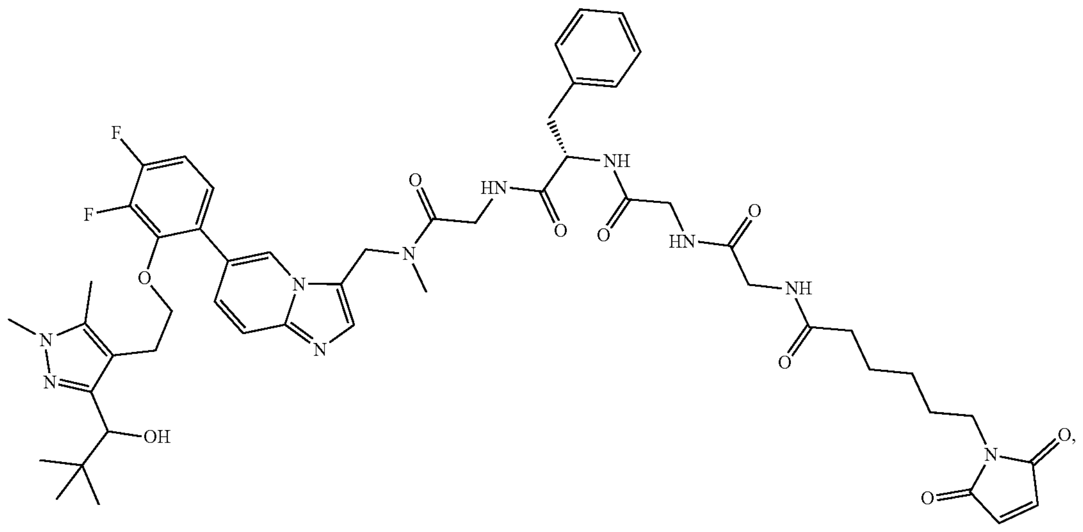 [SMILES: Cc1c(CCOc2c(-c3ccc4ncc(CN(C)C(=O)CNC(=O)[C@H](Cc5ccccc5)NC(=O)CNC(=O)CNC(=O)CCCCCN5C(=O)C=CC5=O)n4c3)ccc(F)c2F)c(C(O)C(C)(C)C)nn1C]

or a salt thereof.

17. The drug conjugate according to claim 16, wherein the drug conjugate is conjugated to a functional group on an amino acid side chain.

18. The drug conjugate according to claim 16, wherein the drug conjugate is conjugated to a chain terminus.

19. The drug conjugate according to claim 16, wherein the drug conjugate is conjugated to a N-terminus.

20. The drug conjugate according to claim 16, wherein the drug conjugate, or salt thereof, is conjugated to a chain terminus or a functional group on an amino acid side chain at a functional group of the linker, wherein the functional group of the linker is maleimide.

21. A pharmaceutical composition comprising the drug conjugate or salt thereof according to claim 20, and a pharmaceutically acceptable carrier.

22. A method for the treatment of cancer, which comprises administering to the subject a therapeutically effective amount of the drug conjugate or salt thereof according to claim 20.

23. The method according to claim 22, wherein the cancer is breast cancer, bladder cancer, lung cancer, prostate cancer, kidney cancer, esophageal carcinoma, colorectal cancer, gallbladder carcinoma, brain tumor, lymphoma, leukemia or neuroblastoma.

* * * * *

SEQUENCE LISTING

```
Sequence total quantity: 8
SEQ ID NO: 1            moltype = AA  length = 214
FEATURE                 Location/Qualifiers
source                  1..214
                        mol_type = protein
                        organism = synthetic construct
SEQUENCE: 1
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 2            moltype = AA  length = 450
FEATURE                 Location/Qualifiers
source                  1..450
                        mol_type = protein
                        organism = synthetic construct
SEQUENCE: 2
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
```

-continued

```
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 3            moltype = AA  length = 213
FEATURE                 Location/Qualifiers
source                  1..213
                        mol_type = protein
                        organism = synthetic construct
SEQUENCE: 3
QIVLSQSPAI LSASPGEKVT MTCRASSSVS YIHWFQQKPG SSPKPWIYAT SNLASGVPVR  60
FSGSGSGTSY SLTISRVEAE DAATYYCQQW TSNPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 4            moltype = AA  length = 451
FEATURE                 Location/Qualifiers
source                  1..451
                        mol_type = protein
                        organism = synthetic construct
SEQUENCE: 4
QVQLQQPGAE LVKPGASVKM SCKASGYTFT SYNMHWVKQT PGRGLEWIGA IYPGNGDTSY  60
NQKFKGKATL TADKSSSTAY MQLSSLTSED SAVYYCARST YYGGDWYFNV WGAGTTVTVS  120
AASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKAE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 5            moltype = AA  length = 213
FEATURE                 Location/Qualifiers
source                  1..213
                        mol_type = protein
                        organism = synthetic construct
SEQUENCE: 5
EIVLTQSPAT LSLSPGERAT LSCRASSRLI YMHWYQQKPG QAPRPLIYAT SNLASGIPAR  60
FSGSGSGTDF TLTISSLEPE DFAVYYCQQW NSNPPTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 6            moltype = AA  length = 452
FEATURE                 Location/Qualifiers
source                  1..452
                        mol_type = protein
                        organism = synthetic construct
SEQUENCE: 6
QVQLVQSGAE VKKPGSSVKV SCKASGYTFT NYVMHWVRQA PGQGLEWMGY INPYNDDVKY  60
NEKFKGRVTI TADESTSTAY MELSSLRSED TAVYYCARWG YYGSPLYYFD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 7            moltype = AA  length = 214
FEATURE                 Location/Qualifiers
source                  1..214
                        mol_type = protein
                        organism = synthetic construct
SEQUENCE: 7
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 8            moltype = AA  length = 451
FEATURE                 Location/Qualifiers
source                  1..451
                        mol_type = protein
                        organism = synthetic construct
```

-continued

SEQUENCE: 8

| | | | | | |
|---|---|---|---|---|---|
| QVQLQQSGSE | LKKPGASVKV | SCKASGYTFT | NYGMNWVKQA | PGQGLKWMGW | INTYTGEPTY 60 |
| TDDFKGRFAF | SLDTSVSTAY | LQISSLKADD | TAVYFCARGG | FGSSYWYFDV | WGQGSLVTVS 120 |
| SASTKGPSVF | PLAPSSKSTS | GGTAALGCLV | KDYFPEPVTV | SWNSGALTSG | VHTFPAVLQS 180 |
| SGLYSLSSVV | TVPSSSLGTQ | TYICNVNHKP | SNTKVDKRVE | PKSCDKTHTC | PPCPAPELLG 240 |
| GPSVFLFPPK | PKDTLMISRT | PEVTCVVVDV | SHEDPEVKFN | WYVDGVEVHN | AKTKPREEQY 300 |
| NSTYRVVSVL | TVLHQDWLNG | KEYKCKVSNK | ALPAPIEKTI | SKAKGQPREP | QVYTLPPSRE 360 |
| EMTKNQVSLT | CLVKGFYPSD | IAVEWESNGQ | PENNYKTTPP | VLDSDGSFFL | YSKLTVDKSR 420 |
| WQQGNVFSCS | VMHEALHNHY | TQKSLSLSPG | K | | 451 |